(12) United States Patent
Jia et al.

(10) Patent No.: US 11,807,616 B2
(45) Date of Patent: Nov. 7, 2023

(54) ORGANIC COMPOUND, AND ELECTRONIC ELEMENT AND ELECTRONIC DEVICE USING SAME

(71) Applicant: Shaanxi Lighte Optoelectronics Material Co., Ltd., Xi'an (CN)

(72) Inventors: Zhiyan Jia, Xi'an (CN); Yun Liu, Xi'an (CN); Youngkook Kim, Xi'an (CN); Yingwen Li, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 18/027,991

(22) PCT Filed: Apr. 21, 2022

(86) PCT No.: PCT/CN2022/088176
§ 371 (c)(1),
(2) Date: Mar. 23, 2023

(87) PCT Pub. No.: WO2022/267661
PCT Pub. Date: Dec. 29, 2022

(65) Prior Publication Data
US 2023/0265063 A1 Aug. 24, 2023

(30) Foreign Application Priority Data

Jun. 25, 2021 (CN) .......................... 202110713428.0
Aug. 20, 2021 (CN) .......................... 202110963124.X

(51) Int. Cl.
*C07D 307/91* (2006.01)
*H10K 85/60* (2023.01)
(Continued)

(52) U.S. Cl.
CPC .......... *C07D 307/91* (2013.01); *C07C 211/54* (2013.01); *C07D 209/82* (2013.01);
(Continued)

(58) Field of Classification Search
CPC .... C07D 307/91; H10K 85/40; H10K 85/622; H10K 85/633; H10K 85/636
See application file for complete search history.

(56) References Cited

FOREIGN PATENT DOCUMENTS

| CN | 107922335 A | 4/2018 |
|----|-------------|--------|
| CN | 109748802 A | 5/2019 |

(Continued)

OTHER PUBLICATIONS

International Search Report from corresponding International Application No. PCT/CN2022/088176, dated Jul. 25, 2022, 4 pages including translation.

*Primary Examiner* — Anthony Ho
(74) *Attorney, Agent, or Firm* — TUCKER ELLIS LLP

(57) ABSTRACT

The present application belongs to the field of organic materials, and relates to an organic compound, and an electronic element and an electronic device using same. The organic compound has a structure as represented by Formula I, and the organic compound can significantly improve the performance of an organic electroluminescent device when applied to the device.

(Continued)

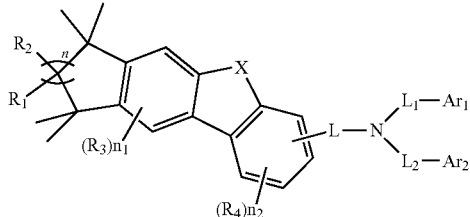

Formula I

10 Claims, 2 Drawing Sheets

(51) Int. Cl.
C07D 409/12 (2006.01)
C07D 333/76 (2006.01)
C07D 209/82 (2006.01)
C07F 7/08 (2006.01)
H10K 85/40 (2023.01)
C07C 211/54 (2006.01)
H10K 50/15 (2023.01)

(52) U.S. Cl.
CPC ......... *C07D 333/76* (2013.01); *C07D 409/12* (2013.01); *C07F 7/0812* (2013.01); *H10K 50/15* (2023.02); *H10K 85/40* (2023.02); *H10K 85/622* (2023.02); *H10K 85/633* (2023.02); *H10K 85/636* (2023.02); *H10K 85/6572* (2023.02); *H10K 85/6574* (2023.02); *H10K 85/6576* (2023.02); *C07B 2200/05* (2013.01)

(56) References Cited

FOREIGN PATENT DOCUMENTS

| CN | 113773290 A | 12/2021 |
| WO | 2021107711 A1 | 6/2021 |
| WO | 2021107743 A1 | 6/2021 |

ORGANIC COMPOUND, AND ELECTRONIC ELEMENT AND ELECTRONIC DEVICE USING SAME

CROSS REFERENCE TO RELATED APPLICATIONS

The present application claims the priority of Chinese patent application CN202110713428.0 filed on Jun. 25, 2021, and the priority of Chinese patent application CN202110963124.X filed on Aug. 20, 2021, and the full content of the above Chinese patent applications is incorporated herein by reference.

TECHNICAL FIELD

The present application relates to the technical field of organic electroluminescence, and particularly provides an organic compound, and an electronic element and an electronic device using the same.

BACKGROUND

An organic electroluminescent technology has been regarded as a next generation display and lighting technology due to the advantages of active luminescence, high luminescence efficiency, low power consumption, lightness, thinness, fast response speed, large viewing angle, and the like. An organic electroluminescent device consists of a substrate, an anode, a hole injection layer, a hole transporting layer, a hole adjusting layer, an electron blocking layer, an organic luminescence layer, an electron transporting layer, a hole blocking layer, an electron injection layer, a cathode, and the like. Electrons and holes are injected from the cathode and the anode, respectively, and then pass through the electron transporting layer and the hole transporting layer to be recombined in the organic luminescence layer to form excitons, and the excitons return to a ground state to emit light.

Although organic electroluminescent devices (OLEDs) have been widely used now, properties such as the luminescence efficiency and service life of the devices have yet to be further improved due to the scarcity of excellent transporting materials, efficient luminescence materials, and injection materials with respect to the application requirements of products. At present, the reported organic hole adjusting layer materials have low glass transition temperature due to their low molecular weight, the materials are easy to crystallize due to repeated charge and discharge during use of the materials, and the film uniformity is damaged, thus affecting the service life of the materials. Therefore, it is of a great practical value to develop stable and efficient organic hole adjusting layer materials to improve the charge mobility, reduce the driving voltage, improve the luminescence efficiency of the device, and prolong the service life of the device.

SUMMARY

The objective of the present application is to provide an organic compound, and an electronic element and an electronic device using the same, and when the organic compound is used in an organic electroluminescent device, the performance of the device can be improved.

A first aspect of the present application provides an organic compound having a structure as shown in Formula I:

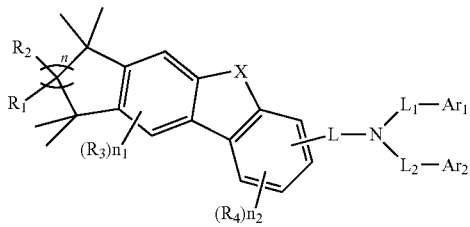

Formula I where $R_1$ and $R_2$ are the same or different, and are each independently selected from hydrogen, deuterium, a methyl or a phenyl;

n is selected from 1 or 2;

X is selected from $C(R_5R_6)$, O or S;

$R_5$ and $R_6$ are the same or different, and are each independently selected from an alkyl with 1 to 10 carbon atoms or an aryl with 6 to 20 carbon atoms; and optionally, $R_5$ and $R_6$ are connected to each other to form a saturated or unsaturated 5- to 15-membered ring;

L is selected from a single bond, a substituted or unsubstituted arylene with 6 to 30 carbon atoms, a substituted or unsubstituted heteroarylene with 3 to 30 carbon atoms, or an alkylene with 1 to 10 carbon atoms;

$L_1$ and $L_2$ are the same or different, and are each independently selected from a single bond, a substituted or unsubstituted arylene with 6 to 30 carbon atoms, or a substituted or unsubstituted heteroarylene with 3 to 30 carbon atoms;

$Ar_1$ and $Ar_2$ are the same or different, and are each independently selected from a substituted or unsubstituted aryl with 6 to 30 carbon atoms, or a substituted or unsubstituted heteroaryl with 3 to 30 carbon atoms;

$R_3$ and $R_4$ are the same or different, and are each independently selected from deuterium, a cyano, a halogen group, an alkyl with 1 to 10 carbon atoms, an aryl with 6 to 12 carbon atoms, a heteroaryl with 3 to 12 carbon atoms, a trialkylsilyl with 3 to 12 carbon atoms, or a haloalkyl with 1 to 10 carbon atoms;

$n_1$ represents the number of $R_3$, and is selected from 0, 1 or 2, and when $n_1$ is 2, each $R_3$ is the same or different; and $n_2$ represents the number of $R_4$, and is selected from 0, 1, 2 or 3, and when $n_2$ is greater than 1, each $R_4$ is the same or different; and substituents of L, $L_1$, $L_2$, $Ar_1$, and $Ar_2$ are the same or different, and are each independently selected from deuterium, a cyano, a halogen, an alkyl with 1 to 10 carbon atoms, a haloalkyl with 1 to 10 carbon atoms, a trialkylsilyl with 3 to 12 carbon atoms, a triphenylsilyl, an aryl with 6 to 20 carbon atoms, a heteroaryl with 3 to 20 carbon atoms, or a cycloalkyl with 3 to 10 carbon atoms; and optionally, any two adjacent substituents form a saturated or unsaturated 3- to 15-membered ring.

In the organic compound of the present application, a substituted cycloalkyl fused specific dibenzo five-membered ring is used a core, and is combined with triarylamine to make the molecular spatial configuration more steric, thereby increasing the Ti (triplet energy level) level, effectively blocking the diffusion of excitons and increasing the service life of the device; and in addition, the organic compound of the present application has better hole mobility, improving the matching between a hole transporting layer and an organic luminescence layer, thereby improving the luminescence efficiency of the device. Therefore, when the organic compound of the present application is used in a hole adjusting layer in an organic electroluminescent device, in particular a red light device, the luminescence efficiency and the service life of the device can be effectively improved while maintaining a lower driving voltage.

A second aspect of the present application provides an electronic element, including an anode and a cathode which are oppositely disposed, and a functional layer disposed between the anode and the cathode; where the functional layer includes the organic compound described above.

A third aspect of the present application provides an electronic device, including the electronic element described above.

Other features and advantages of the present application will be described in detail in the subsequent detailed description.

BRIEF DESCRIPTION OF THE DRAWINGS

The drawings are used to provide a further understanding of the present application and constitute a part of the description, and are used to explain the present application together with the following specific embodiments, but do not constitute limitations on the present application.

REFERENCE NUMERALS

Figure 1:
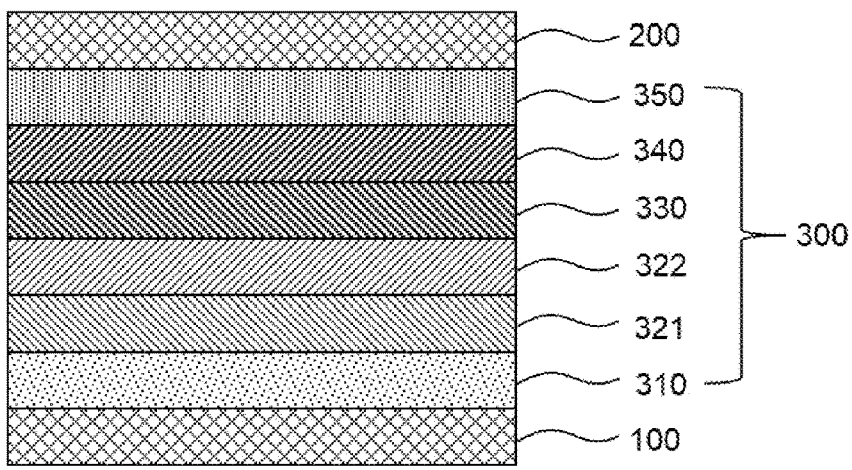
FIG. 1 is a structural schematic diagram of an organic electroluminescent device according to one embodiment of the present application.

100, anode; 200, cathode; 300, functional layer; 310, hole injection layer; 321, hole transporting layer; 322, hole adjusting layer; 330, organic luminescence layer; 340, electron transporting layer; 350, electron injection layer; 320, hole transporting layer; 360, photoelectric conversion layer; 400, first electronic device; and 500, second electronic device.

DETAILED DESCRIPTION

The specific embodiments of the present application are described in detail below in combination with the drawings. It should be understood that the specific embodiments described herein are only used to illustrate and interpret the present application, but are not to limit the present application.

A first aspect of the present application provides an organic compound having a structure as shown in Formula I.

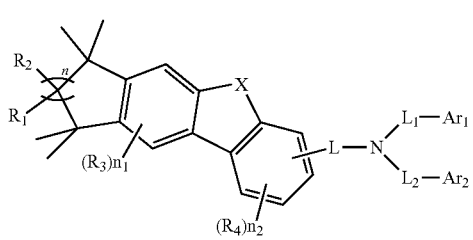

Formula I where $R_1$ and $R_2$ are the same or different, and are each independently selected from hydrogen, deuterium, a methyl or a phenyl;

n is selected from 1 or 2;

X is selected from $C(R_5R_6)$, O or S;

$R_5$ and $R_6$ are the same or different, and are each independently selected from an alkyl with 1 to 10 carbon atoms or an aryl with 6 to 20 carbon atoms; and optionally, $R_5$ and $R_6$ are connected to each other to form a saturated or unsaturated 5- to 15-membered ring;

L is selected from a single bond, a substituted or unsubstituted arylene with 6 to 30 carbon atoms, a substituted or unsubstituted heteroarylene with 3 to 30 carbon atoms, or an alkylene with 1 to 10 carbon atoms;

$L_1$ and $L_2$ are the same or different, and are each independently selected from a single bond, a substituted or unsubstituted arylene with 6 to 30 carbon atoms, or a substituted or unsubstituted heteroarylene with 3 to 30 carbon atoms;

$Ar_1$ and $Ar_2$ are the same or different, and are each independently selected from a substituted or unsubstituted aryl with 6 to 30 carbon atoms, or a substituted or unsubstituted heteroaryl with 3 to 30 carbon atoms;

$R_3$ and $R_4$ are the same or different, and are each independently selected from deuterium, a cyano, a halogen, an alkyl with 1 to 10 carbon atoms, an aryl with 6 to 12 carbon atoms, a heteroaryl with 3 to 12 carbon atoms, a trialkylsilyl with 3 to 12 carbon atoms, or a haloalkyl with 1 to 10 carbon atoms;

$n_1$ represents the number of $R_3$, and is selected from 0, 1 or 2, and when $n_1$ is 2, each $R_3$ is the same or different; and $n_2$ represents the number of $R_4$, and is selected from 0, 1, 2 or 3, and when $n_2$ is greater than 1, each $R_4$ is the same or different; and substituents of L, $L_1$, $L_2$, $Ar_1$, and $Ar_2$ are the same or different, and are each independently selected from deuterium, a cyano, a halogen (e.g., fluorine), an alkyl with 1 to 10 carbon atoms, a haloalkyl with 1 to 10 carbon atoms, a trialkylsilyl with 3 to 12 carbon atoms, a triphenylsilyl, an aryl with 6 to 20 carbon atoms, a heteroaryl with 3 to 20 carbon atoms, or a cycloalkyl with 3 to 10 carbon atoms; and optionally, any two adjacent substituents form a saturated or unsaturated 3- to 15-membered ring.

In the present application, "$R_5$ and $R_6$ are the same or different, and are each independently selected from an alkyl with 1 to 10 carbon atoms or an aryl with 6 to 20 carbon atoms, and optionally, $R_5$ and $R_6$ are connected to each other to form a saturated or unsaturated 5- to 15-membered ring", which has the same meaning as "$R_5$ and $R_6$ are the same or different, and are each independently selected from an alkyl with 1 to 10 carbon atoms or an aryl with 6 to 20 carbon atoms, or $R_5$ and $R_6$ are connected to each other to form a saturated or unsaturated 5- to 15-membered ring".

In the present application, the term such as "substituted or unsubstituted" means that a functional group described behind the term may have or may not have a substituent (hereinafter, the substituent is collectively referred to as $R_c$ in order to facilitate description). For example, the "substituted or unsubstituted aryl" refers to aryl having the substituent $R_c$ or unsubstituted aryl. The above substituent, i.e., Rc, can be, for example, deuterium, a halogen group, a cyano, a heteroaryl, an aryl, a trialkylsilyl, a triphenylsilyl, an alkyl, a haloalkyl, a cycloalkyl, or the like. The number of the substituent $R_c$ may be one or more. When two substituents $R_c$ are connected to a same atom, the two substituents $R_c$ can independently exist or are connected with each other to form a ring with the atom; and when two adjacent substituents $R_c$ exist on the functional group, the two adjacent substituents $R_c$ can independently exist or are fused with the functional group to which they are connected to form a ring.

In the present application, the terms "optional" and "optionally" mean that the subsequently described event or circumstance may but need not occur, and that the description includes instances where the event or circumstance occurs or does not occur. For example, "optionally, two adjacent substituents form a ring", which means that the two substituents can, but need not, form a ring, including scenarios in which two adjacent substituents form a ring and scenarios in which two adjacent substituents do not form a ring.

In the present application, the adopted description manners "are each independently", " . . . are respectively and independently" and " . . . are independently selected from" can be interchanged, and should be understood in a broad sense, which means that in different groups, specific options expressed between the same symbols do not influence each other, or in a same group, specific options expressed between the same symbols do not influence each other. For example, the meaning of

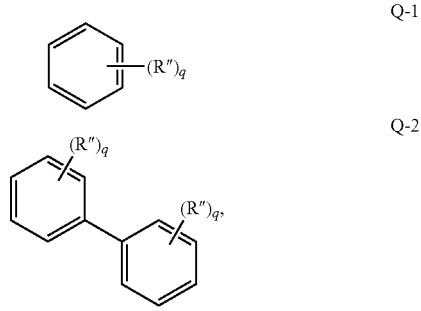

where each q is independently 0, 1, 2 or 3, and each R" is independently selected from hydrogen, deuterium, a fluorine or a chlorine" is as follows: a formula Q-1 represents that q substituents R" exist on a benzene ring, each R" can be the same or different, and options of each R" do not influence each other; and a formula Q-2 represents that each benzene ring of biphenyl has q substituents R", the number q of the substituents R" on the two benzene rings can be the same or different, each R" can be the same or different, and options of each R" do not influence each other.

In the present application, the number of carbon atoms in a substituted or unsubstituted functional group refers to the number of all carbon atoms. For example, if $L_1$ is substituted arylene with 12 carbon atoms, the number of all carbon atoms of the arylene and substituents of the arylene is 12.

In the present application, aryl refers to an optional functional group or substituent derived from an aromatic carbocyclic ring. The aryl may be a monocyclic aryl (e.g., phenyl) or a polycyclic aryl, in other words, the aryl can be a monocyclic aryl, a fused-ring aryl, two or more monocyclic aryls conjugatedly connected through carbon-carbon bonds, a monocyclic aryl and a fused-ring aryl conjugatedly connected through a carbon-carbon bond, or two or more fused-ring aryls conjugatedly connected through carbon-carbon bonds. That is, unless otherwise noted, two or more aromatic groups conjugatedly connected through carbon-carbon bonds can also be regarded as aryl in the present application. The fused-ring aryl may include, for example, a bicyclic fused aryl (e.g., a naphthyl), a tricyclic fused aryl (e.g., phenanthryl, fluorenyl, and anthryl), and the like. Examples of the aryl include, but are not limited to, phenyl, naphthyl, fluorenyl, anthracenyl, phenanthryl, biphenyl, terphenyl, benzo[9,10]phenanthryl, pyrenyl, benzofluoranthenyl, chrysenyl, and the like.

In the present application, the arylene involved refers to a divalent group formed by further loss of one hydrogen atom from aryl.

In the present application, the substituted aryl may be that one or two or more hydrogen atoms in the aryl are substituted by groups such as deuterium atom, halogen group, —CN, aryl, heteroaryl, trialkylsilyl, triphenylsilyl, alkyl, cycloalkyl, haloalkyl, and the like. Specific examples of heteroaryl-substituted aryl include, but are not limited to, dibenzofuranyl-substituted phenyl, dibenzothienyl-substituted phenyl, pyridyl-substituted phenyl, and the like. It should be understood that the number of carbon atoms in the substituted aryl refers to the total number of carbon atoms of the aryl and substituents of the aryl, for example, substituted aryl with 18 carbon atoms means that the total number of carbon atoms of the aryl and substituents of the aryl is 18.

In the present application, the heteroaryl refers to a monovalent aromatic ring containing at least one heteroatom in the ring or a derivative thereof, and the heteroatom can be at least one of B, O, N, P, Si, Se and S. The heteroaryl may be a monocyclic heteroaryl or a polycyclic heteroaryl, in other words, the heteroaryl may be a system of a single aromatic ring or a system of multiple aromatic rings conjugatedly connected through carbon-carbon bonds, and any one aromatic ring system is one aromatic monocyclic ring or one aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, phenothiazinyl, silafluorenyl, dibenzofuranyl, N-phenylcarbazolyl, N-pyridylcarbazolyl, N-methylcarbazolyl and the like, but is not limited thereto. The thienyl, furyl, phenanthrolinyl and the like are heteroaryls of the single aromatic ring system, and N-phenylcarbazolyl and N-pyridylcarbazolyl are heteroaryls of the multiple aromatic rings system conjugatedly connected through carbon-carbon bonds.

In the present application, the heteroarylene involved refers to a divalent group formed by further loss of one hydrogen atom from heteroaryl.

In the present application, the substituted heteroaryl can be that one or two or more hydrogen atoms in the heteroaryl are substituted by groups such as deuterium atom, halogen group, —CN, aryl, heteroaryl, trialkylsilyl, triphenylsilyl, alkyl, cycloalkyl, haloalkyl, and the like. Specific examples of heteroaryl substituted by aryl include, but are not limited to, phenyl-substituted dibenzofuranyl, phenyl-substituted dibenzothienyl, phenyl-substituted pyridyl and the like. It should be understood that the number of carbon atoms of the substituted heteroaryl refers to the total number of carbon atoms of heteroaryl and substituents of the heteroaryl.

In the present application, the number of carbon atoms of the aryl as a substituent can be 6 to 20, for example, the number of carbon atoms is 6, 7, 8, 9, 10, 11, 12, 13, 14, 15, 16, 17, 18, 19, or 20, and specific examples of the aryl as a substituent include, but are not limited to, phenyl, biphenyl, naphthyl, anthryl, phenanthryl, and chrysenyl.

In the present application, the number of carbon atoms of the heteroaryl as a substituent can be 3 to 20, for example, the number of carbon atoms is 3, 4, 5, 6, 7, 8, 9, 10, 11, 12, 13, 14, 15, 16, 17, 18, 19, or 20, and specific examples of the heteroaryl as a substituent include, but are not limited to, pyridyl, pyrimidinyl, carbazolyl, dibenzofuranyl, dibenzothienyl, quinolyl, quinazolinyl, quinoxalinyl, and isoquinolyl.

In the present application, the alkyl with 1 to 10 carbon atoms may include linear alkyl with 1 to 10 carbon atoms and branched alkyl with 3 to 10 carbon atoms. The number of carbon atoms of the alkyl can be, for example, 1, 2, 3, 4, 5, 6, 7, 8, 9, or 10, and specific examples of the alkyl include, but are not limited to, methyl, ethyl, n-propyl, isopropyl, n-butyl, isobutyl, tert-butyl, n-pentyl, isopentyl, neopentyl, n-hexyl, n-heptyl, n-octyl, 2-ethylhexyl, nonyl, decyl, 3,7-dimethyloctyl, and the like.

In the present application, the halogen group can be, for example, fluorine, chlorine, bromine or iodine, preferably fluorine.

In the present application, specific examples of trialkylsilyl include, but are not limited to, trimethylsilyl, triethylsilyl, and the like.

In the present application, specific examples of haloalkyl include, but are not limited to, trifluoromethyl.

In the present application, specific examples of cycloalkyl include, but are not limited to, cyclopentyl, cyclohexyl, and adamantyl.

In the present application, " 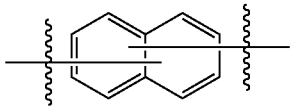 " refers to a connecting bond bonded to other substituents or binding sites.

In the present application, an non-positioned connecting bond refers to a single bond " 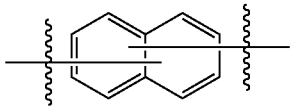 " extending out from a ring system, which means that one end of the connecting bond can be connected to any position in the ring system through which the bond penetrates, and the other end of the connecting bond is connected to the rest part of a compound molecule structure. For example, as shown in the following formula (f), naphthyl represented by the formula (f) is connected to other positions of a molecule through two non-positioned connecting bonds penetrating through double rings, and its meaning includes any one possible connecting mode represented by formulas (f-1) to (f-10):

 (f)

 (f-1)

(f-2)

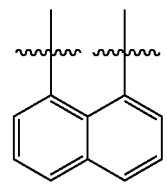

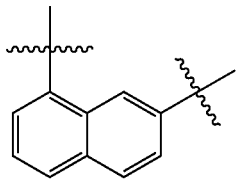

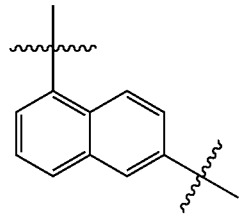 (f-3)

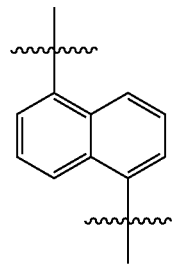 (f-4)

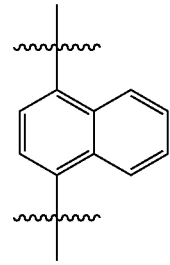 (f-5)

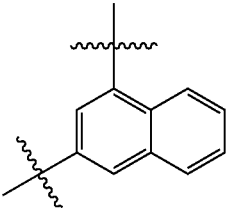 (f-6)

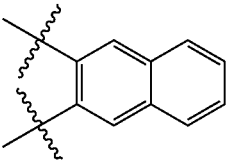 (f-7)

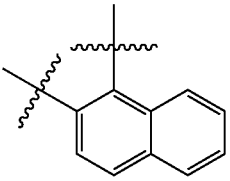 (f-8)

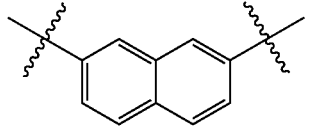 (f-9)

(f-10)

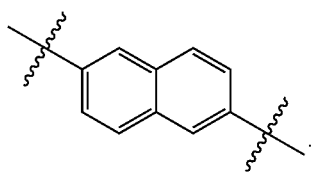

For example, as shown in the following formula (X'), phenanthryl represented by the formula (X') is connected with other positions of a molecule through one non-positioned connecting bond extending out from the center of a benzene ring on one side, and its meaning includes any possible connecting mode represented by formulas (X'-1) to (X'-4):

(X')

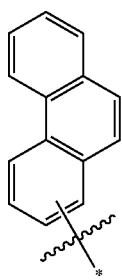

(X'-1)

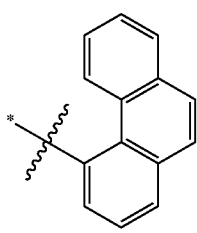

(X'-2)

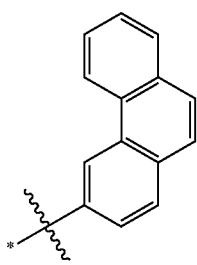

(X'-3)

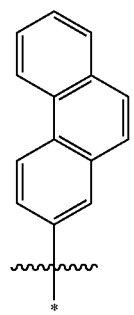

(X'-4)

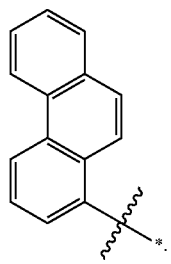

In the present application, a non-positioned substituent refers to a substituent connected through a single bond extending out from the center of a ring system, which means that the substituent can be connected to any possible position in the ring system. For example, as shown in the following formula (Y), a substituent R' represented by the formula (Y) is connected with a quinoline ring through one non-positioned connecting bond, and its meaning includes any possible connecting mode represented by formulas (Y-1) to (Y-7):

(Y)

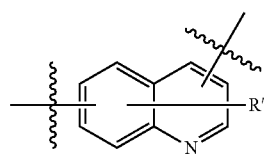

(Y-1)

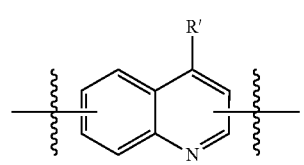

(Y-2)

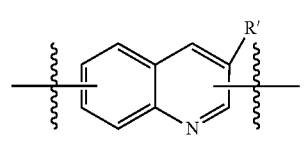

(Y-3)

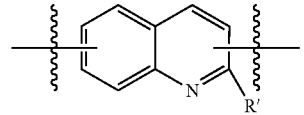

(Y-4)

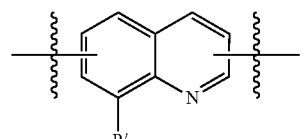

(Y-5)

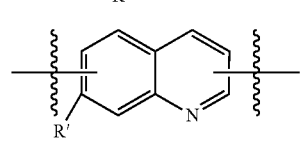

(Y-6)

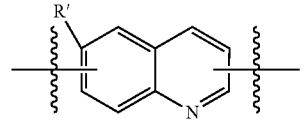

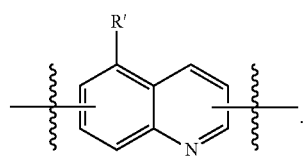
(Y-7)

In the present application, the Formula I can have a structure represented by Formula I-1 or Formula I-2:

Formula I-1

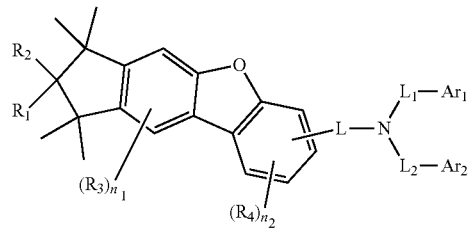

Formula I-1-A

Formula I-2

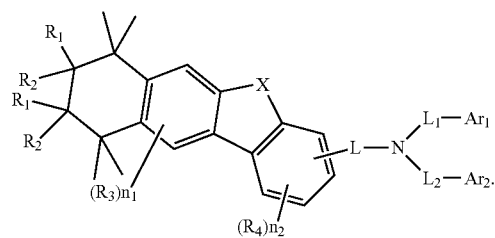

Formula I-2-A

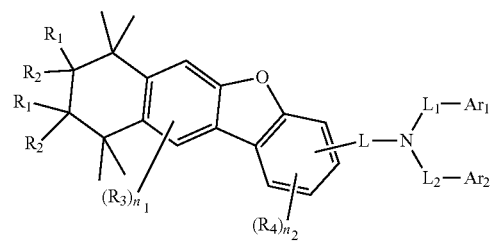

Formula I-1-B

In the Formula I-2, both $R_1$ can be the same or different, and both $R_2$ can be the same or different.

Preferably, X is selected from $C(R_5R_6)$ or O.

Optionally, $R_1$ and $R_2$ are the same or different, and are each independently selected from hydrogen or a methyl.

Optionally, $R_5$ and $R_6$ are the same or different, and are each independently selected from a methyl, an ethyl, an isopropyl, a tert-butyl, a phenyl, a naphthyl, or a biphenyl; and optionally, $R_5$ and $R_6$ are connected to each other to form a cyclopentane, a cyclohexane, a norbornane or a fluorene ring.

Optionally, $R_3$ and $R_4$ are the same or different, and are each independently selected from deuterium, a cyano, a fluorine, a methyl, an ethyl, an isopropyl, a tert-butyl, a phenyl, a naphthyl, a biphenyl, a pyridyl, a dibenzofuranyl, a dibenzothienyl, a carbazolyl, a trimethylsilyl, or a trifluoromethyl.

Optionally, $n_1+n_2=0$, 1 or 2.

In one embodiment of the present application, the structure of the organic compound is selected from the group consisting of the following structural formulas:

Formula I-2-B

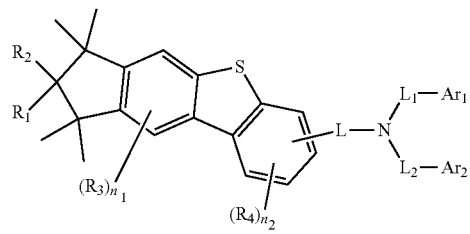

Formula I-1-C

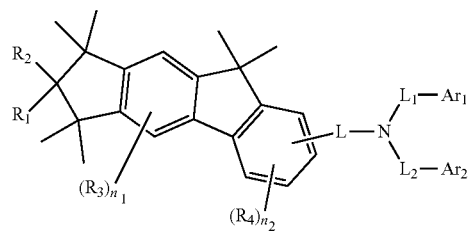

Formula I-2-C

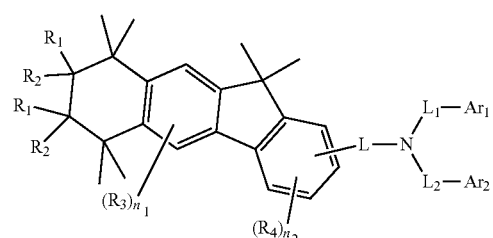

Formula I-1-D

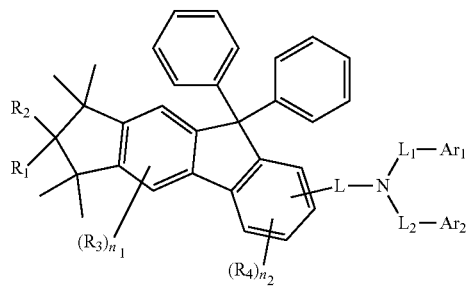

Formula I-2-D

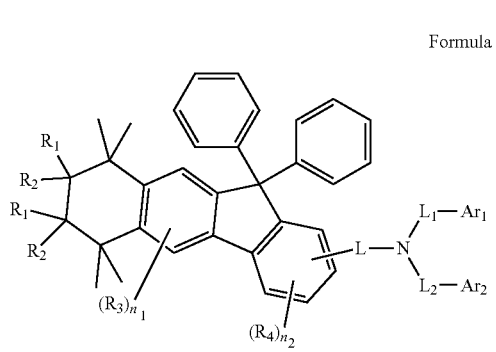

Formula I-1-E

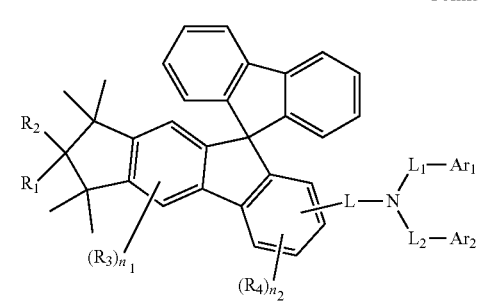

Formula I-2-E

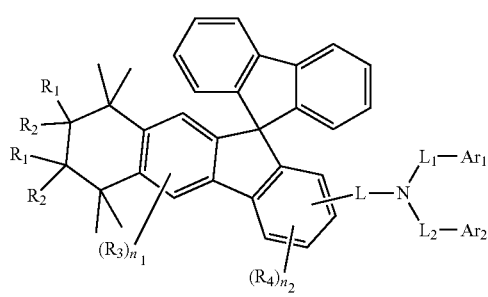

Formula I-1-F

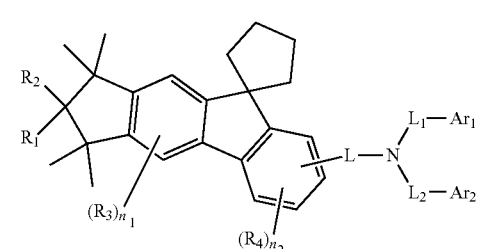

Formula I-2-F

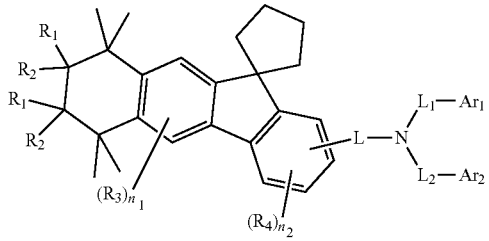

Formula I-1-G

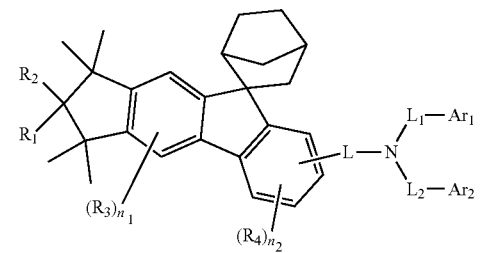

Formula I-2-G

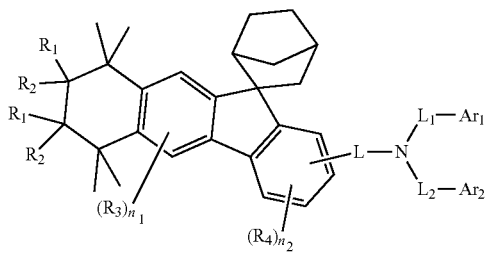

Formula I-1-H

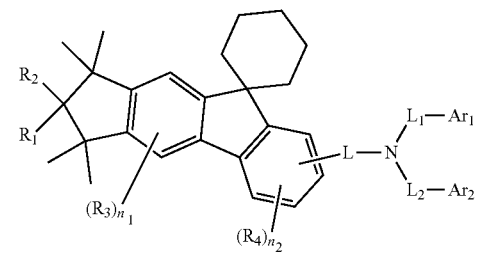

Formula I-2-H

Optionally, substituents of L, $L_1$, $L_2$, $Ar_1$, and $Ar_2$ are the same or different, and are each independently selected from deuterium, a cyano, a halogen group (e.g., fluorine), an alkyl with 1 to 5 carbon atoms, a fluoroalkyl with 1 to 5 carbon atoms, a trialkylsilyl with 3 to 7 carbon atoms, an aryl with 6 to 15 carbon atoms, a heteroaryl with 5 to 15 carbon atoms, or a cycloalkyl with 5 to 10 carbon atoms.

In the present application, specific examples of the substituents of L, $L_1$, $L_2$, $Ar_1$, and $Ar_2$ respectively include, but are not limited to, deuterium, cyano, fluorine, methyl, ethyl, n-propyl, isopropyl, tert-butyl, trifluoromethyl, trimethylsilyl, phenyl, naphthyl, biphenyl, carbazolyl, dibenzofuranyl, dibenzothienyl, quinolyl, cyclopentyl, cyclohexyl, or adamantyl; and optionally, any two adjacent substituents form a fluorene ring, a cyclopentane or a cyclohexane.

In one embodiment of the present application, L is selected from a single bond, a substituted or unsubstituted arylene with 6 to 15 carbon atoms, or a substituted or unsubstituted heteroarylene with 3 to 12 carbon atoms. For example, L is selected from a single bond; a substituted or unsubstituted arylene with 6, 7, 8, 9, 10, 11, 12, 13, 14, or 15 carbon atoms; or a substituted or unsubstituted heteroarylene with 3, 4, 5, 6, 7, 8, 9, 10, 11, or 12 carbon atoms.

Optionally, L is selected from a single bond, a substituted or unsubstituted phenylene, a substituted or unsubstituted biphenylene, or a substituted or unsubstituted naphthylene.

In one embodiment of the present application, $L_1$ and $L_2$ are each independently selected from a single bond, a substituted or unsubstituted arylene with 6 to 15 carbon atoms, or a substituted or unsubstituted heteroarylene with 5 to 12 carbon atoms. For example, $L_1$ and $L_2$ are each independently selected from single bond; a substituted or unsubstituted arylene with 6, 7, 8, 9, 10, 11, 12, 13, 14, or 15 carbon atoms; or a substituted or unsubstituted heteroarylene with 5, 6, 7, 8, 9, 10, 11, or 12 carbon atoms.

Optionally, $L_1$ and $L_2$ are each independently selected from a single bond, a substituted or unsubstituted phenylene, a substituted or unsubstituted biphenylene, a substituted or unsubstituted naphthylene, a substituted or unsubstituted fluorenylene, a substituted or unsubstituted dibenzofurylene, a substituted or unsubstituted dibenzothienylene, or a substituted or unsubstituted carbazolylene.

Optionally, substituents of L, $L_1$, and $L_2$ are each independently selected from deuterium, a fluorine, a cyano, an alkyl with 1 to 5 carbon atoms, a trimethylsilyl, or a phenyl.

In one specific embodiment of the present application, L, $L_1$ and $L_2$ are each independently selected from a single bond or a group A; where the group A is selected from the group consisting of the following groups:

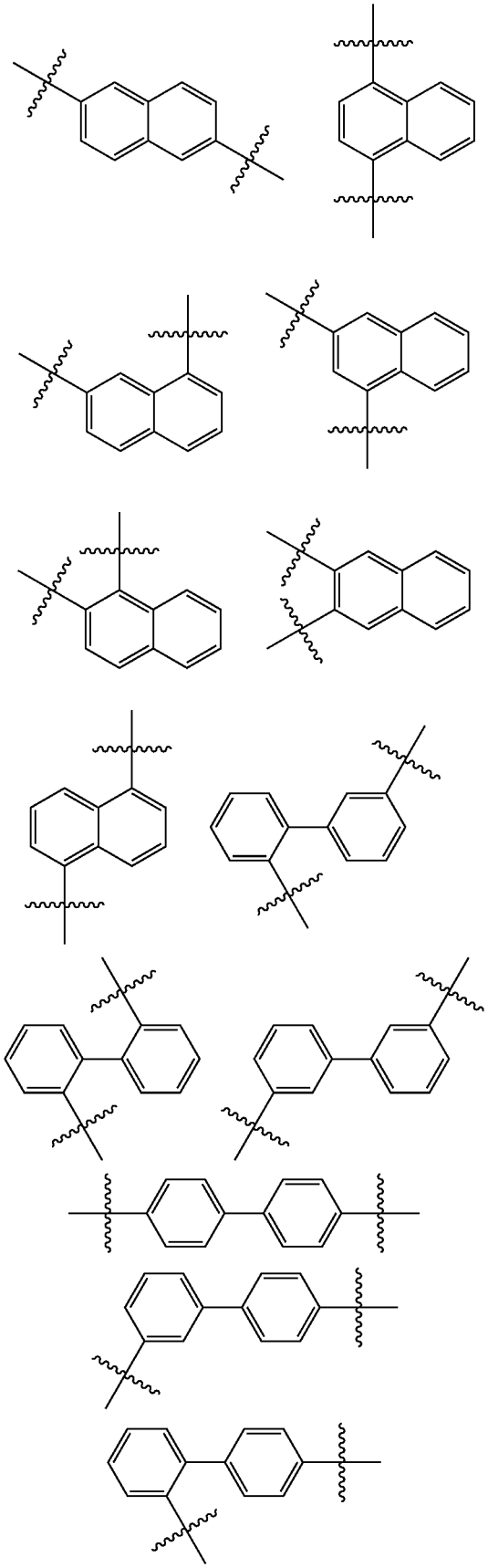

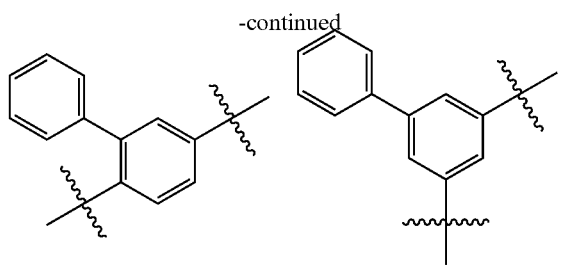

In some embodiments of the present application, Ar₁ and Ar₂ are each independently selected from a substituted or unsubstituted aryl with 6 to 25 carbon atoms or a substituted or unsubstituted heteroaryl with 5 to 20 carbon atoms. For example, Ar₁ and Ar₂ are each independently selected from a substituted or unsubstituted aryl with 6, 7, 8, 9, 10, 11, 12, 13, 14, 15, 16, 17, 18, 19, 20, 21, 22, 23, 24, or 25 carbon atoms; or a substituted or unsubstituted heteroaryl with 5, 6, 7, 8, 9, 10, 11, 12, 13, 14, 15, 16, 17, 18, 19, or 20 carbon atoms.

Optionally, substituents of Ar₁ and Ar₂ are each independently selected from deuterium, a cyano, a fluorine, an alkyl with 1 to 5 carbon atoms, a haloalkyl with 1 to 5 carbon atoms, a trialkylsilyl with 3 to 7 carbon atoms, an aryl with 6 to 12 carbon atoms, a heteroaryl with 5 to 12 carbon atoms, or a cycloalkyl with 5 to 10 carbon atoms; and optionally, any two adjacent substituents form a fluorene ring, a cyclopentane or a cyclohexane.

In some embodiments of the present application, Ar₁ and Ar₂ are each independently selected from a substituted or unsubstituted phenyl, a substituted or unsubstituted naphthyl, a substituted or unsubstituted biphenyl, a substituted or unsubstituted pyridyl, a substituted or unsubstituted quinolyl, a substituted or unsubstituted dibenzothienyl, a substituted or unsubstituted dibenzofuranyl, a substituted or unsubstituted fluorenyl, a substituted or unsubstituted carbazolyl, a substituted or unsubstituted phenanthryl, a substituted or unsubstituted spirobifluorenyl, a substituted or unsubstituted triphenylene, or a substituted or unsubstituted terphenyl.

Preferably, Ar₁ and Ar₂ are each independently selected from a substituted or unsubstituted phenyl, a substituted or unsubstituted naphthyl, a substituted or unsubstituted biphenyl, a substituted or unsubstituted pyridyl, a substituted or unsubstituted quinolyl, a substituted or unsubstituted dibenzothienyl, a substituted or unsubstituted dibenzofuranyl, a substituted or unsubstituted fluorenyl, a substituted or unsubstituted carbazolyl, a substituted or unsubstituted phenanthryl, a substituted or unsubstituted spirobifluorenyl, or a substituted or unsubstituted triphenylene.

Optionally, substituents of Ar₁ and Ar₂ are each independently selected from deuterium, a fluorine, a cyano, a methyl, an ethyl, an isopropyl, a tert-butyl, a trifluoromethyl, a trimethylsilyl, a phenyl, a naphthyl, a cyclopentyl, a cyclohexyl, or an adamantyl; and optionally, any two adjacent substituents form a fluorene ring, a cyclopentane or a cyclohexane.

In one embodiment of the present application, Ar₁ and Ar₂ are each independently selected from a substituted or unsubstituted group V, or a substituted or unsubstituted group W; where the unsubstituted group V is selected from the group consisting of the following groups:

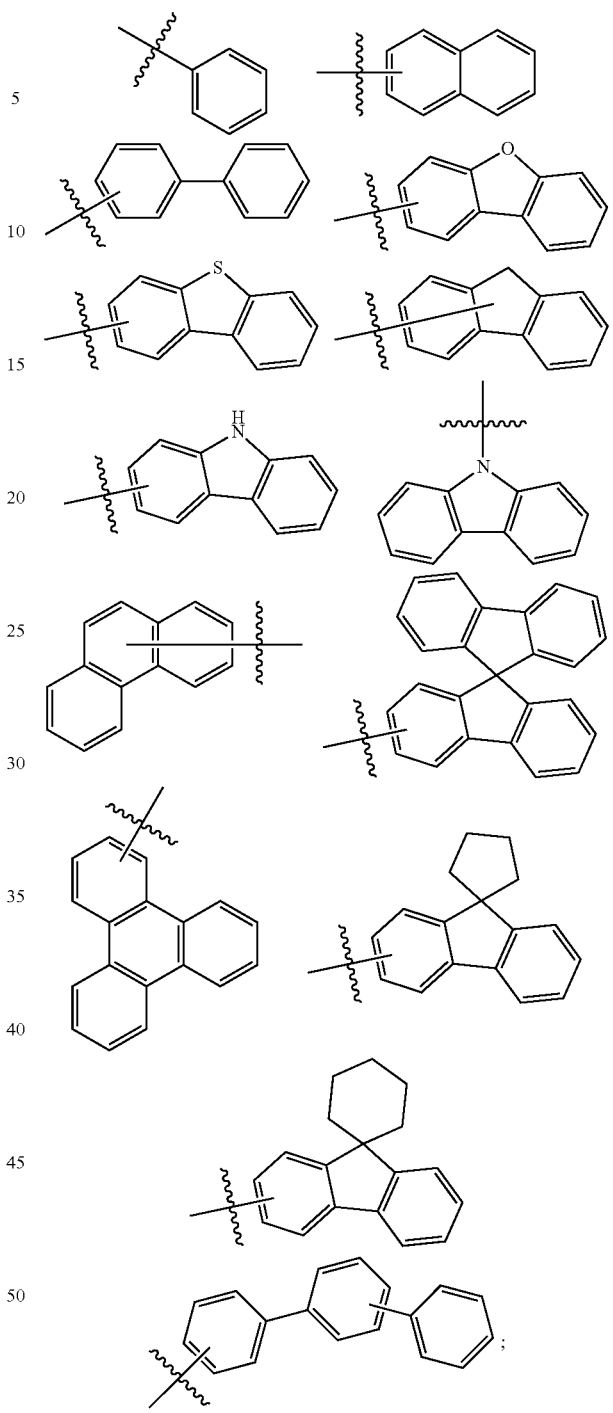

where ⨉ represents a chemical bond; the substituted group V has one or two or more substituents, the substituents are each independently selected from deuterium, a fluorine, a cyano, a methyl, an ethyl, an isopropyl, a tert-butyl, a trifluoromethyl, a trimethylsilyl, a phenyl, a naphthyl, a cyclopentyl, a cyclohexyl, or an adamantyl; and when the number of the substituents is greater than 1, the substituents are the same or different;

the unsubstituted group W is selected from the group consisting of the following groups:

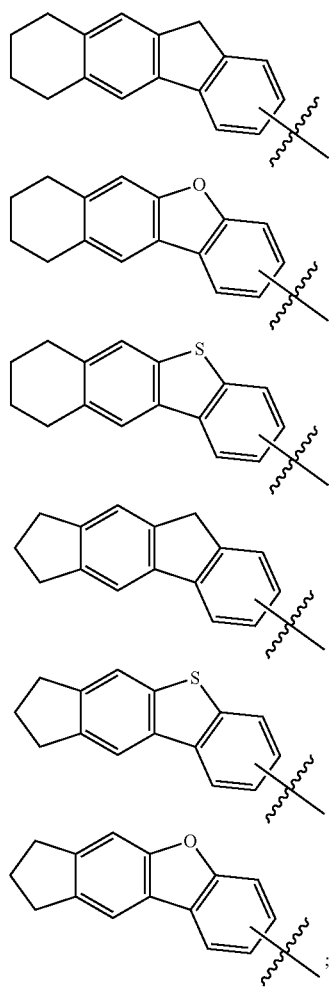

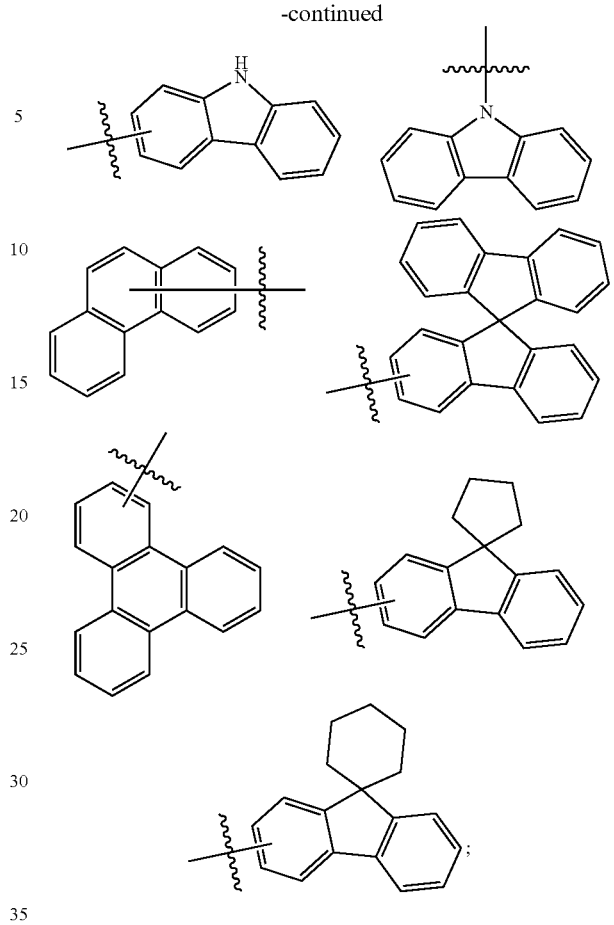

where ⁃ represents a chemical bond; the substituted group W has one or two or more substituents, the substituents are each independently selected from deuterium, a fluorine, a cyano, a methyl, an ethyl, an isopropyl, or a tert-butyl; and when the number of the substituents is greater than 1, the substituents are the same or different.

Preferably, $Ar_1$ and $Ar_2$ are each independently selected from a substituted or unsubstituted group V'; where the unsubstituted group V' is selected from the group consisting of the following groups:

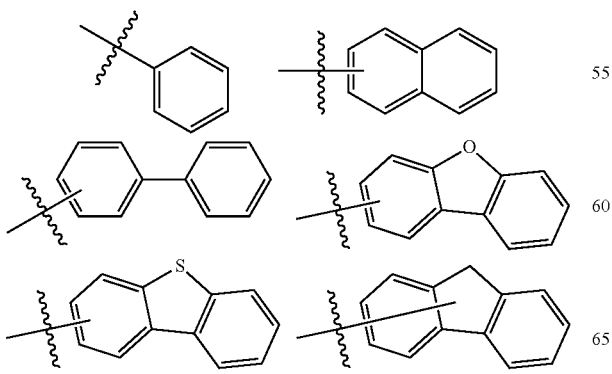

where the substituted group V has one or two or more substituents, the substituents are each independently selected from deuterium, a fluorine, a cyano, a methyl, an ethyl, an isopropyl, a tert-butyl, a trifluoromethyl, a trimethylsilyl, a phenyl, a naphthyl, a cyclopentyl, a cyclohexyl, or an adamantyl; and when the number of the substituents is greater than 1, the substituents are the same or different.

Optionally, $Ar_1$ and $Ar_2$ are each independently selected from the group consisting of the following groups:

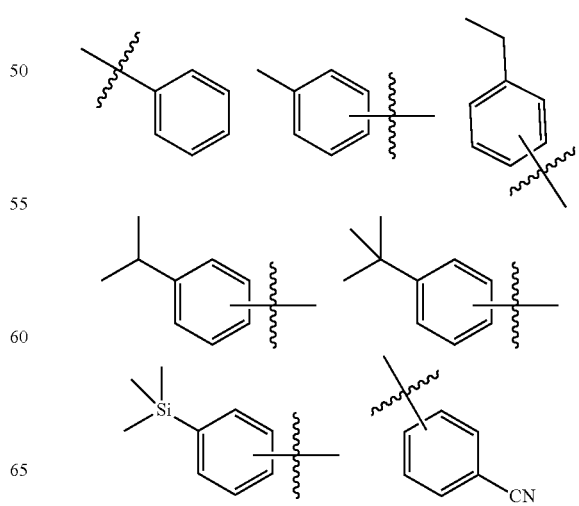

-continued
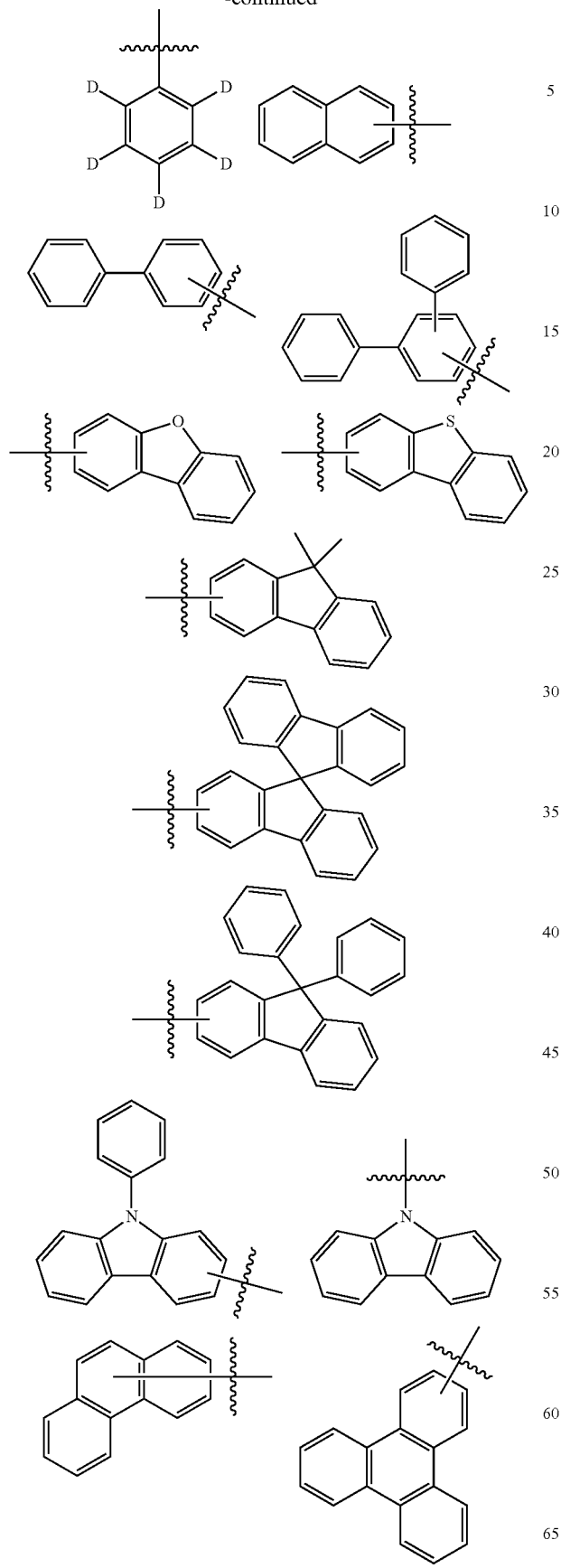
-continued
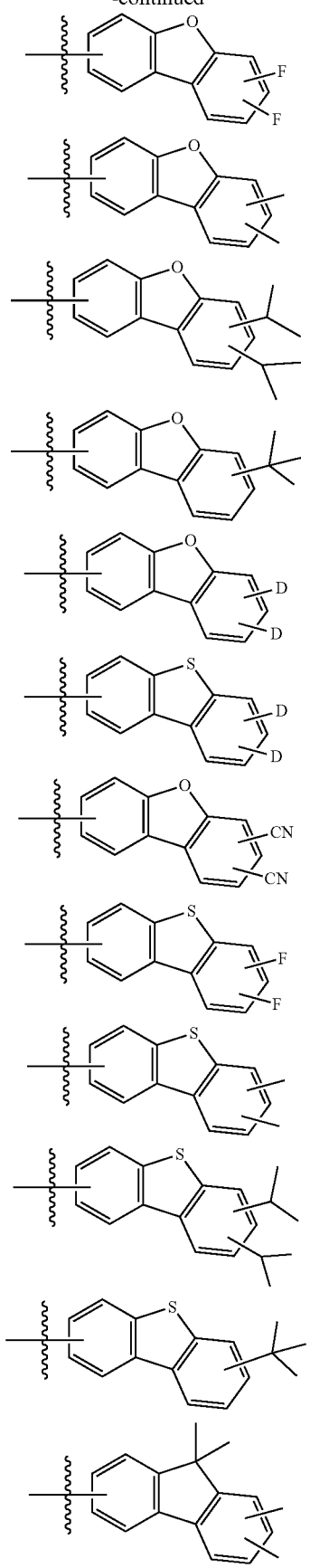

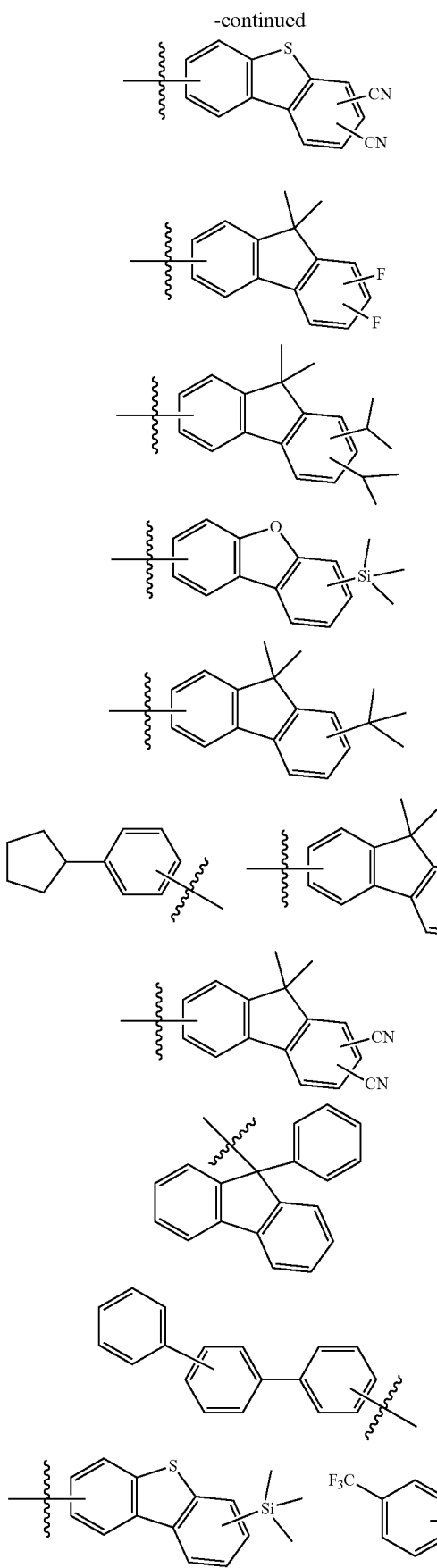
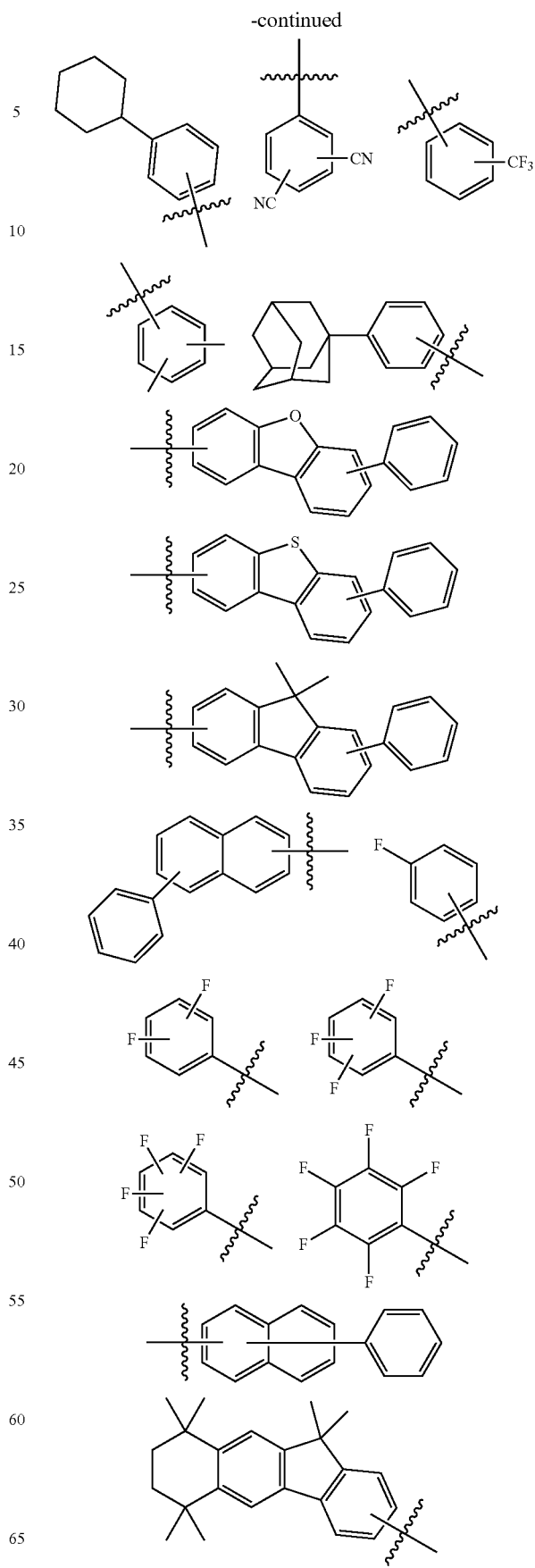

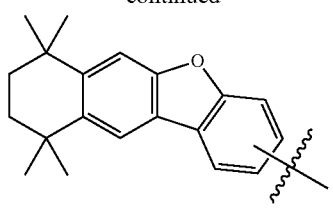
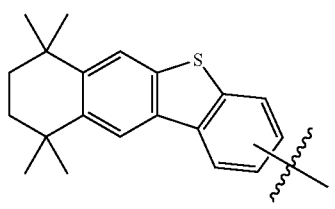
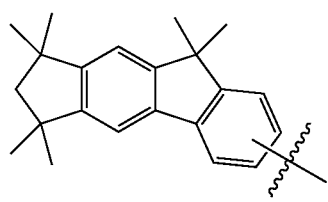
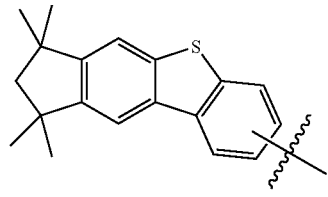
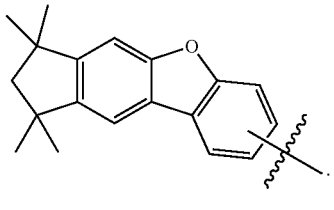
Preferably, Ar$_1$ and Ar$_2$ are each independently selected from the group consisting of the following groups:
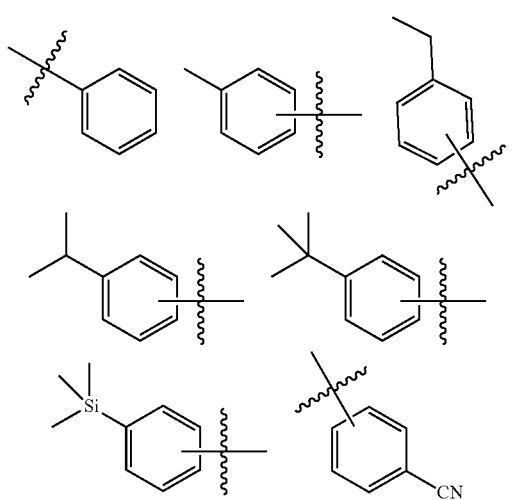
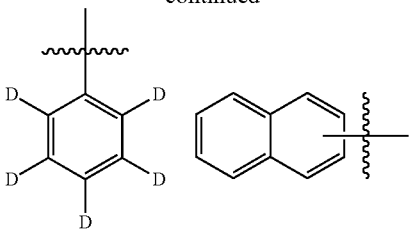
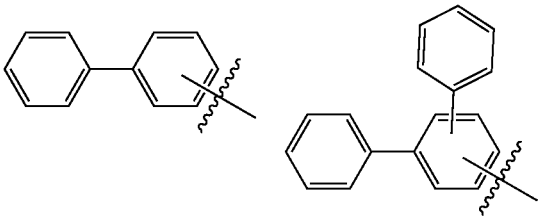
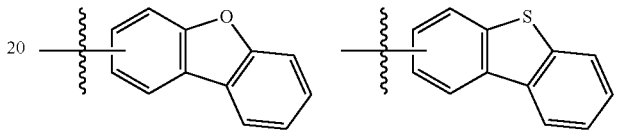
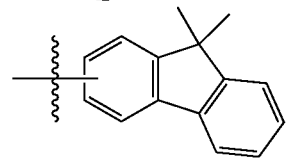
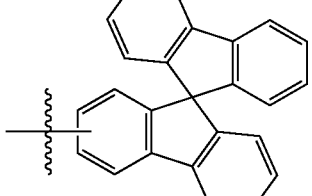
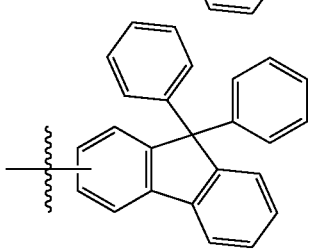
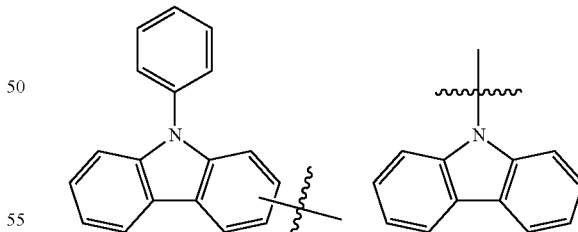
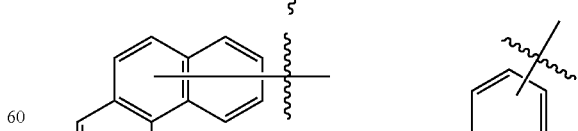
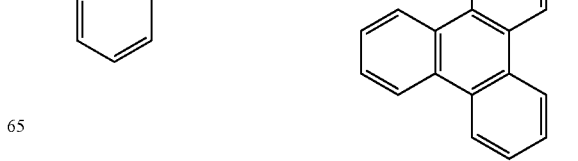

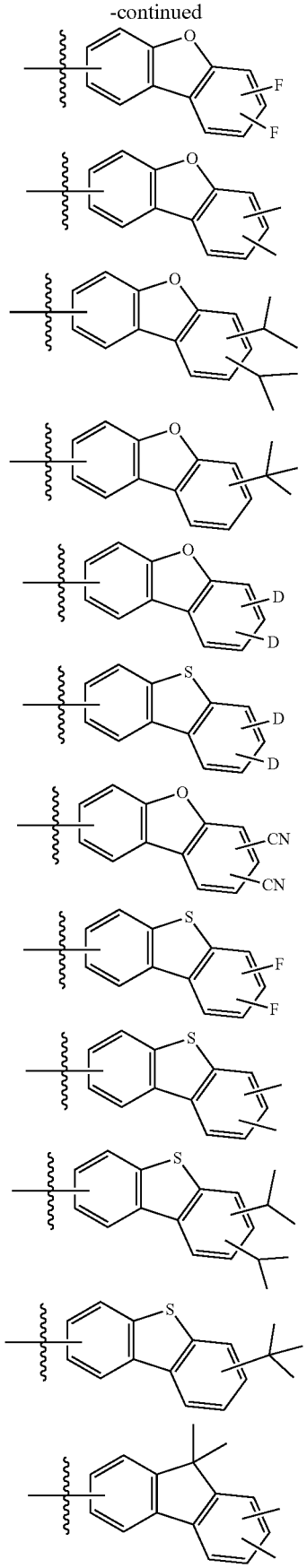
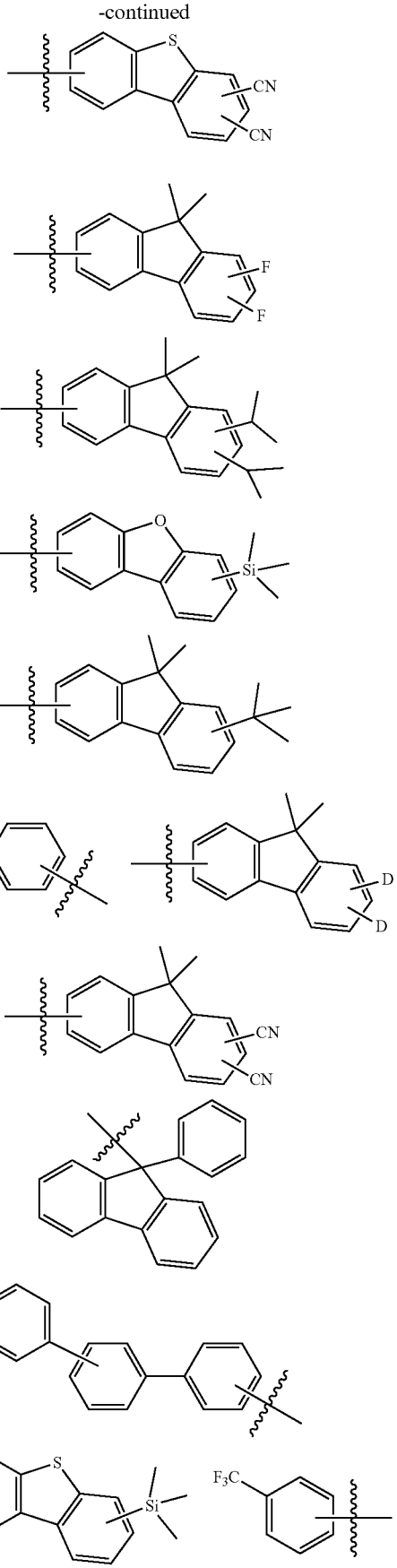

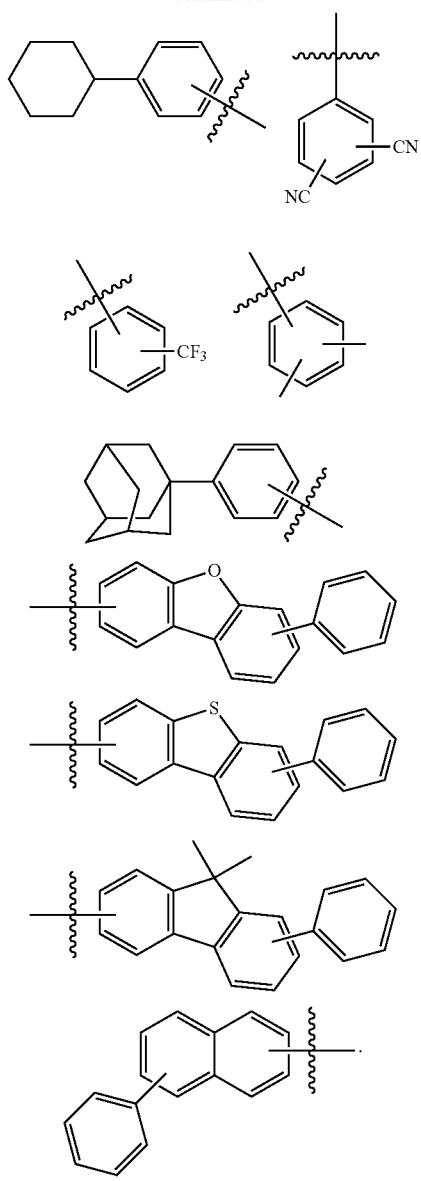
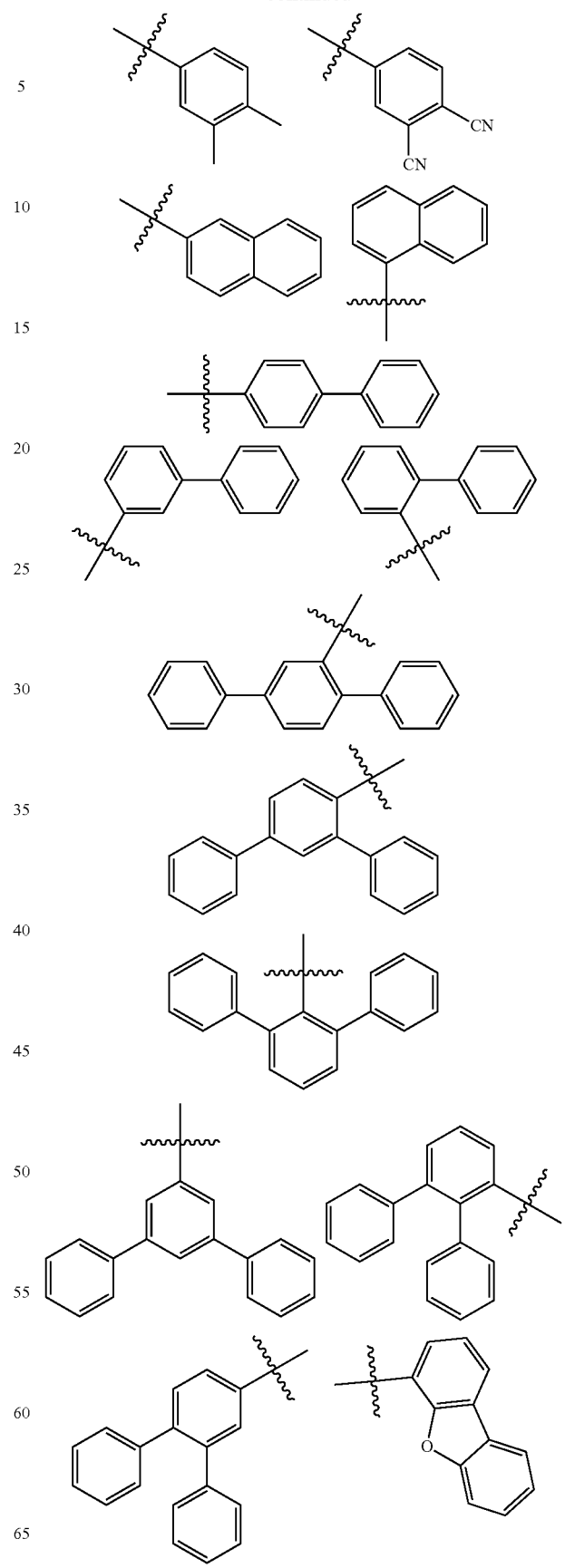
Further optionally, Ar₁ and Ar₂ are each independently selected from the group consisting of the following groups:
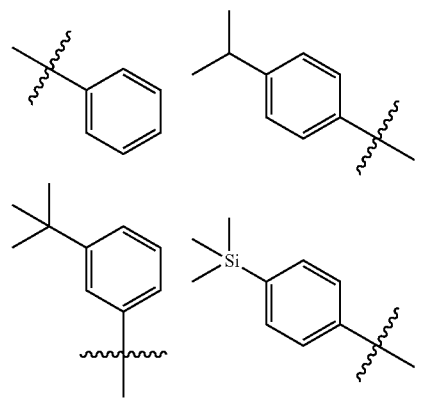

-continued
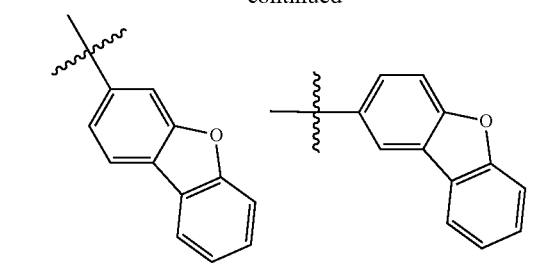
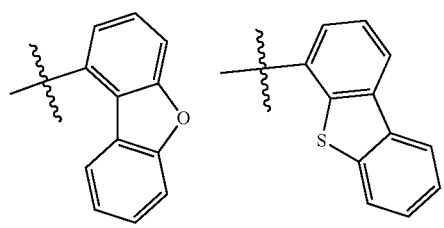
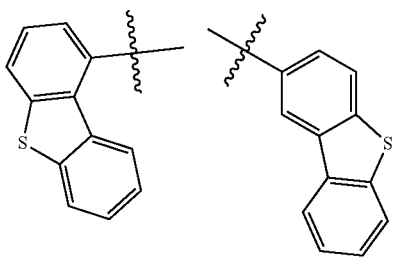
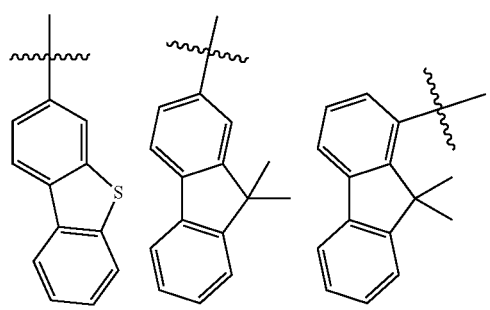
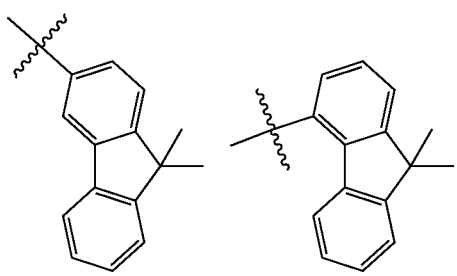
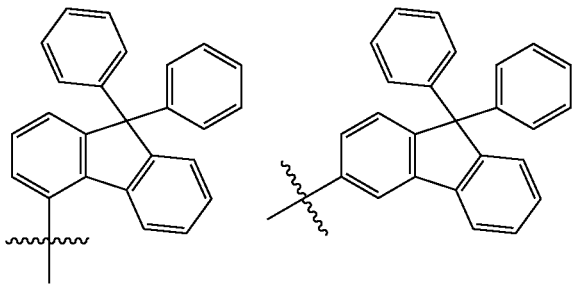
-continued
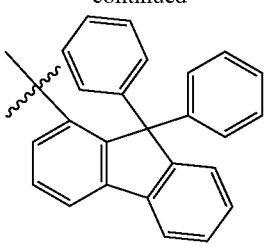
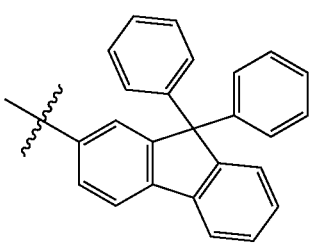
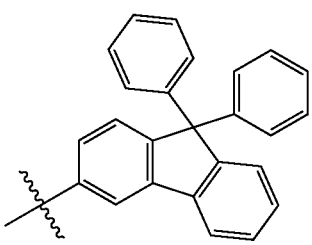
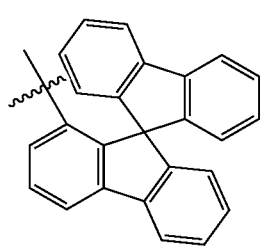
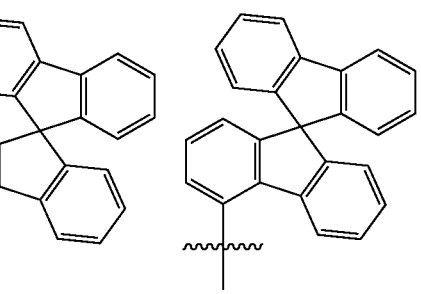
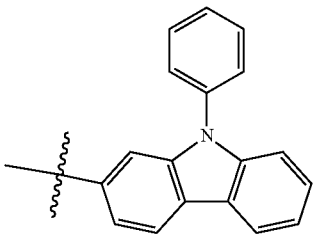

-continued
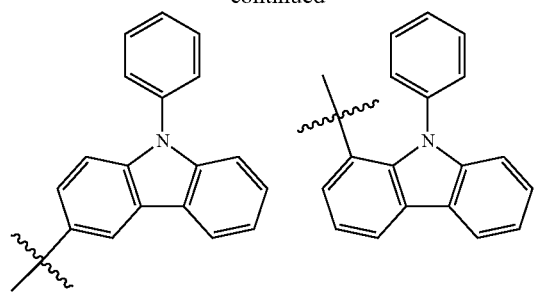
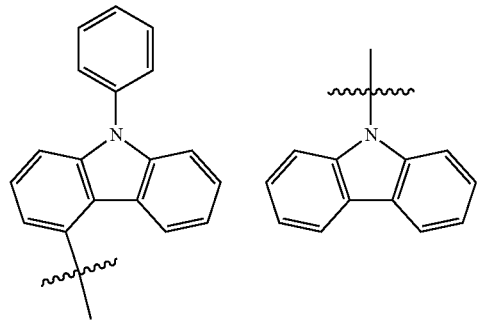
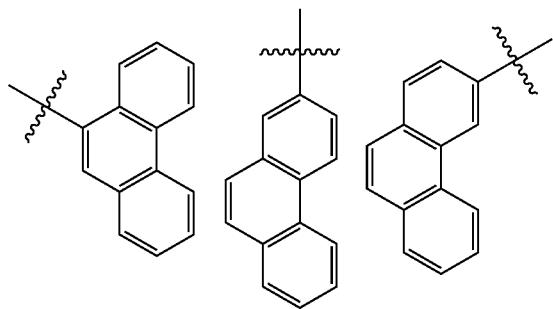
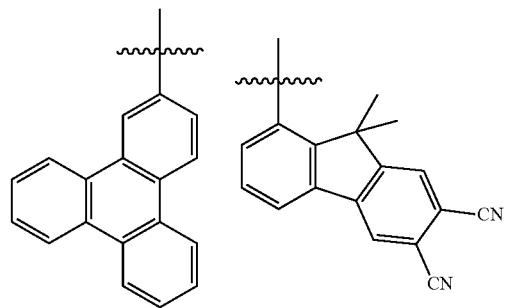
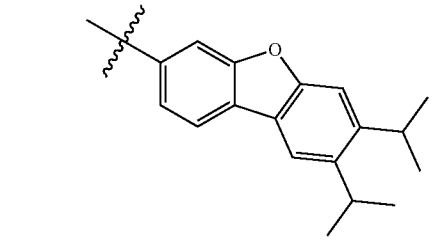
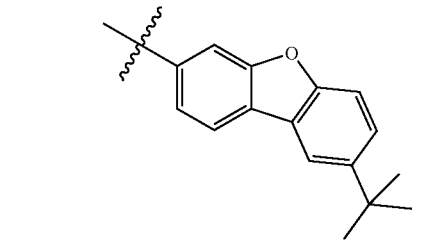
-continued
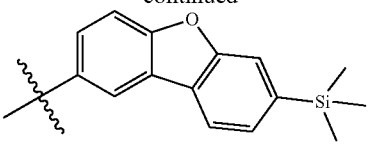
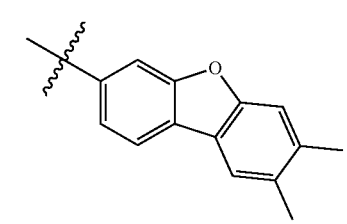
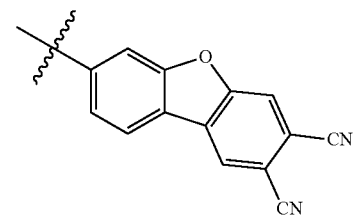
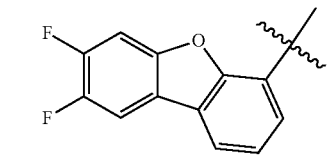
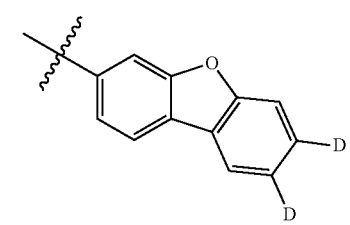
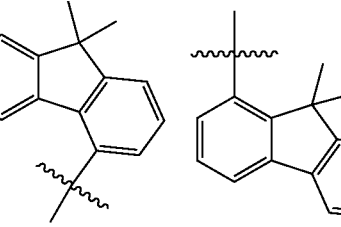
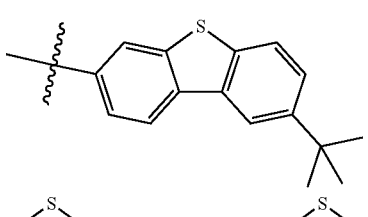
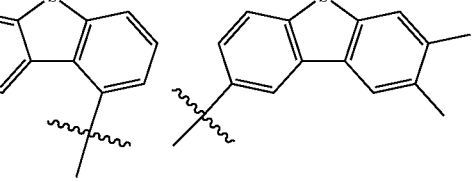

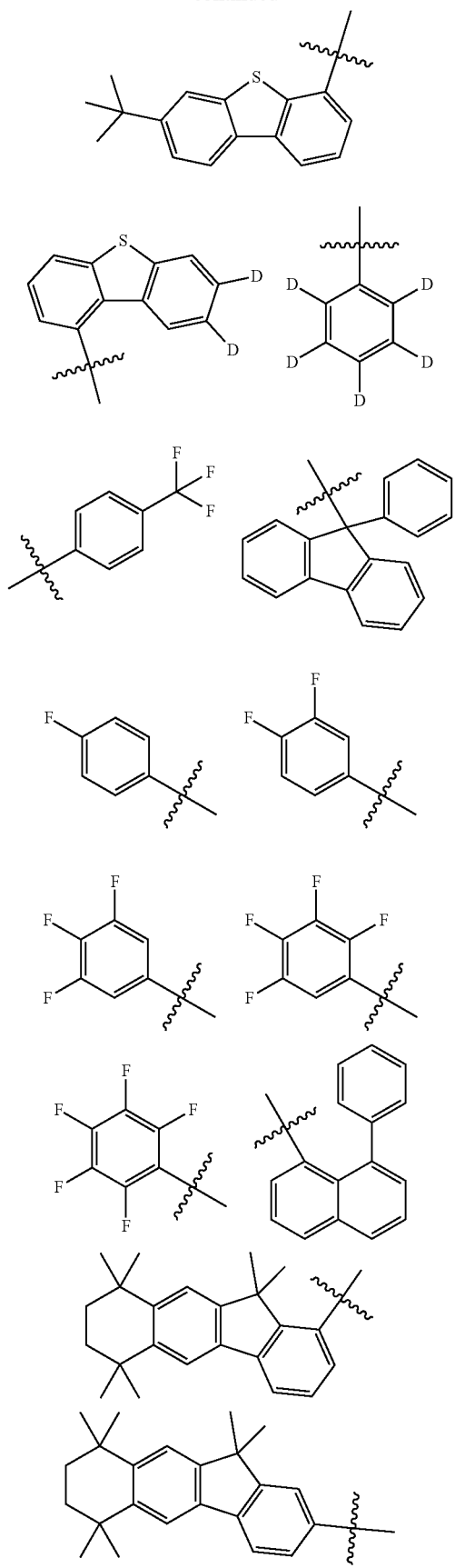
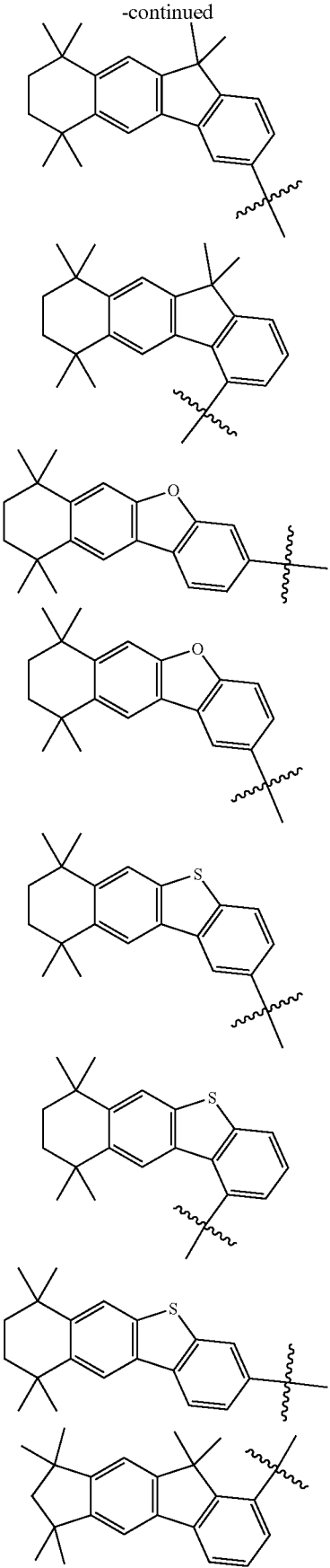

-continued
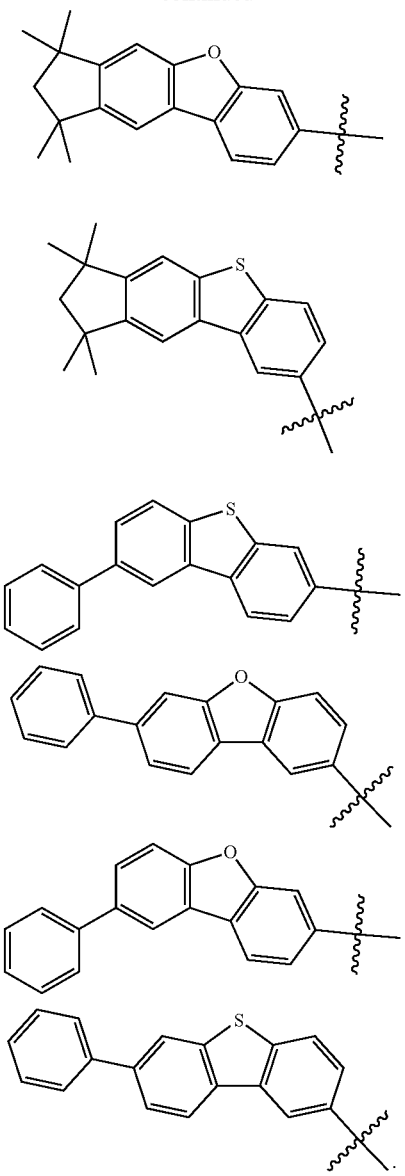
Preferably, $Ar_1$ and $Ar_2$ are each independently selected from the group consisting of the following groups:
-continued
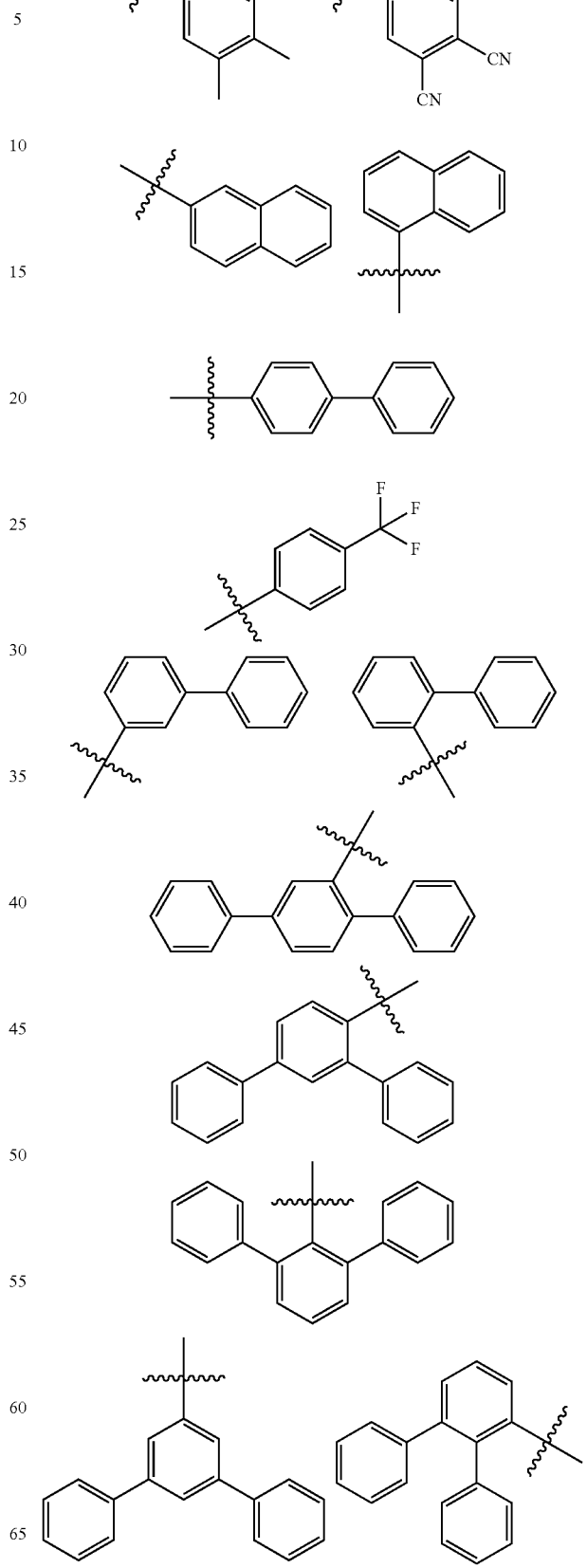

-continued
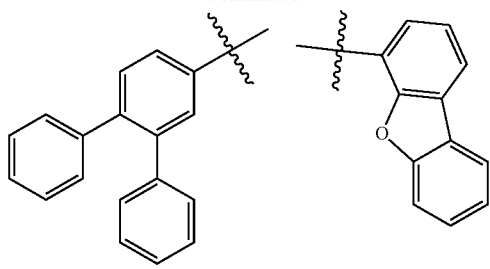
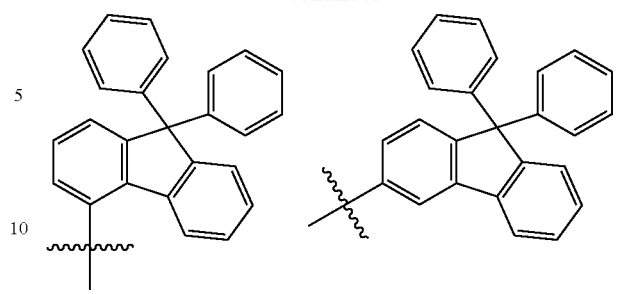
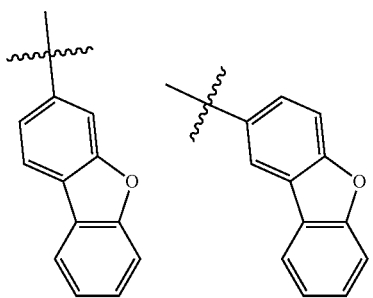
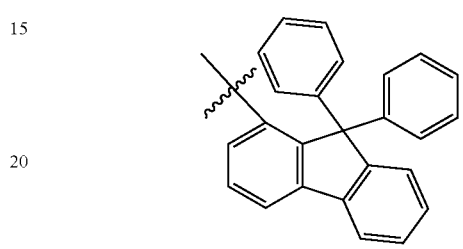
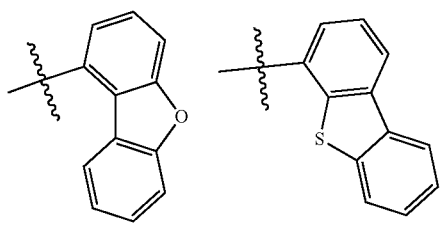
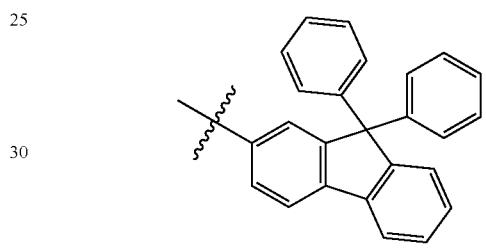
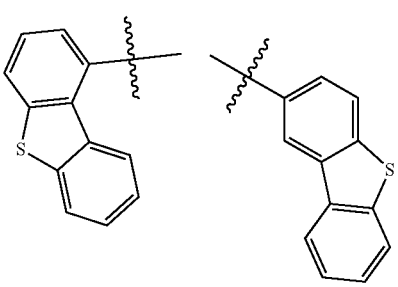
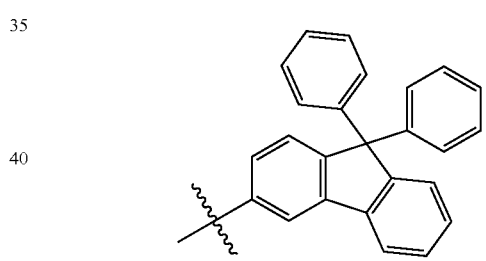
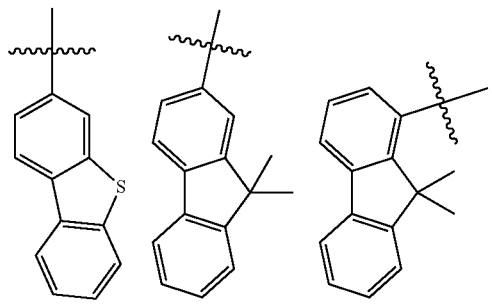
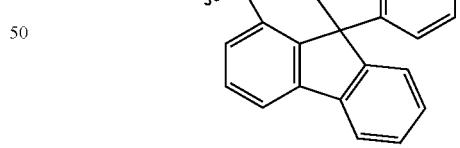
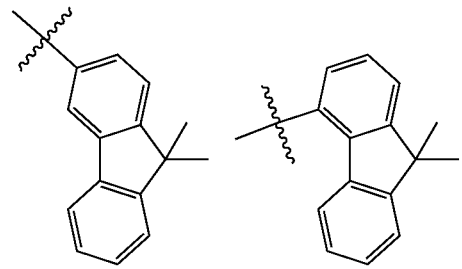
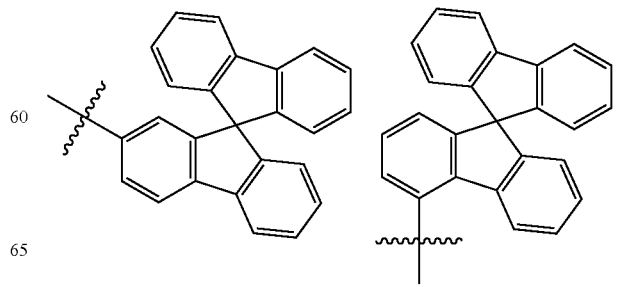

-continued
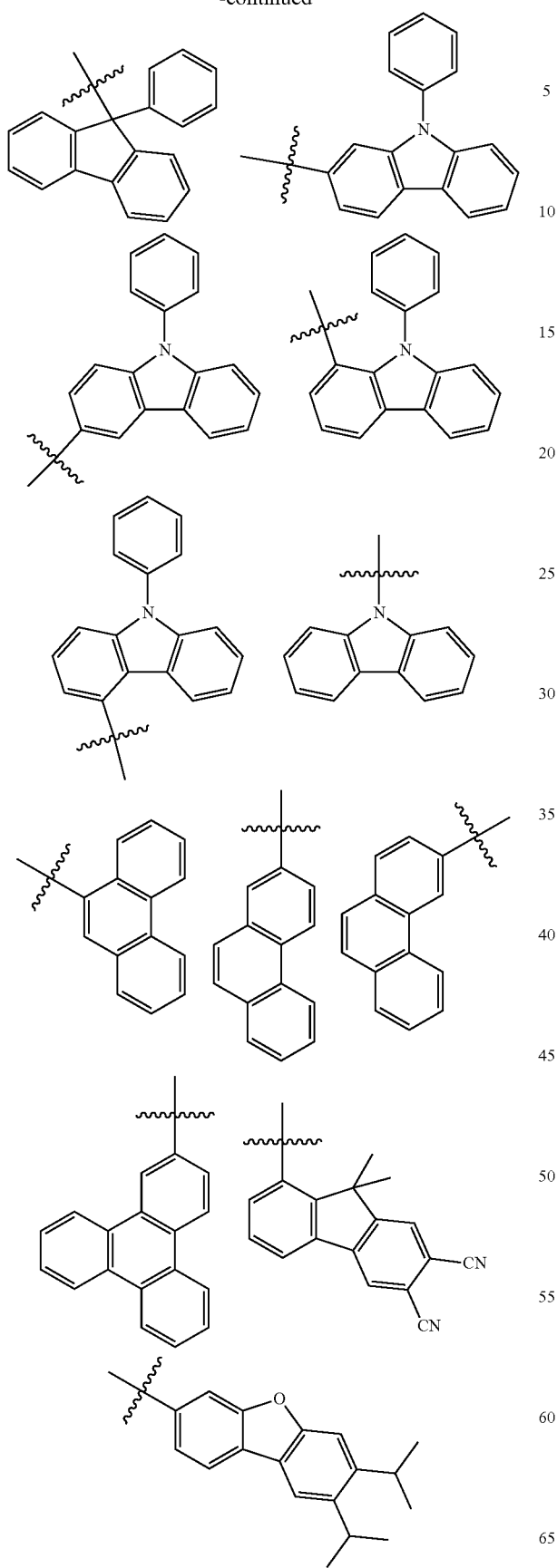
-continued
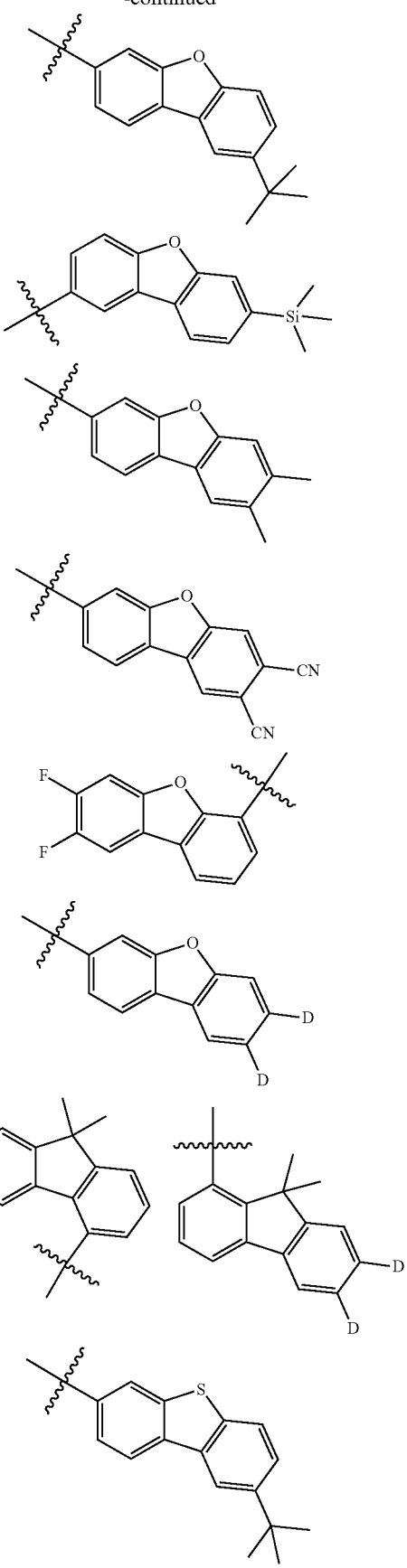

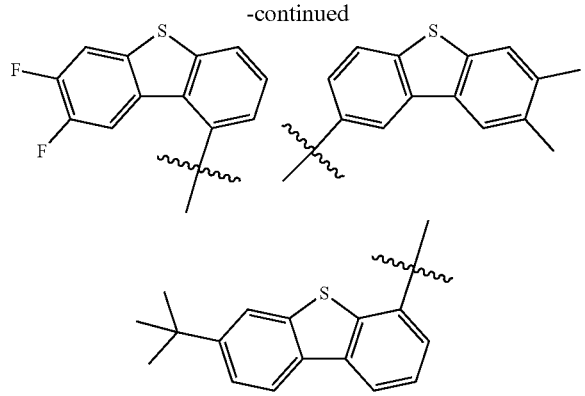
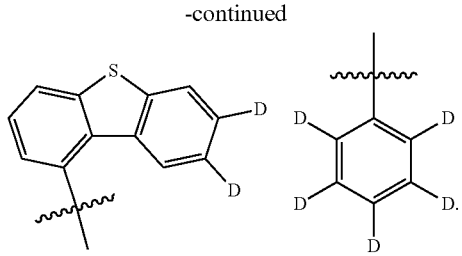
Optionally, the organic compound is selected from the group consisting of the following compounds:
1
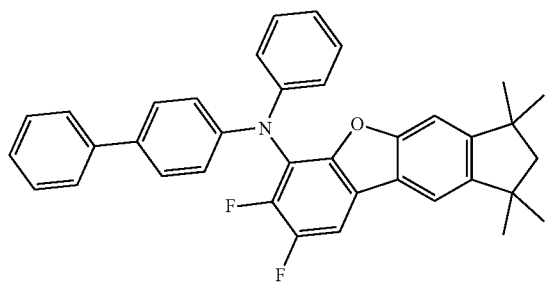
2
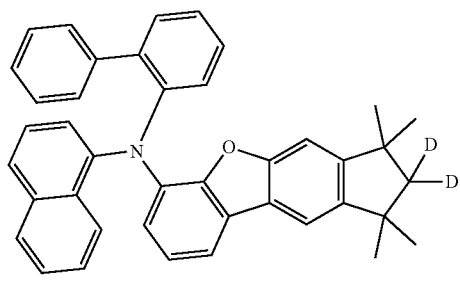
3
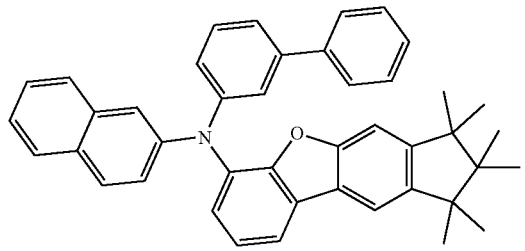
4
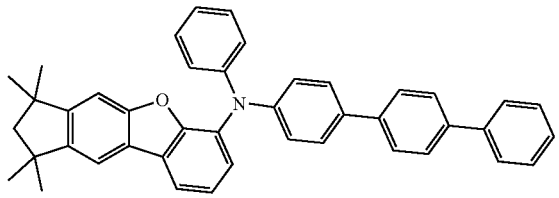
5
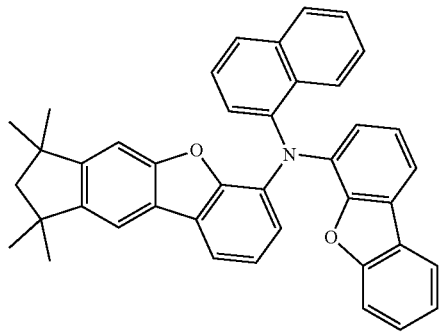
6
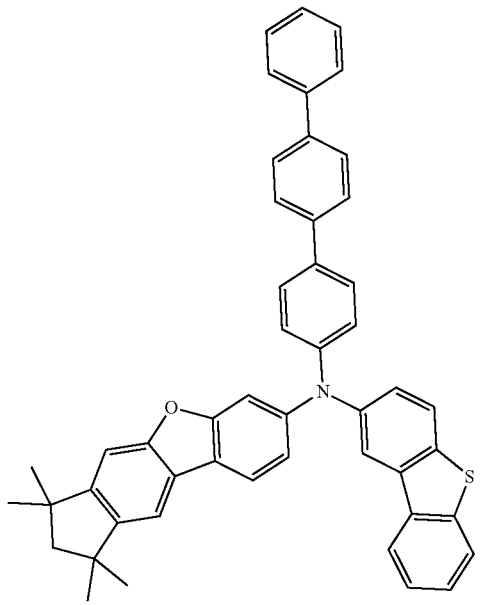

-continued
7
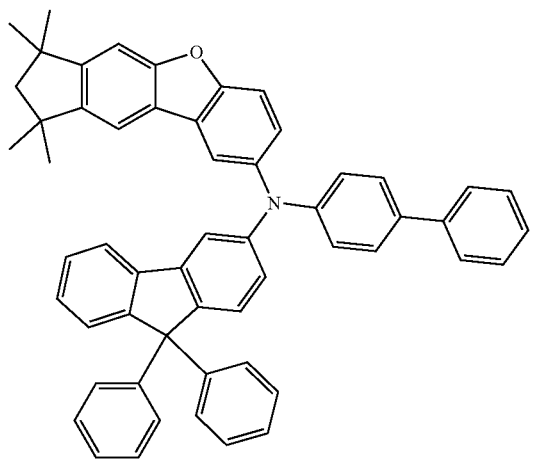
8
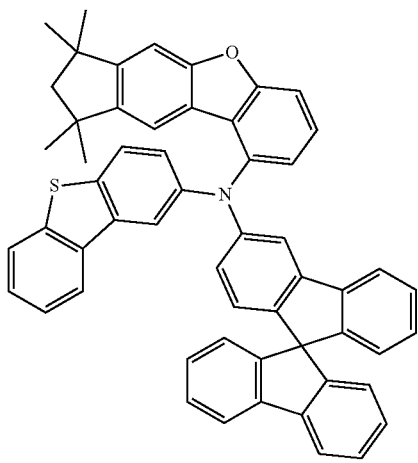
9
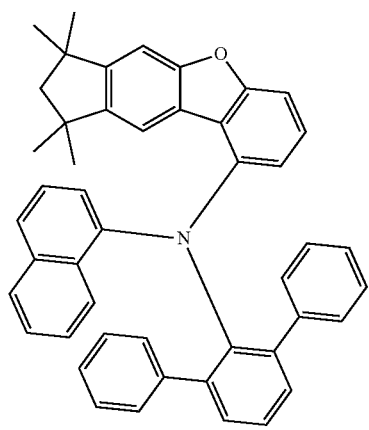
10
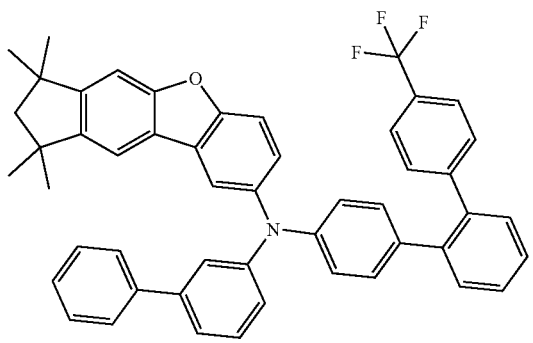
11
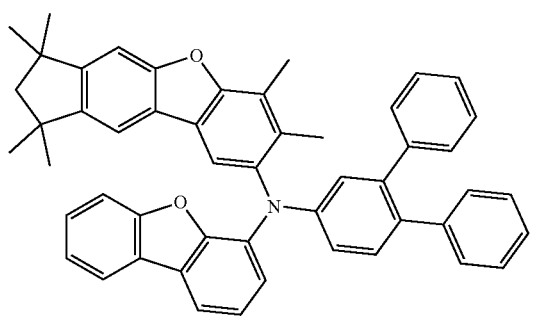
12
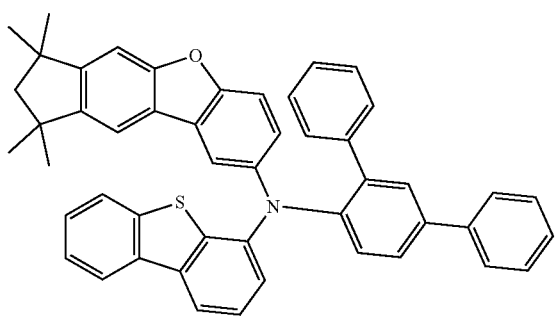
13
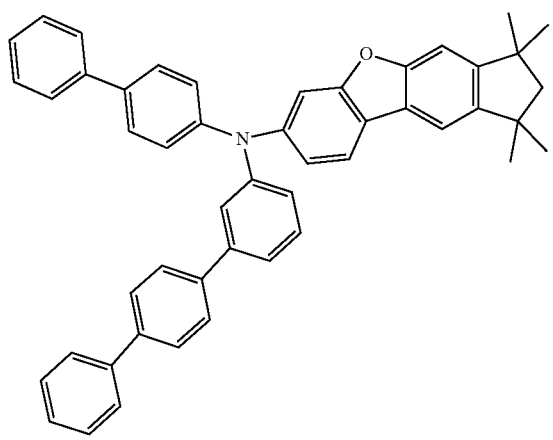
14
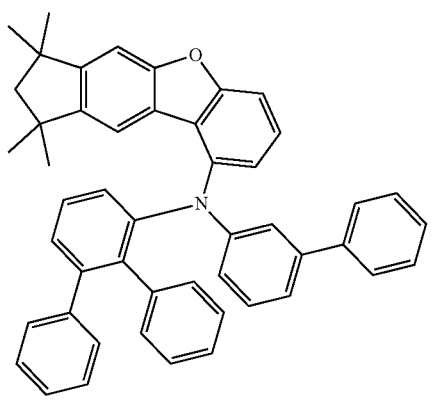

-continued
15
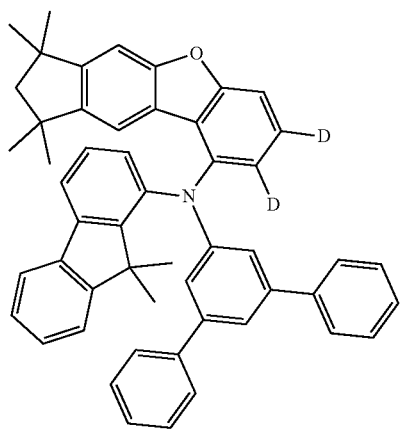
16
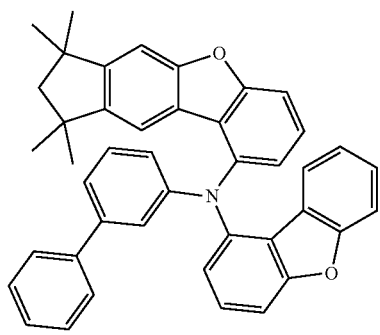
17
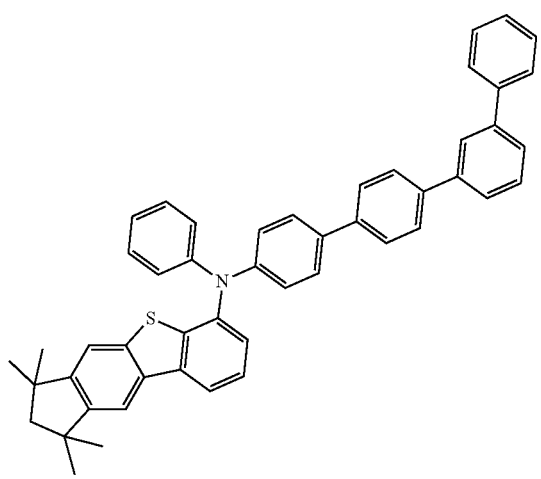
18
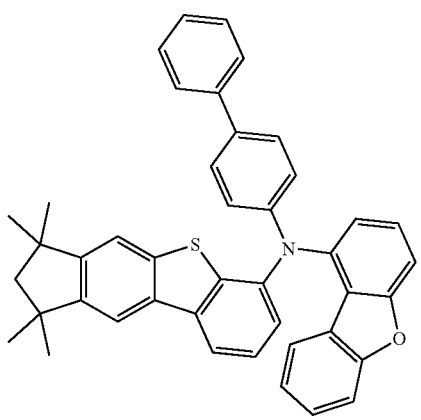
19
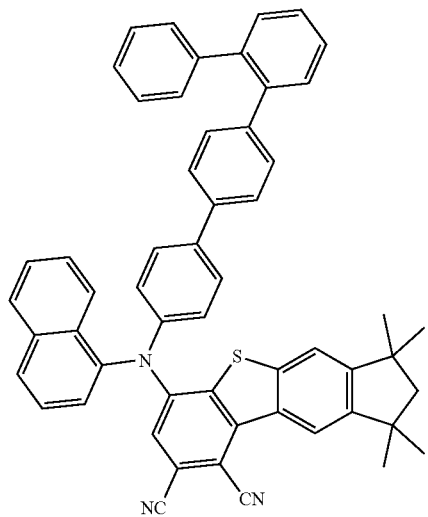
20
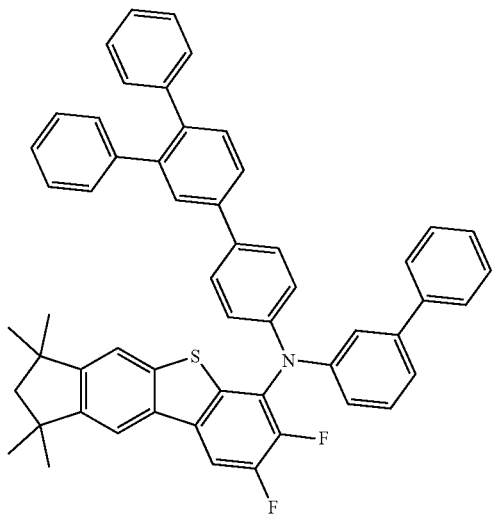

-continued
21
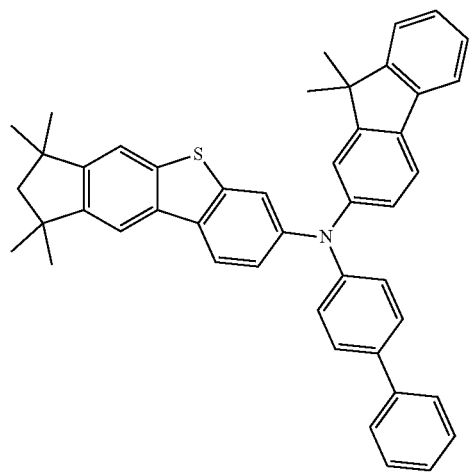
22
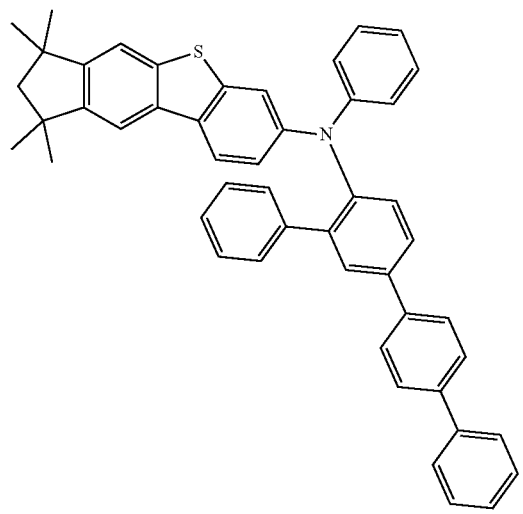
23
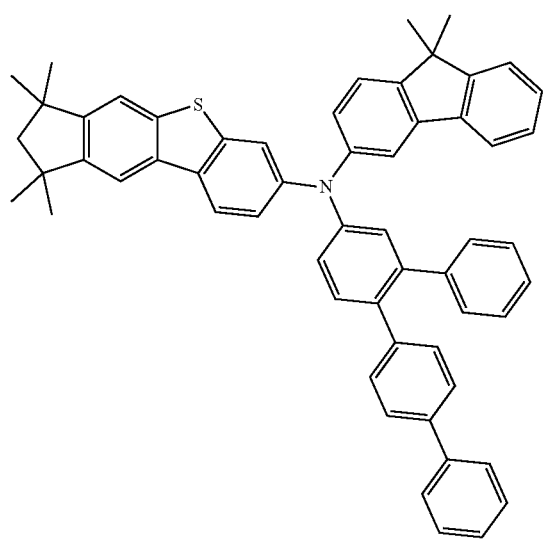
24
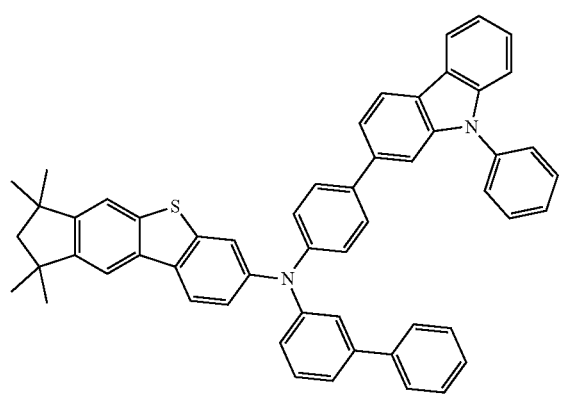
25
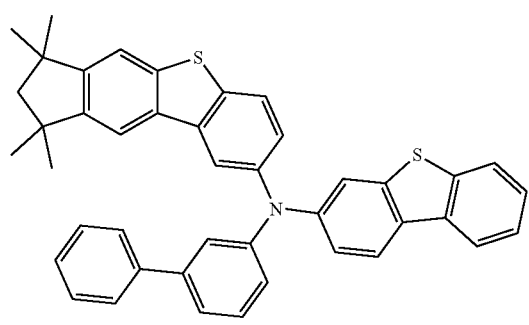
26
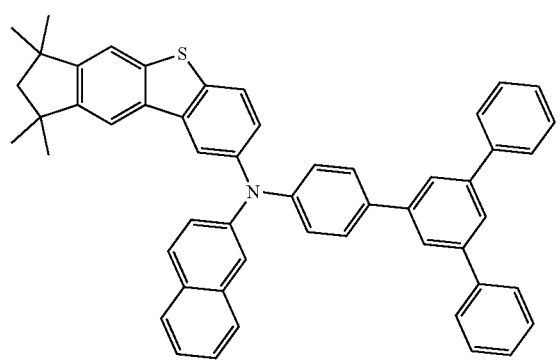

-continued
27
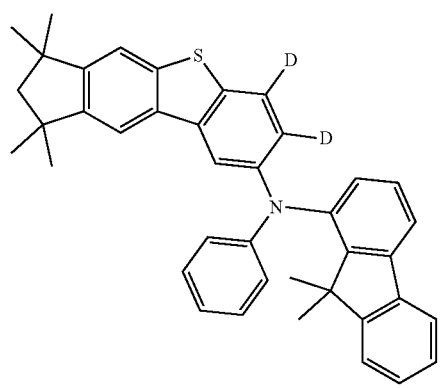
28
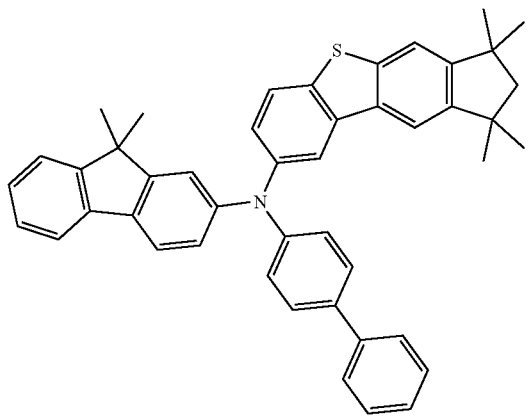
29
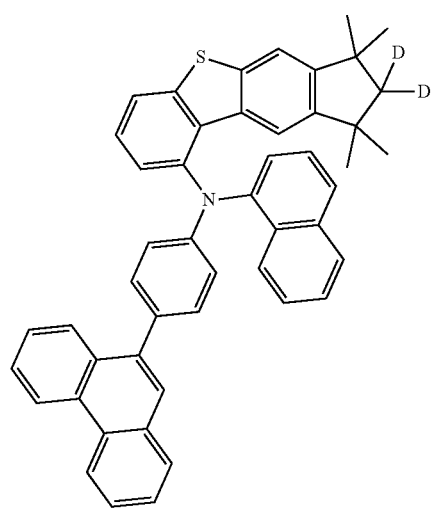
30
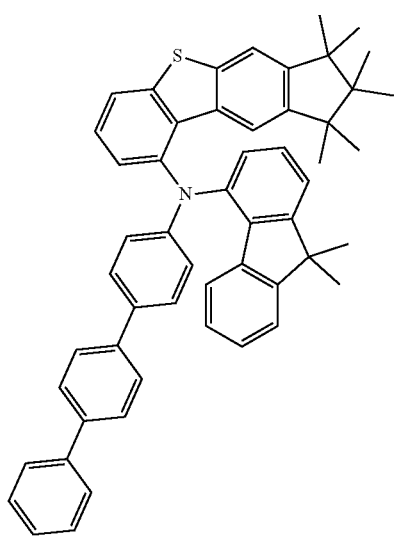
31
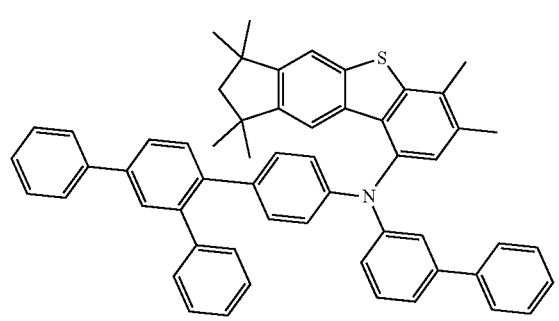
32
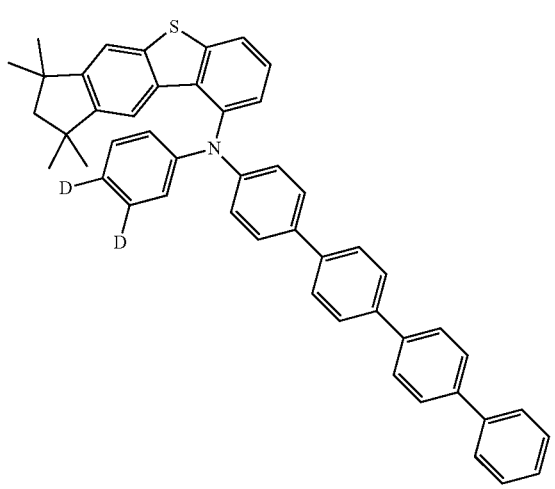

-continued
33
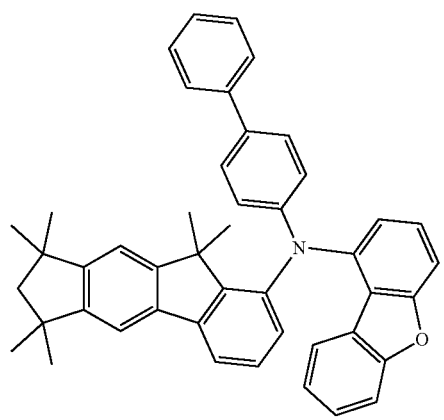
34
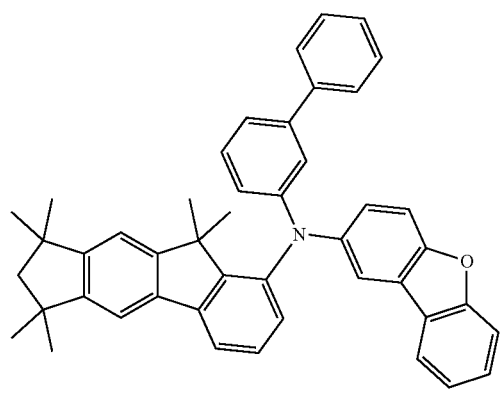
35
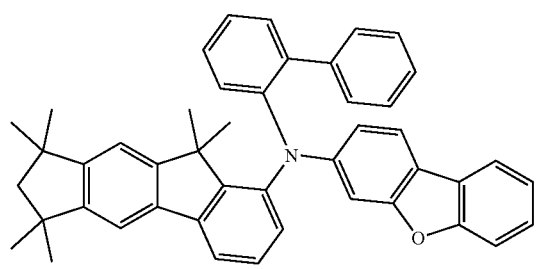
36
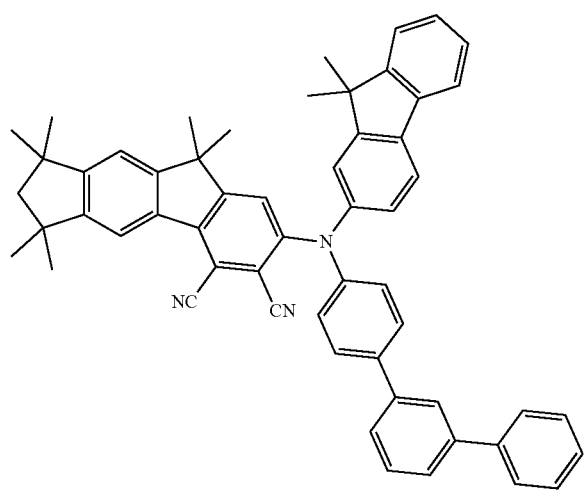
37
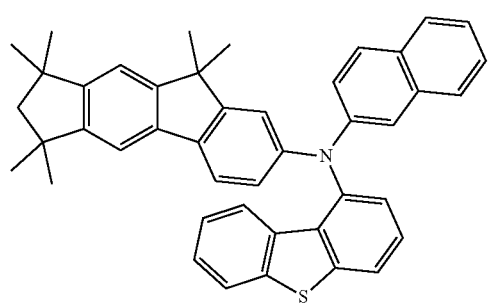
38
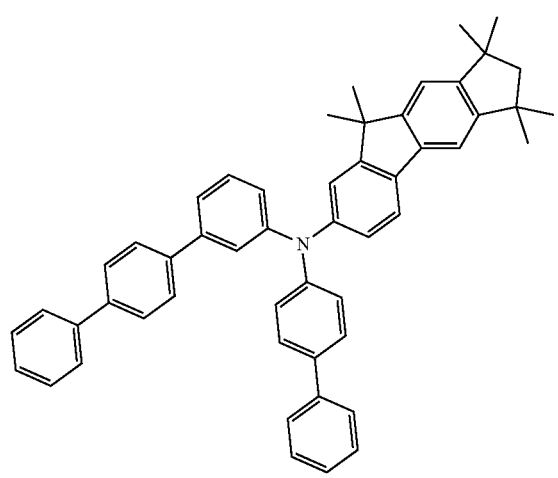

-continued
39
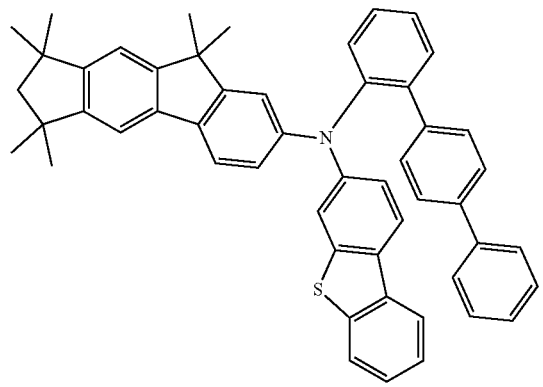
40
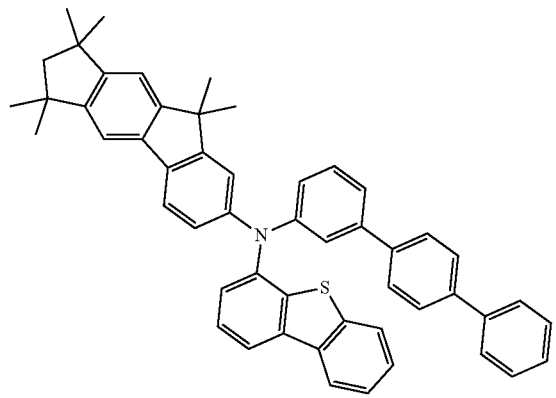
41
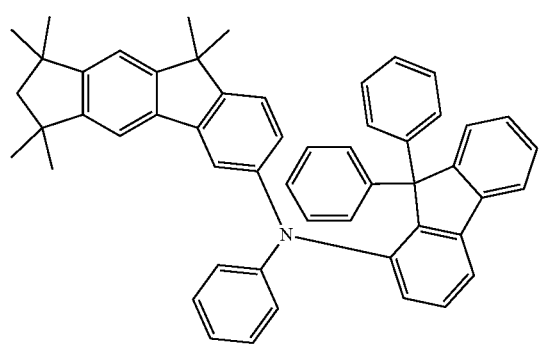
42
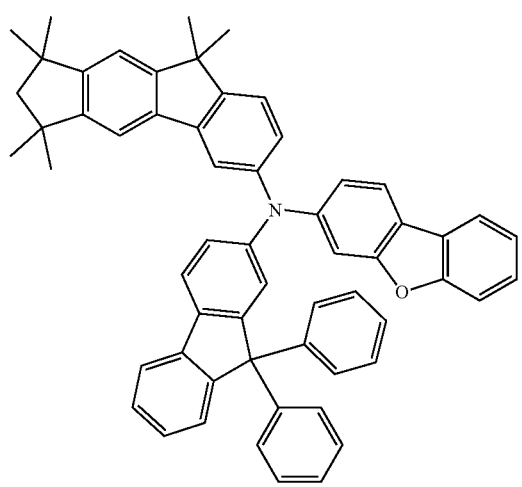
43
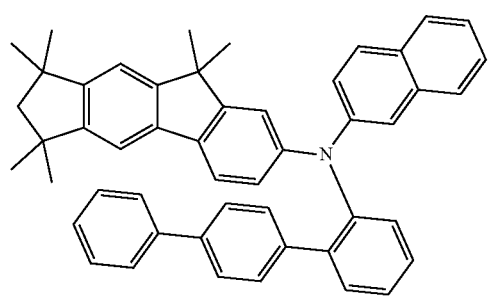
44
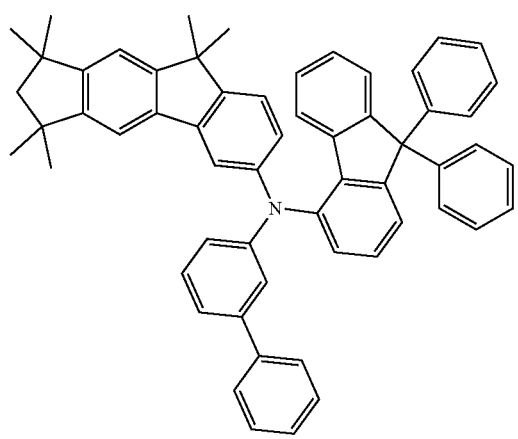

-continued
45
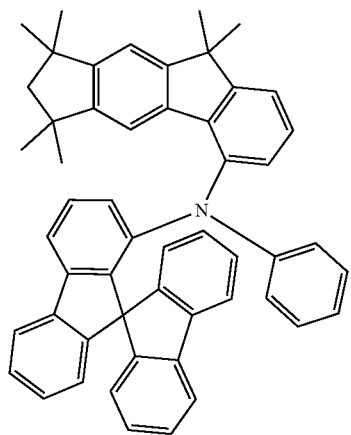
46
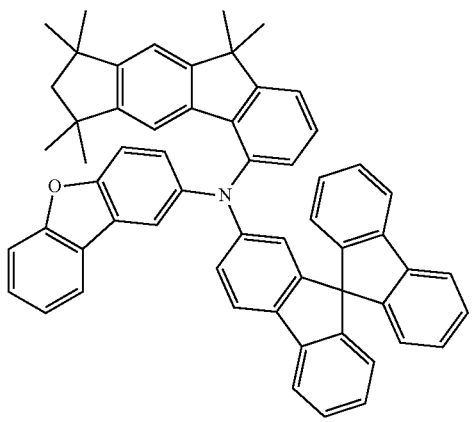
47
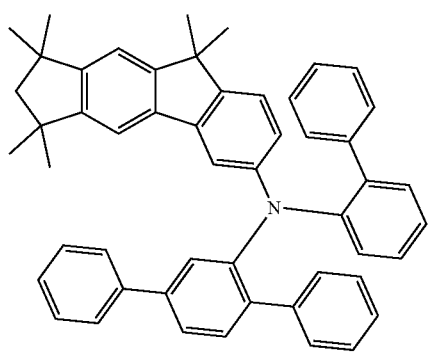
48
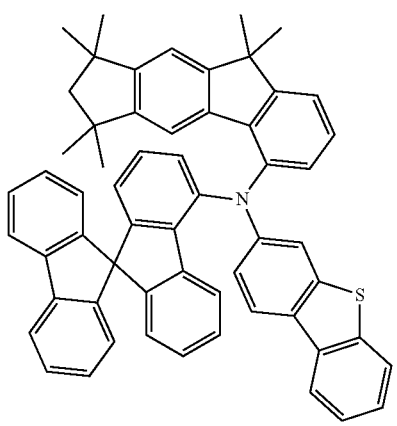
49
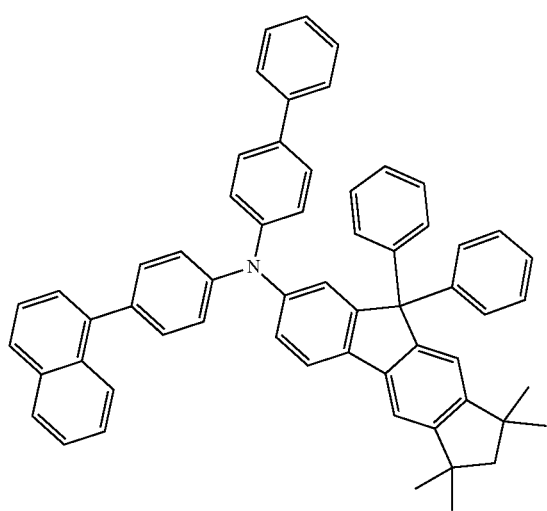
50
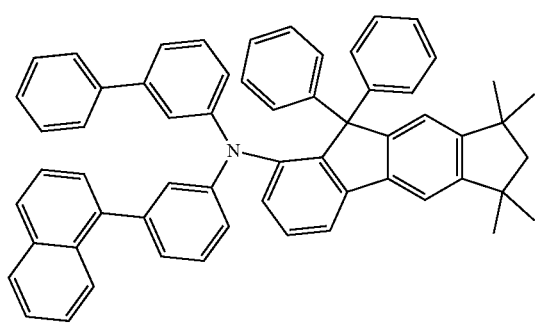

-continued
51
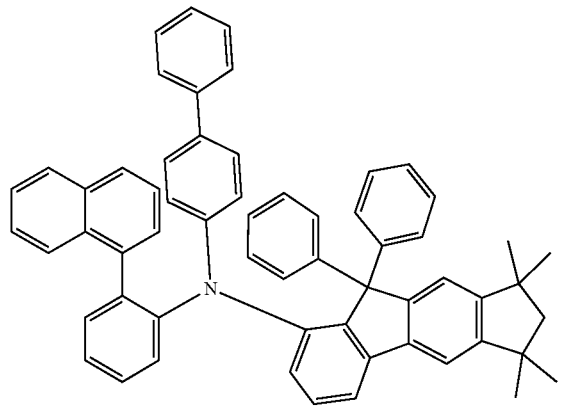
52
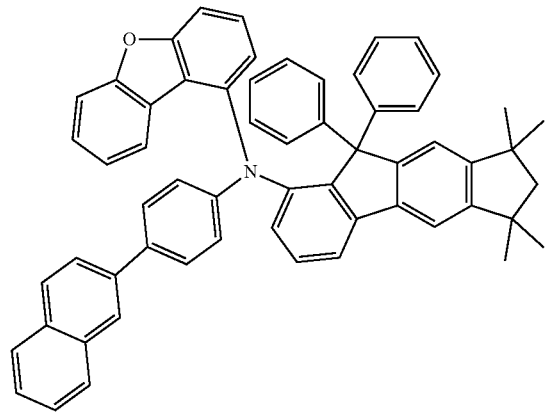
53
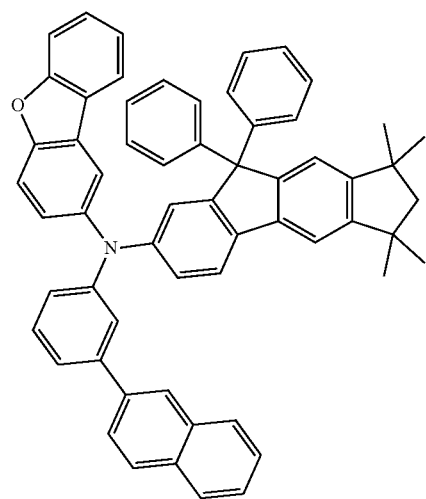
54
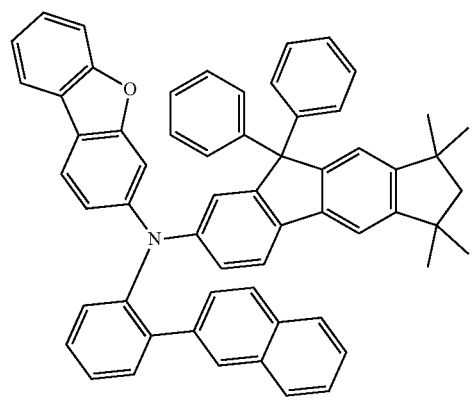
55
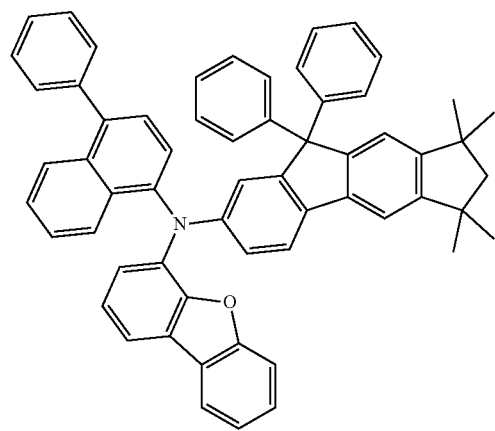
56
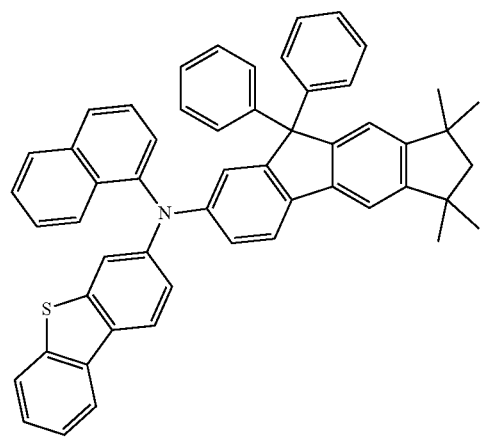

-continued
57
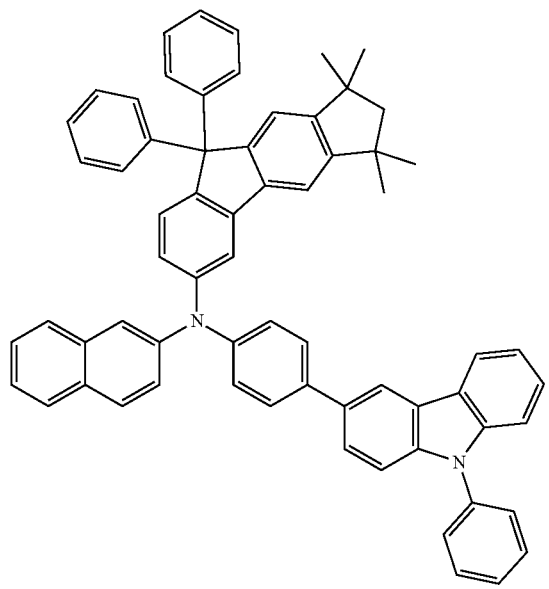
58
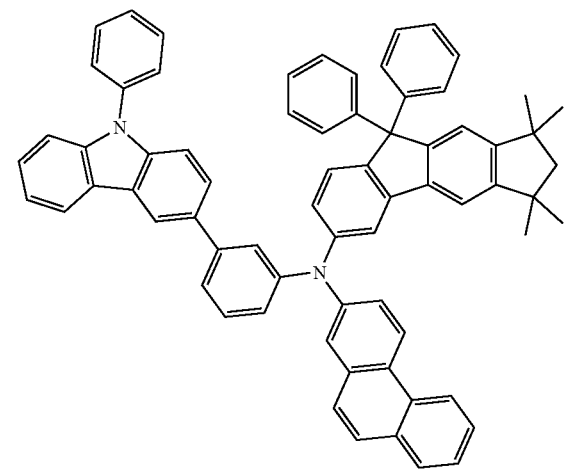
59
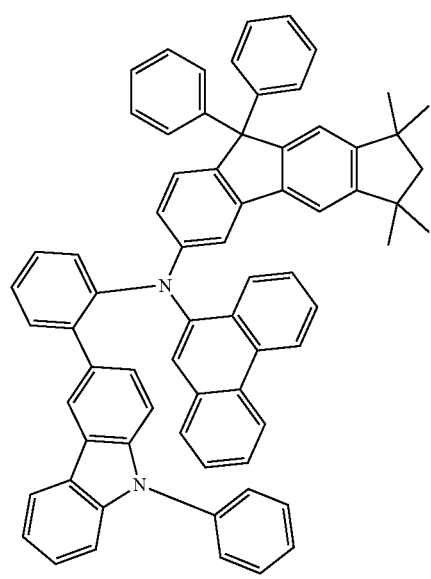
60
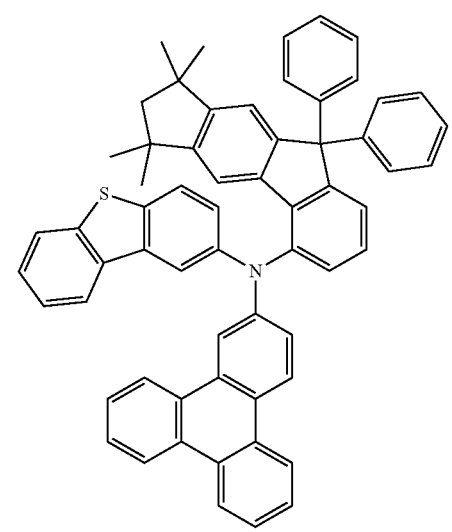
61
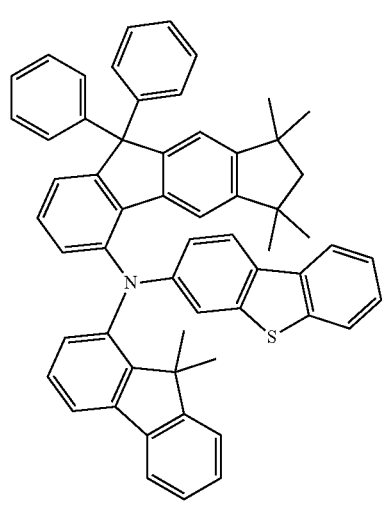
62
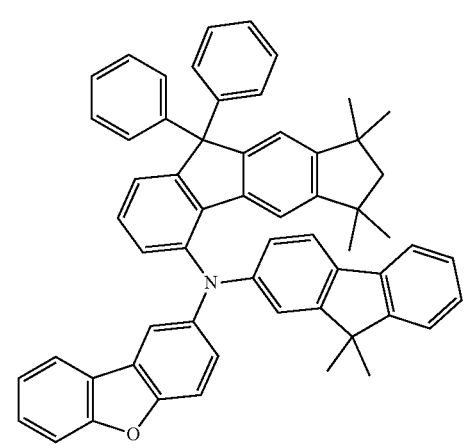

63
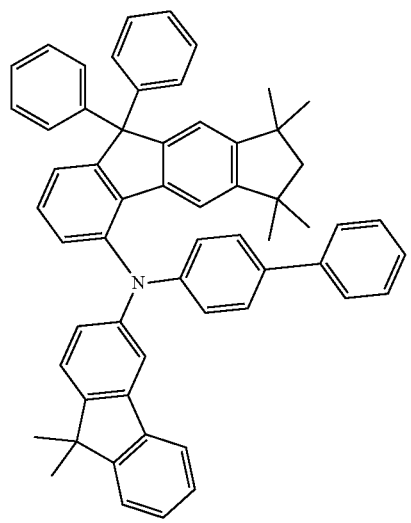
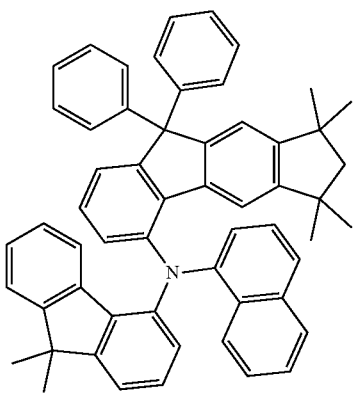
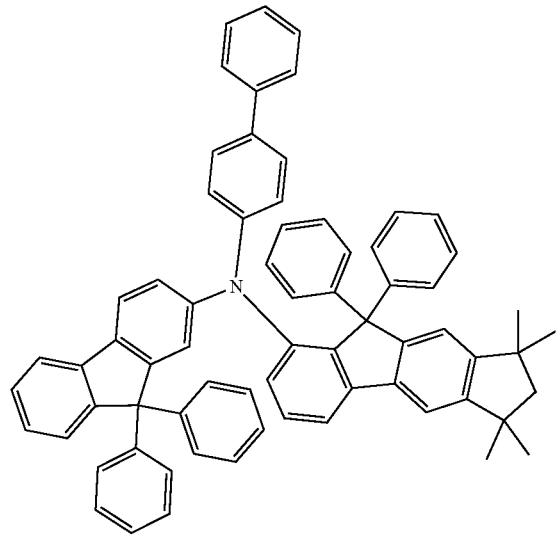
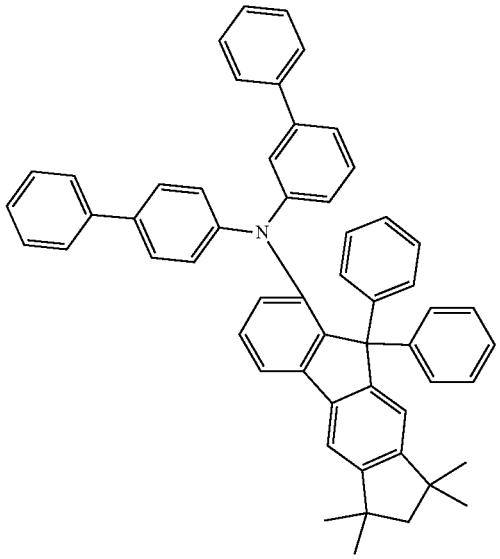
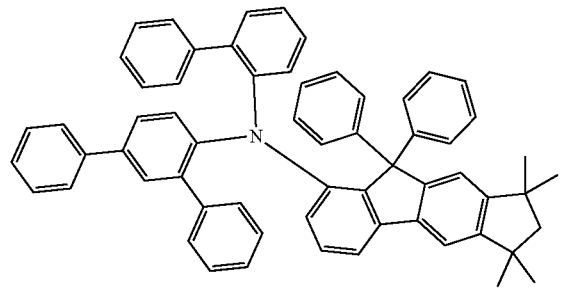
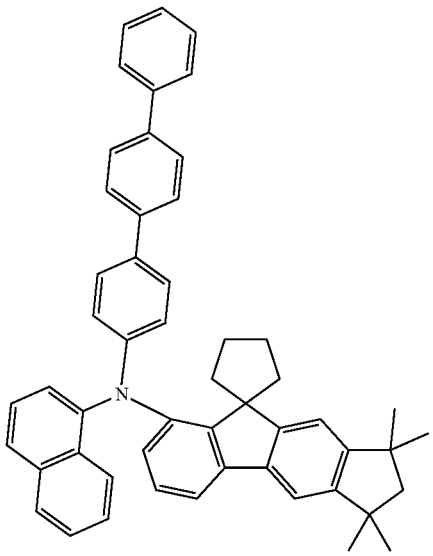

-continued
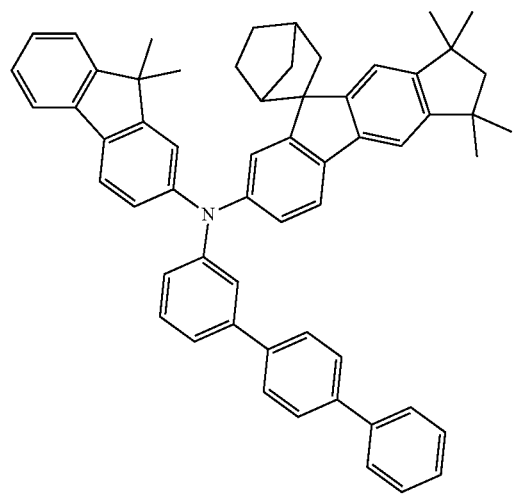
69
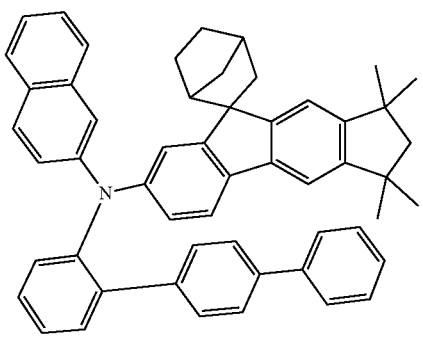
70
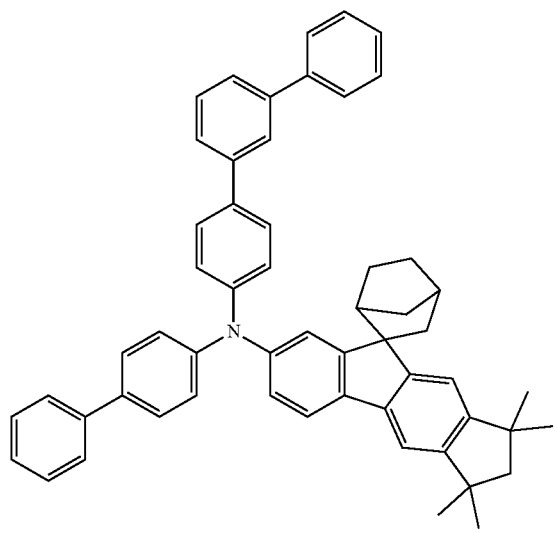
71
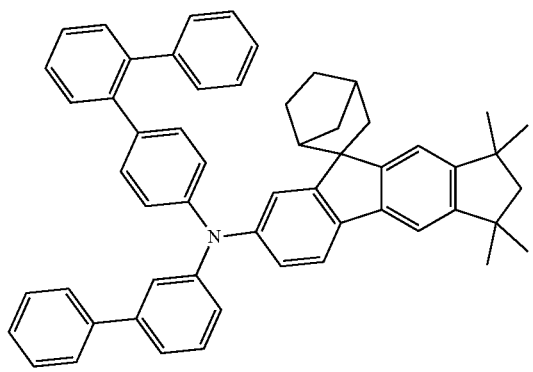
72
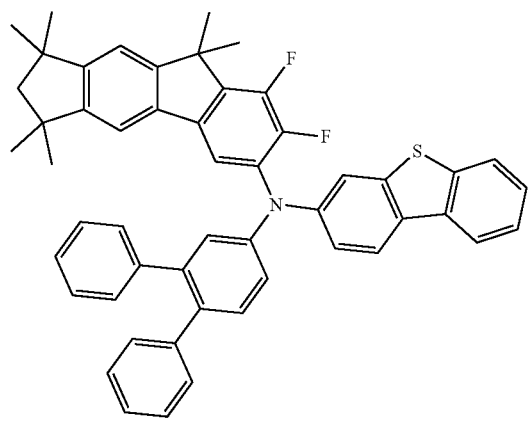
73
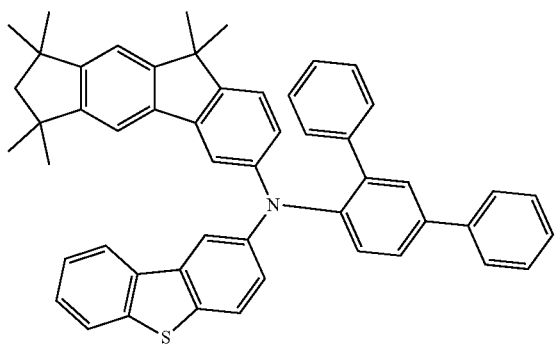
74

-continued
75
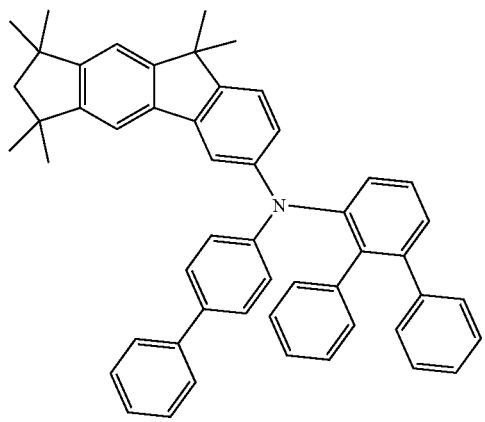
76
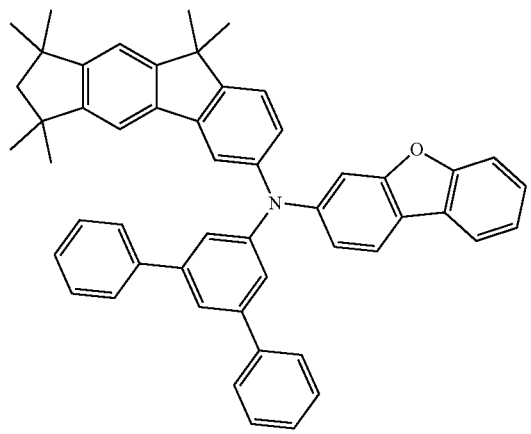
77
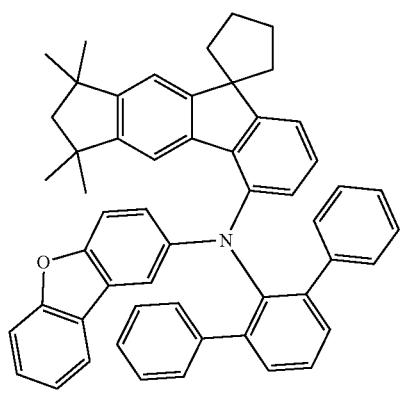
78
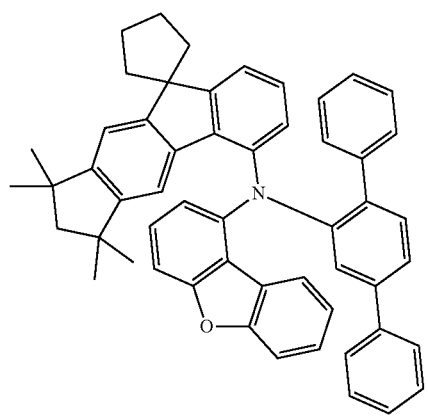
79
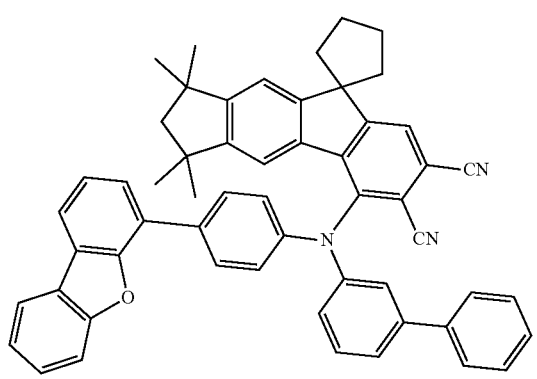
80
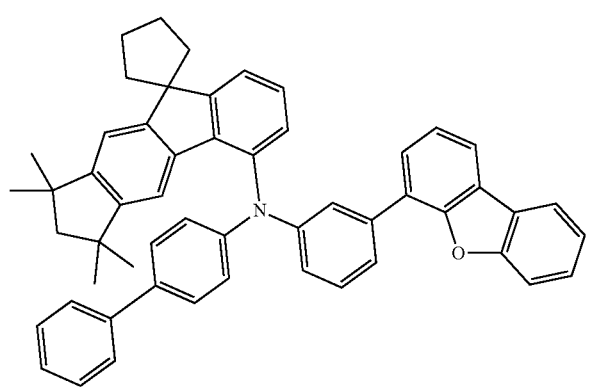
81
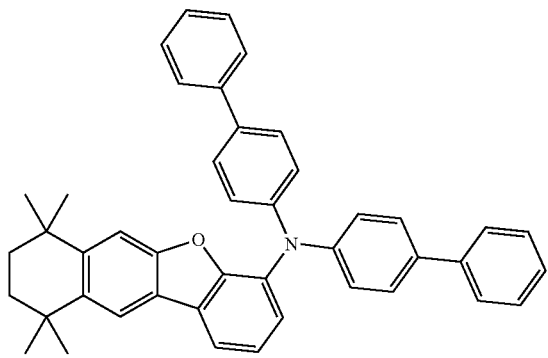
82
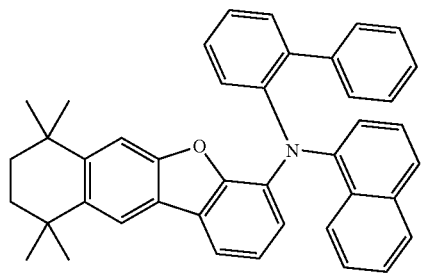

-continued
83
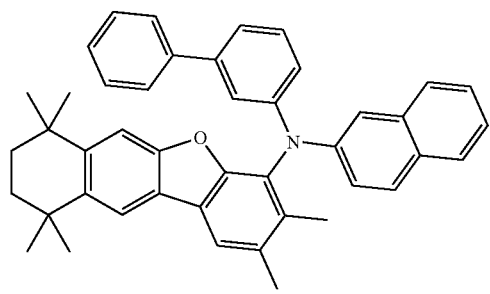
84
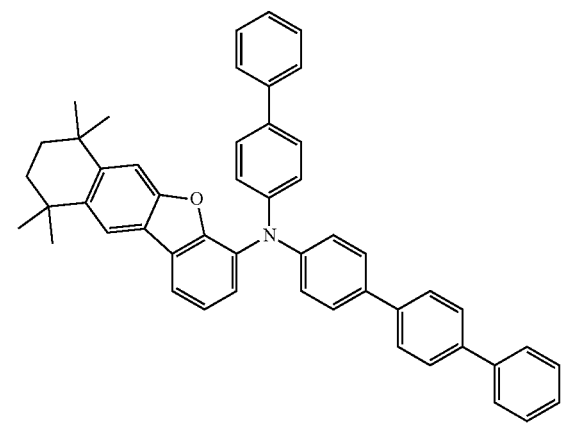
85
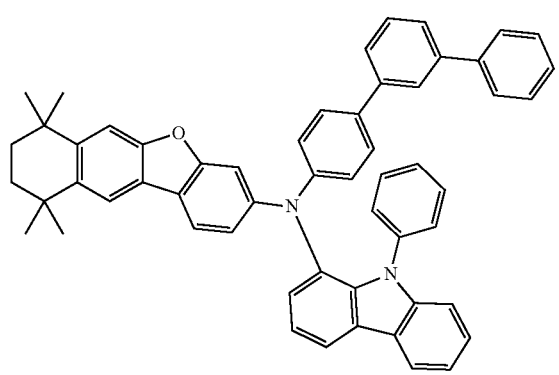
86
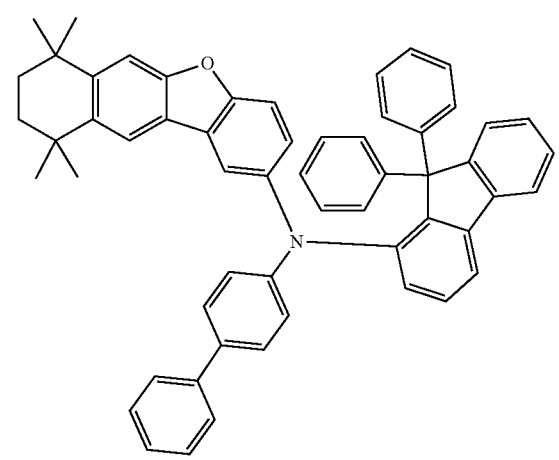
87
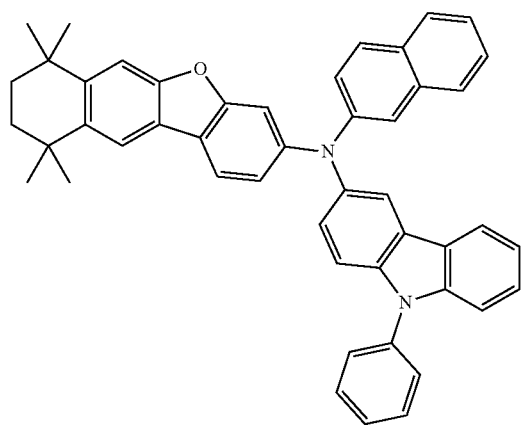
88
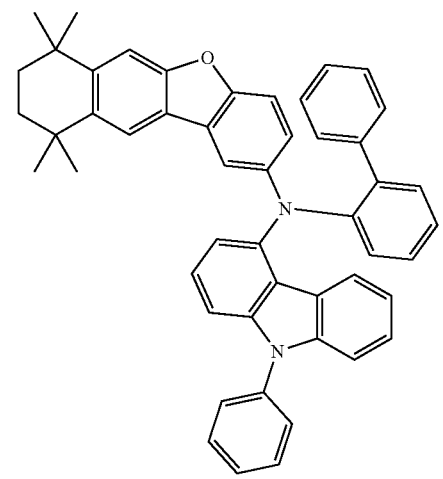

-continued
89
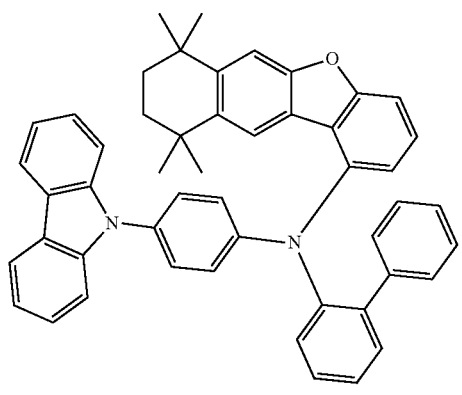
90
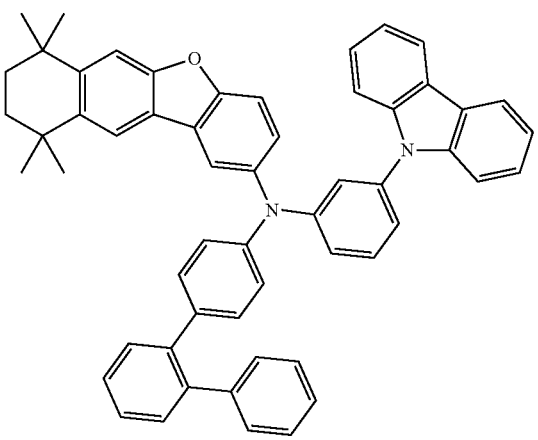
91
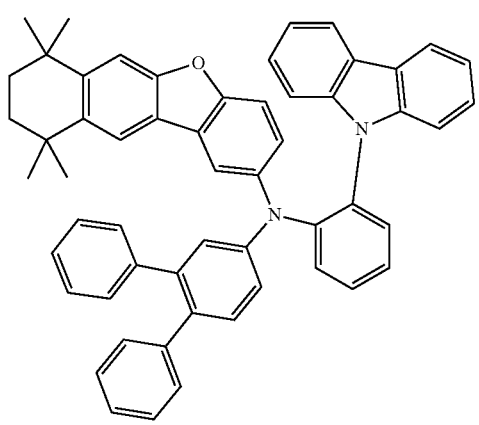
92
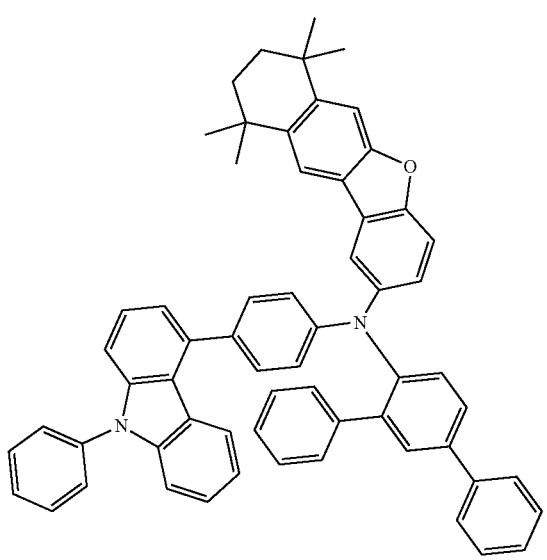
93
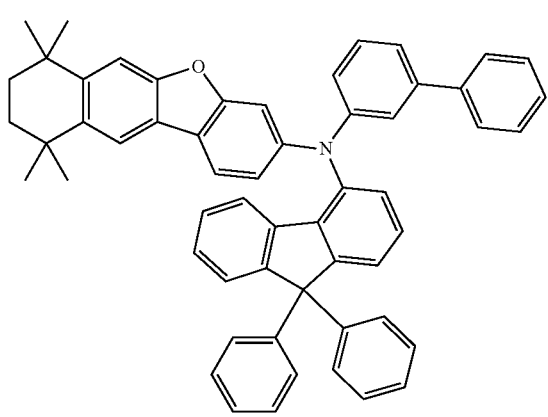
94
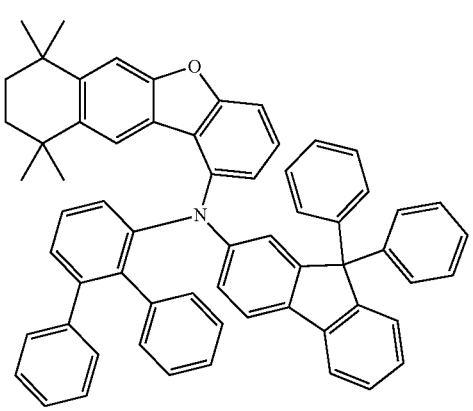

-continued
95
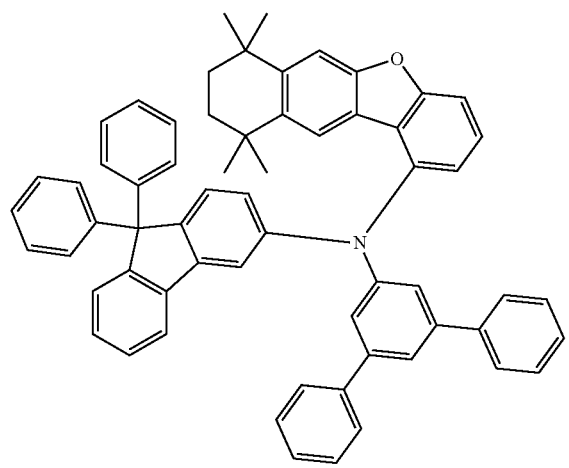
96
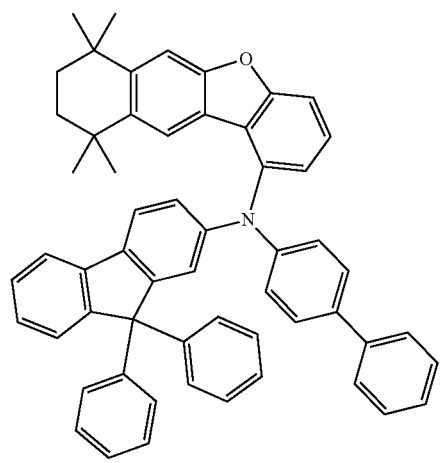
97
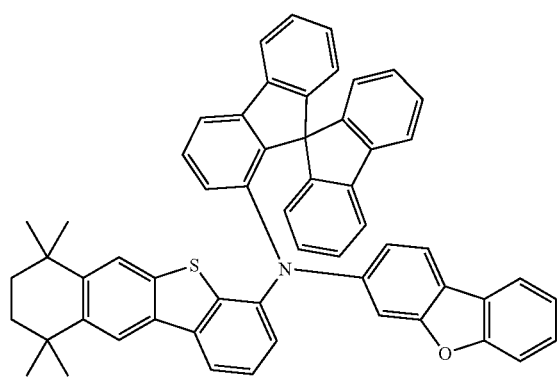
98
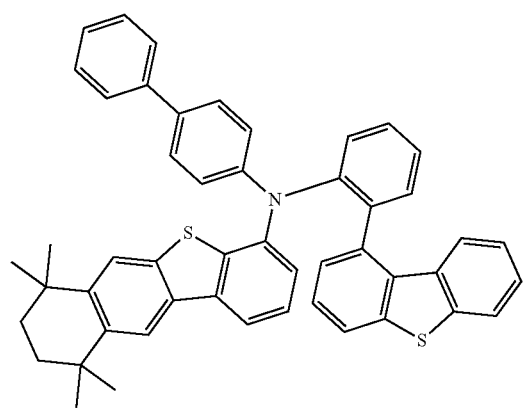
99
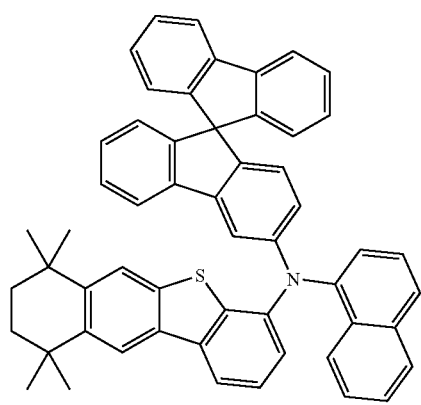
100
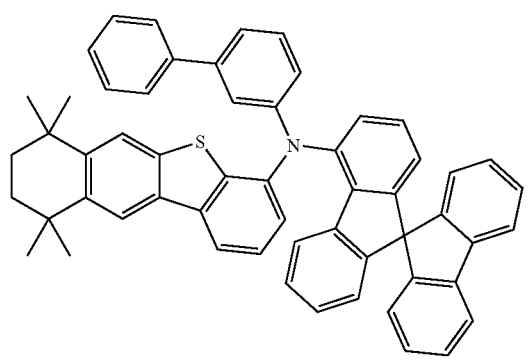

-continued
101
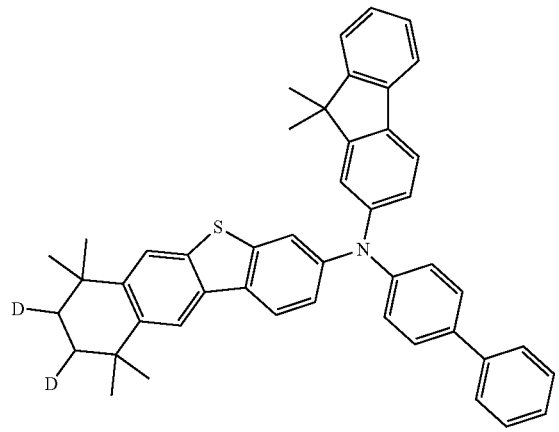
102
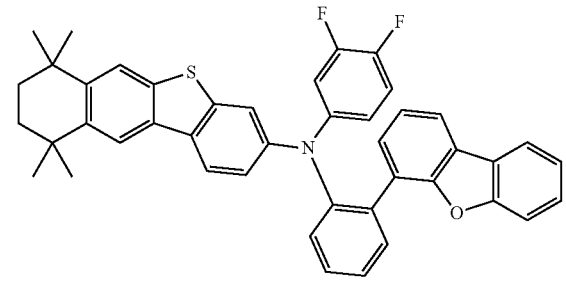
103
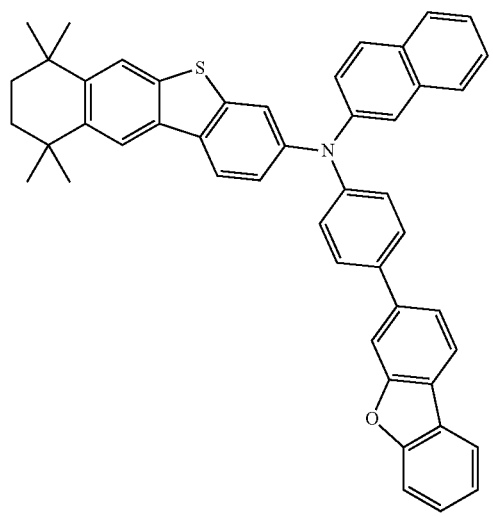
104
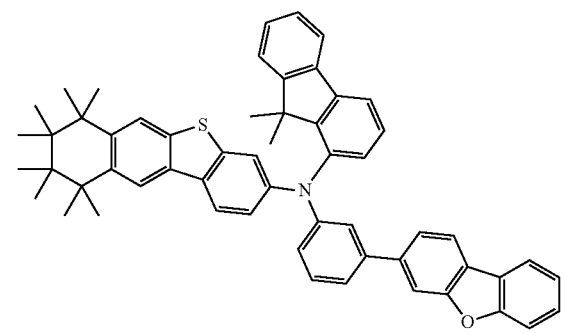
105
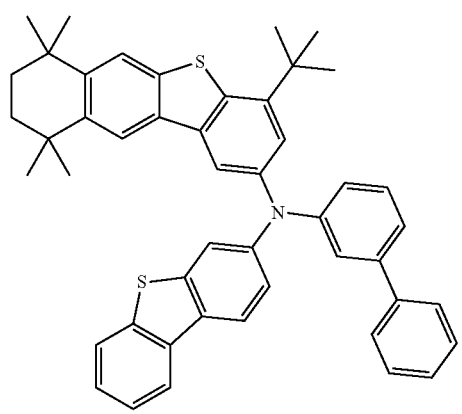
106
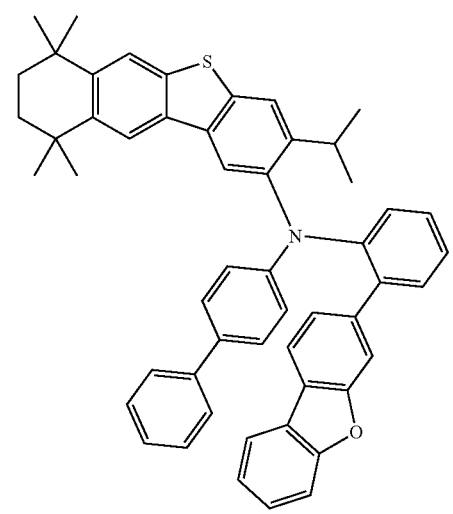

-continued
107
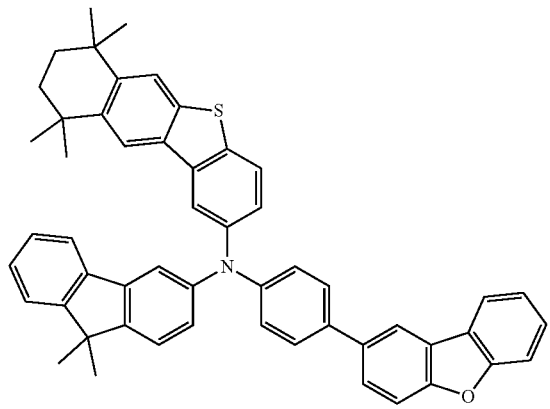
108
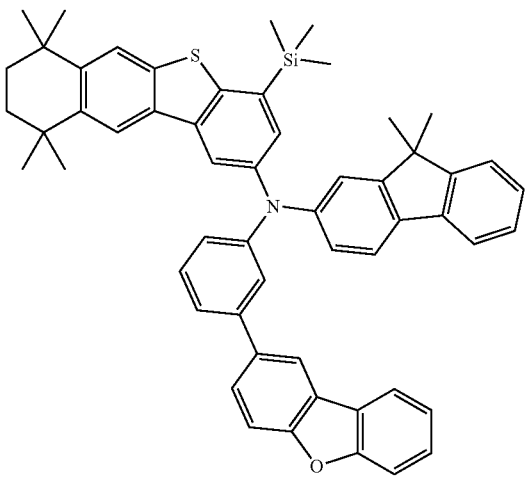
109
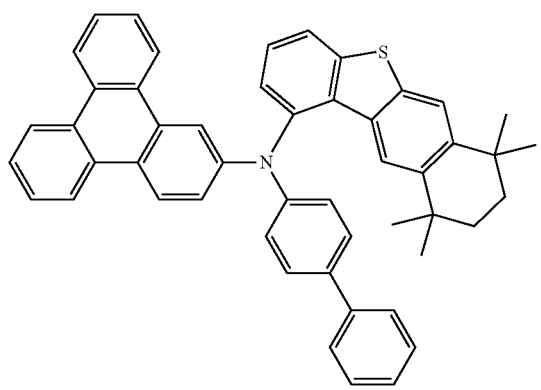
110
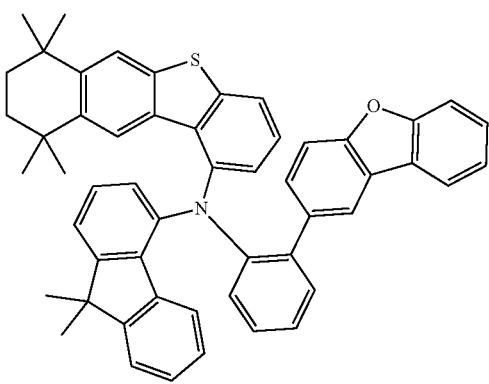
111
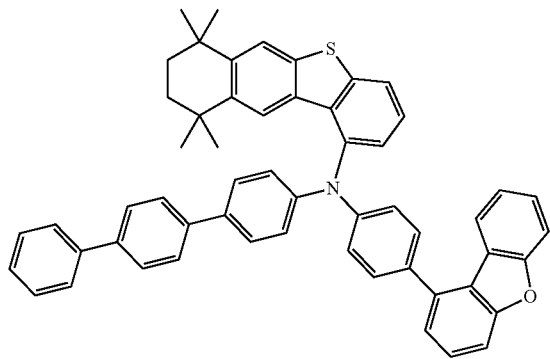
112
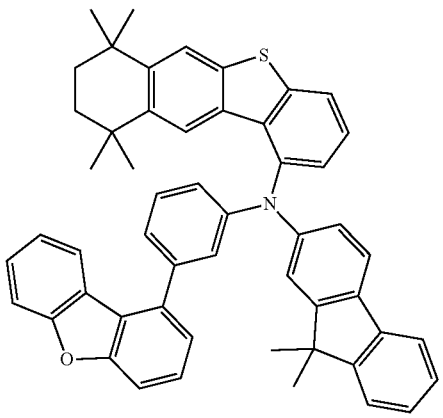
113
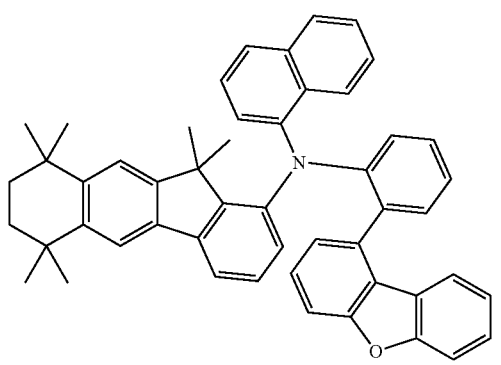
114
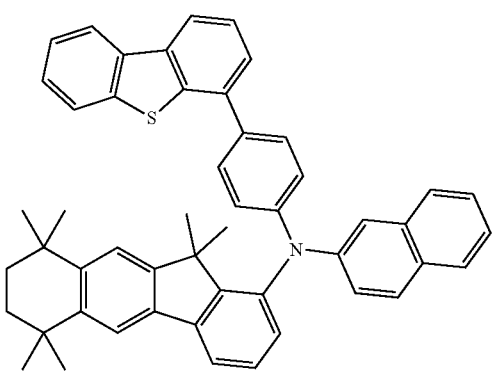

-continued
115
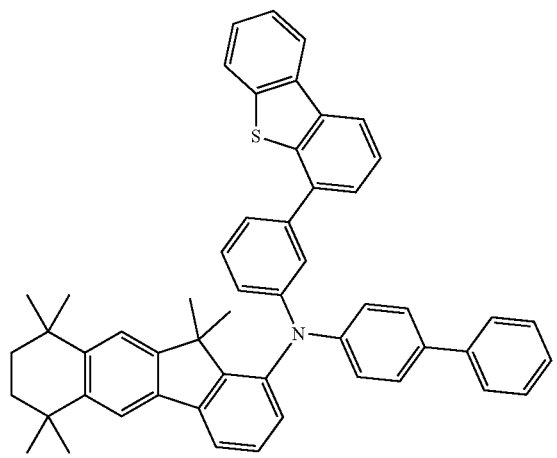
116
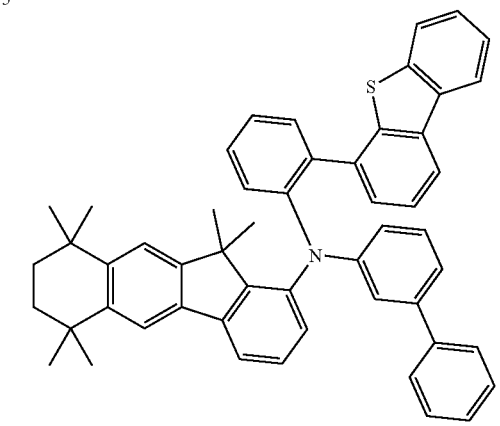
117
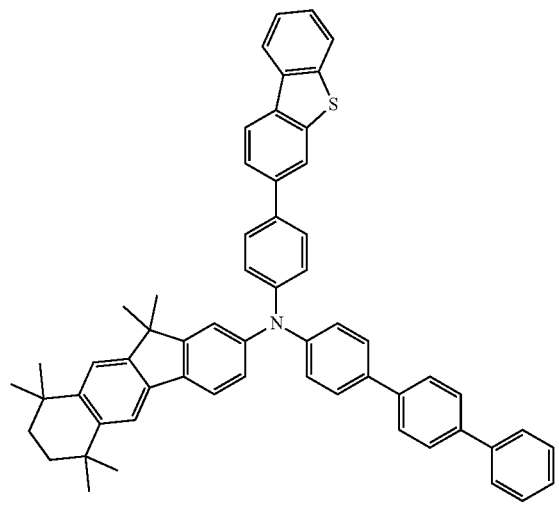
118
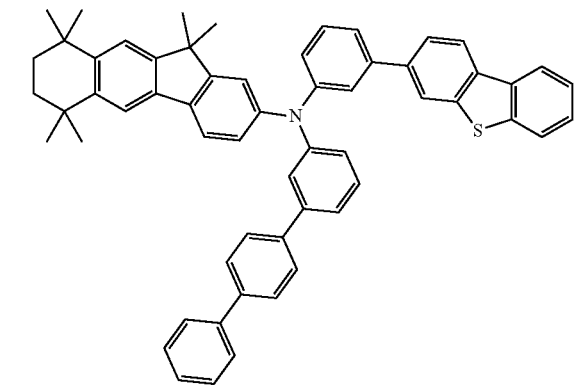
119
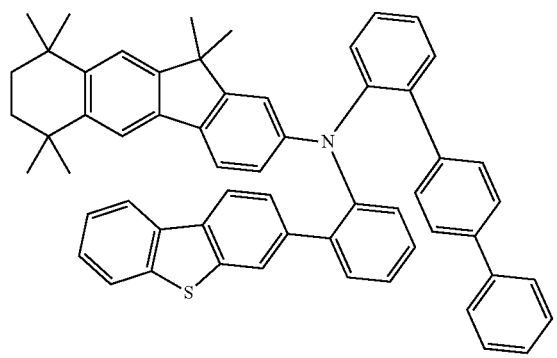
120
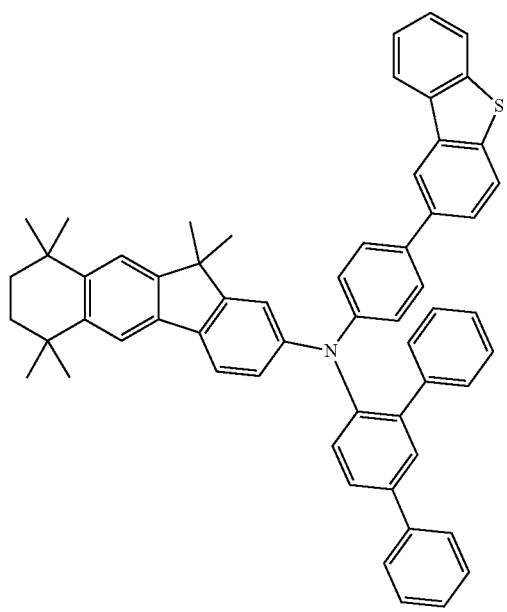

121
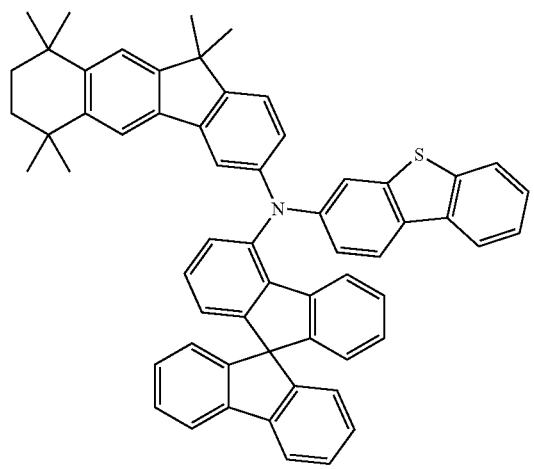
122
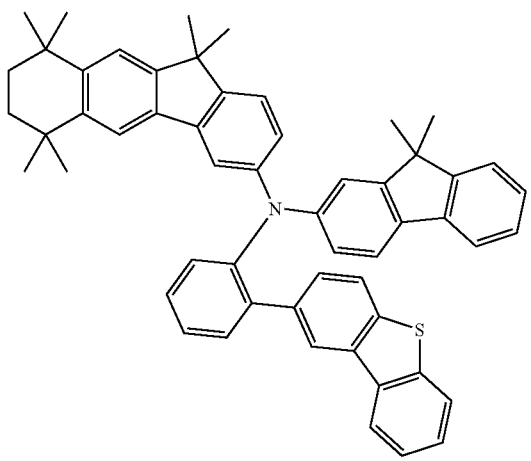
123
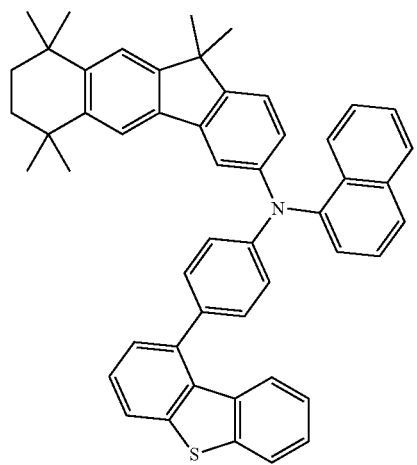
124
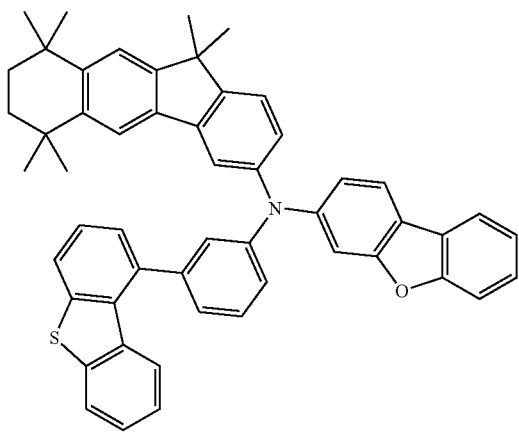
125
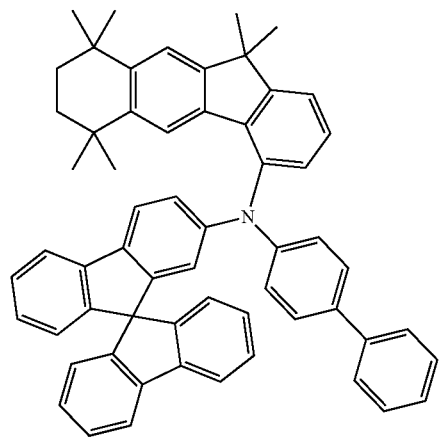
126
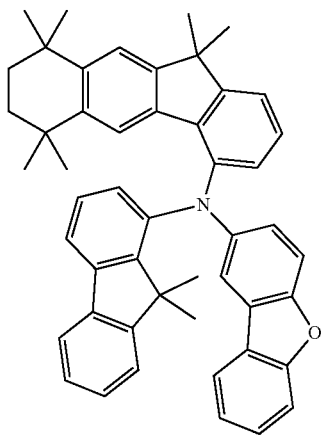

127
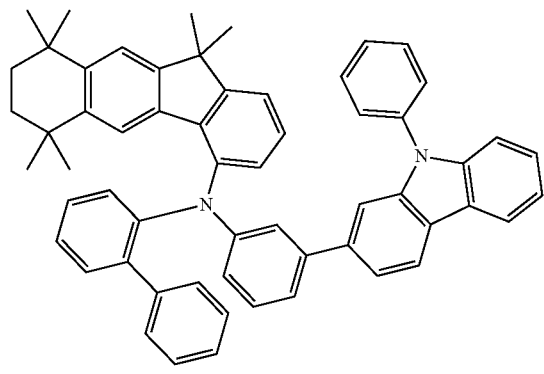
128
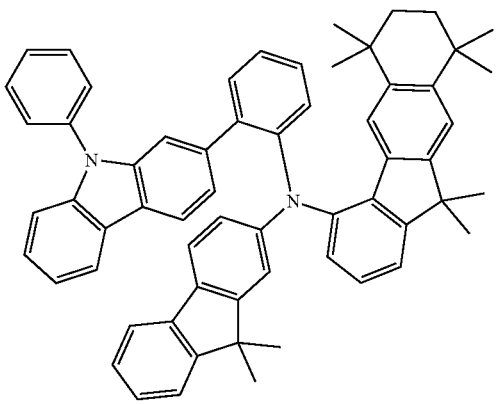
129
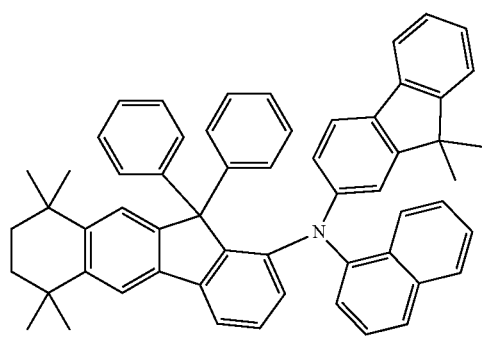
130
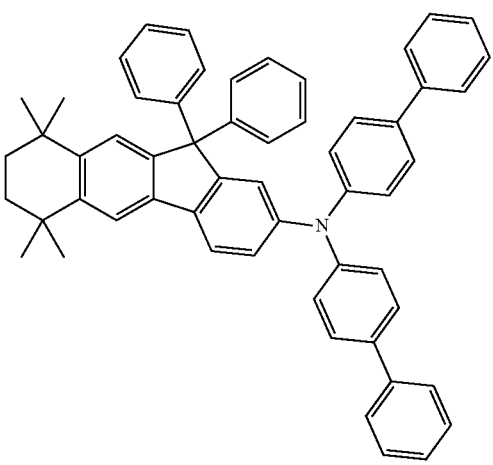
131
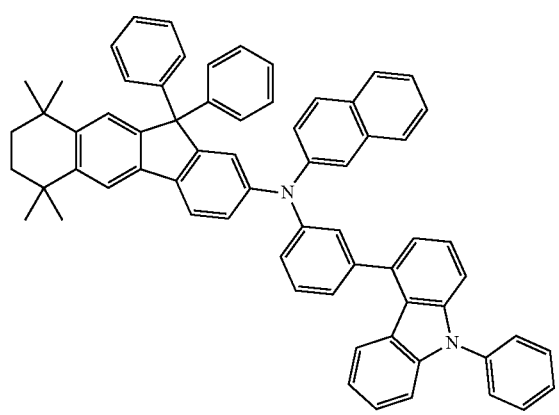
132
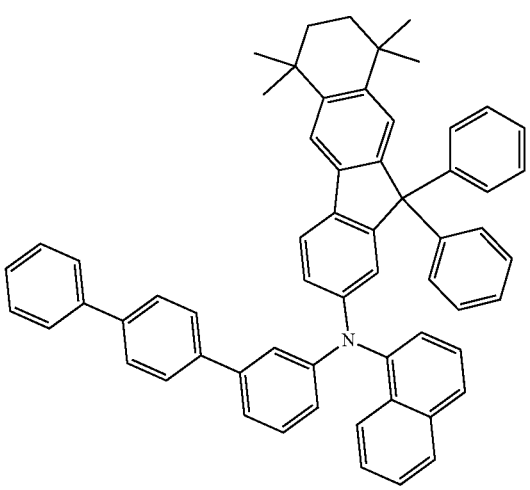

-continued
133
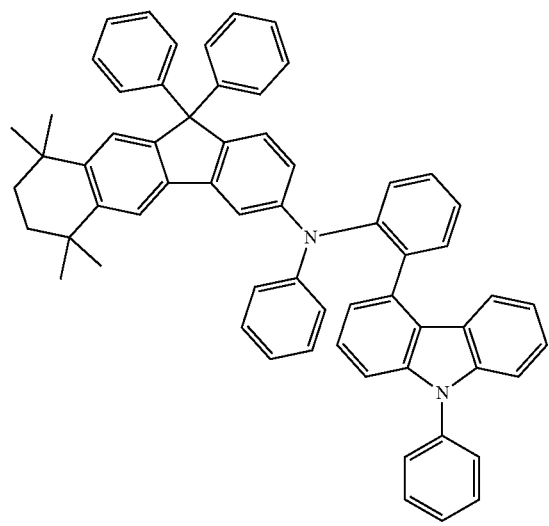
134
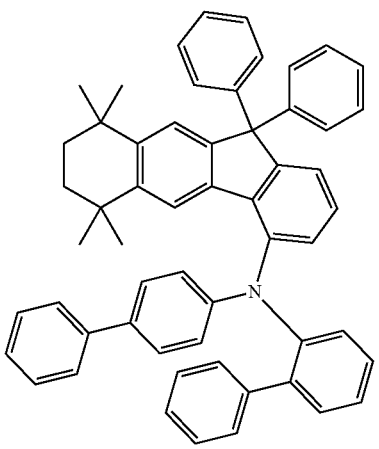
135
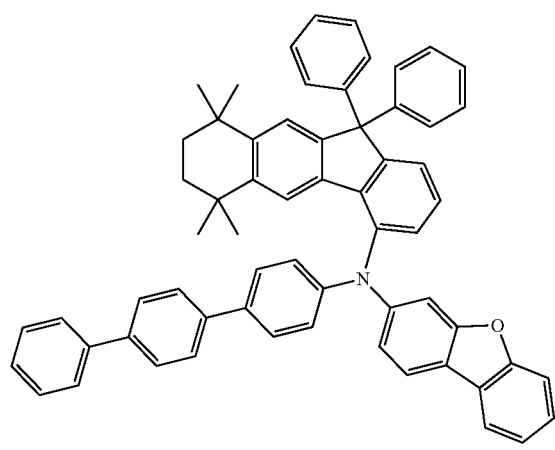
136
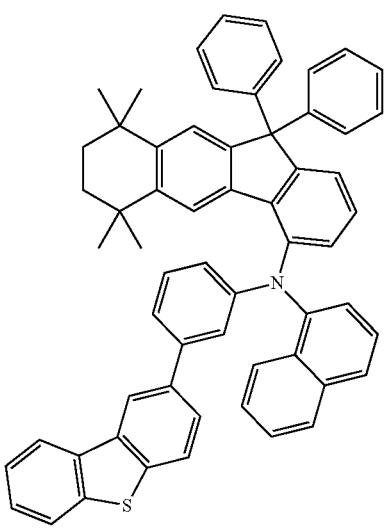
137
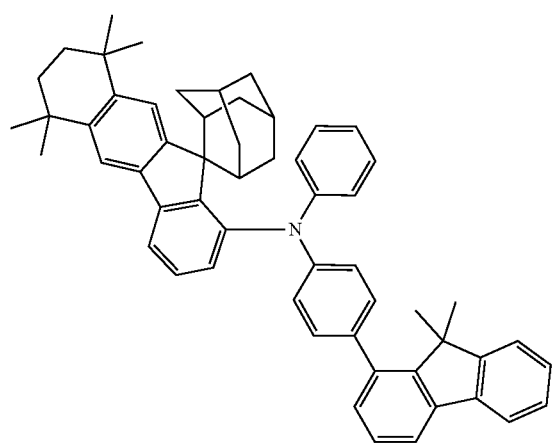
138
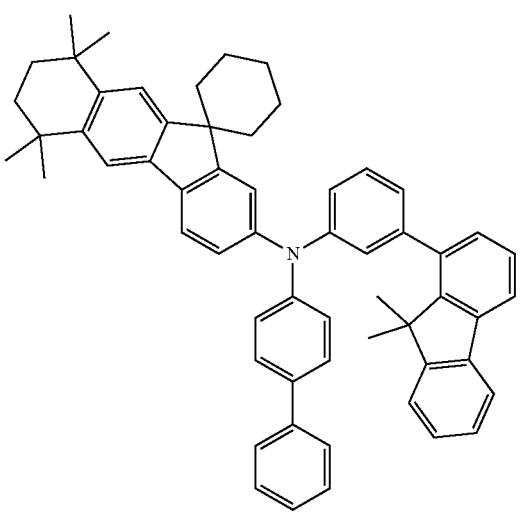

-continued
139
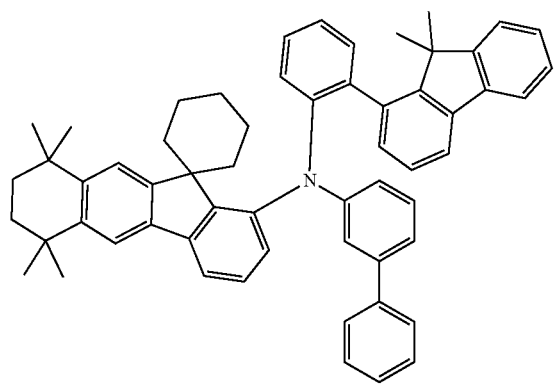
140
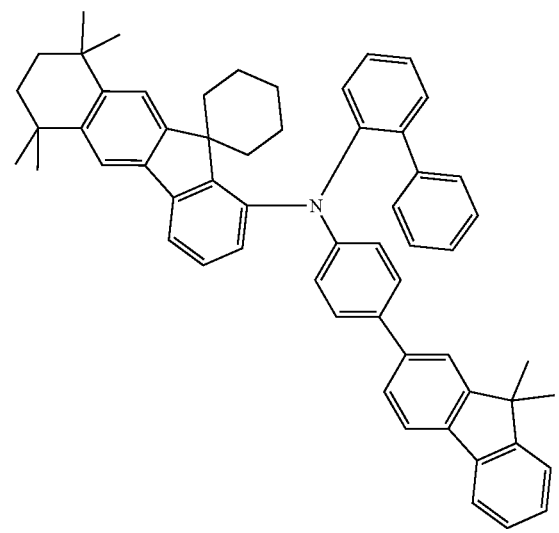
141
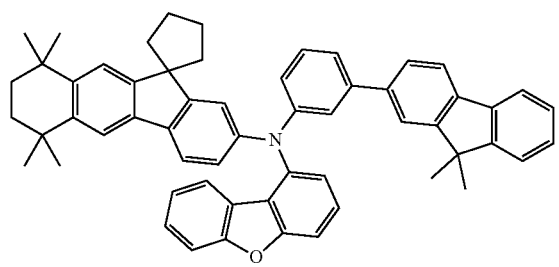
142
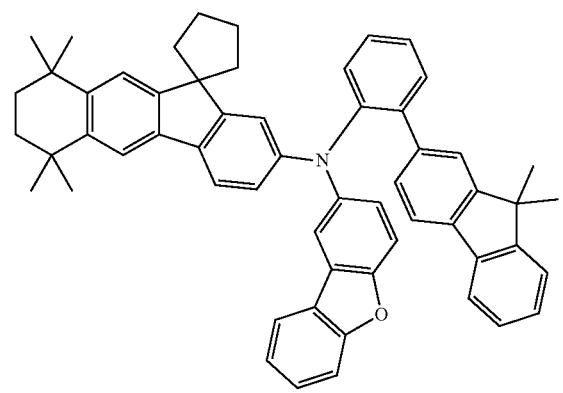
143
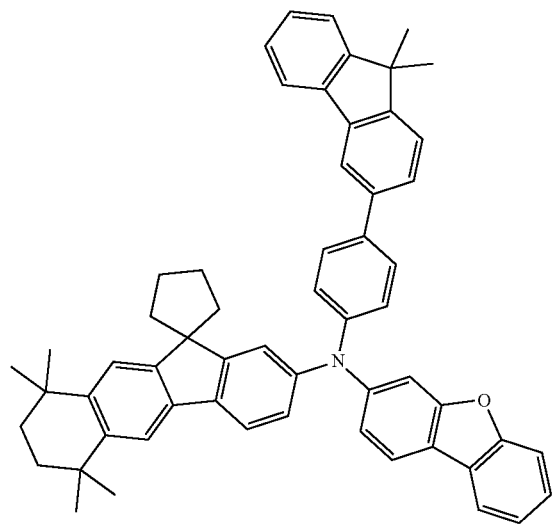
144
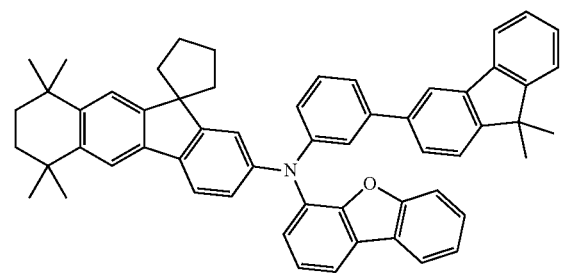

-continued
145
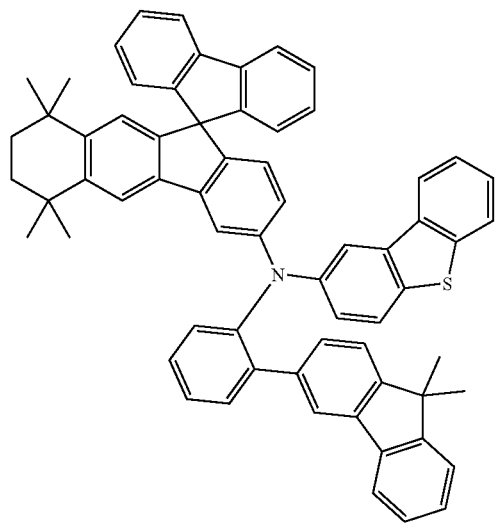
146
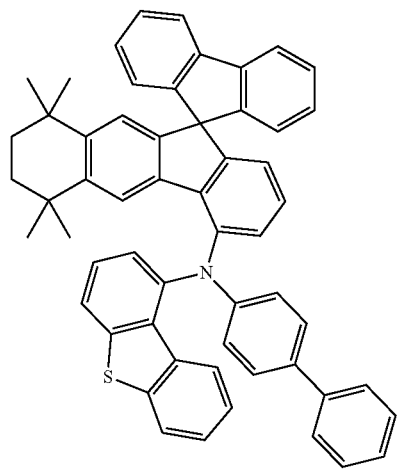
147
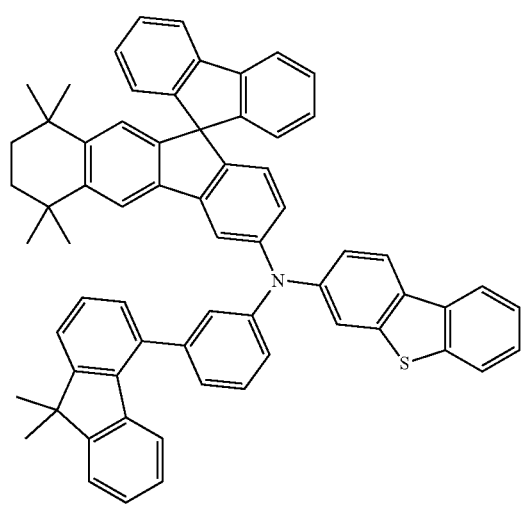
148
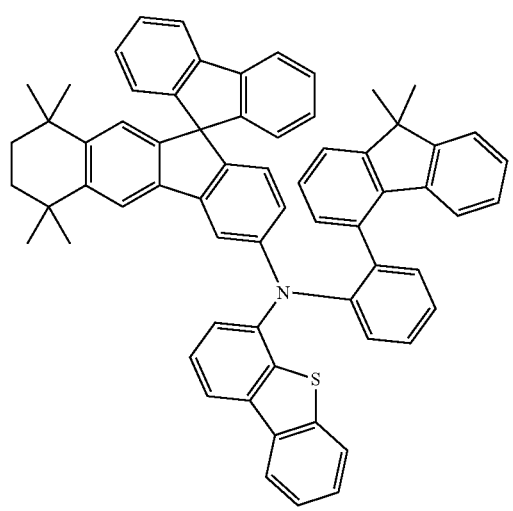
149
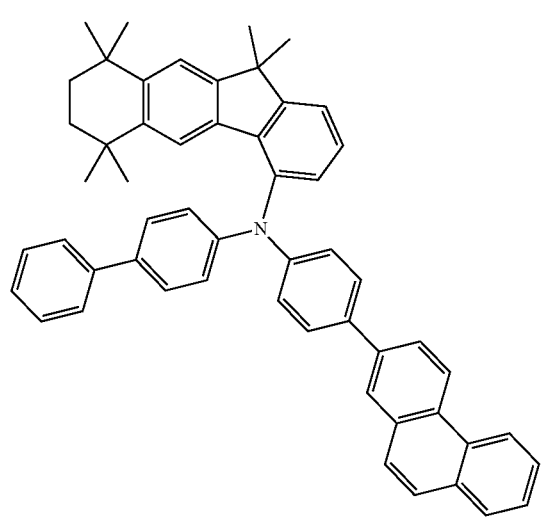
150
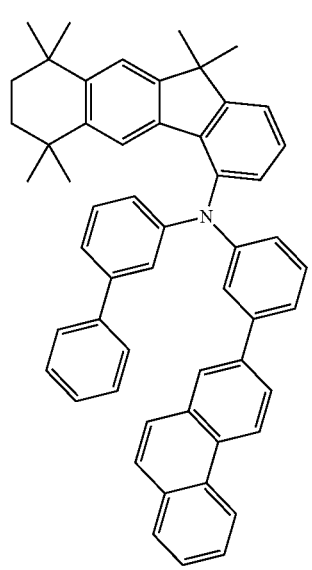

-continued
151 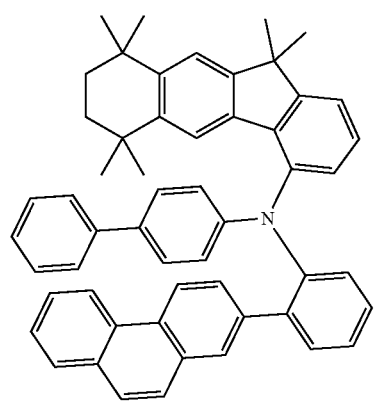
152 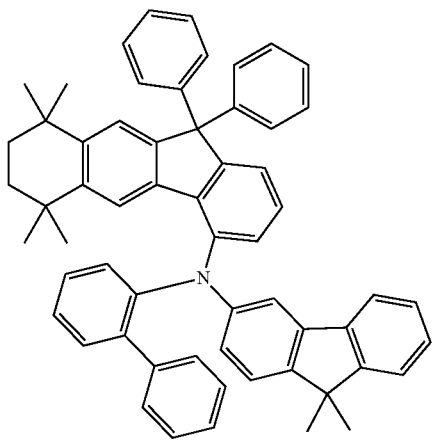
153 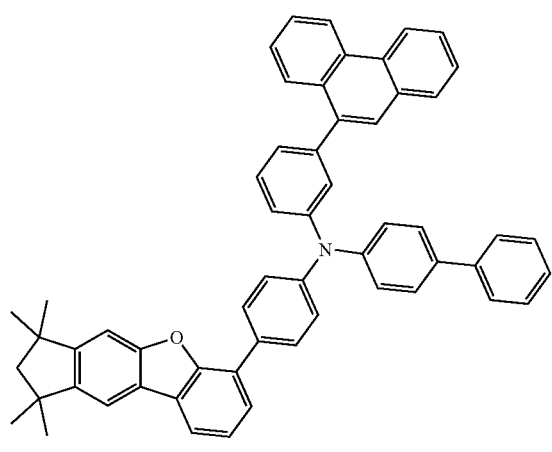
154 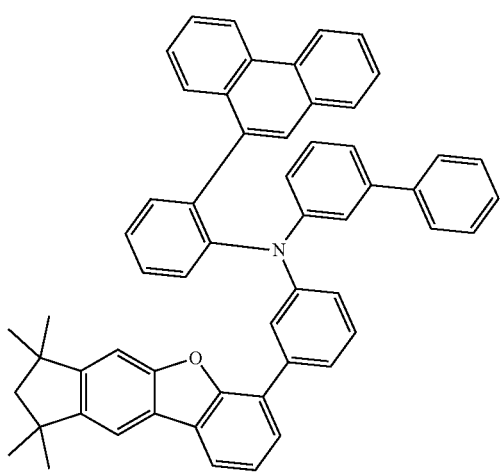
155 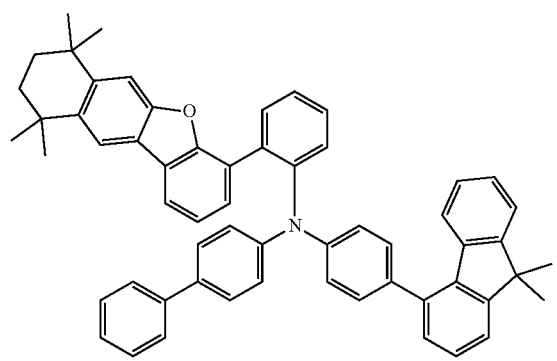
156 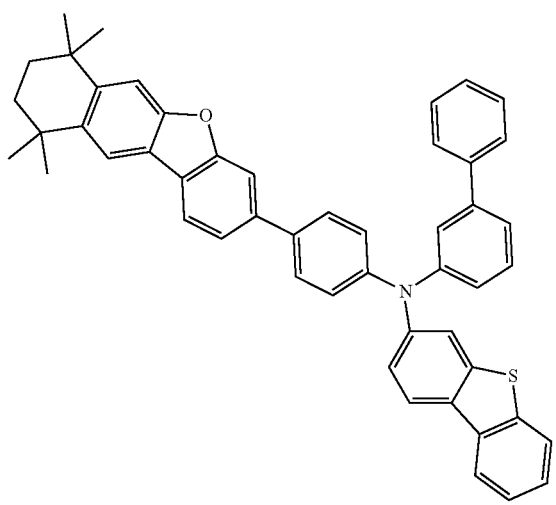

-continued
157
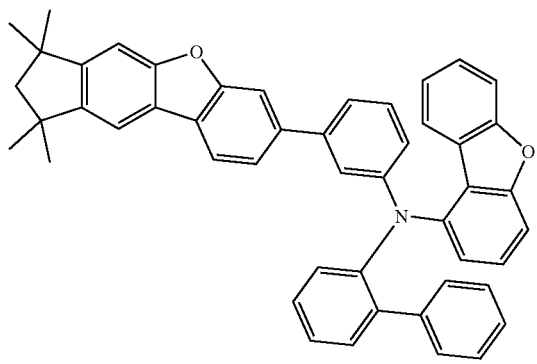
158
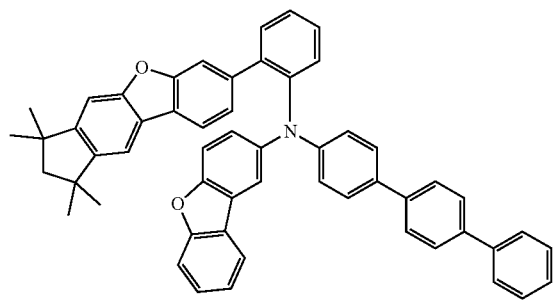
159
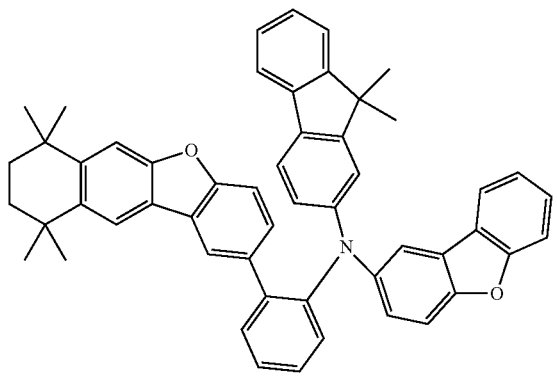
160
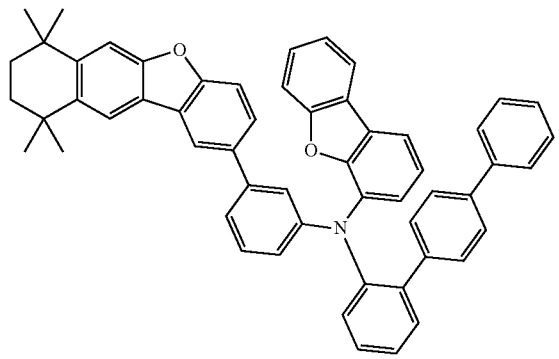
161
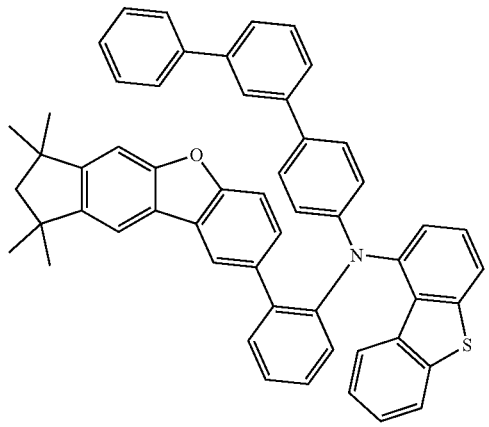
162
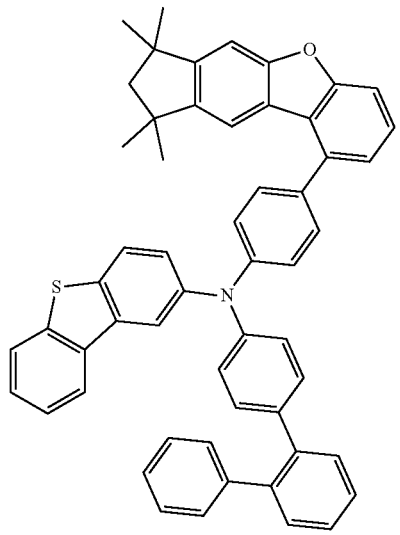

-continued
163
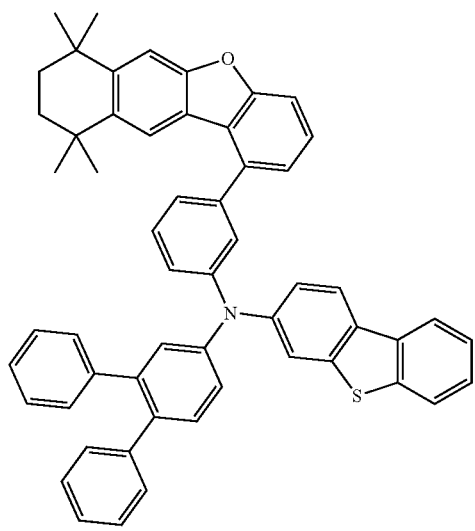
164
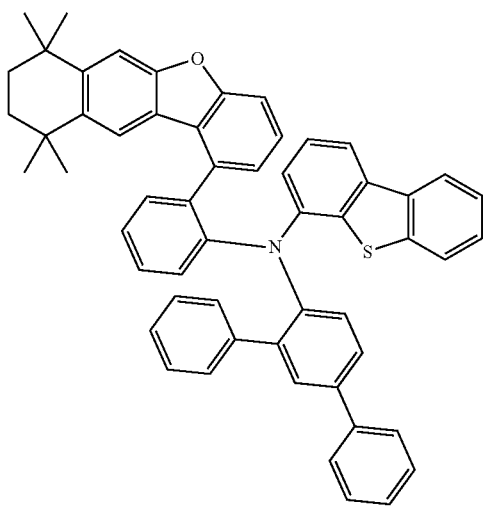
165
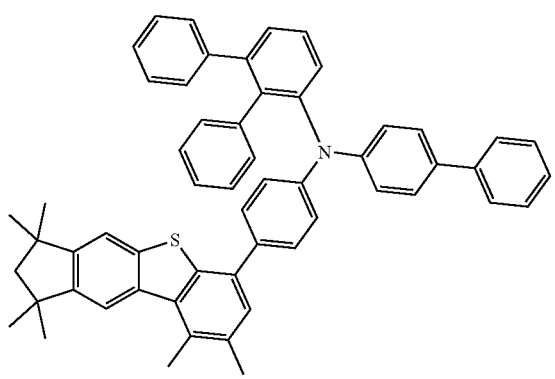
166
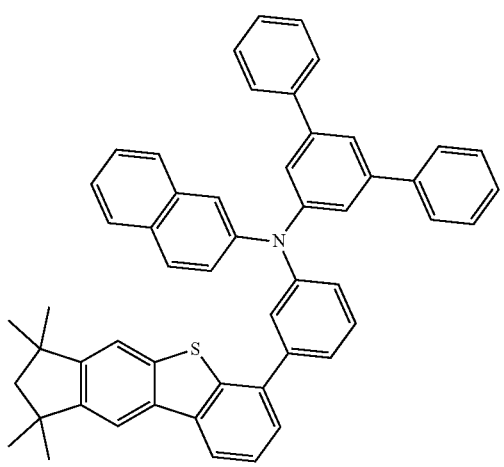
167
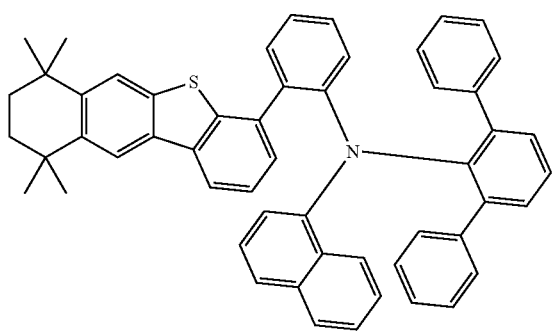
168
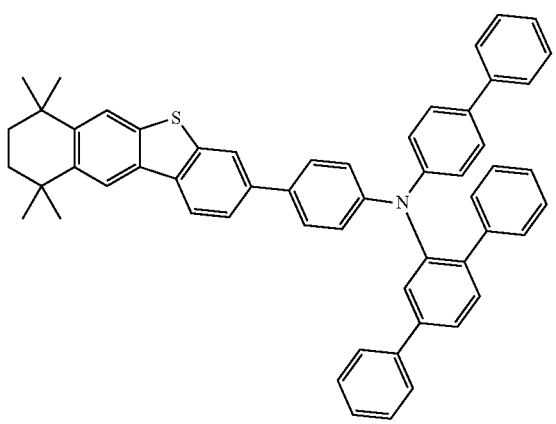

169
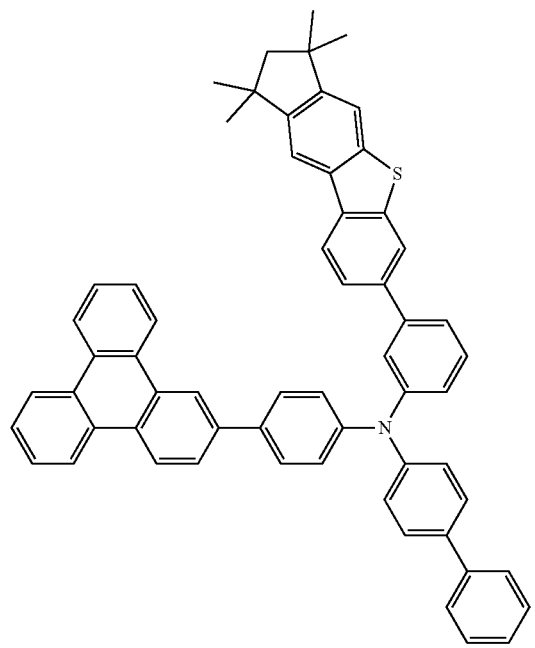
170
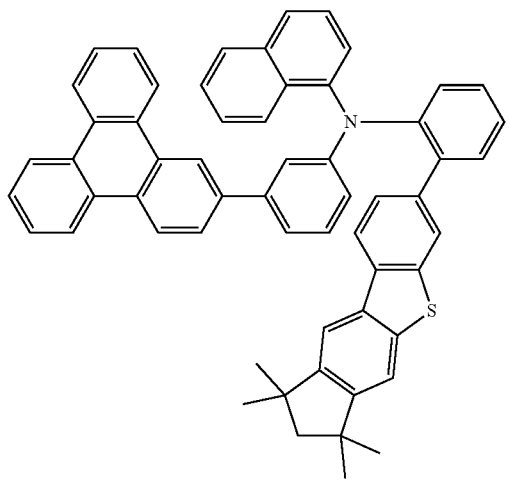
171
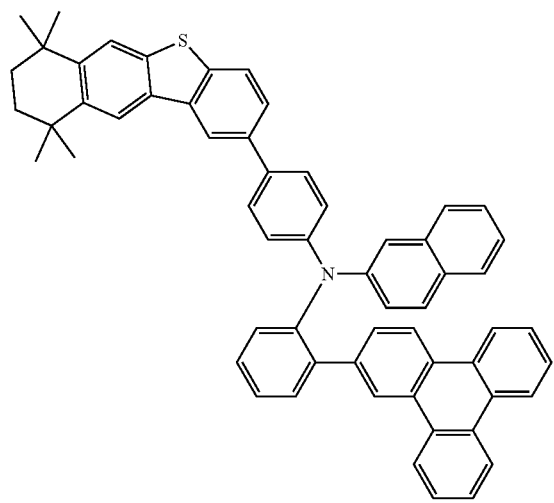
172
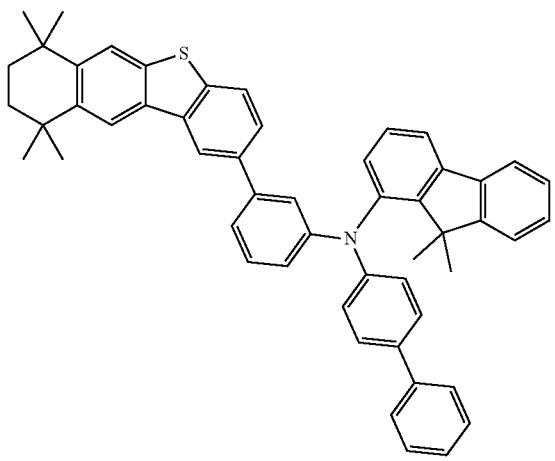

-continued
173 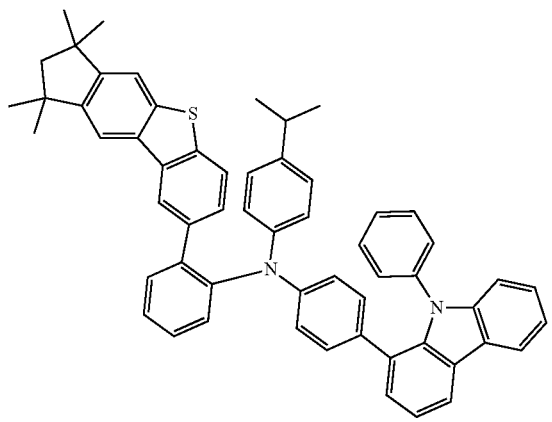
174 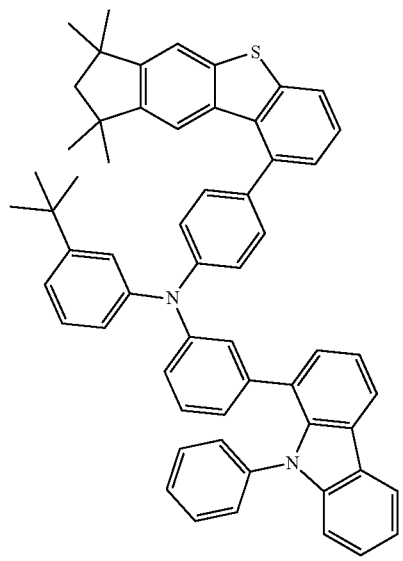
175 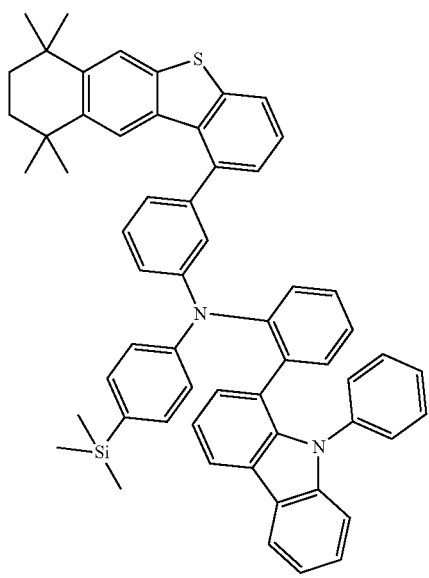
176 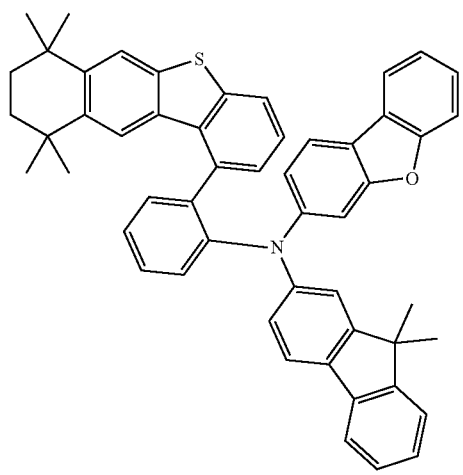
177 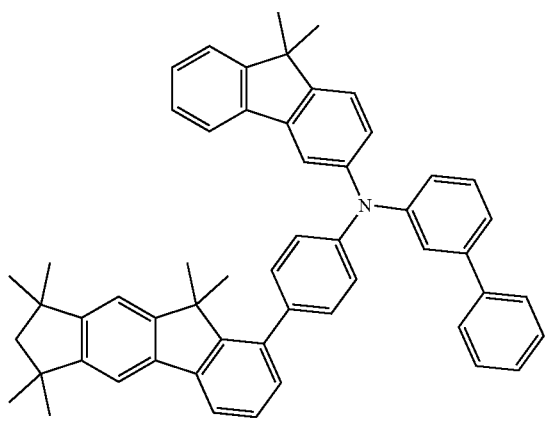
178 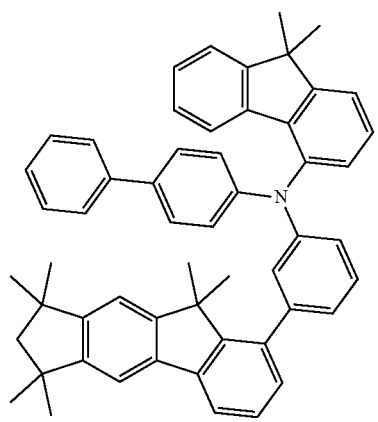

-continued
179
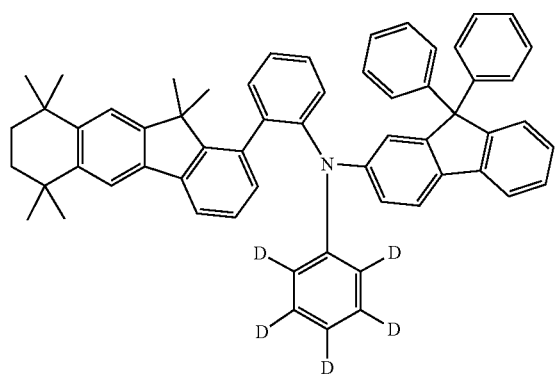
180
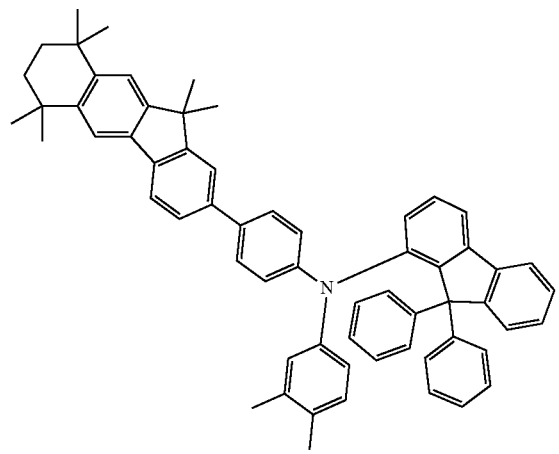
181
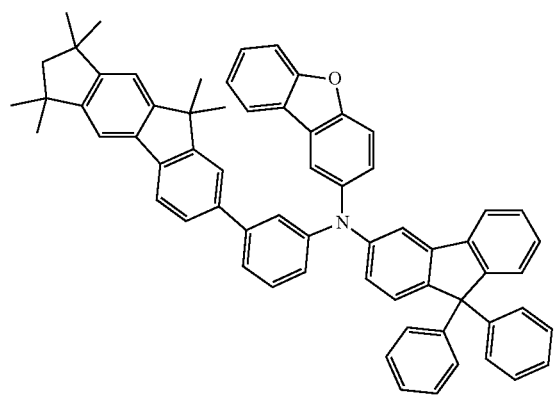
182
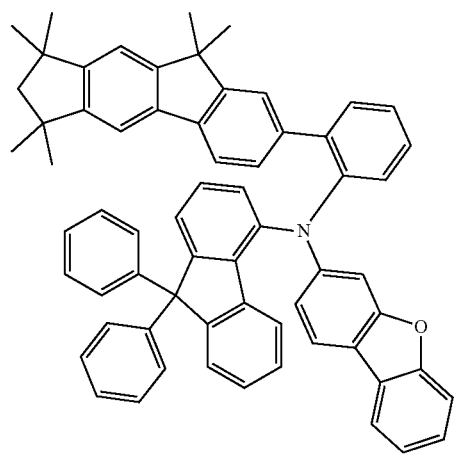
183
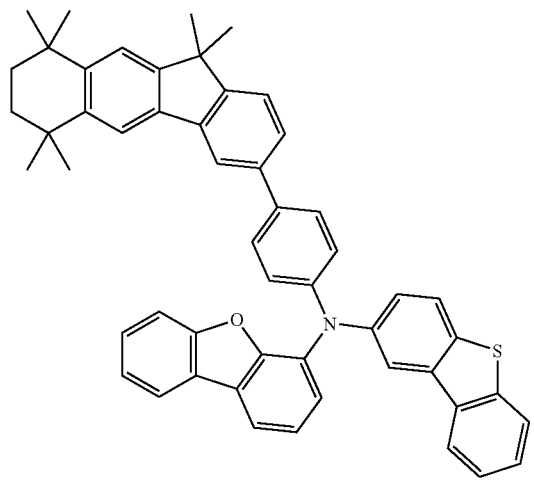
184
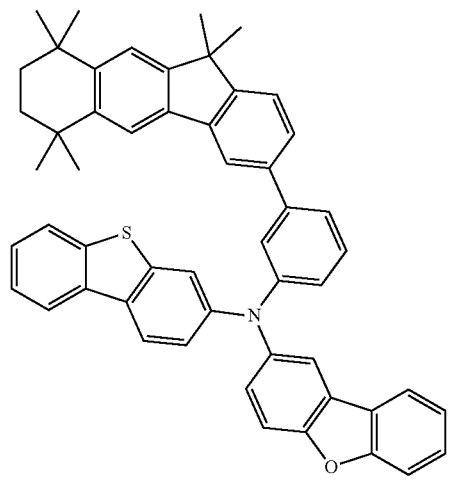

-continued
185 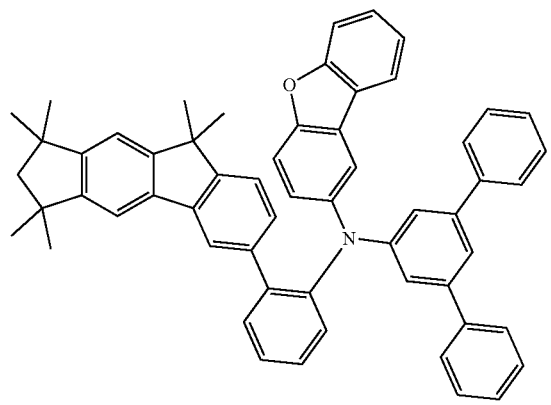
186 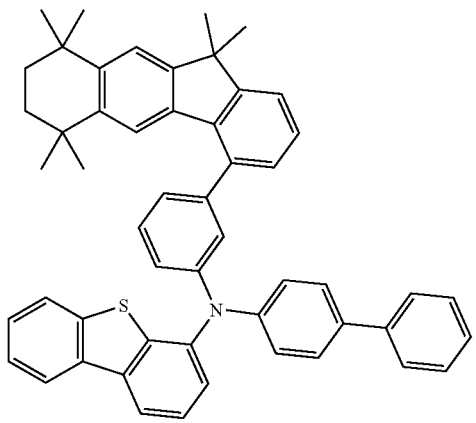
187 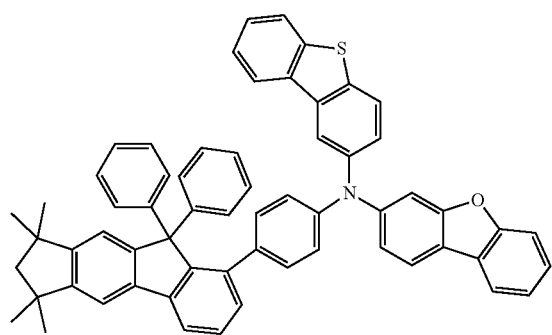
188 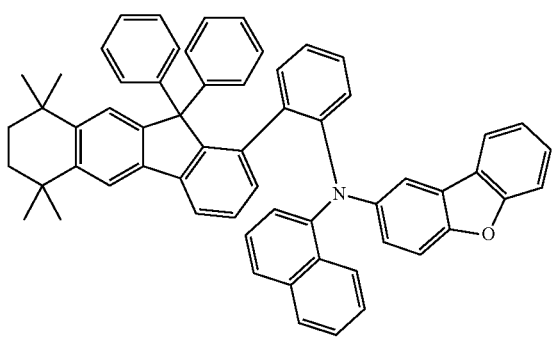
189 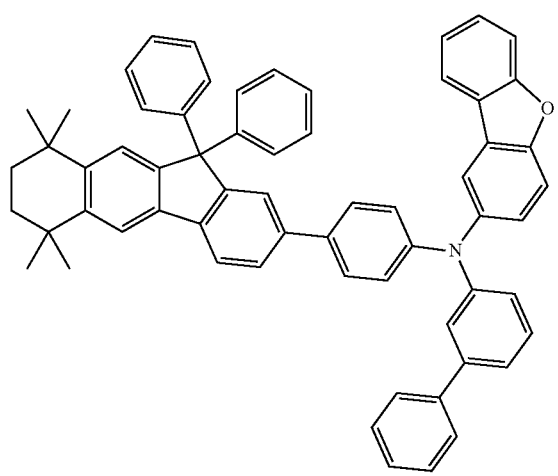
190 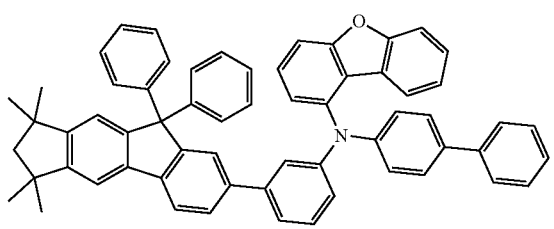

-continued
191
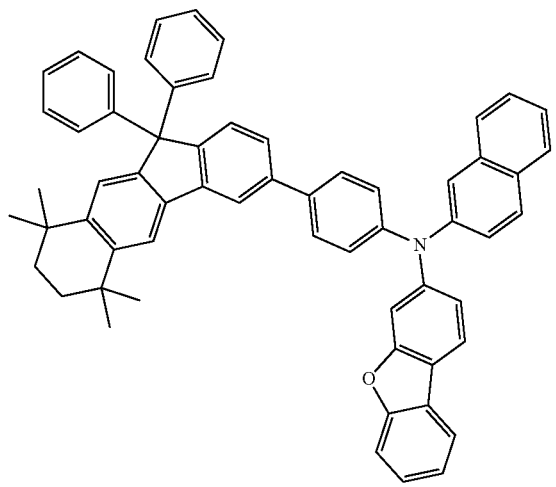
192
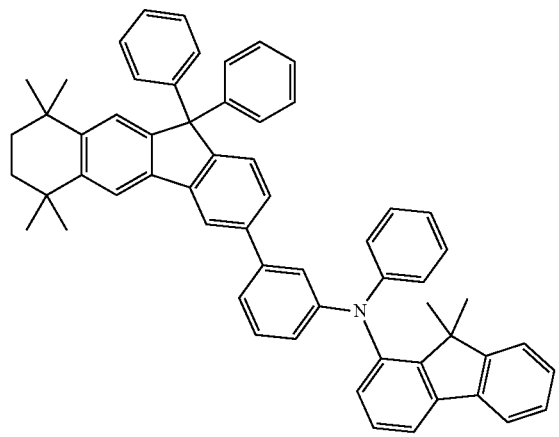
193
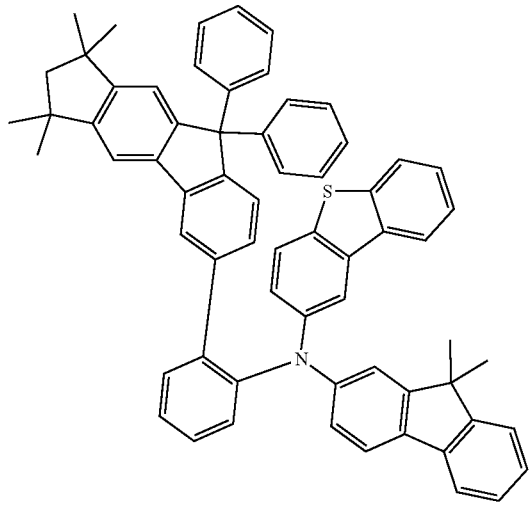
194
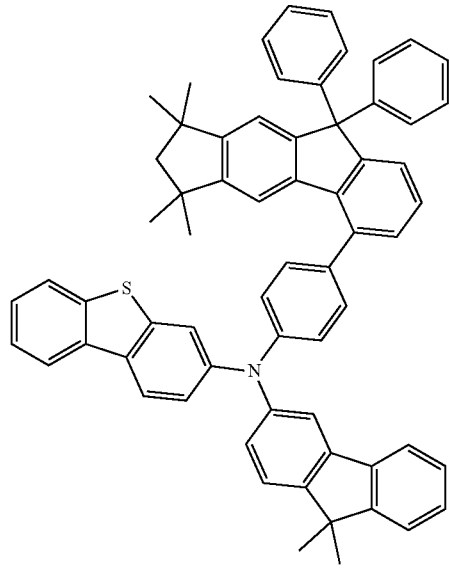
195
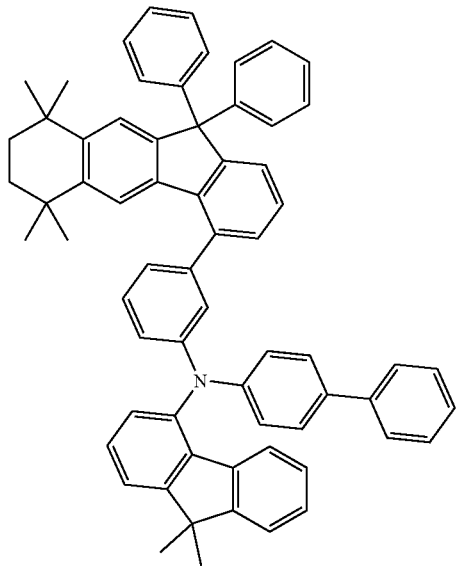
196
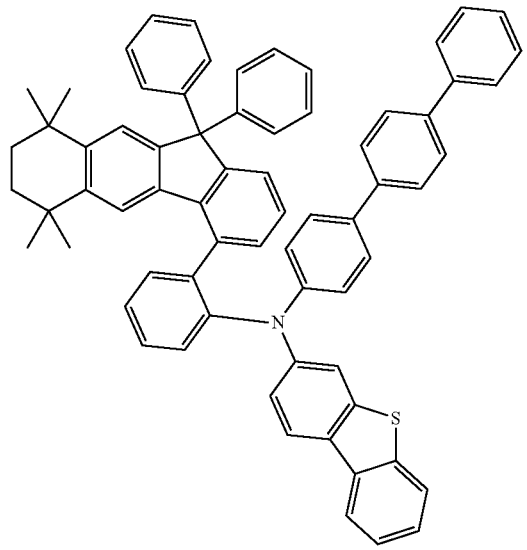

-continued
197
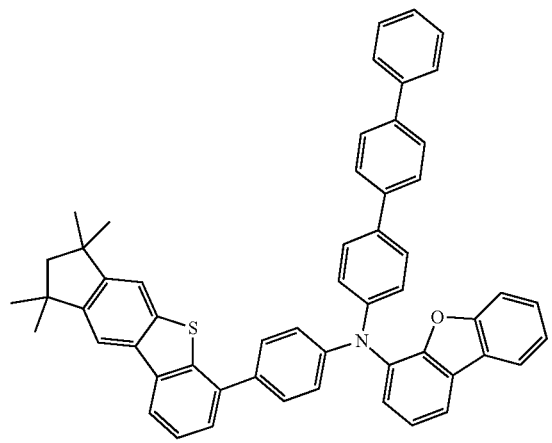
198
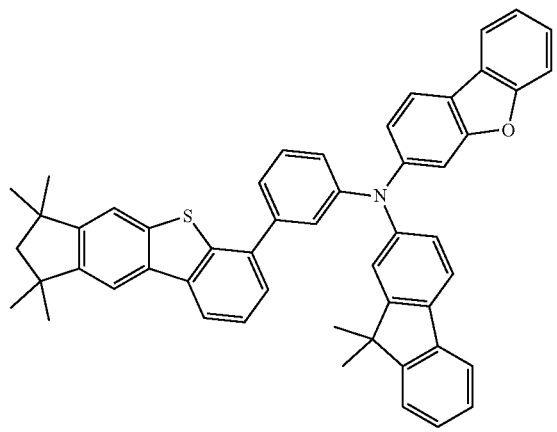
199
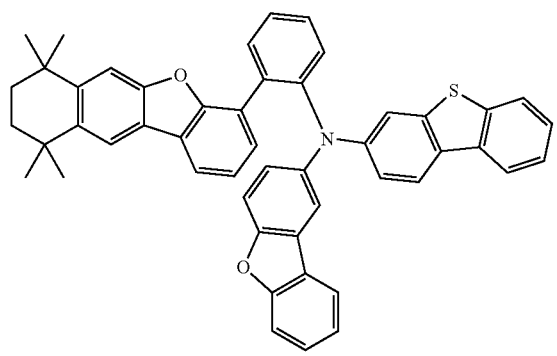
200
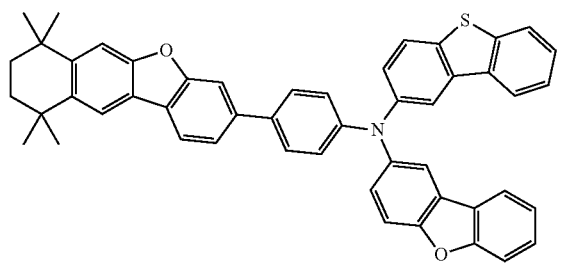
201
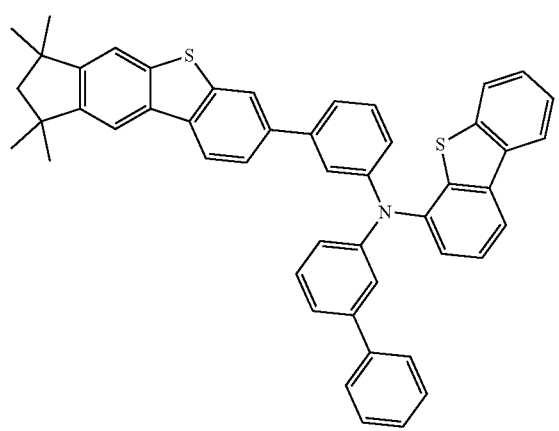
202
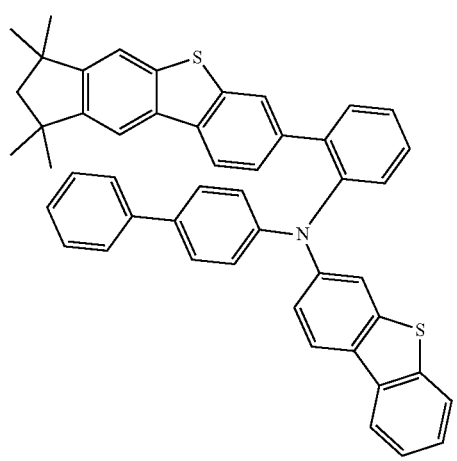

-continued
203
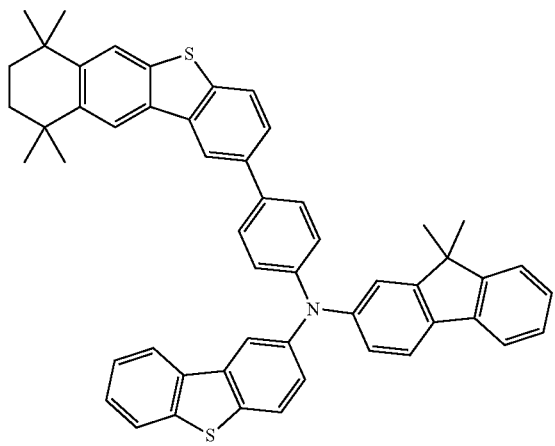
204
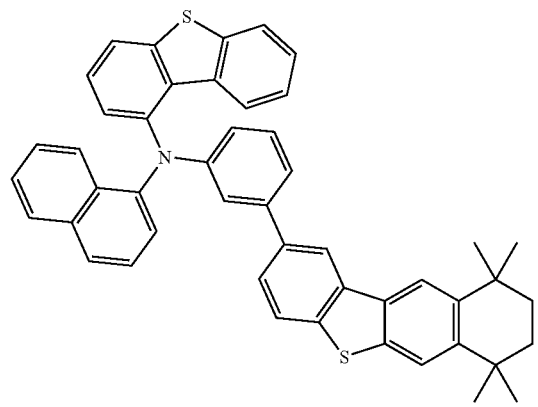
205
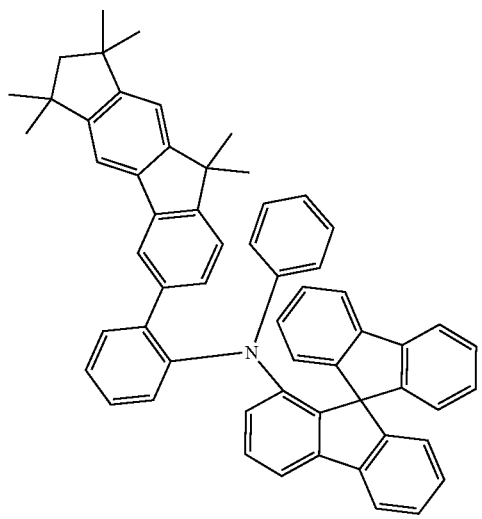
206
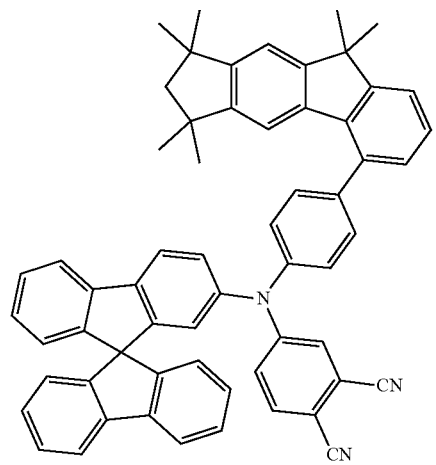
207
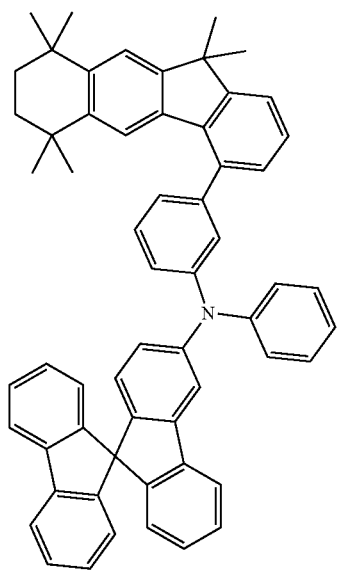
208
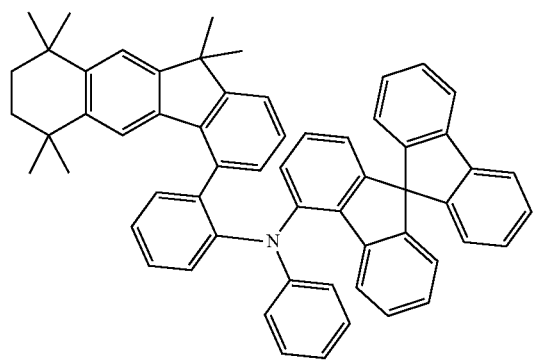

-continued
209
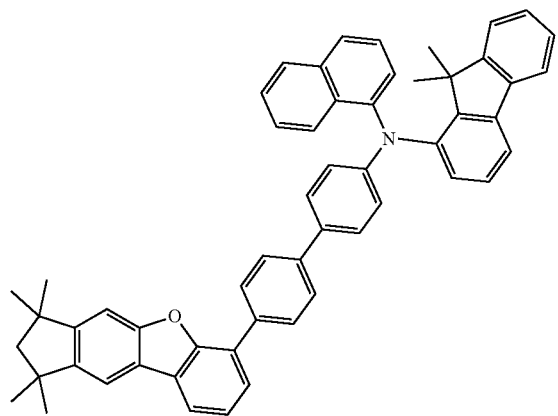
210
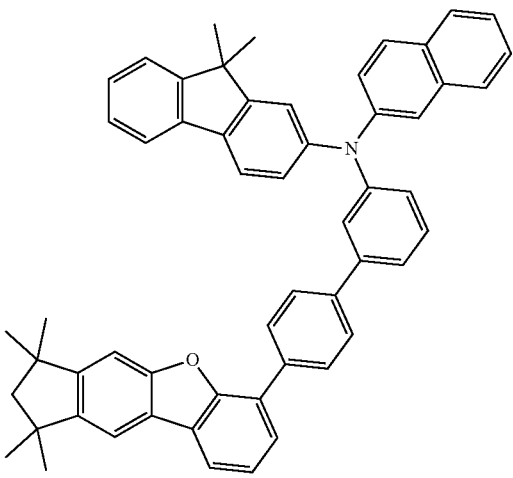
211
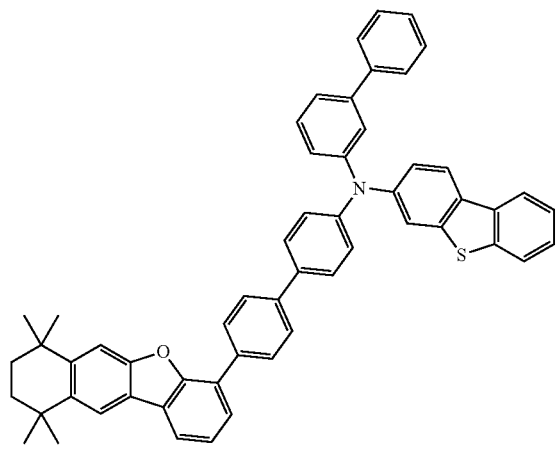
212
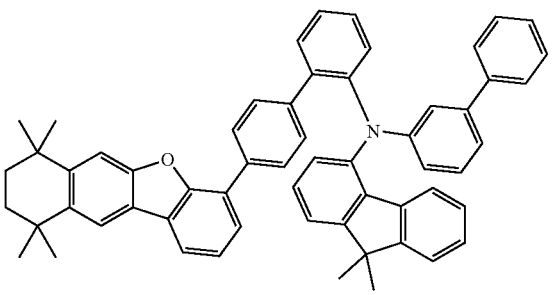
213
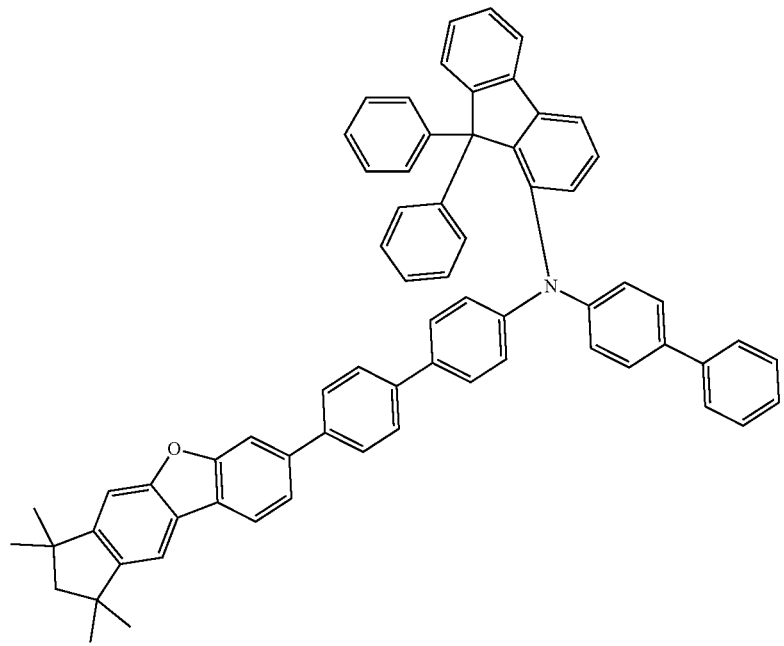

-continued
214
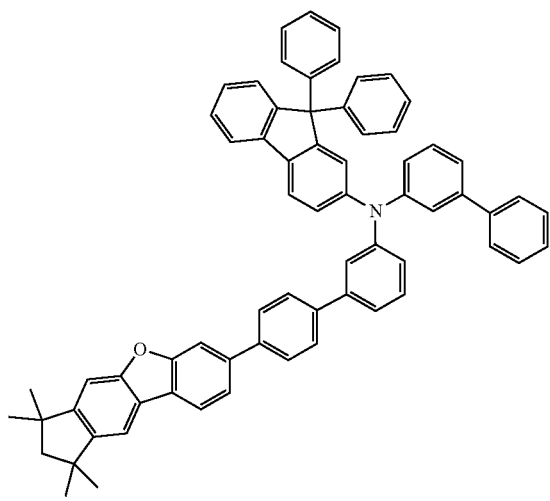
215
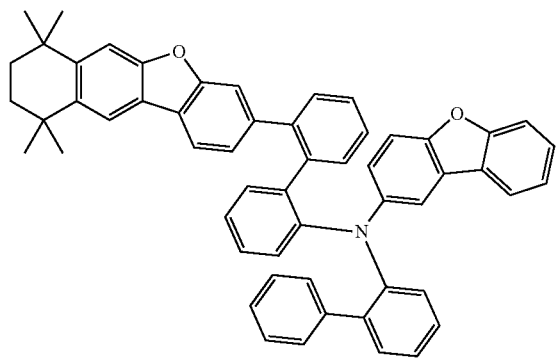
216
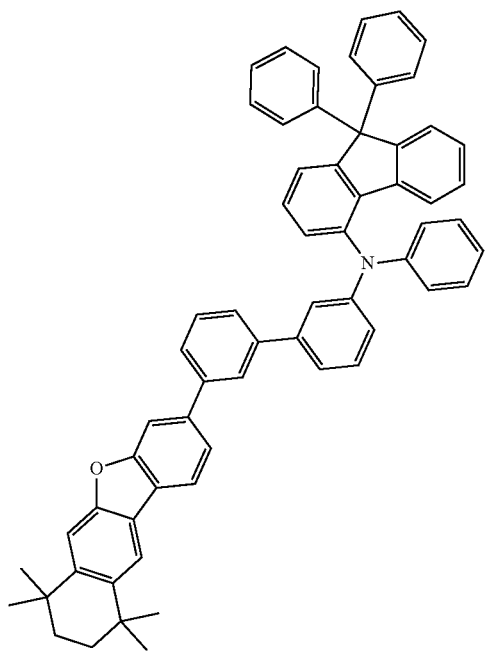
217
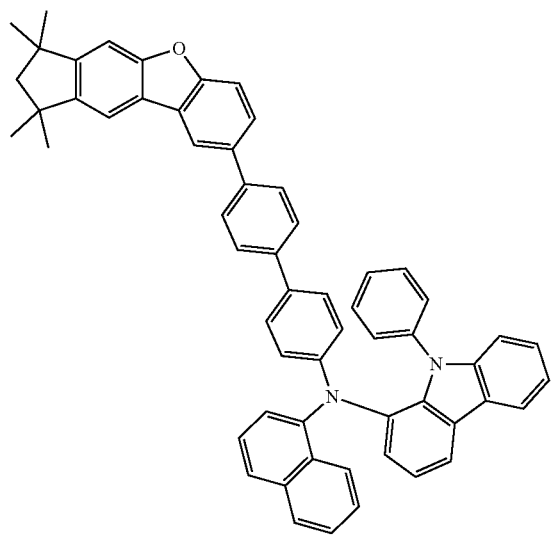

218
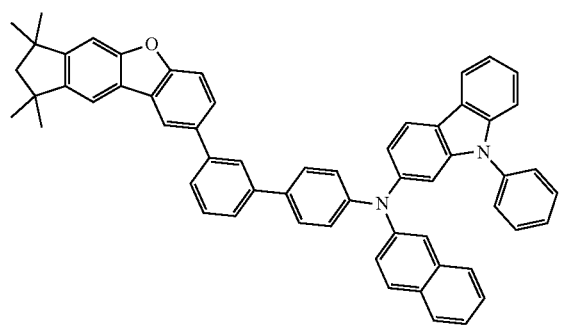
219
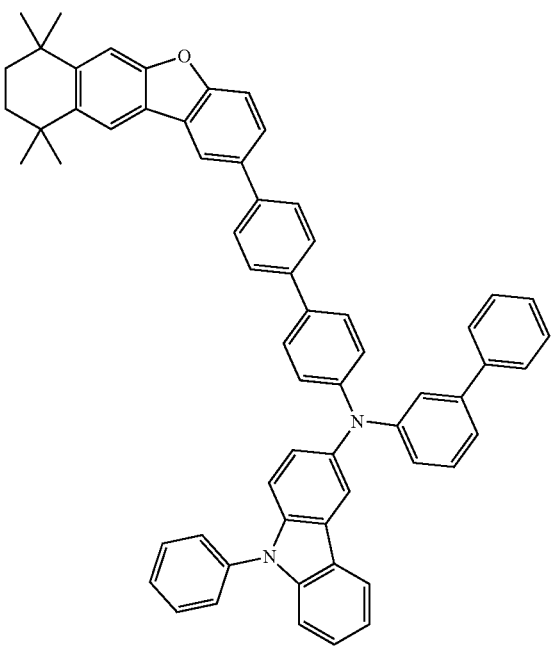
220
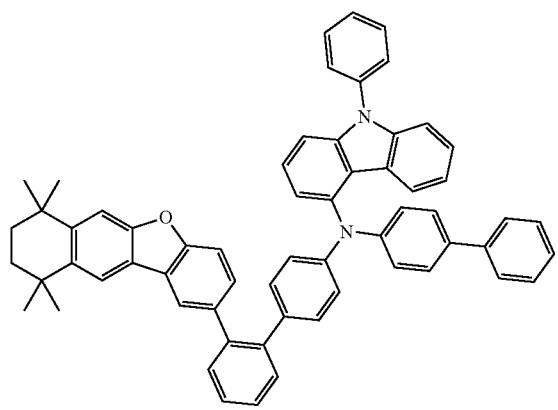
221
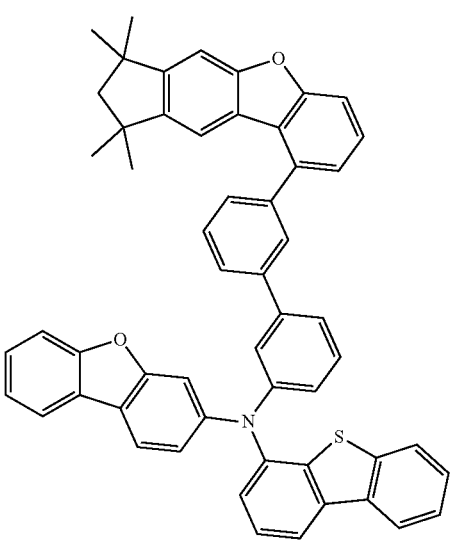

-continued
222
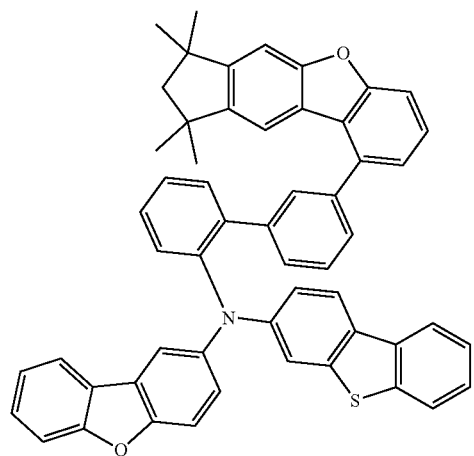
223
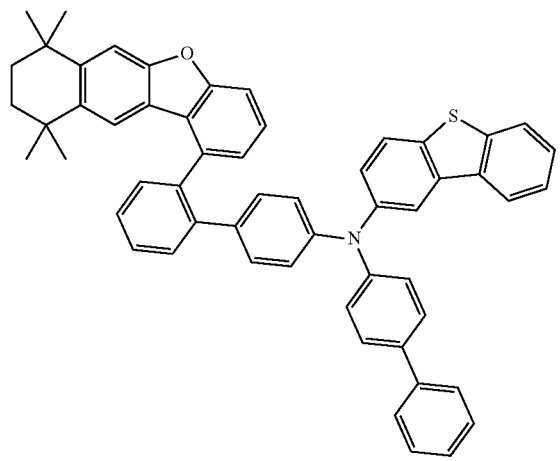
224
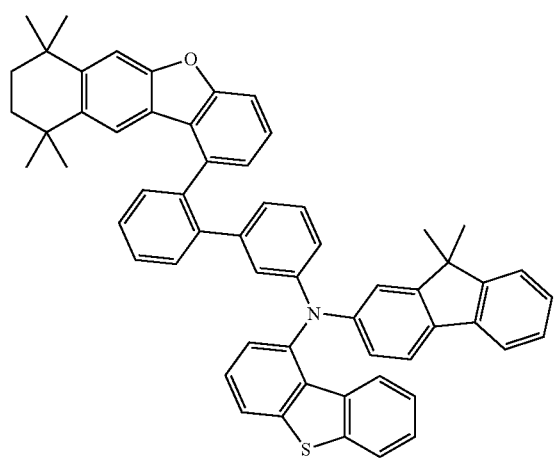
225
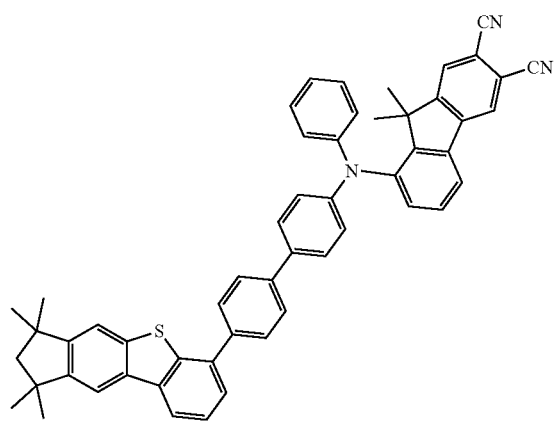
226
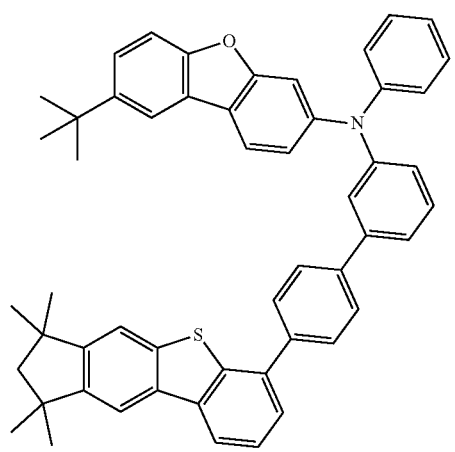
227
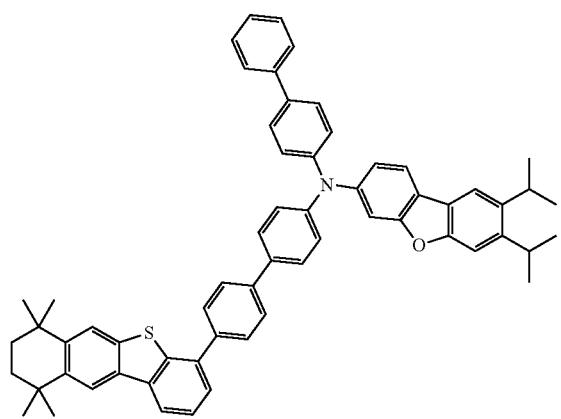

228
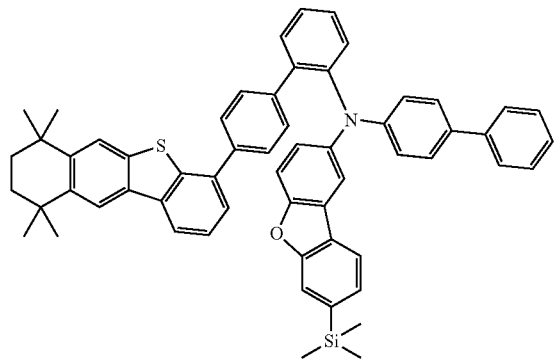
229
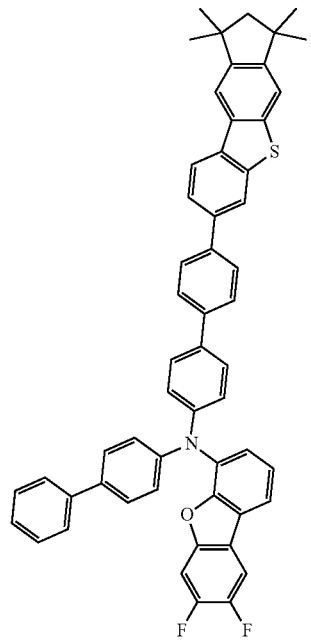
230
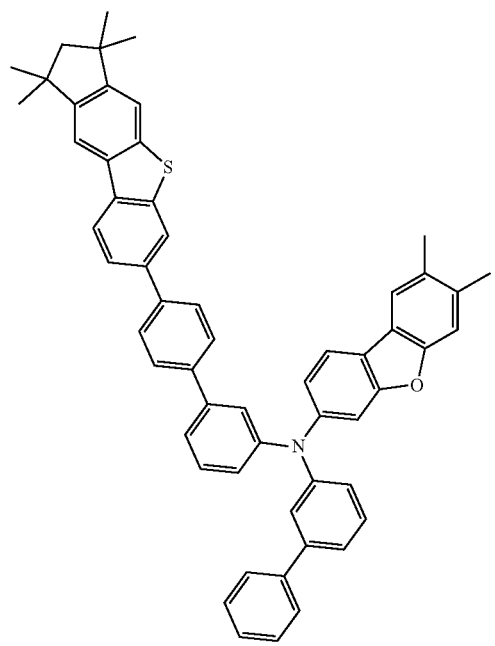
231
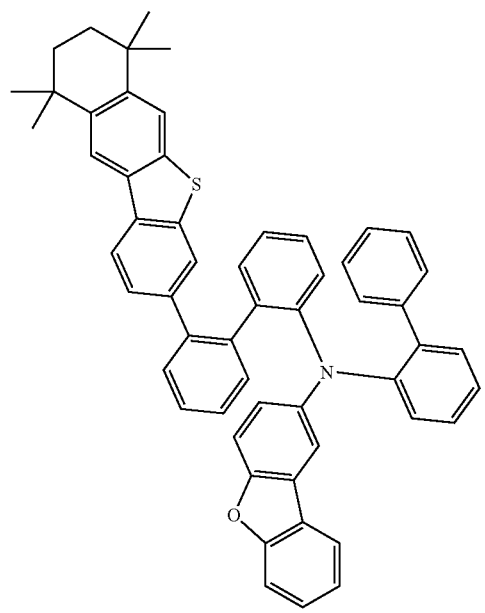

-continued
121
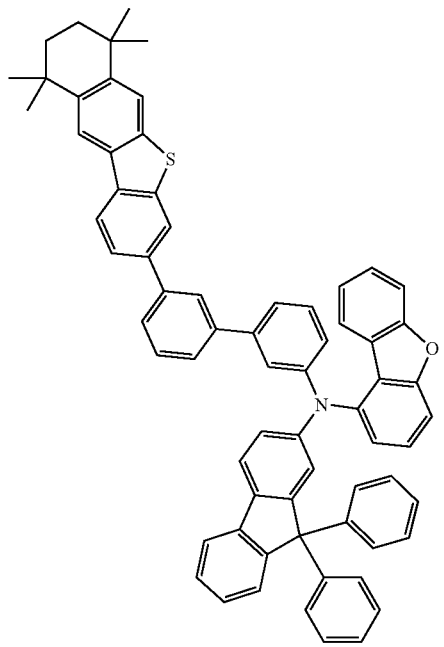
122
232
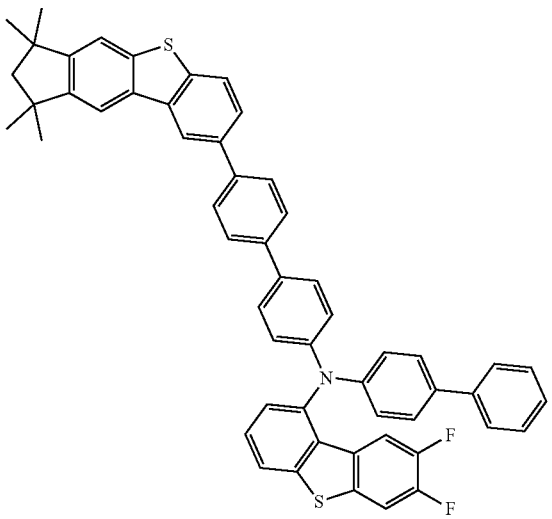
233
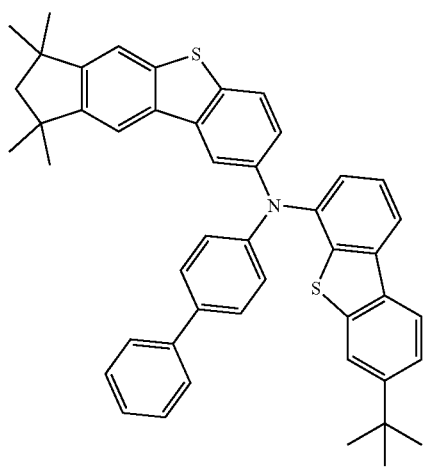
234
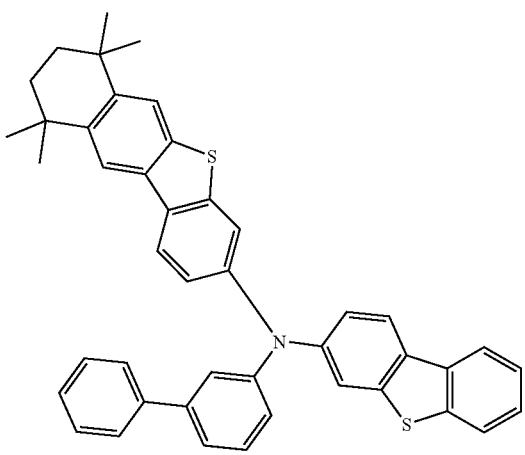
235
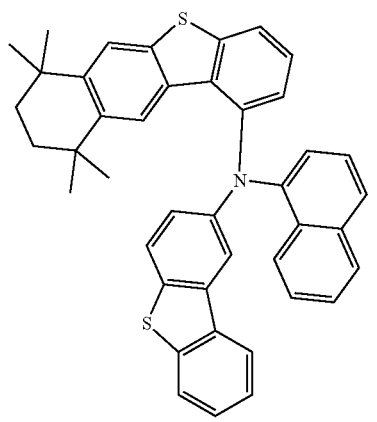
236
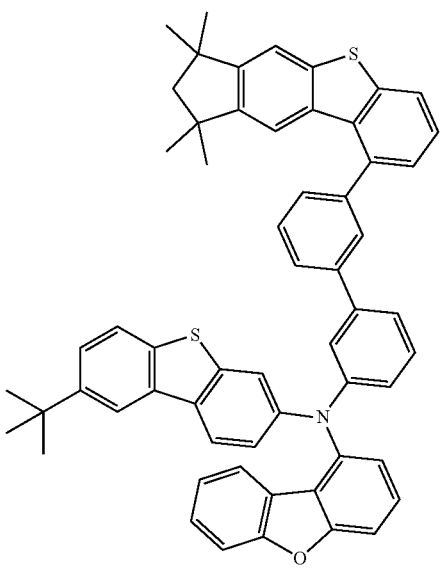
237

-continued
123
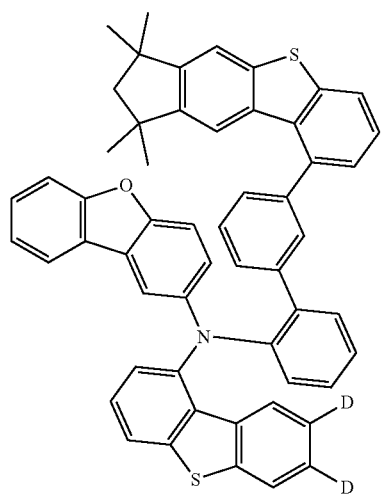
238
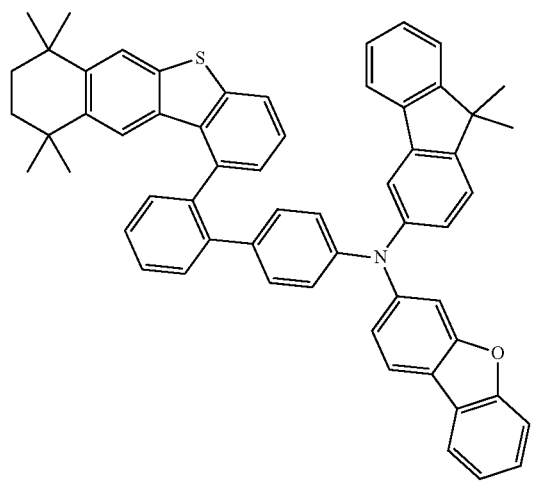
239
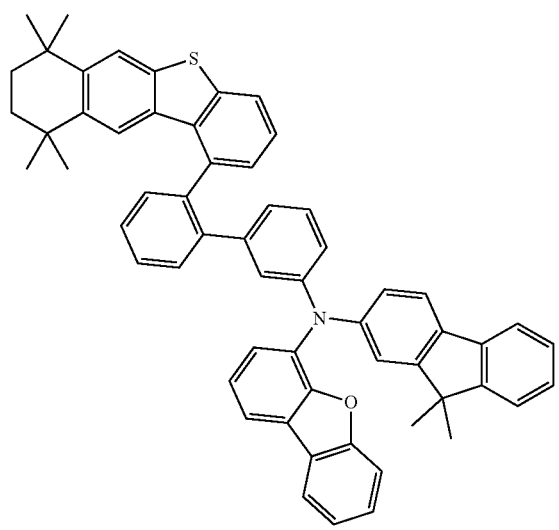
240
124
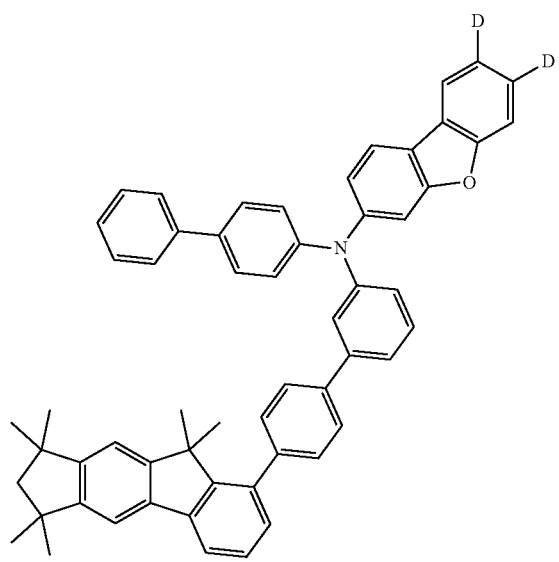
242
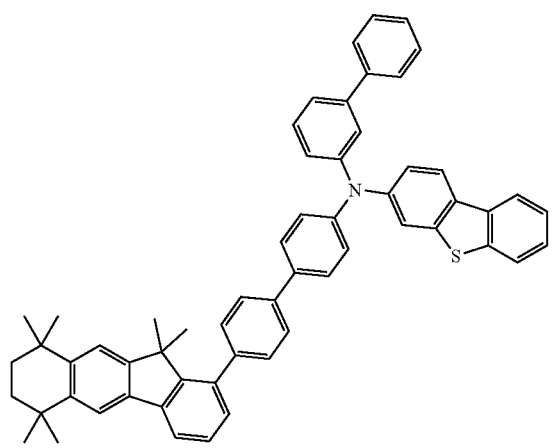
241
243

244
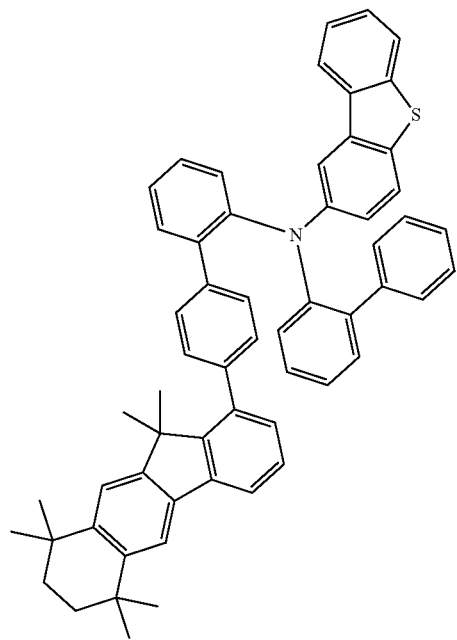
245
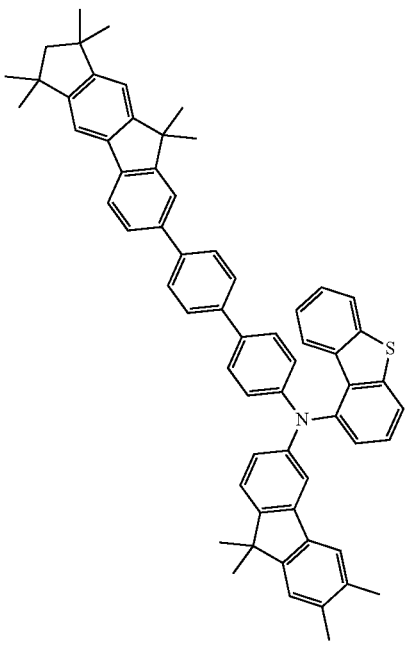
246
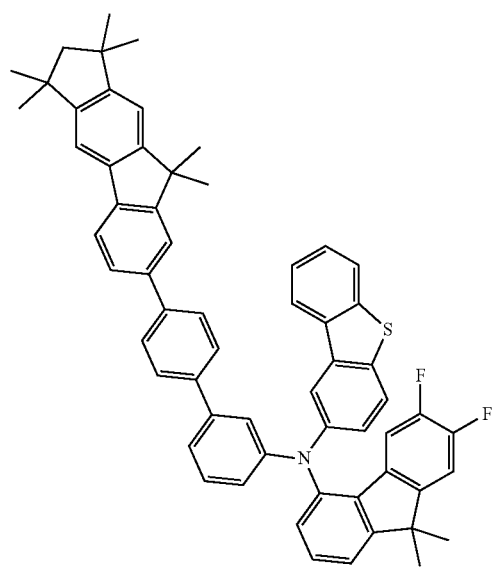
247
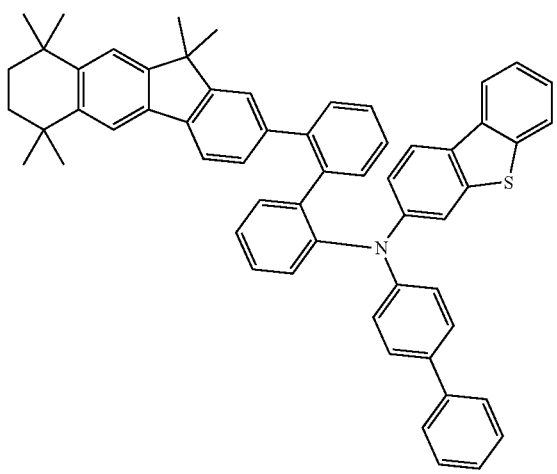

248
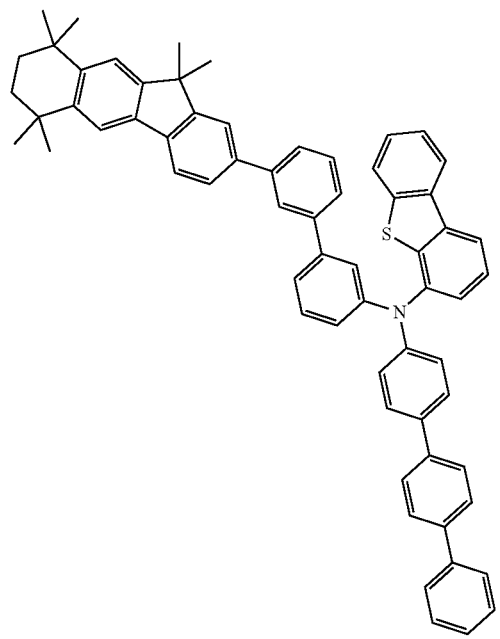
249
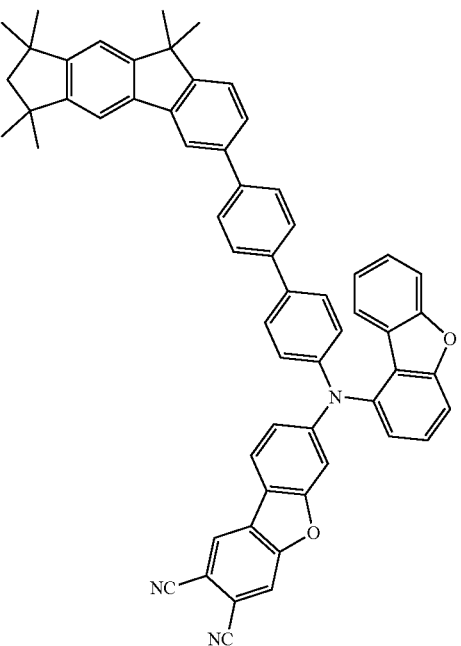
250
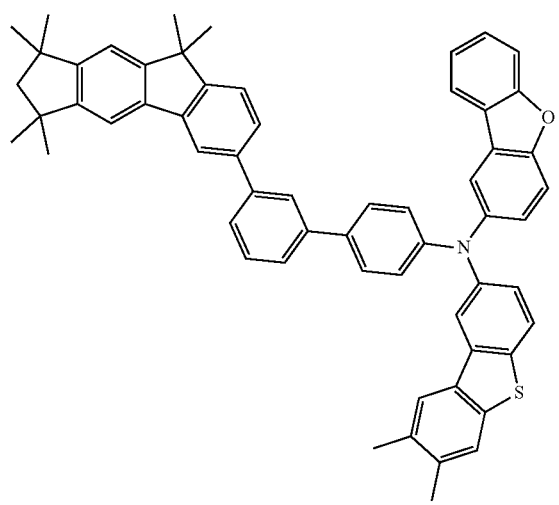
251
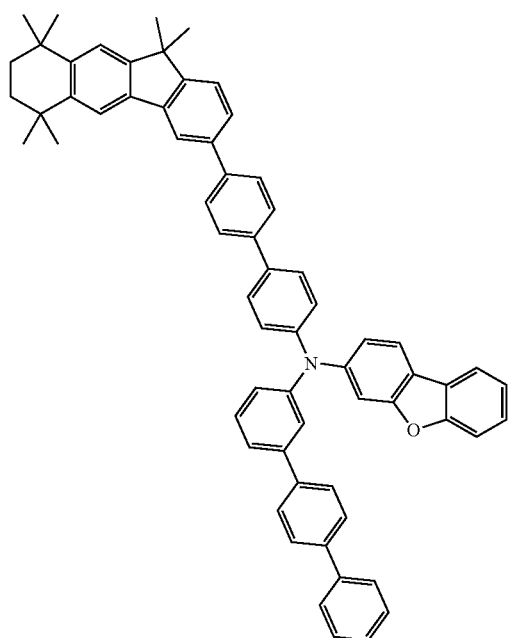

252
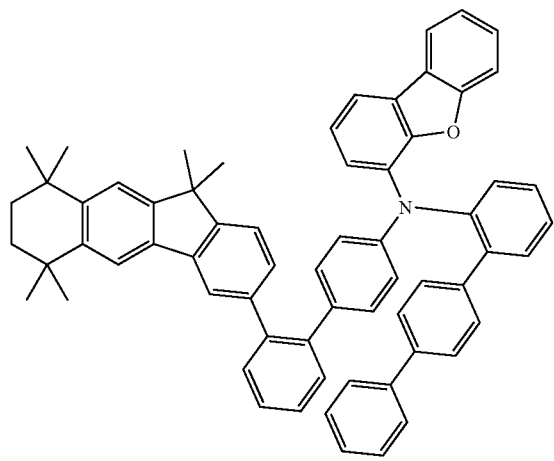
253
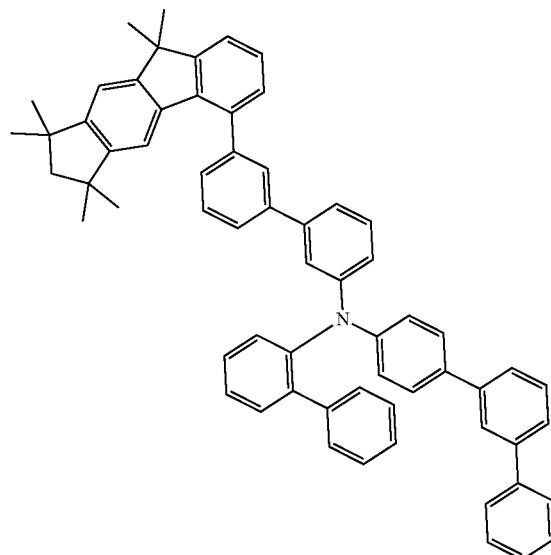
254
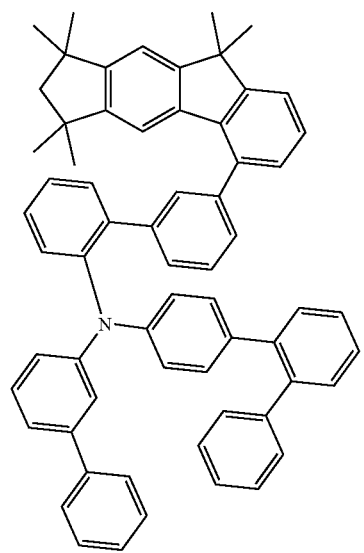
255
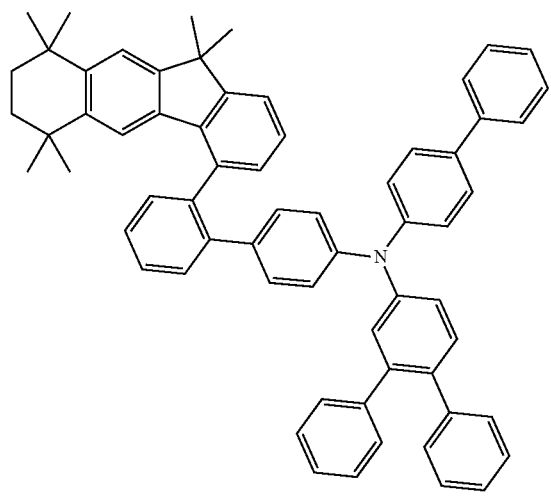

256
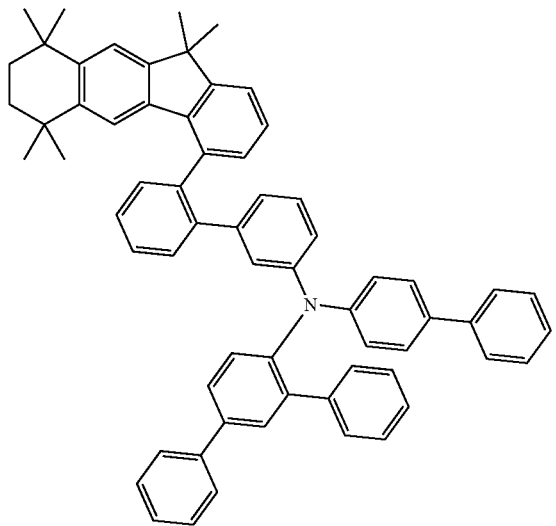
257
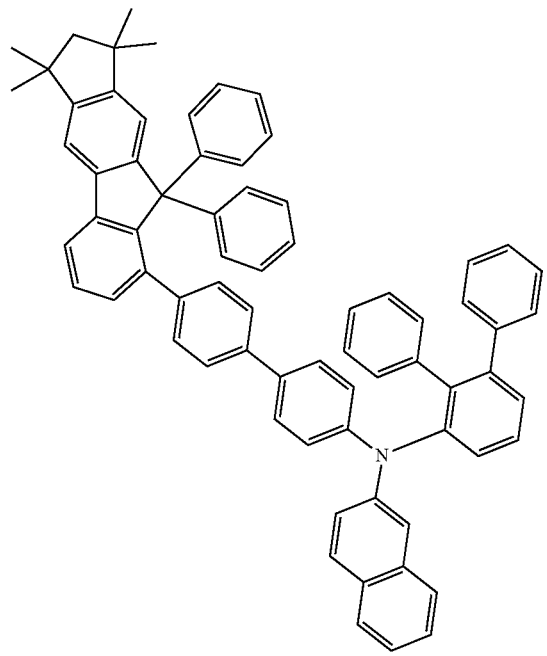
258
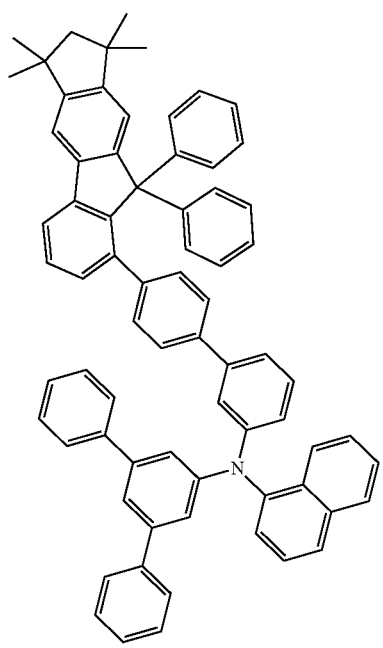
259
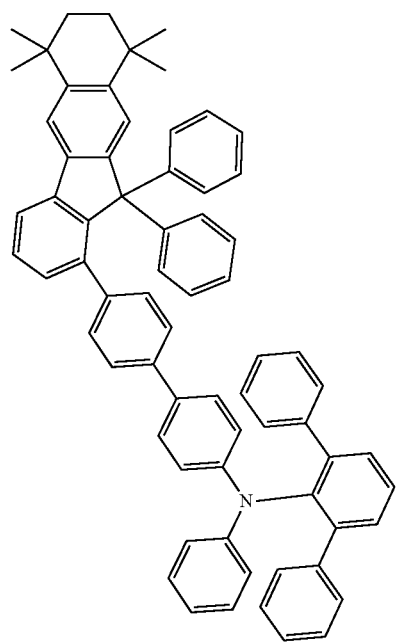

-continued
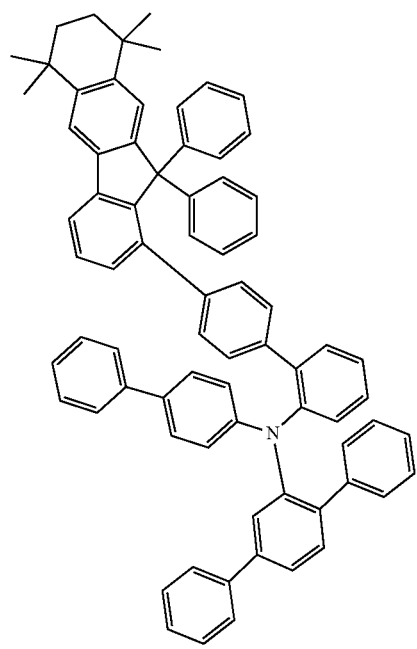
260
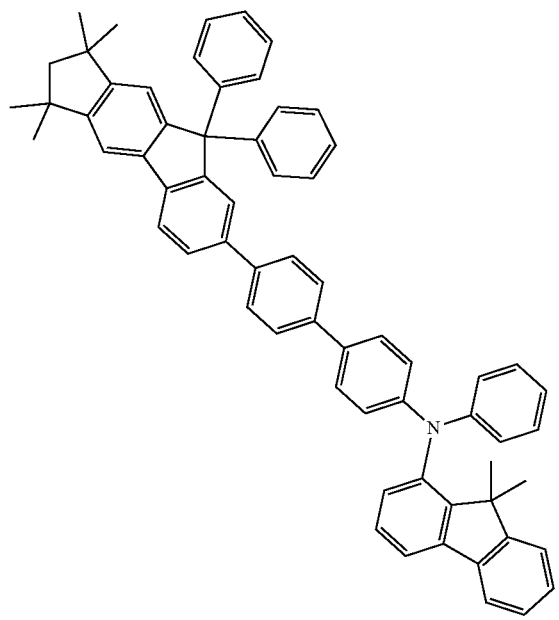
261
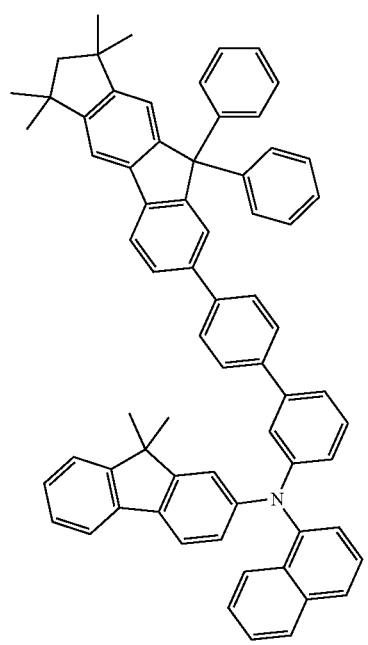
262
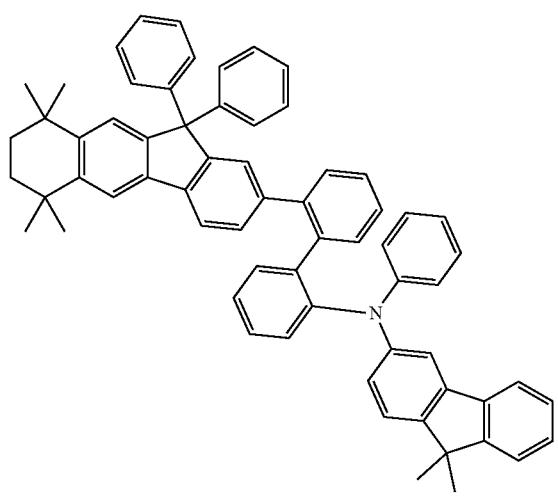
263

264
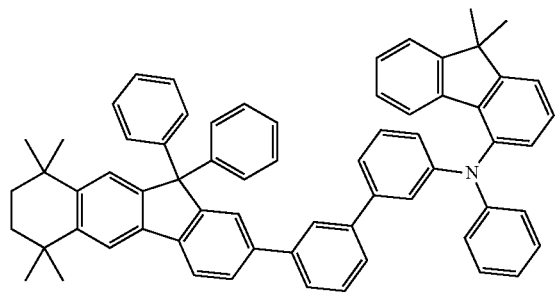
265
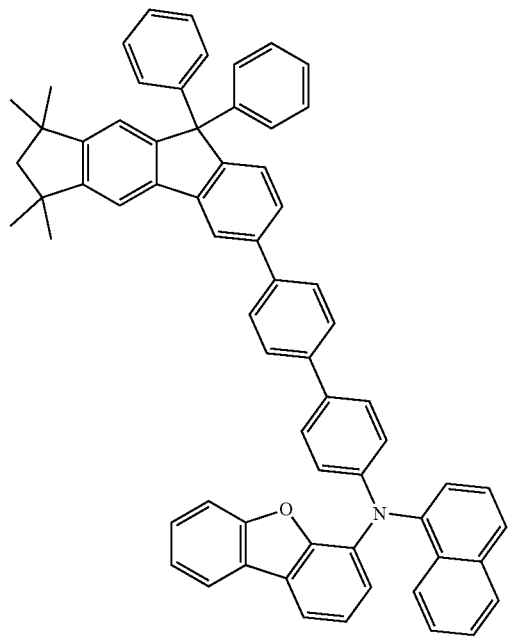
266
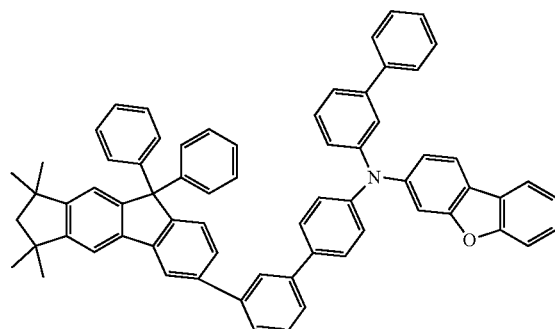
267
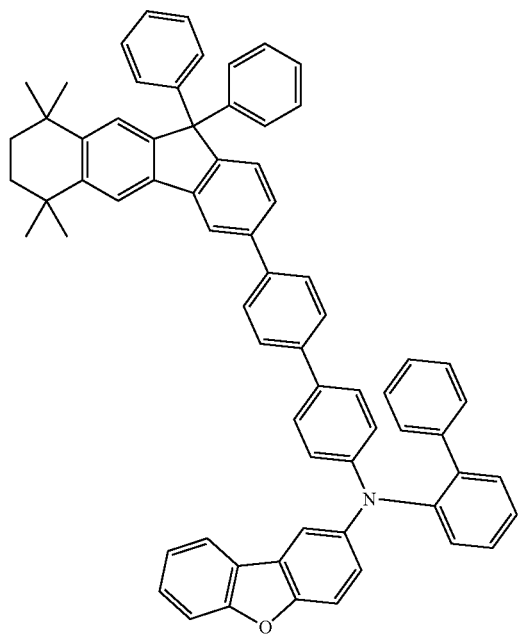

-continued
268
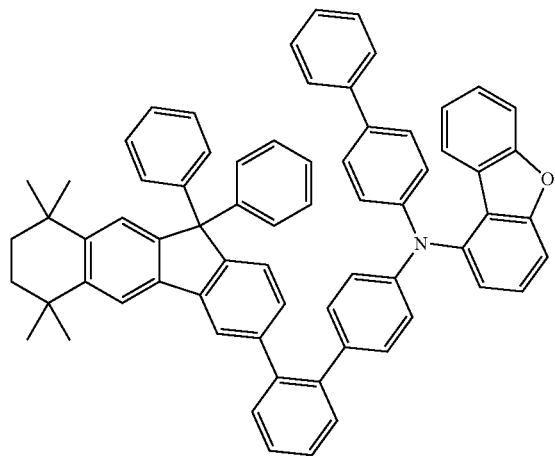
269
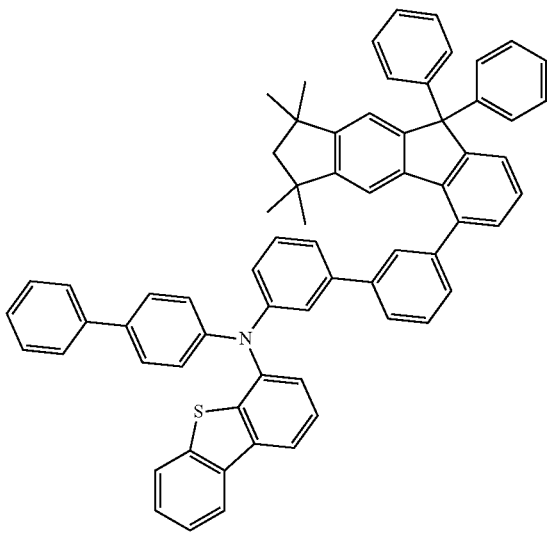
270
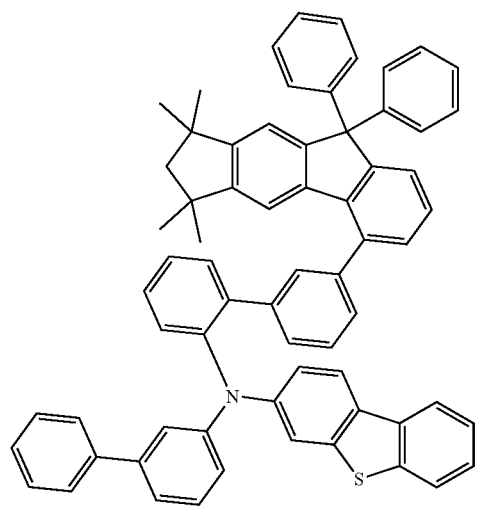
271
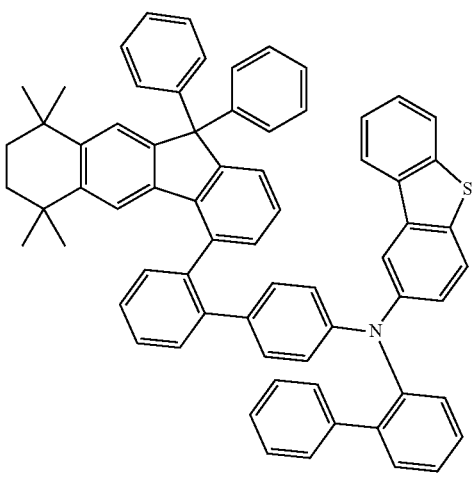
272
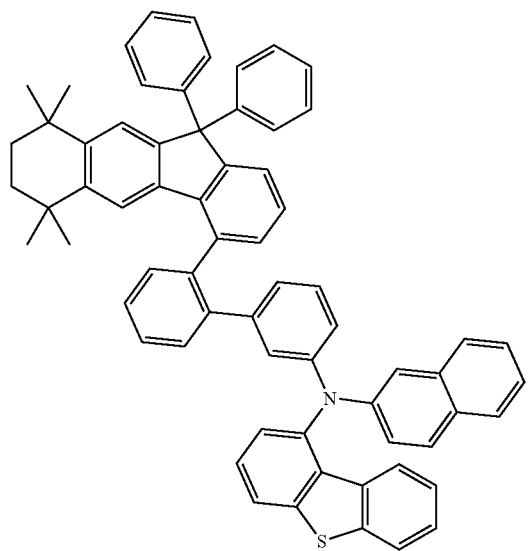
273
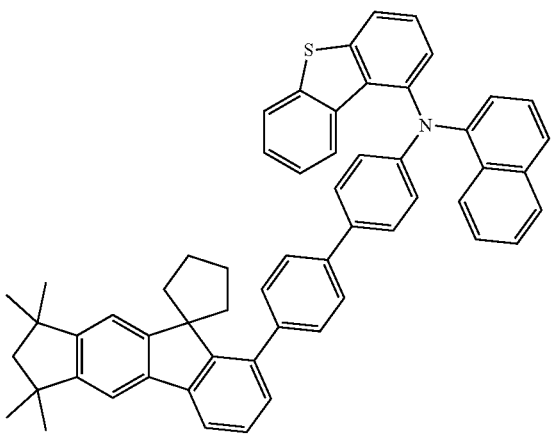

-continued
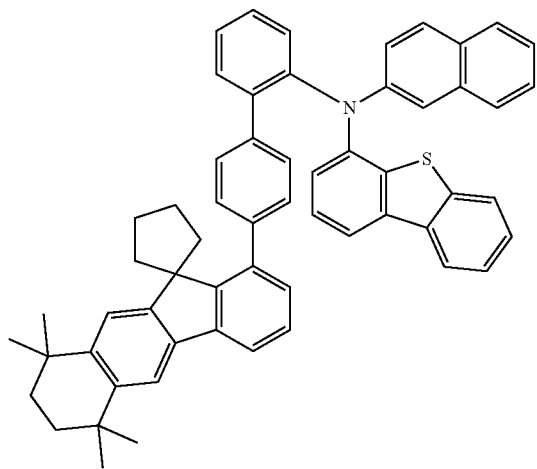
274
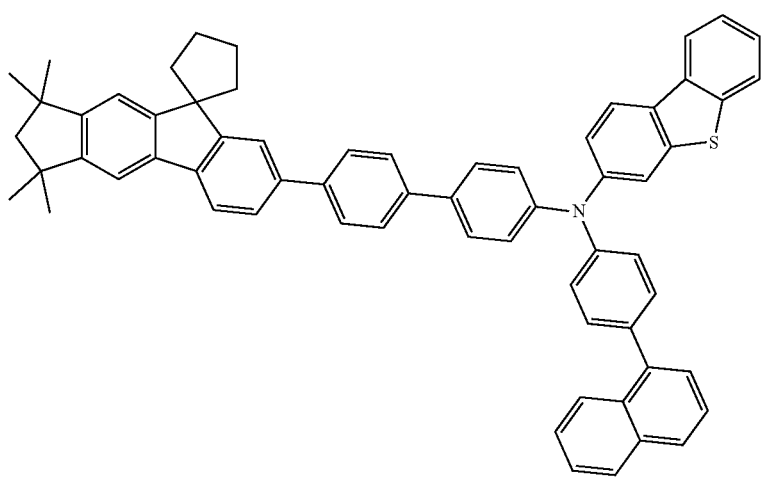
275
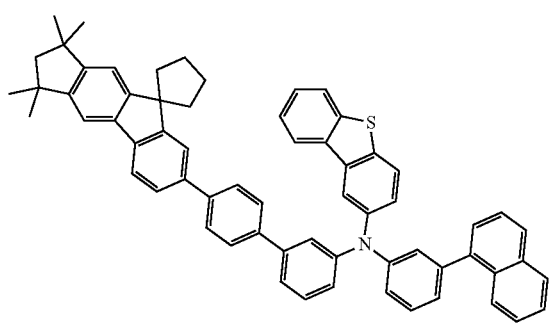
276
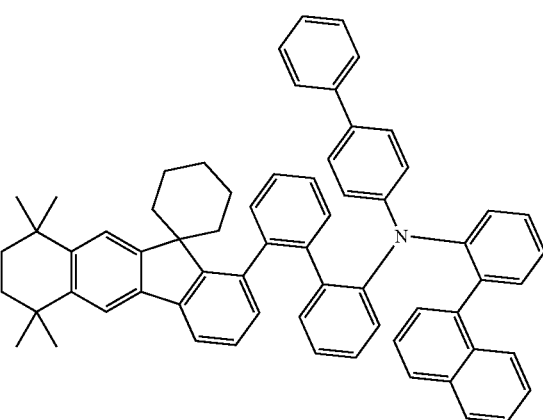
277

278
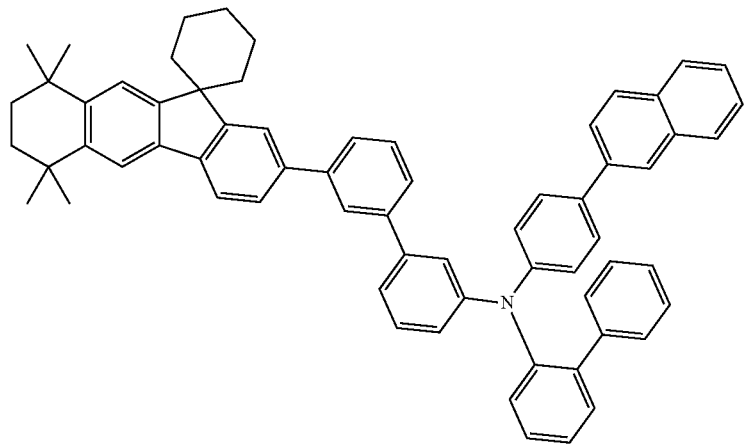
279
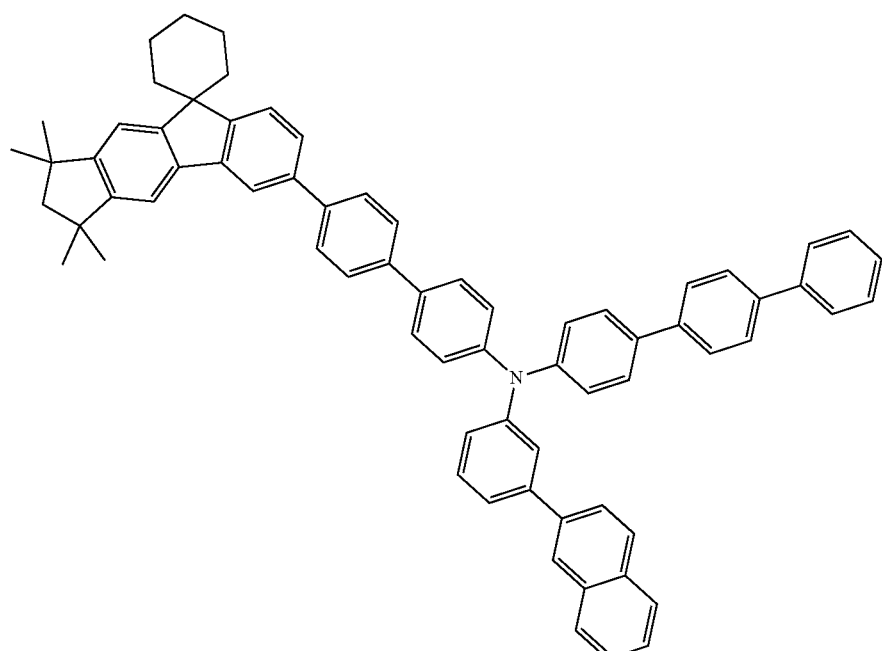
280
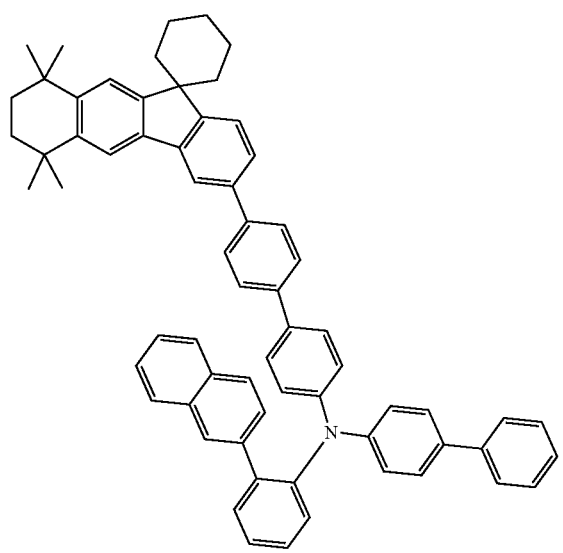
281
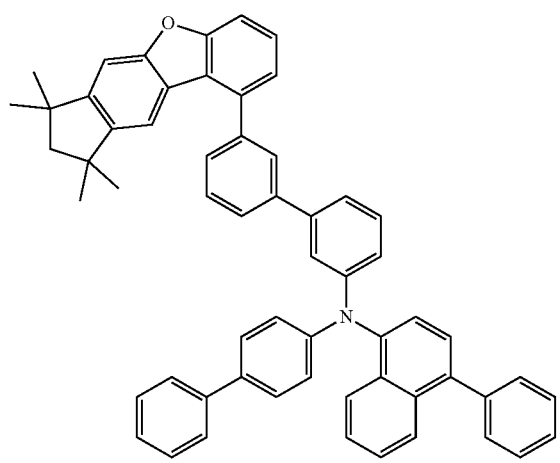

-continued
282
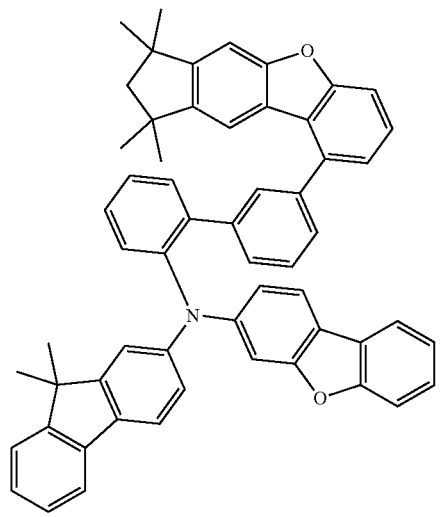
283
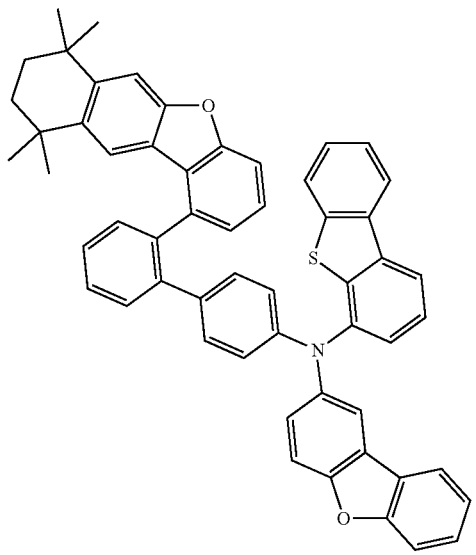
284
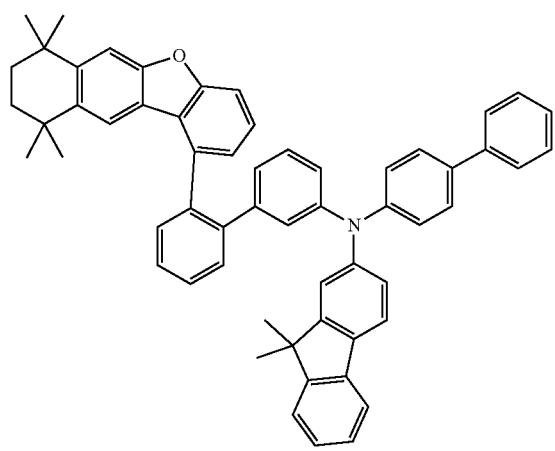
285
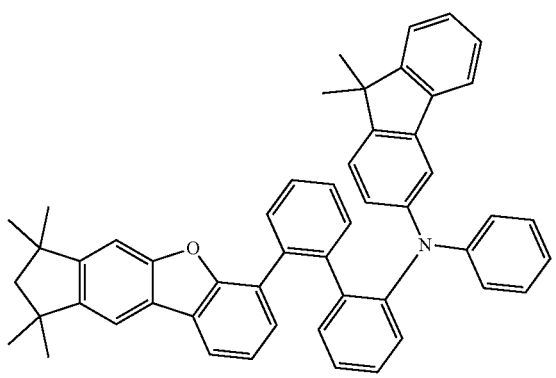
286
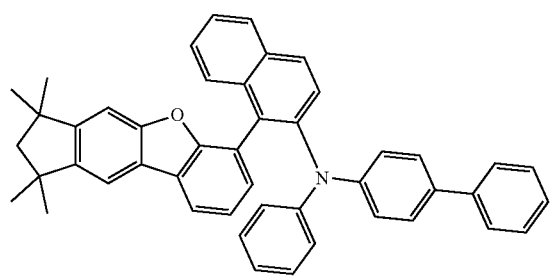
287
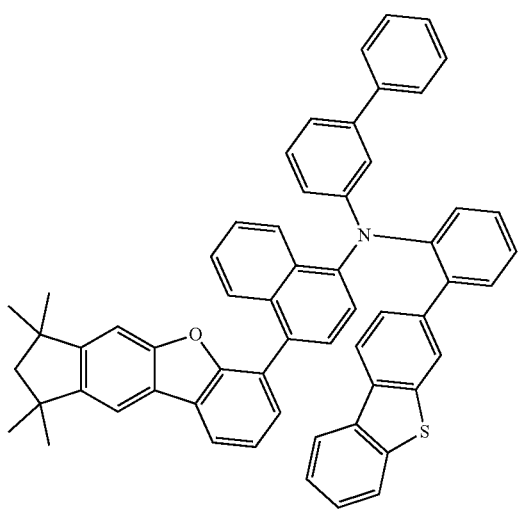

288
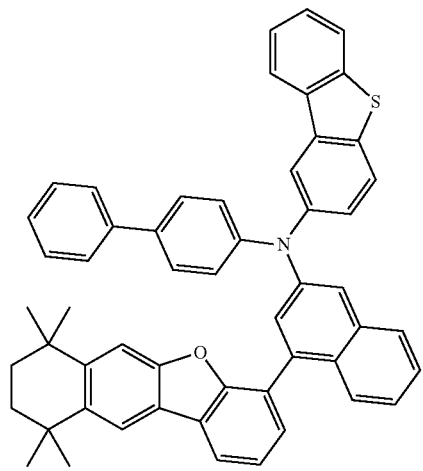
289
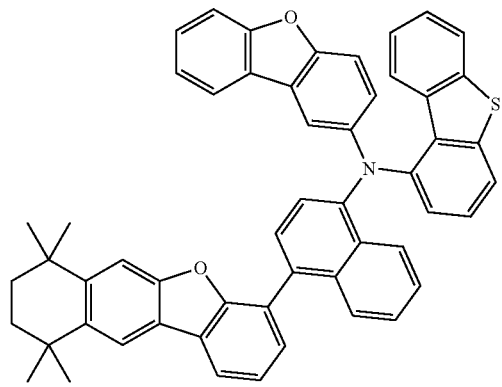
290
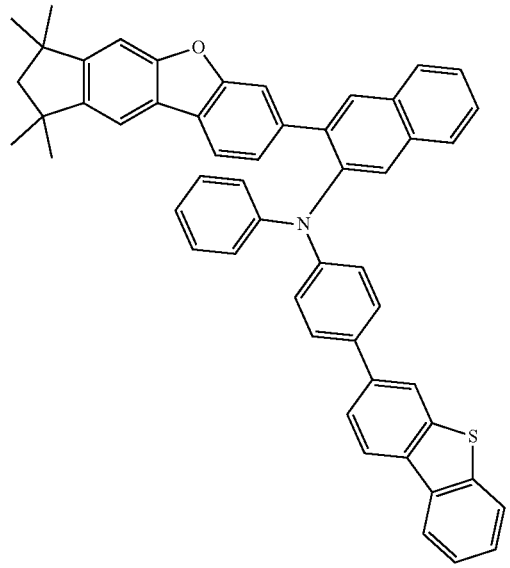
291
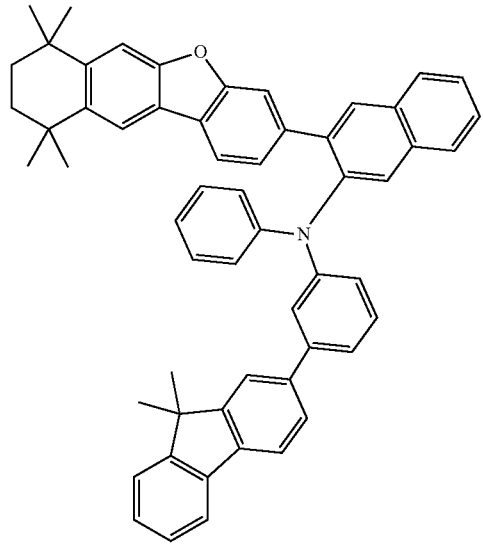
292
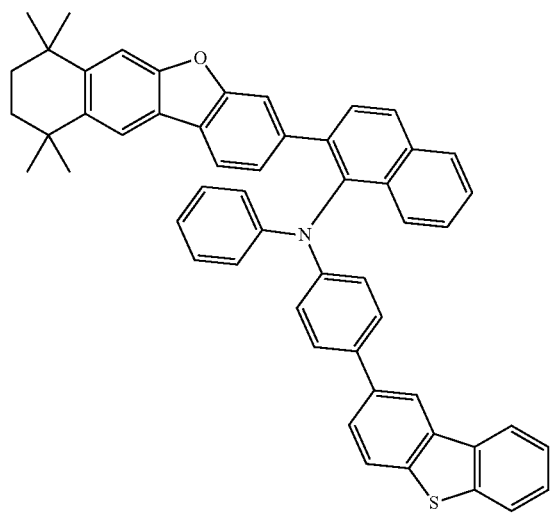
293
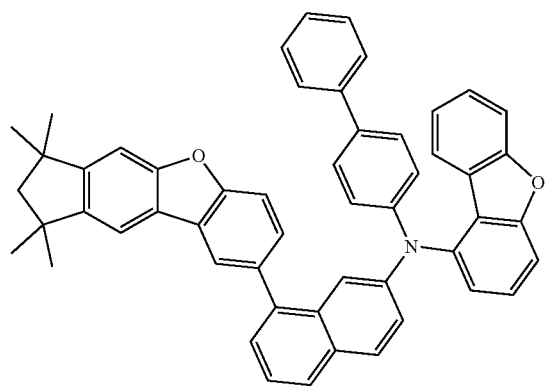

-continued
294 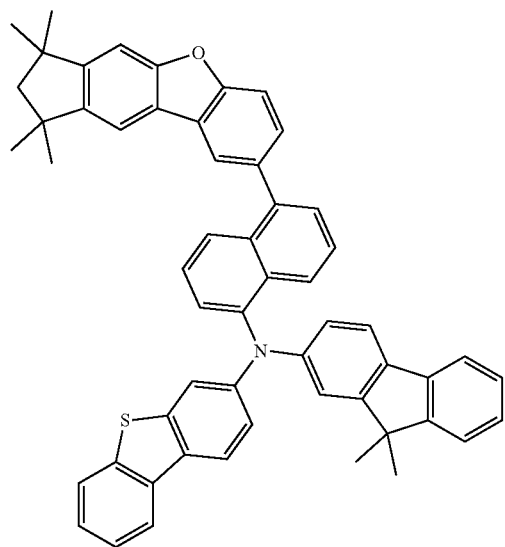
295 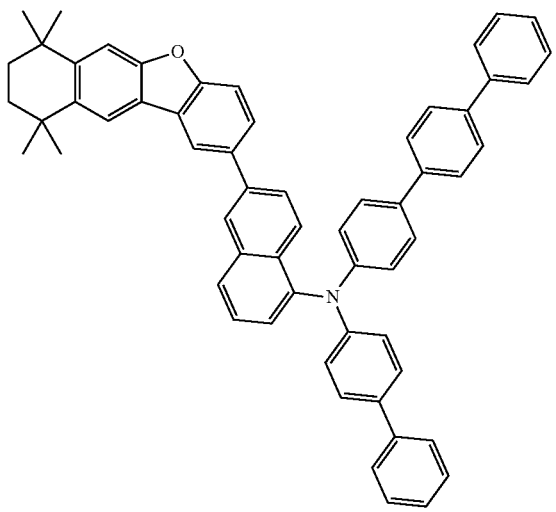
296 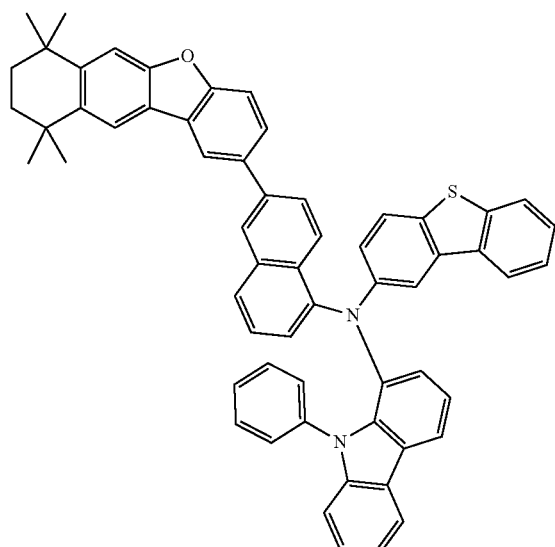
297 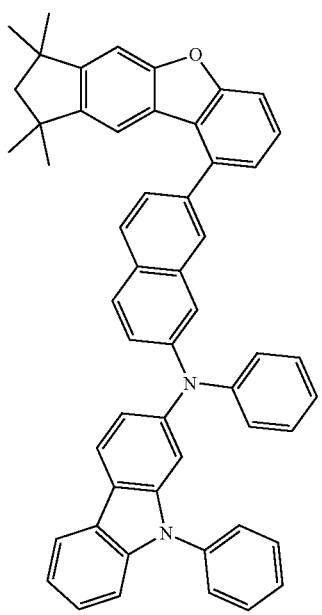

149
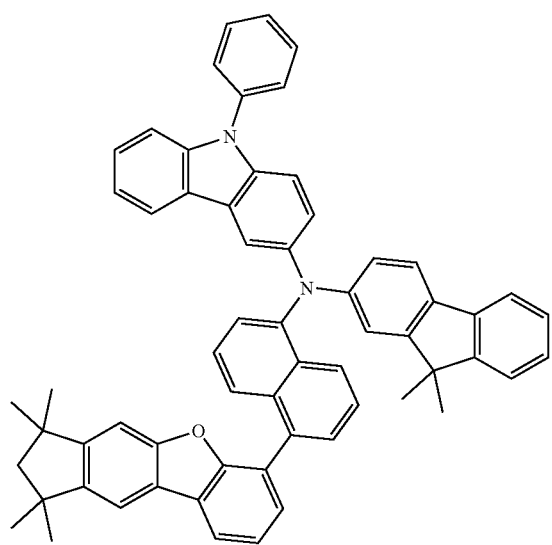
298
150
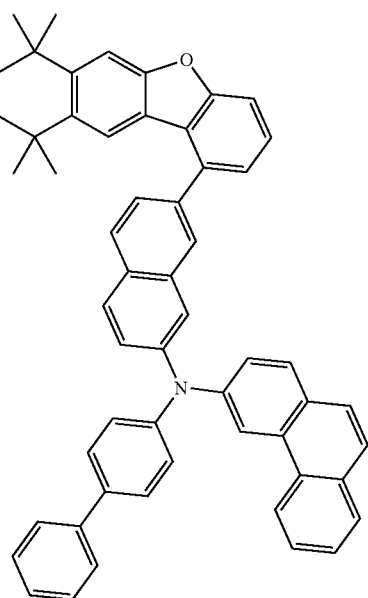
299
-continued
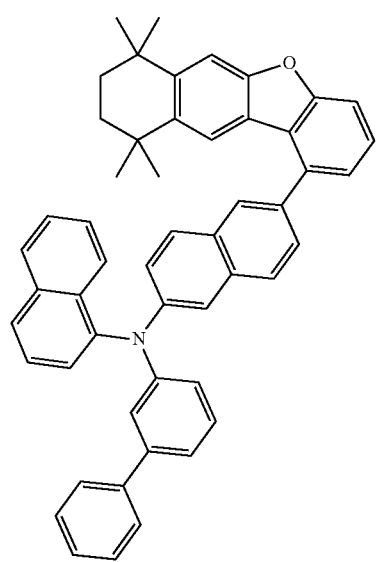
300
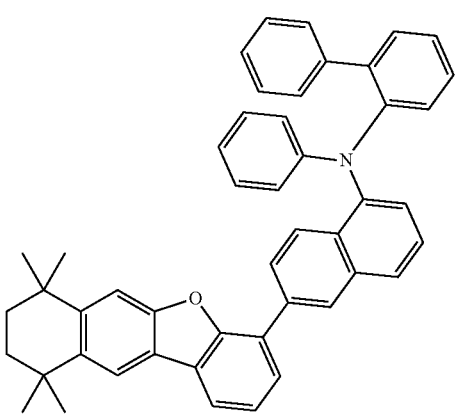
301

-continued
302
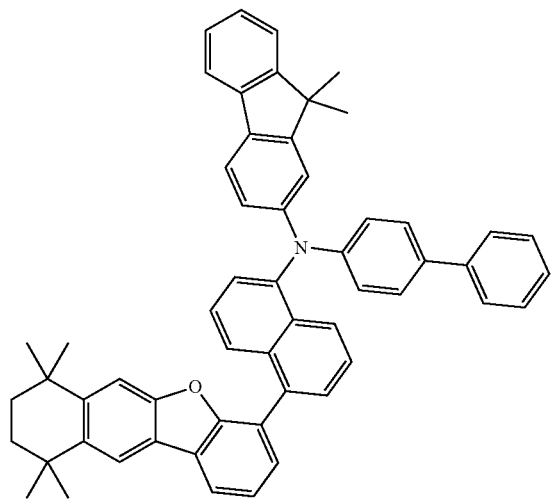
303
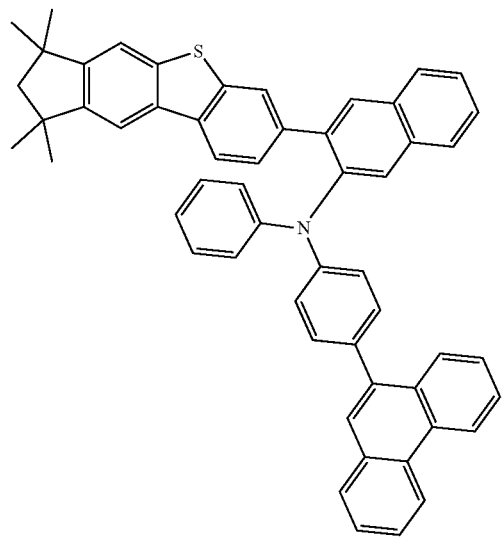
304
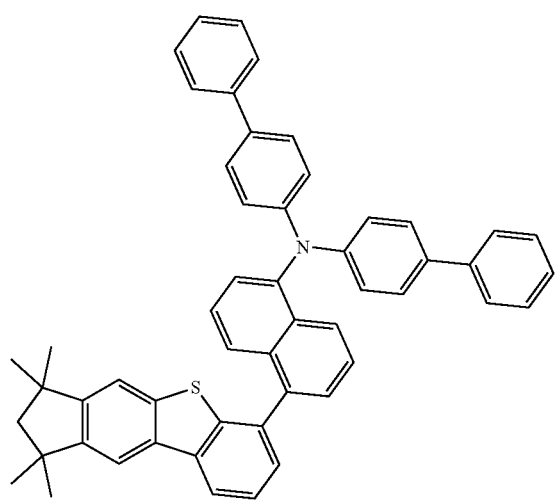
305
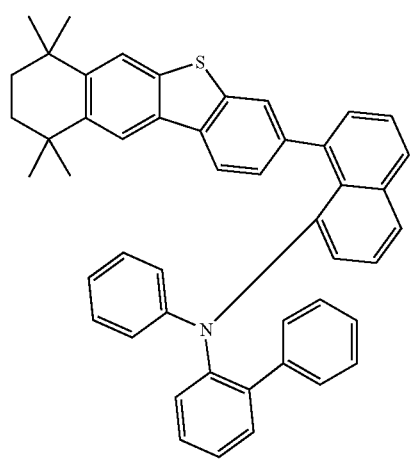
306
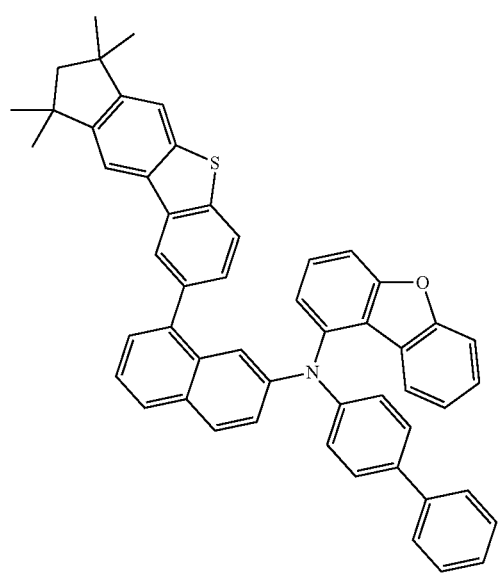
307
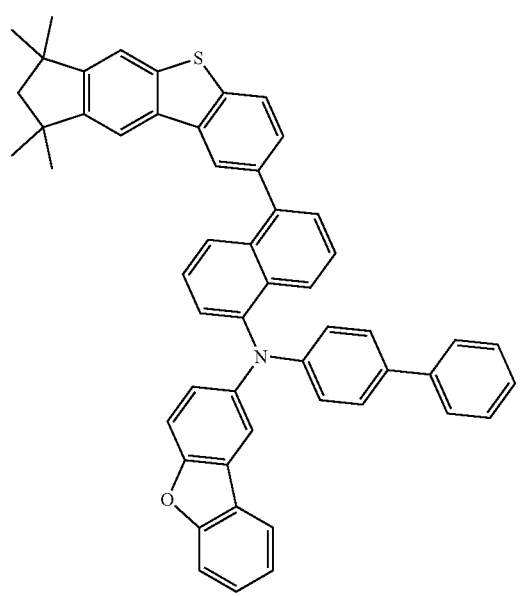

-continued
308
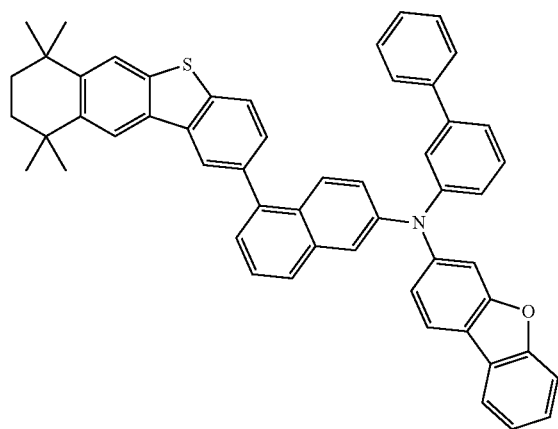
309
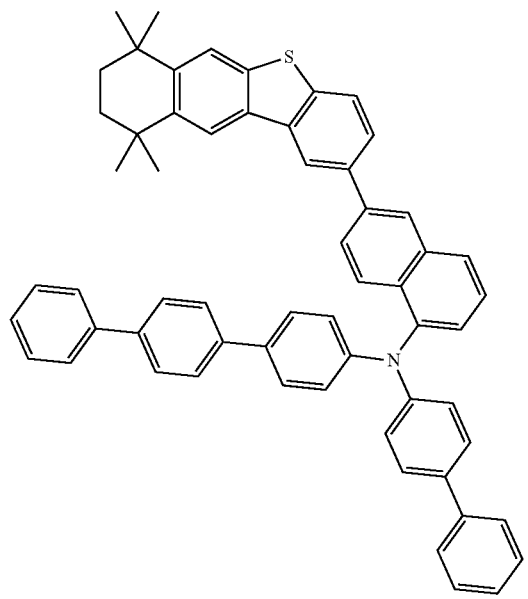
310
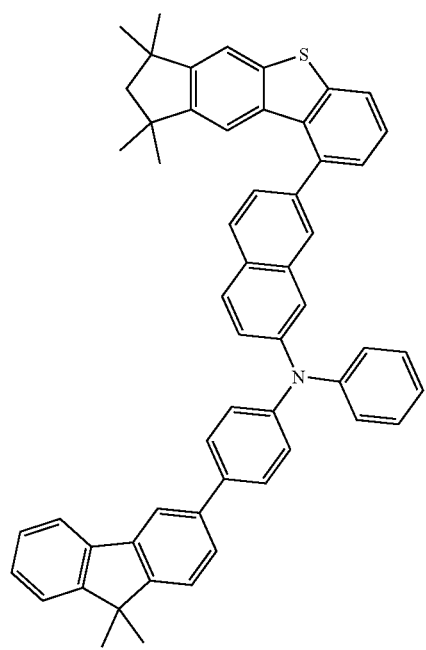
311
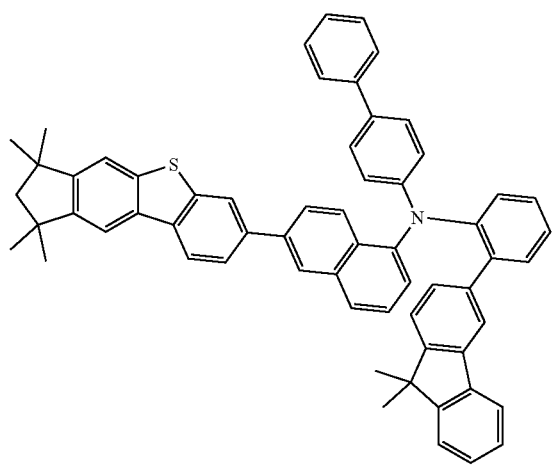

-continued
3312
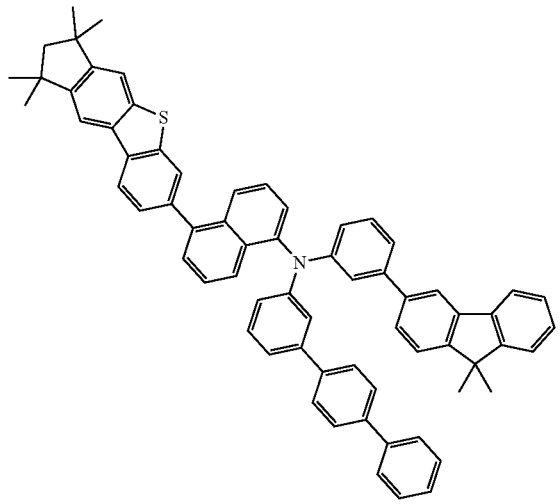
313
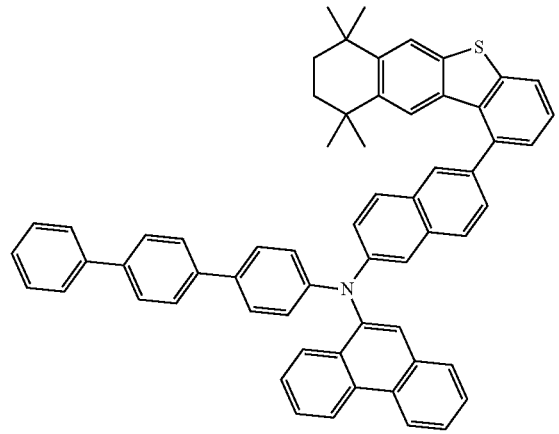
314
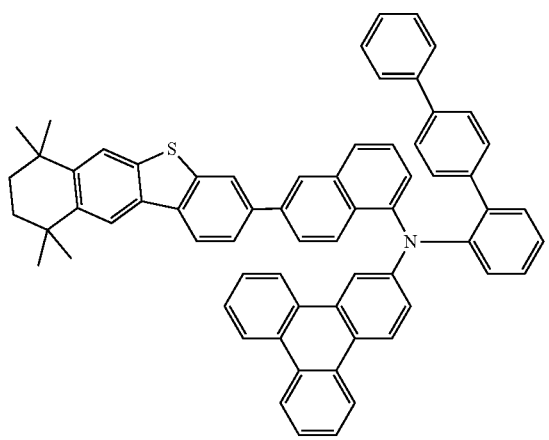
315
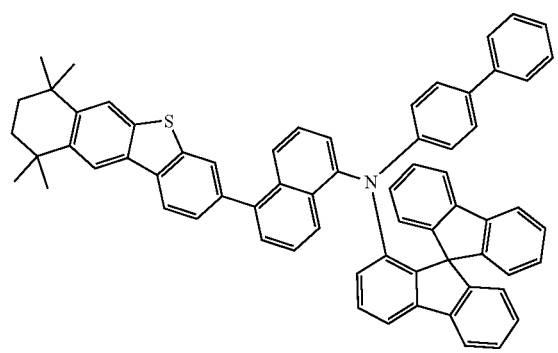
316
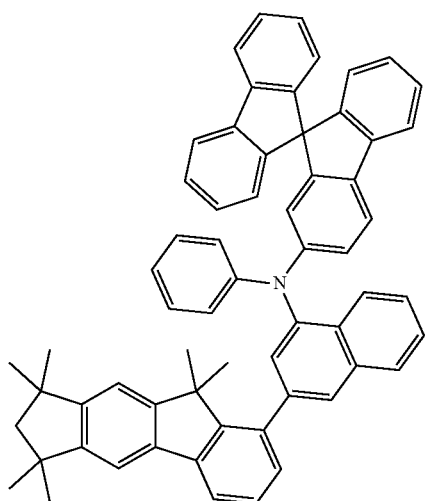
317
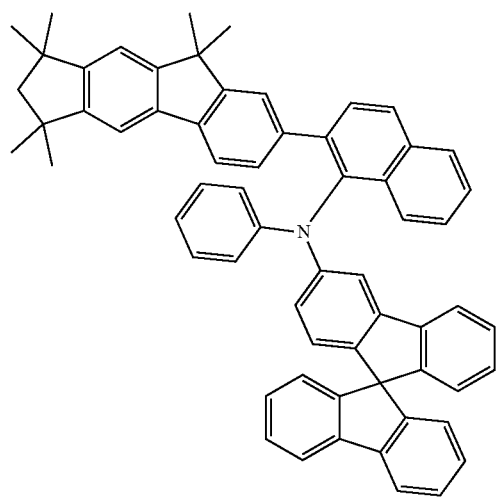

-continued
318
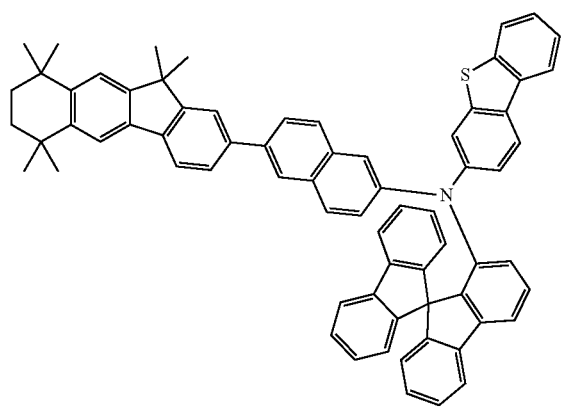
319
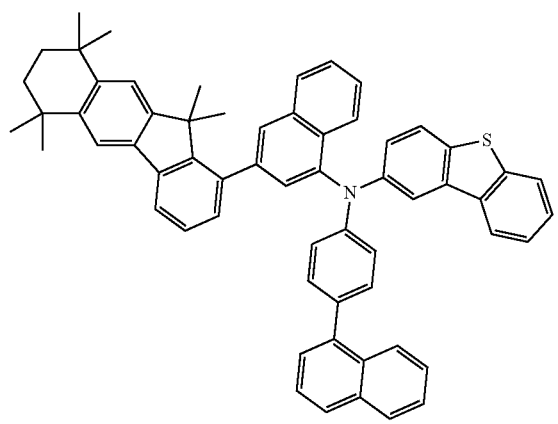
320
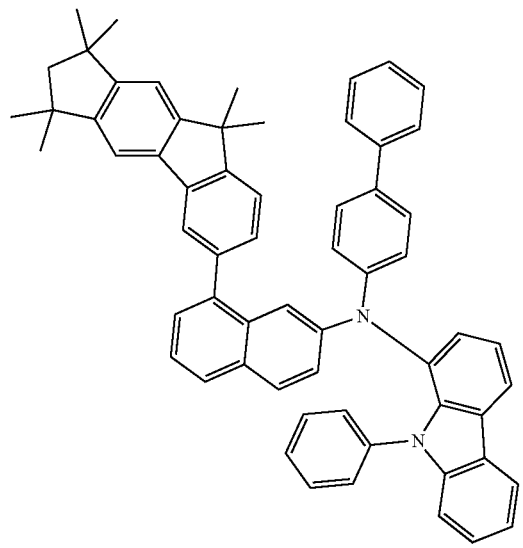
321
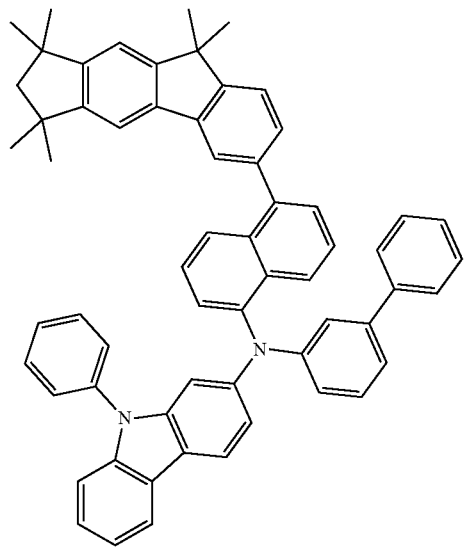
322
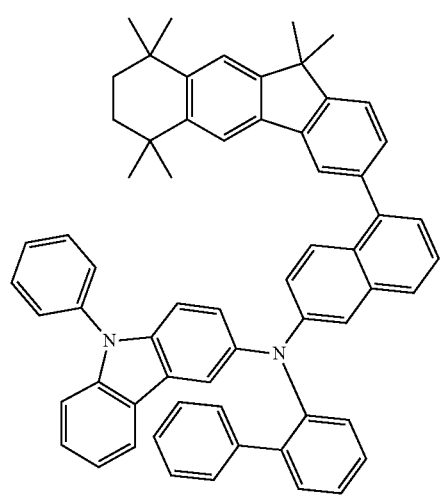
323
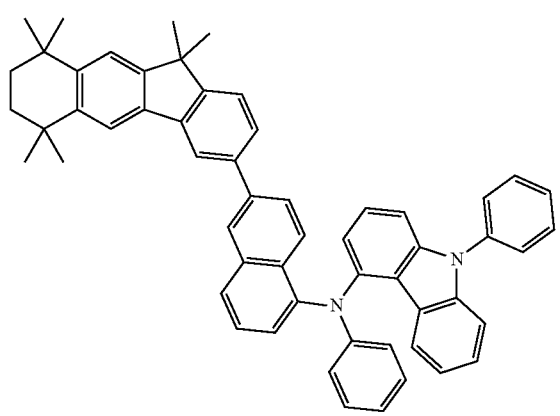

-continued
324
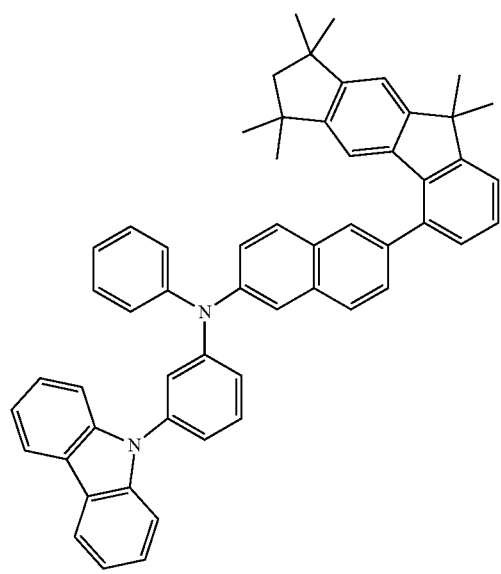
325
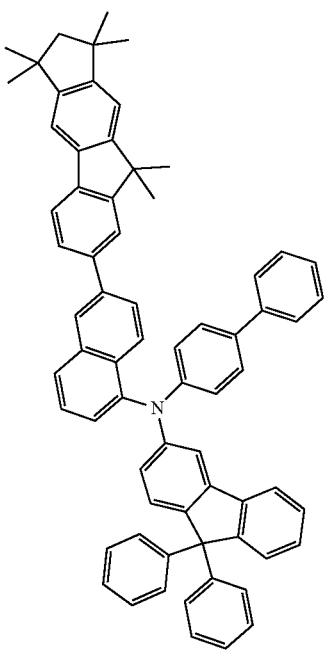
326
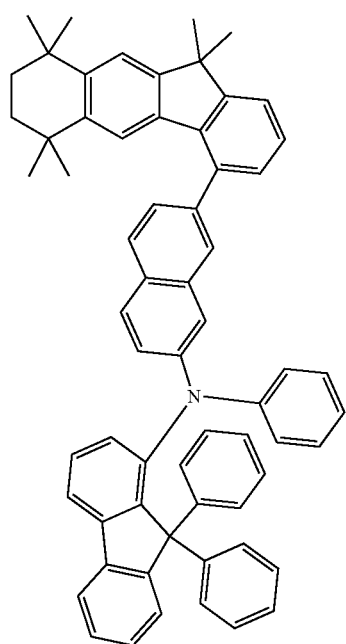
327
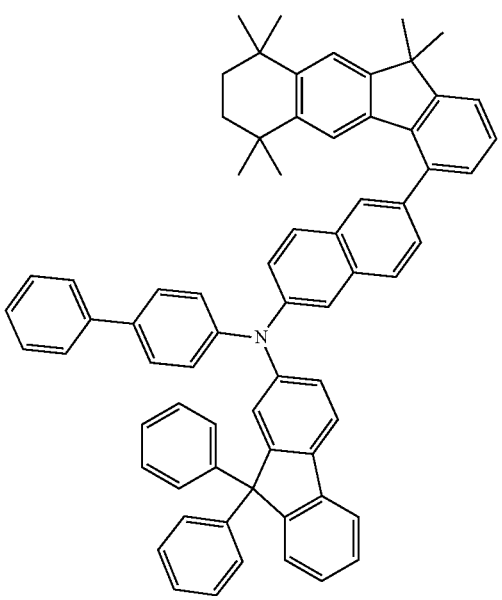

328
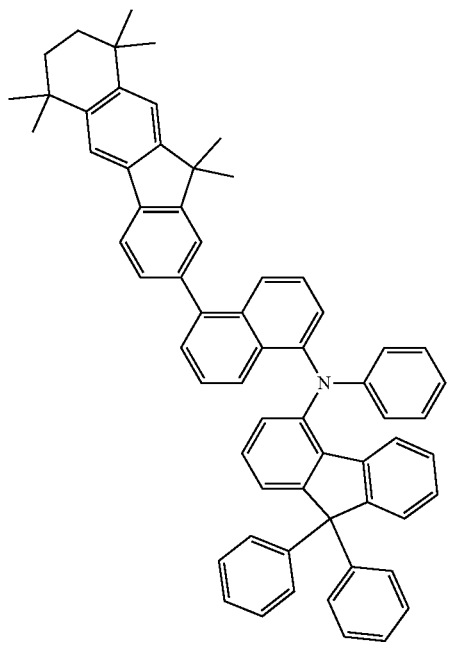
329
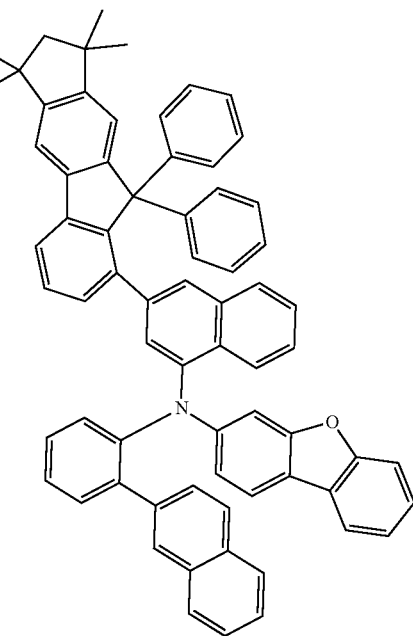
330
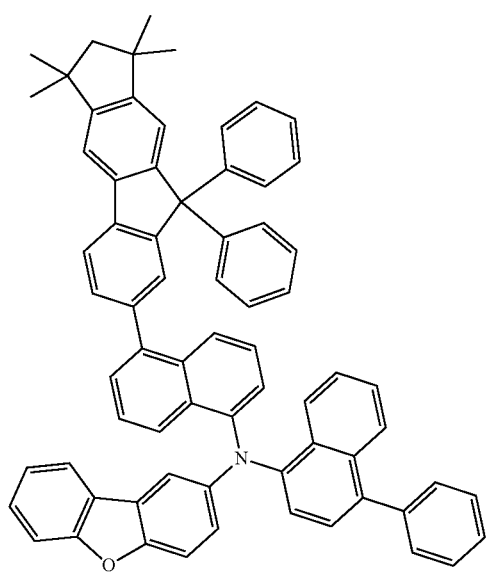
331
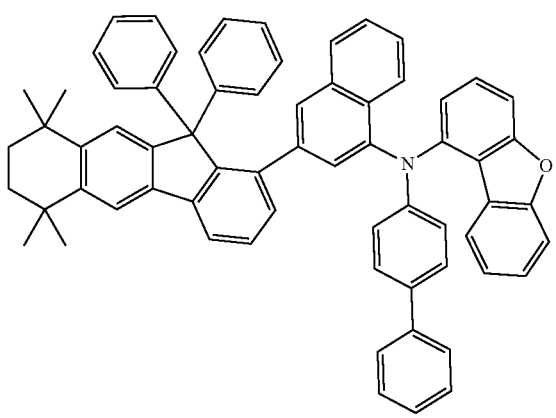

332
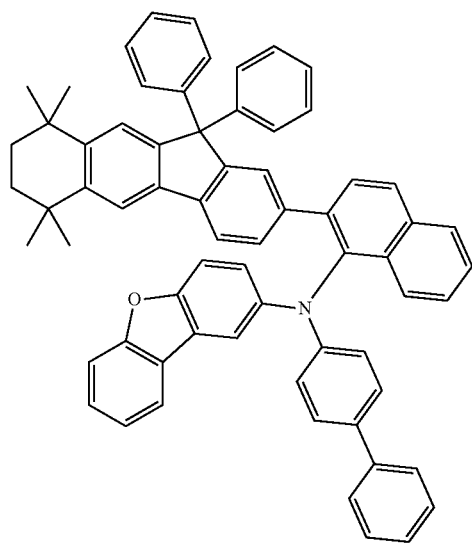
333
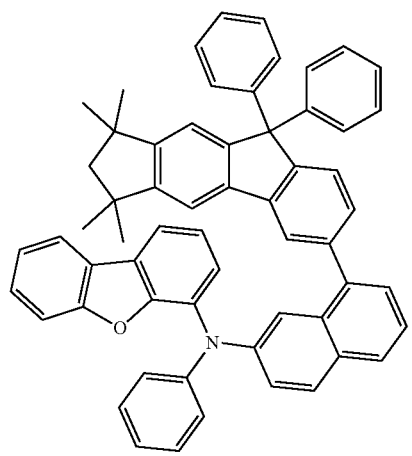
334
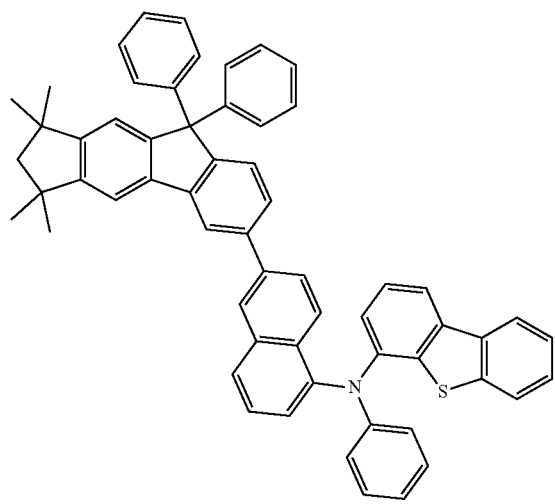
335
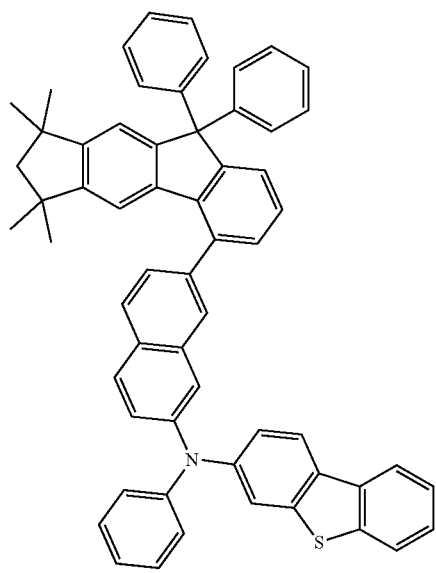

-continued
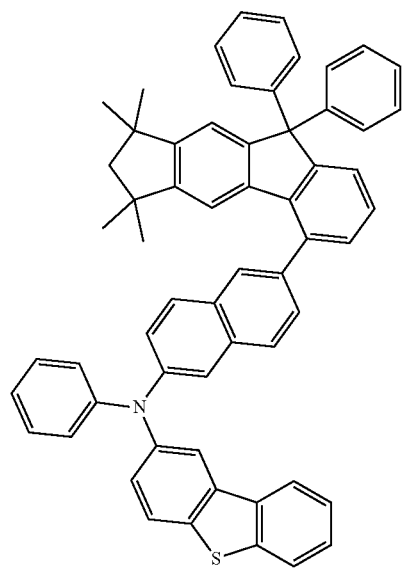
336
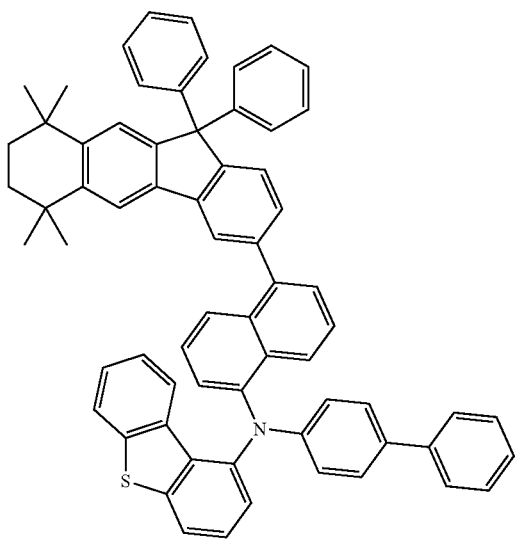
337
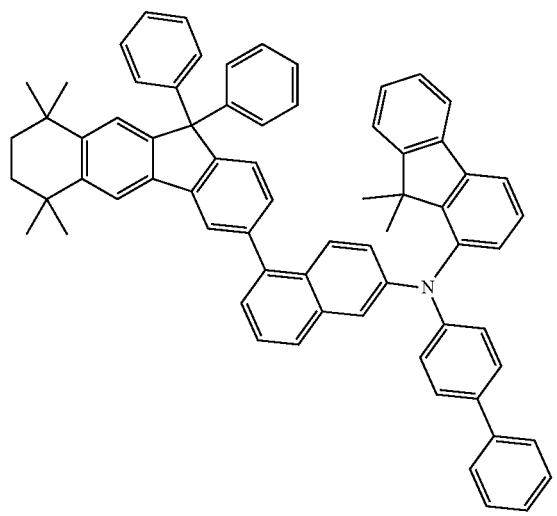
338
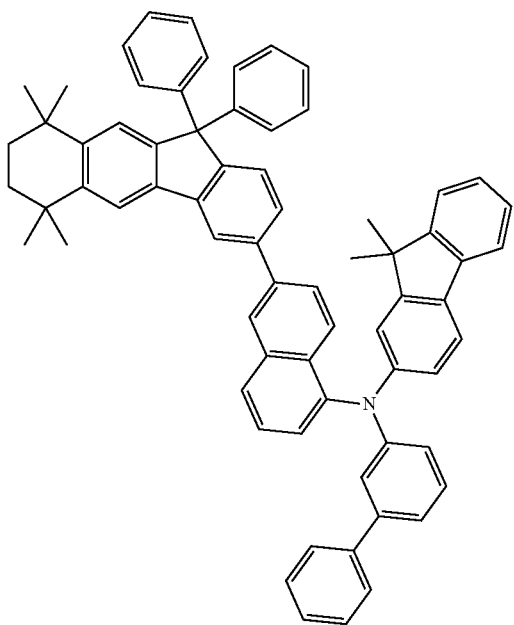
339

-continued
340
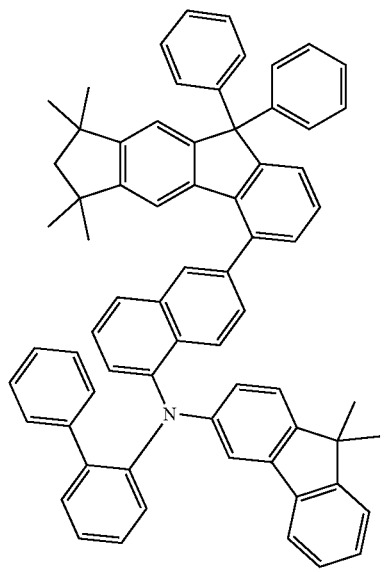
341
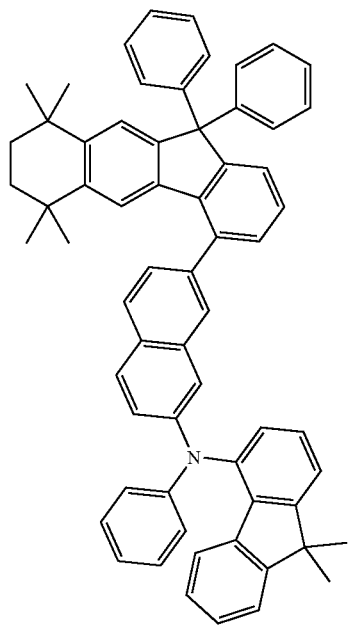
342
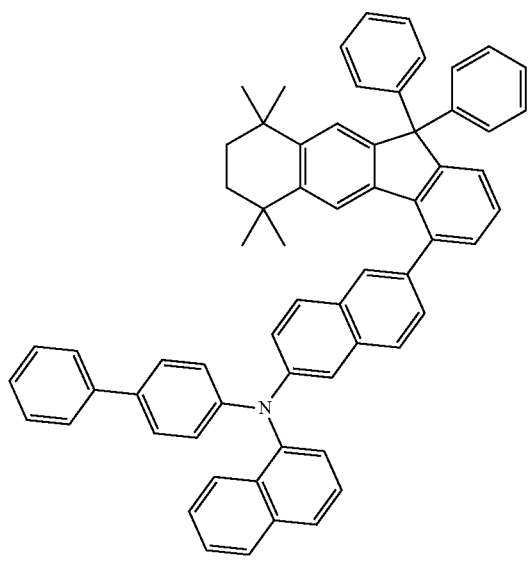
343
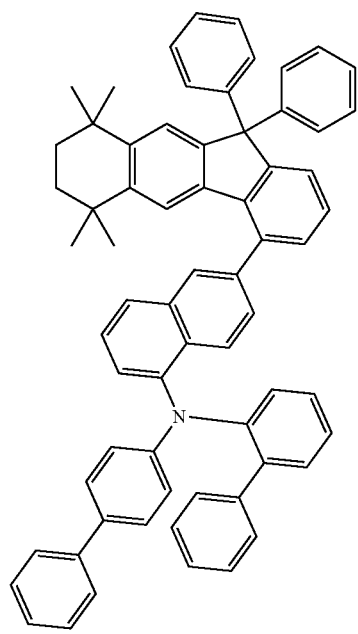

-continued
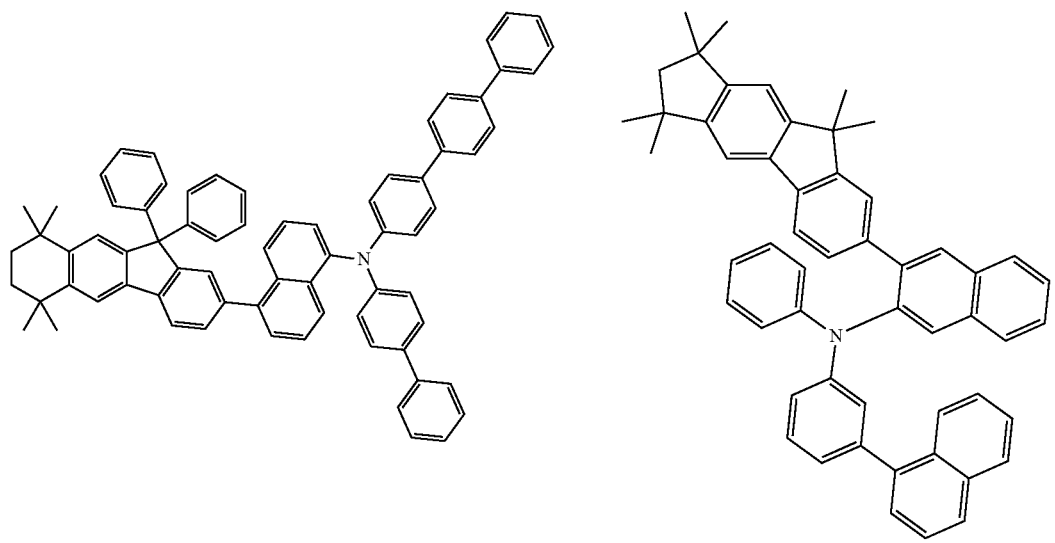
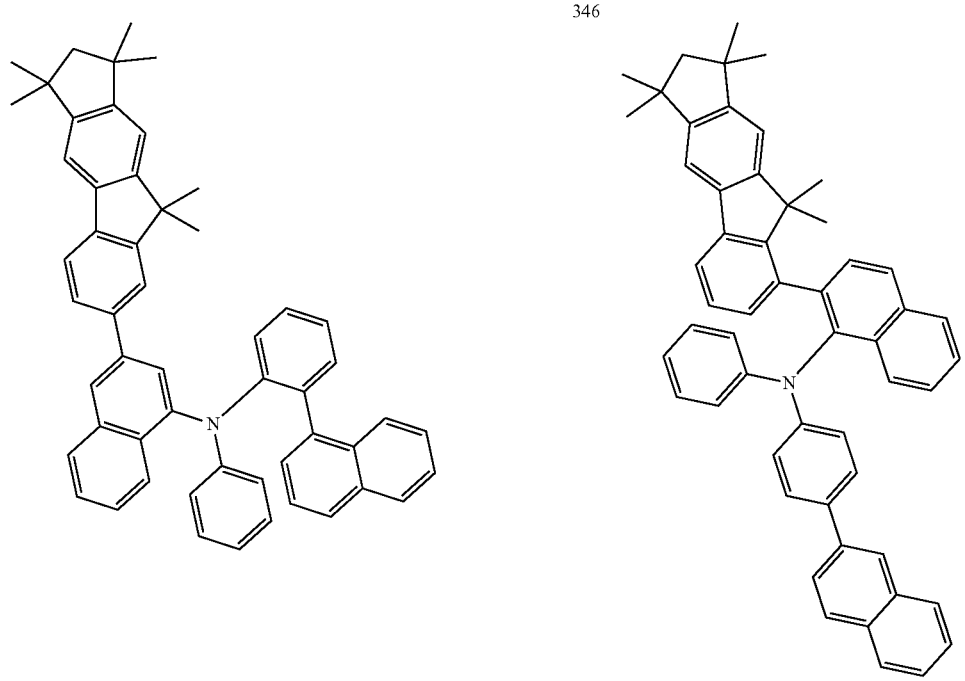

-continued
171
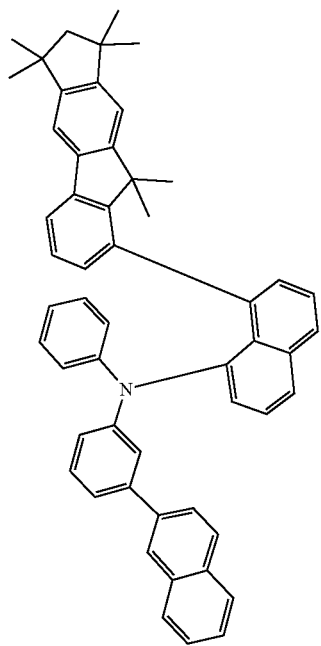
348
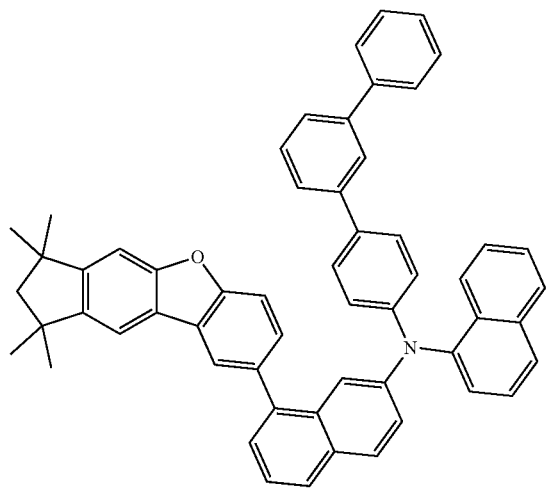
349
172
350
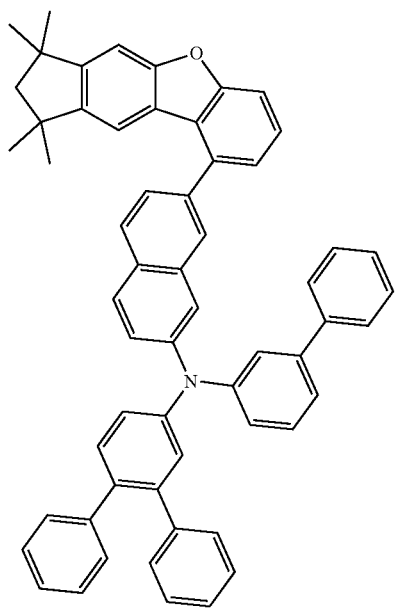
351
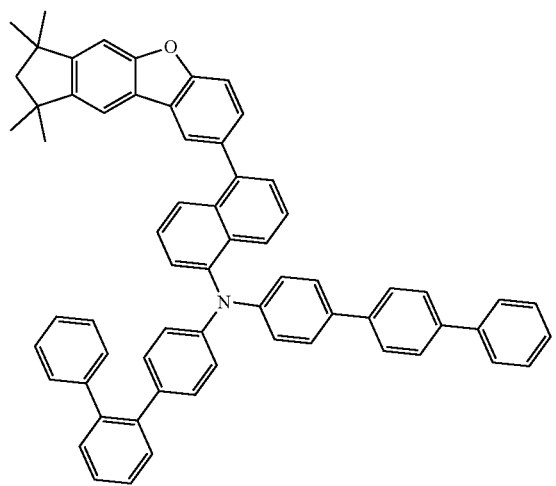

352
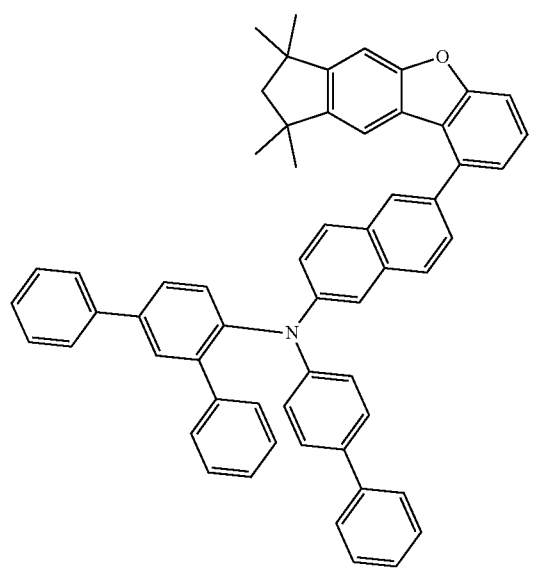
353
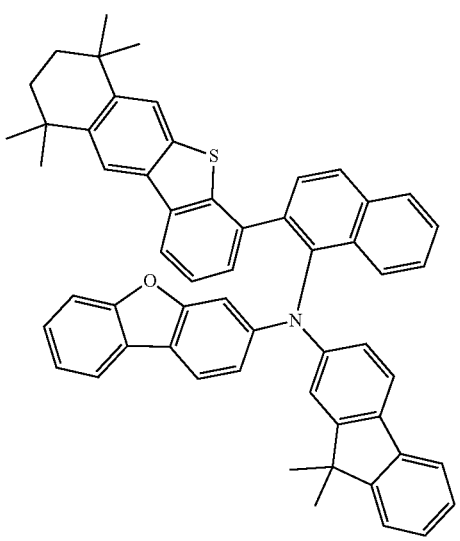
354
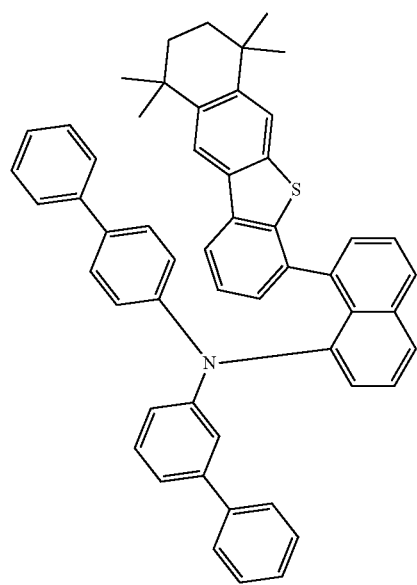
355
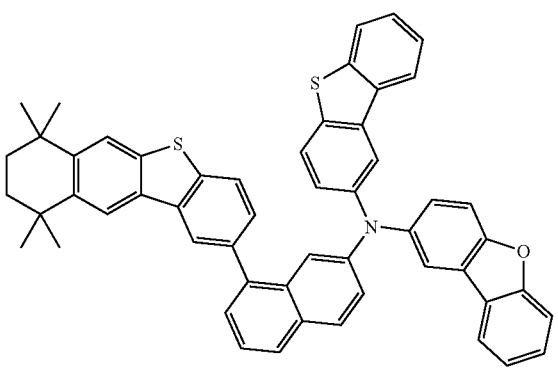

-continued
356
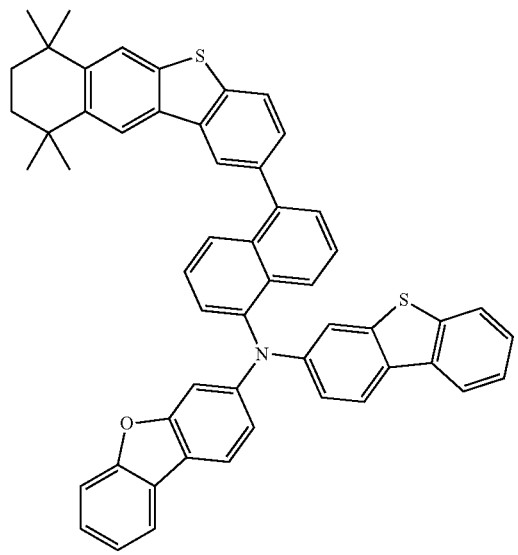
357
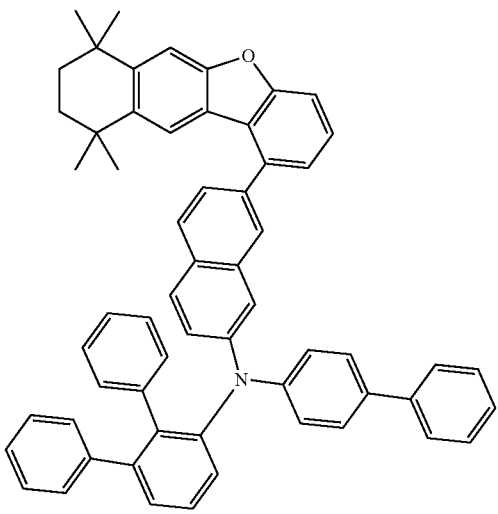
358
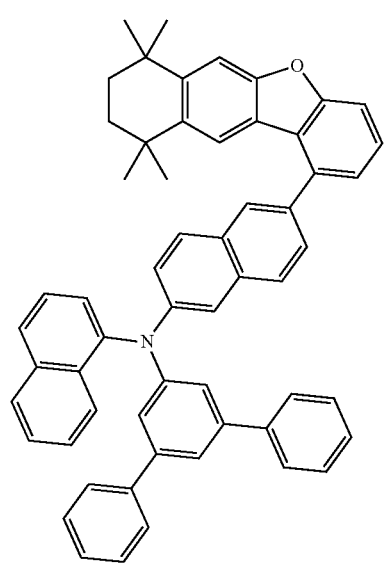
359
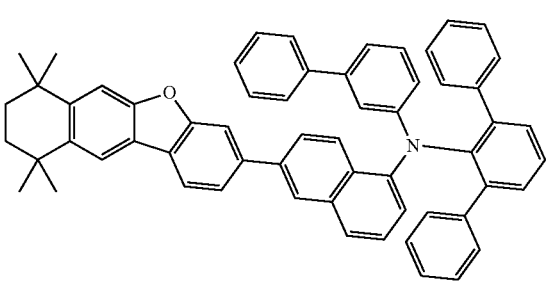
360
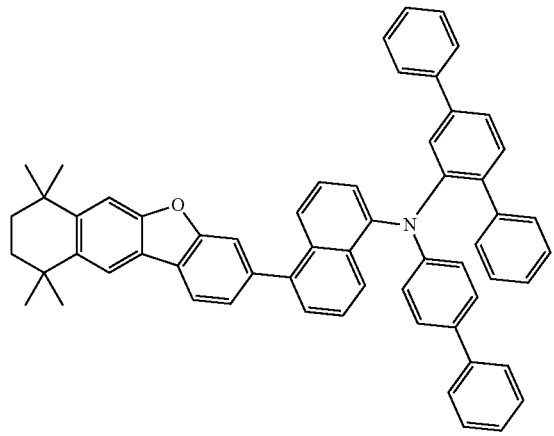
361
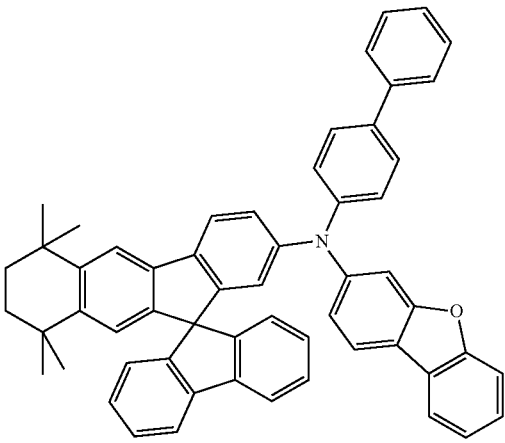

362
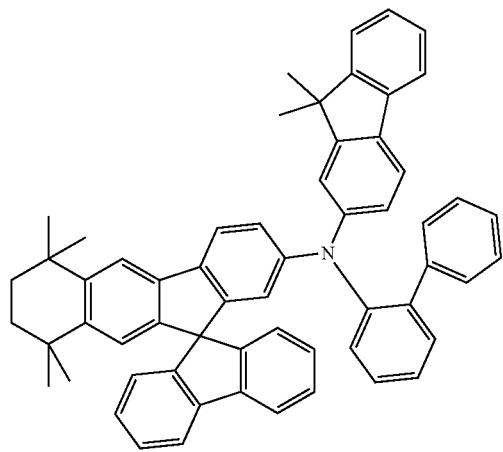
363
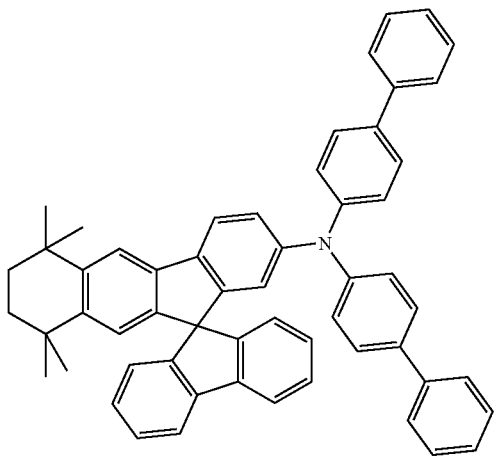
364
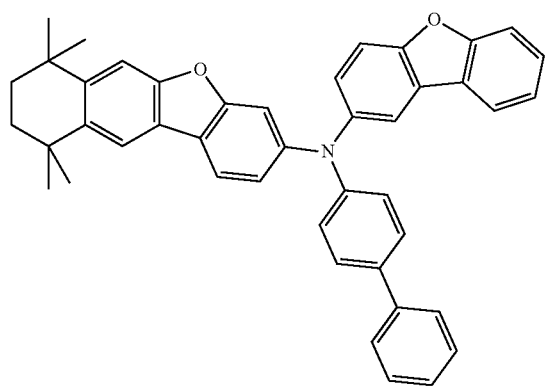
365
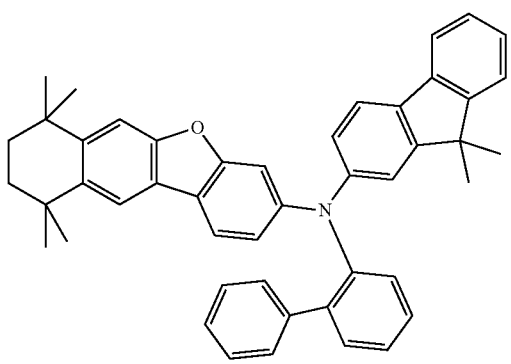
366
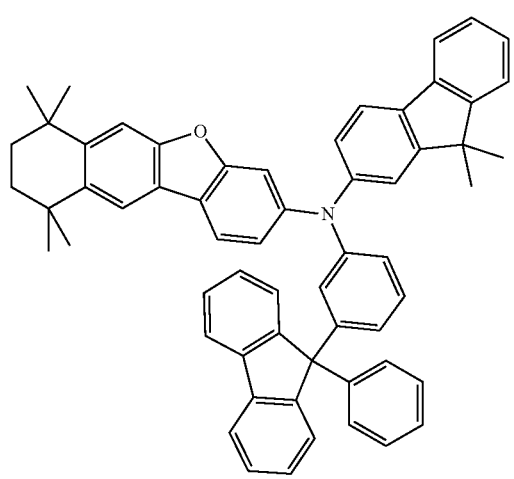
367
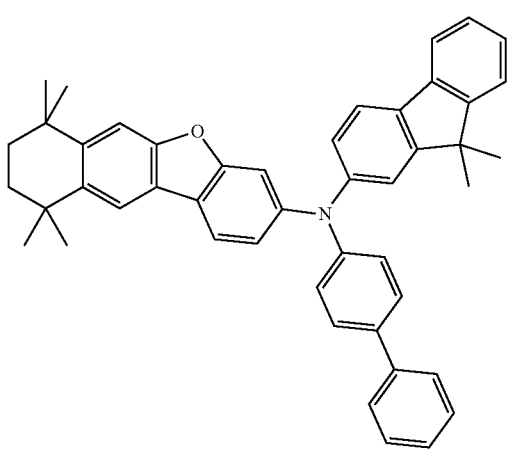

-continued
368
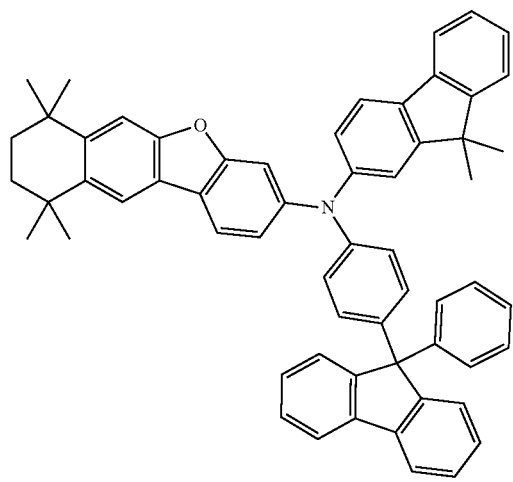
369
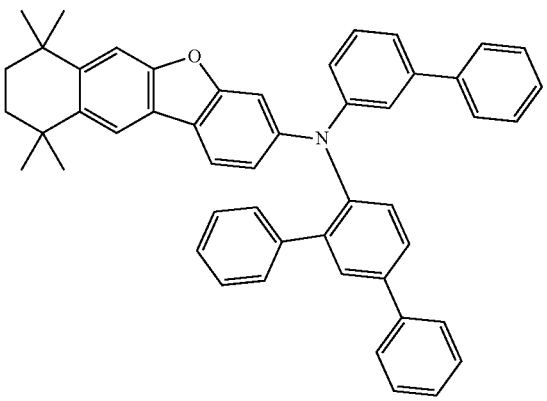
370
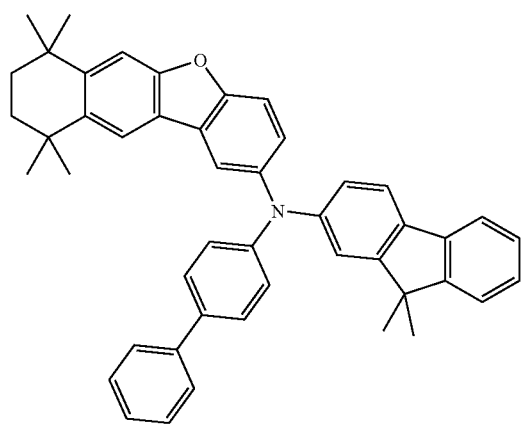
371
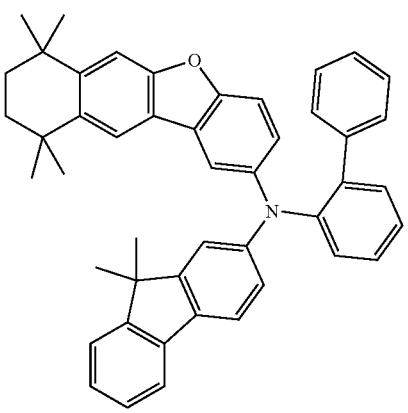
372
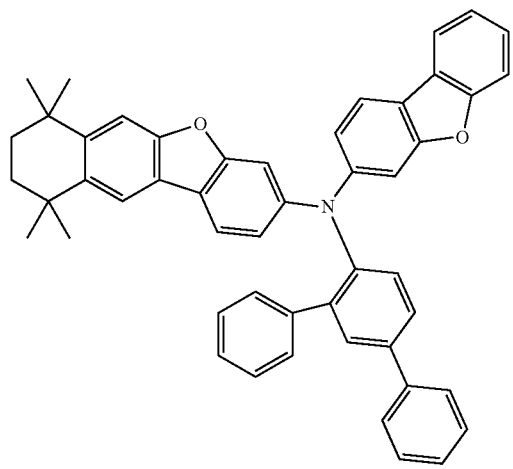
373
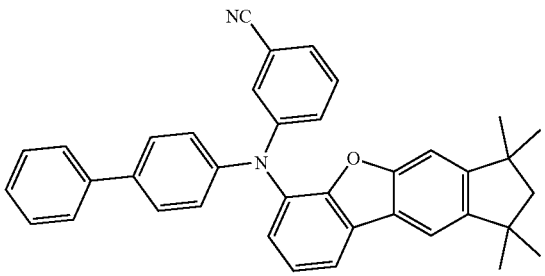

-continued
373
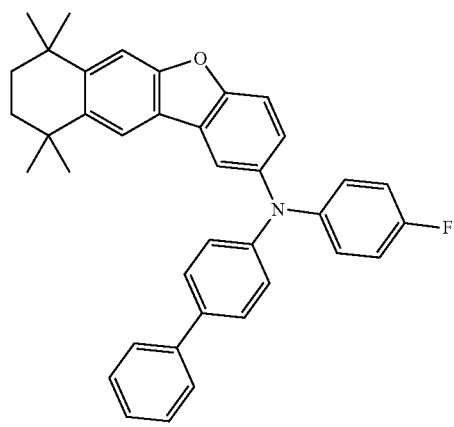
374
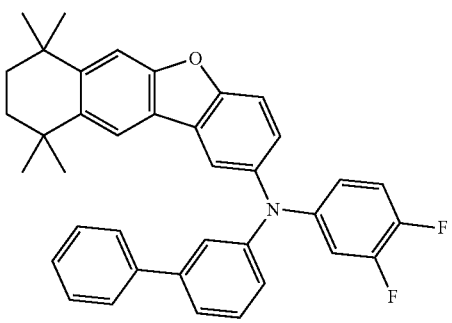
375
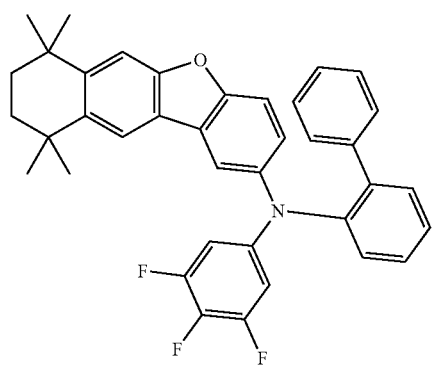
376
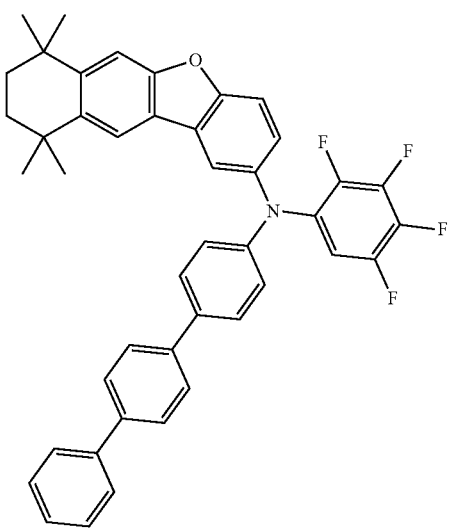
377
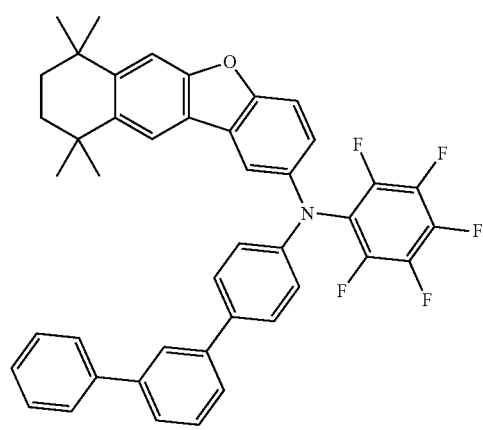
378
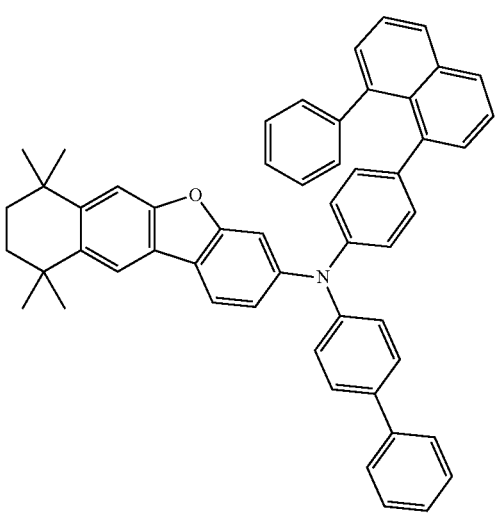

-continued
380
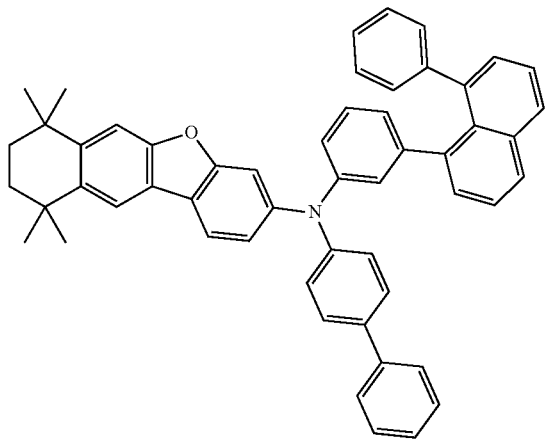
381
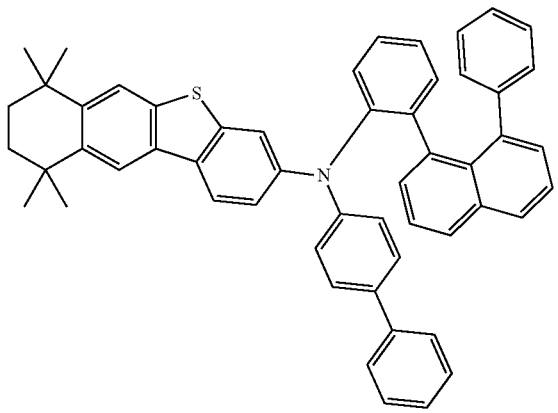
382
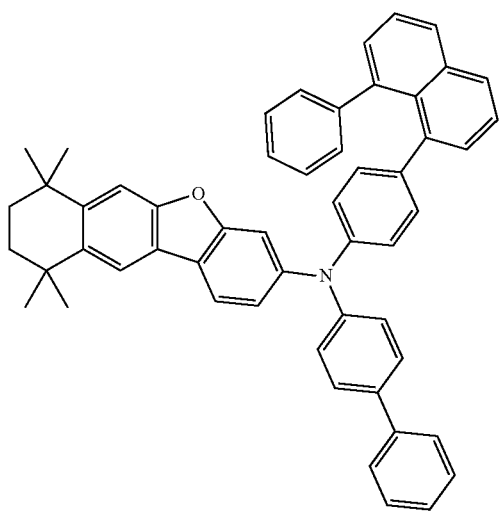
383
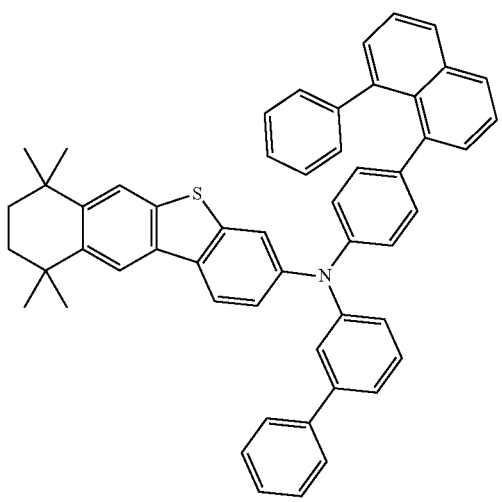
384
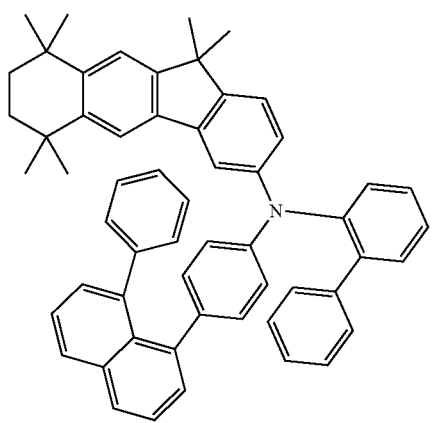
385
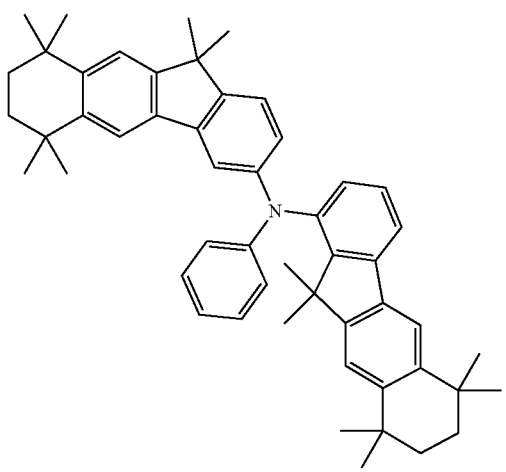

-continued
386
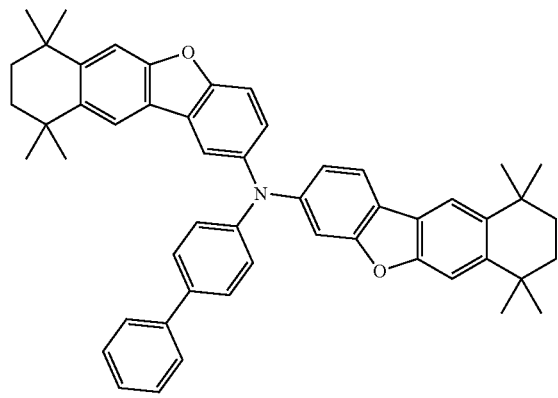
387
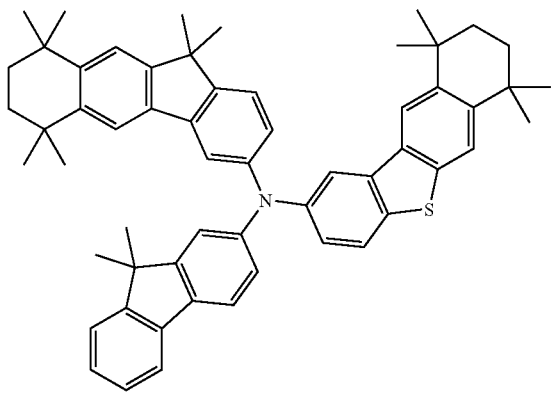
388
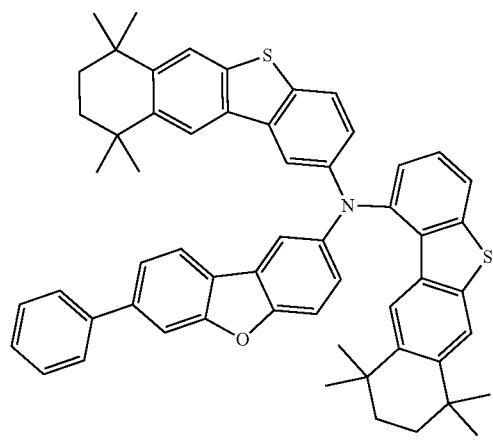
389
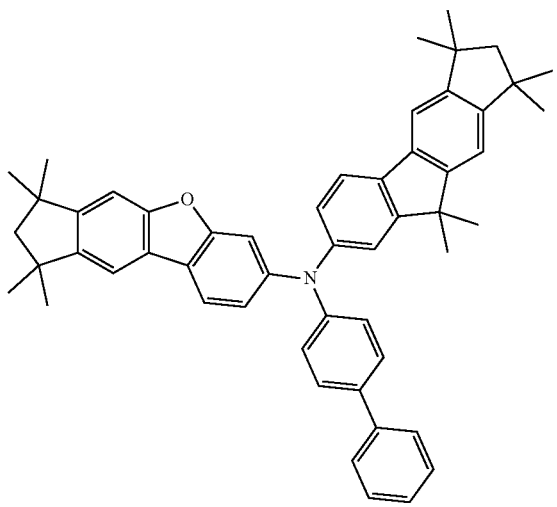
390
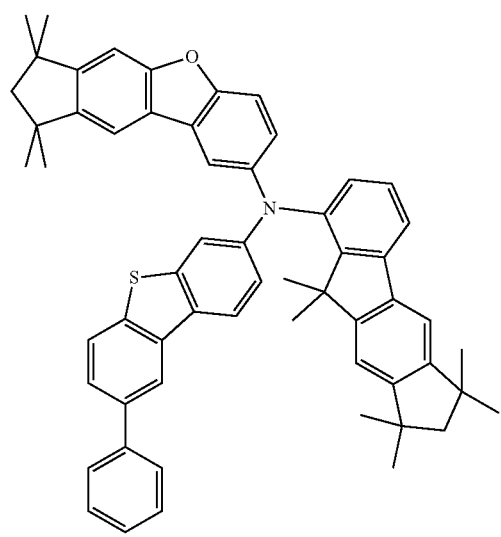
391
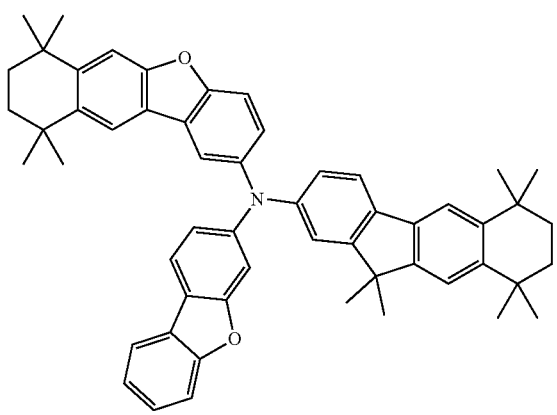

-continued
392
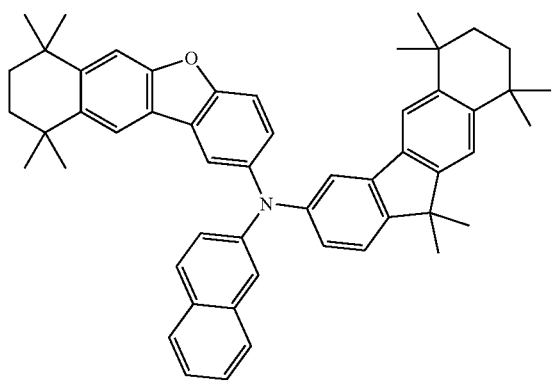
393
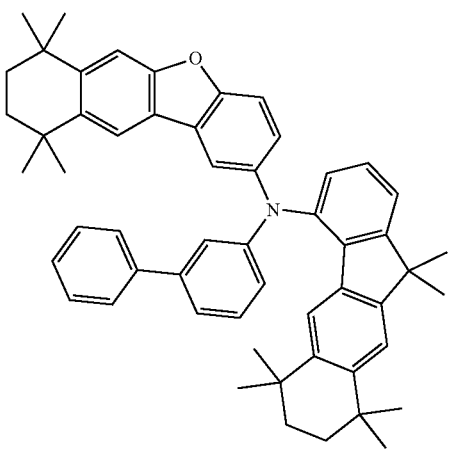
394
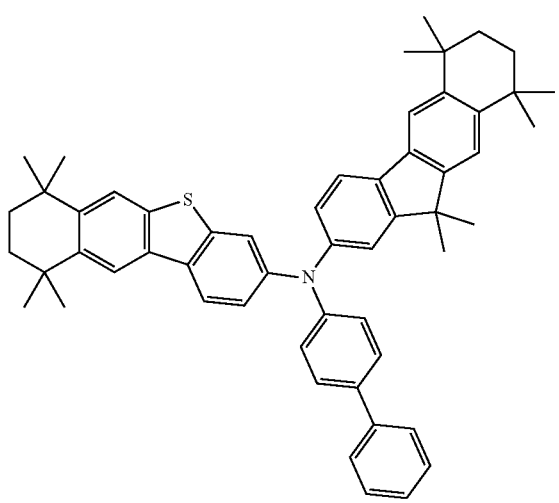
395
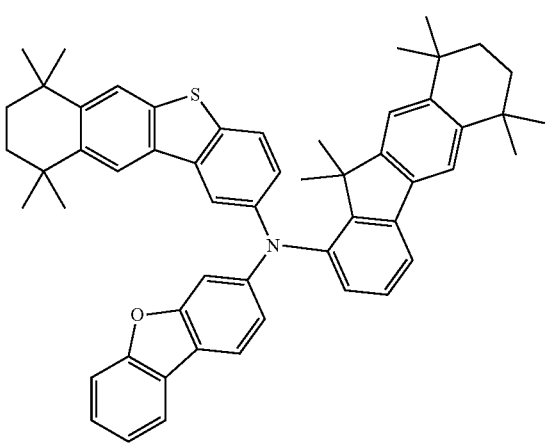
396
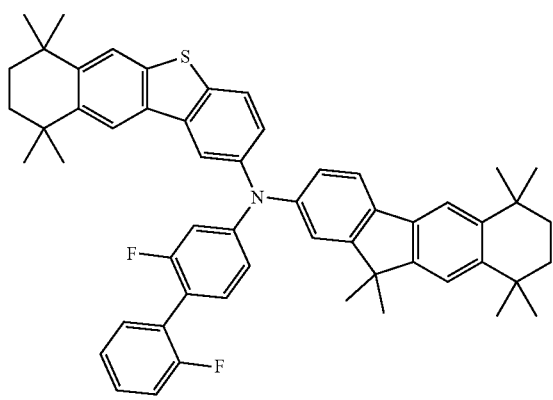
397
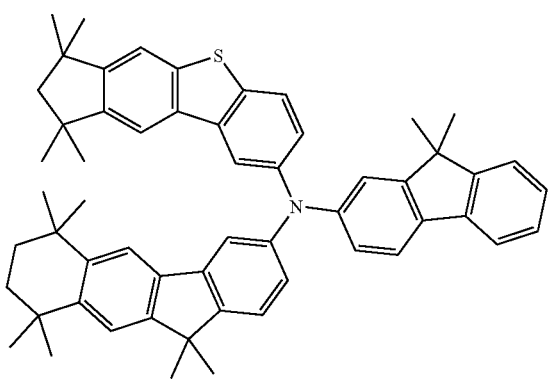

-continued

398

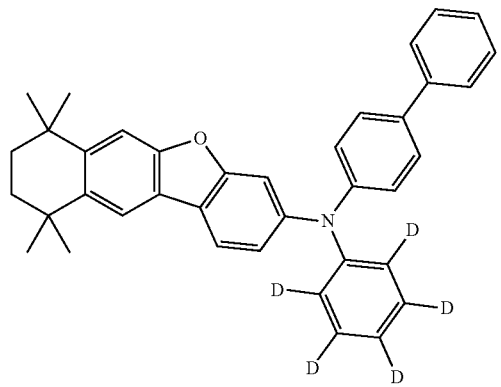

399

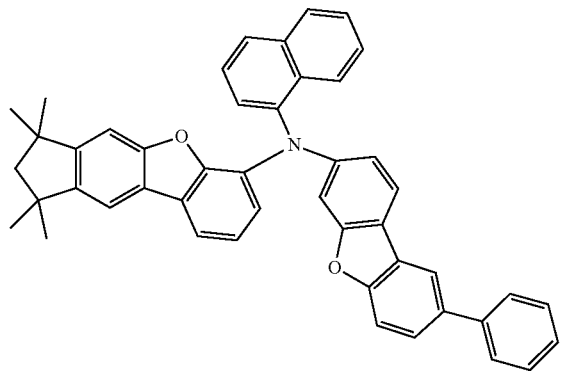

400

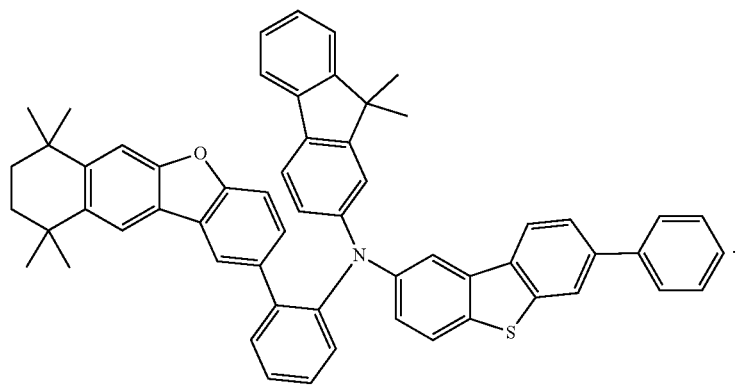

A second aspect of the present application provides an electronic element, including an anode and a cathode which are oppositely disposed, and a functional layer disposed between the anode and the cathode, where the functional layer includes the organic compound according to the present application.

Optionally, the electronic element is an organic electroluminescent device or a photoelectric conversion device.

In one embodiment, the electronic element is an organic electroluminescent device and the functional layer includes a hole adjusting layer, where the hole adjusting layer includes the organic compound of the present application.

In the present application, the organic electroluminescent device can be a red light device, a blue light device or a green light device. Preferably, the organic electroluminescent device is a red light device.

In another embodiment, the electronic element is a photoelectric conversion device and the functional layer includes a hole transporting layer, where the hole transporting layer includes the organic compound of the present application.

In one specific embodiment, the electronic element is an organic electroluminescent device, and as shown in FIG. 1, the organic electroluminescent device may include an anode 100, a hole transporting layer 321, a hole adjusting layer 322, an organic luminescence layer 330, an electron transporting layer 340, and a cathode 200 which are sequentially stacked.

Optionally, the anode 100 includes the following anode materials, which are preferably materials having a large work function that facilitate hole injection into the functional layer. Specific examples of the anode materials include metals such as nickel, platinum, vanadium, chromium, copper, zinc, and gold, or an alloy thereof, metal oxides such as zinc oxide, indium oxide, indium tin oxide (ITO) and indium zinc oxide (IZO); combined metals and oxides, such as ZnO:Al or SnO$_2$:Sb; or conductive polymer such as poly(3-methylthiophene), poly[3,4-(ethylene-1,2-dioxy)thiophene] (PEDT), polypyrrole and polyaniline, but are not limited thereto. A transparent electrode containing indium tin oxide (ITO) as the anode is preferably included.

Optionally, the hole transporting layer 321 includes one or more hole transporting materials, and the hole transporting materials can be selected from a carbazole polymer, carbazole-linked triarylamine compounds or other types of compounds, which are not specially limited in the present application. For example, the hole transporting layer 321 may be composed of compound NPB and the hole adjusting layer 322 may contain the compound of the present application.

Optionally, the organic luminescence layer 330 may be composed of a single luminescence layer material and may also include a host material and a doping material. Optionally, the organic luminescence layer 330 is composed of a host material and a doping material, holes injected into the organic luminescence layer 330 and electrons injected into the organic luminescence layer 330 can be recombined in the organic luminescence layer 330 to form excitons, the excitons transfer energy to the host material, the host material transfers energy to the doping material, which in turn enables the doping material to emit light.

The host material of the organic luminescence layer 330 can be a metal chelated compound, a distyryl derivative, an aromatic amine derivative, a dibenzofuran derivative or other types of materials, which is not specially limited in the present application. In one embodiment of the present application, the host material of the organic luminescence layer 330 is CBP.

The doping material of the organic luminescence layer 330 can be a compound with a condensed aryl ring or a derivative thereof, a compound with a heteroaryl ring or a derivative thereof, an aromatic amine derivative or other materials, which is not specially limited in the present application. In one embodiment of the present application, the doping material of the organic luminescence layer 330 is Ir(piq)$_2$(acac).

The electron transporting layer 340 may be a single-layer structure or a multi-layer structure and may include one or more electron transporting materials, and the electron transporting materials are selected from, but are not limited to, a benzimidazole derivative, an oxadiazole derivative, a quinoxaline derivative, or electron transporting materials such as ET-01, TPBi, and LiQ.

In the present application, the cathode 200 may include a cathode material, which is a material with a small work function that facilitates electron injection into the functional layer. Specific examples of the cathode material include, but are not limited to, metals such as magnesium, calcium, sodium, potassium, titanium, indium, yttrium, lithium, gadolinium, aluminum, silver, tin, and lead, or an alloy thereof; or multilayer materials such as LiF/Al, Liq/Al, LiO$_2$/Al, LiF/Ca, LiF/Al, and BaF$_2$/Ca. A metal electrode including magnesium and silver is preferably included as the cathode.

Optionally, as shown in FIG. 1, a hole injection layer 310 can also be arranged between the anode 100 and the hole transporting layer 321 to enhance the ability of injecting holes into the hole transporting layer 321. The hole injection layer 310 can be made of a benzidine derivative, a starburst arylamine compound, a phthalocyanine derivative or other materials, which is not specially limited in the present application. For example, the hole injection layer 310 may be composed of F4-TCNQ.

Optionally, as shown in FIG. 1, an electron injection layer 350 can also be arranged between the cathode 200 and the electron transporting layer 340 to enhance the ability of injecting electrons into the electron transporting layer 340. The electron injection layer 350 may include an inorganic material such as an alkali metal sulfide, and an alkali metal halide, or may include a complex of an alkali metal and an organic substance. For example, the electron injection layer 350 may include Yb.

Figure 3:
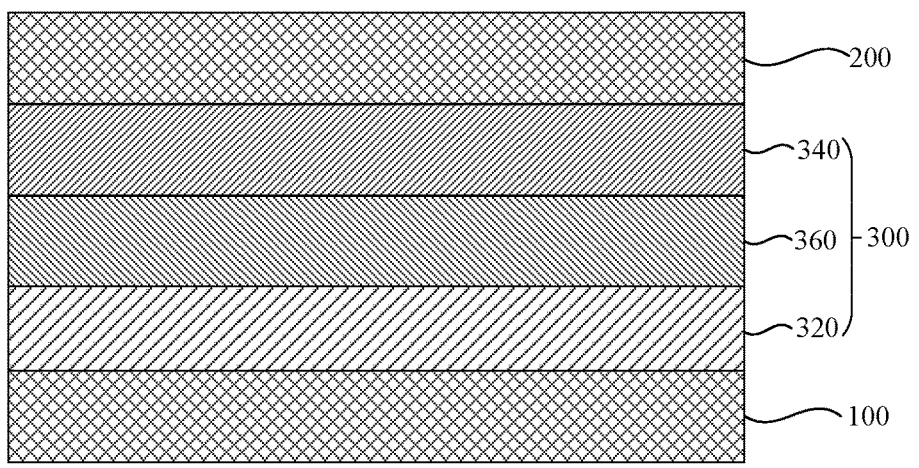
FIG. 3 is a structural schematic diagram of a photoelectric conversion device according to one embodiment of the present application.

According to another specific embodiment, the electronic element is a photoelectric conversion device. As shown in FIG. 3, the photoelectric conversion device may include an anode 100 and a cathode 200 which are oppositely disposed, and a functional layer 300 disposed between the anode 100 and the cathode 200; where the functional layer 300 includes the organic compound provided by the present application.

According to one specific embodiment, as shown in FIG. 3, a photoelectric conversion device may include an anode 100, a hole transporting layer 320, a photoelectric conversion layer 360, an electron transporting layer 340, and a cathode 200 which are sequentially stacked.

Optionally, the photoelectric conversion device can be a solar cell, in particular an organic thin-film solar cell. For example, in one embodiment of the present application, the solar cell may include an anode, a hole transporting layer, an organic luminescence layer, an electron transporting layer, and a cathode which are sequentially stacked, where the hole transporting layer includes the organic compound of the present application.

A third aspect of the present application provides an electronic device, including the electronic element according to the second aspect of the present application.

Figure 2:
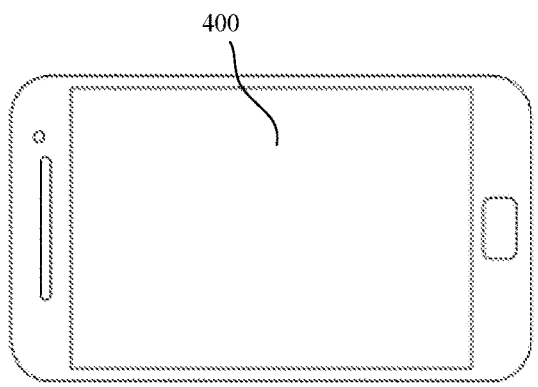
FIG. 2 is a schematic diagram of a first electronic device according to one embodiment of the present application.

According to one embodiment, as shown in FIG. 2, the electronic device is a first electronic device 400, and the first electronic device 400 includes the organic electroluminescent device described above. The first electronic device 400 can be, for example, a display device, a lighting device, an optical communication device or other types of electronic devices, and may include, for example, but is not limited to, a computer screen, a mobile phone screen, a television, electronic paper, an emergency lighting lamp, an optical module and the like.

Figure 4:
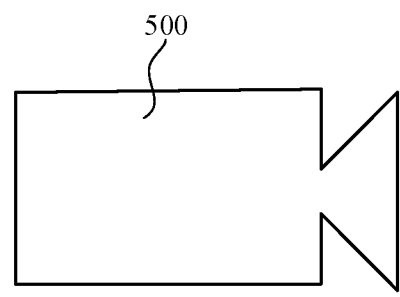
FIG. 4 is a schematic diagram of a second electronic device according to one embodiment of the present application.

According to another embodiment, as shown in FIG. 4, the electronic device is a second electronic device 500, and the second electronic device 500 includes the photoelectric conversion device described above. The second electronic device 500 may be, for example, a solar power generation device, a photodetector, a fingerprint identification device, a light module, a CCD camera, or other types of electronic devices.

A synthesis method of the organic compound of the present application is specifically described below in conjunction with the synthesis examples, but the present application is not limited in any way thereby.

Compounds of which synthesis methods are not mentioned in the present application are all commercially available raw material products.

Synthesis Examples

1. Synthesis of IM YM-1

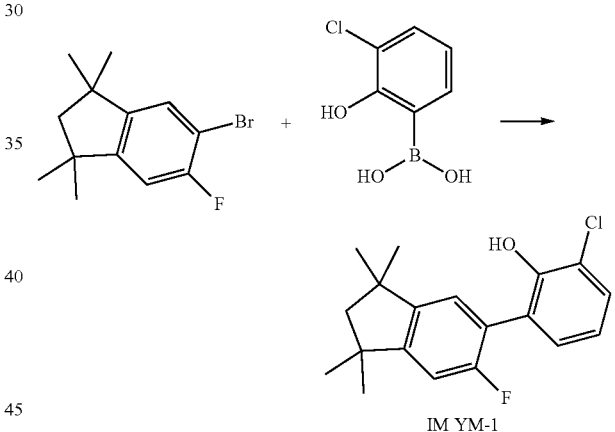

IM YM-1

Under nitrogen atmosphere, 5-bromo-6-fluoro-2,3-dihydro-1,1,3,3-tetramethyl-1H-indene (20 g, 73.8 mmol), 3-chloro-2-hydroxyphenylboronic acid (15.3 g, 88.6 mmol), tetrakis(triphenylphosphine)palladium (0.17 g, 0.15 mmol), potassium carbonate (25.5 g, 184.5 mmol), 160 mL of toluene, 80 mL of ethanol and 40 mL of water were added to a 500 mL of three-necked flask, and the solution was heated to 70-80° C., and refluxed overnight. After cooling to room temperature, the resulting reaction solution was washed with water for three times, and finally extracted with a saturated aqueous ammonium chloride solution, and organic phases were mixed, dried over anhydrous magnesium sulfate, and concentrated by rotary evaporation. The obtained solid material was recrystallized with ethanol to give IM YM-1 (13.8 g, yield: 58.9%).

IM YM-x listed in Table 1 was synthesized with reference to the method for IM YM-1 except that a raw material 1 was used instead of 5-bromo-6-fluoro-2,3-dihydro-1,1,3,3-tetramethyl-1H-indene and a raw material 2 was used instead of 3-chloro-2-hydroxyphenylboronic acid, where the main raw materials used, IM YM-x synthesized and their yields are as shown in Table 1.

TABLE 1

| Raw material 1 | Raw material 2 | IM YM-x | Yield/% |
|---|---|---|---|
| | | IM YM-2 | 68.2 |
| | | IM YM-3 | 65.9 |
| | | IM YM-4 | 57.6 |
| | | IM YM-5 | 67.4 |
| | | IM YM-6 | 66.5 |
| | | IM YM-7 | 55.8 |

TABLE 1-continued
| Raw material 1 | Raw material 2 | IM YM-x | Yield/% |
|---|---|---|---|
| | 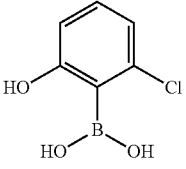 [SMILES: OB(O)c1c(O)cccc1Cl] | 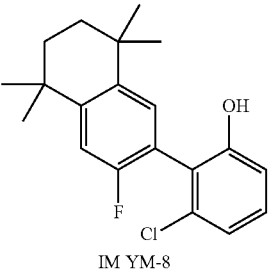 IM YM-8 | 63.6 |
| 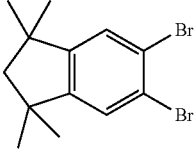 | 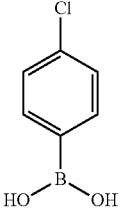 | 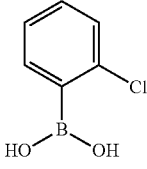 IM YM-9 | 45.5 |
| | 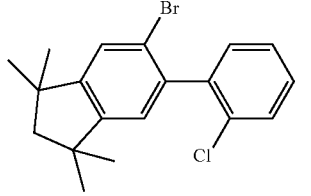 | 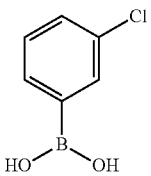 IM YM-10 | 44.8 |
| | 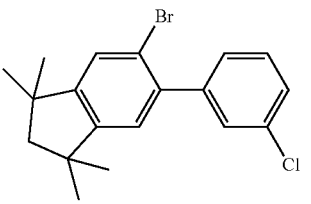 | 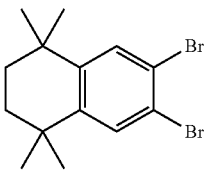 [SMILES: CC1(C)CCC(C)(C)c2cc(Br)c(Br)cc21] IM YM-18 | 45.6 |
| 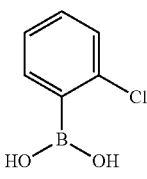 | 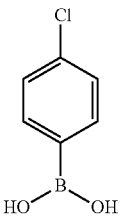 | 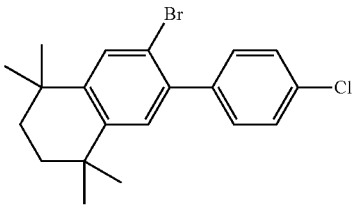 IM YM-11 | 47.3 |
| |  |  IM YM-12 | 45.8 |

TABLE 1-continued

| Raw material 1 | Raw material 2 | IM YM-x | Yield/% |
|---|---|---|---|
| (1,1,4,4-tetramethyl-tetrahydronaphthalene with I) | 4-bromophenylboronic acid | IM YM-15 | 68.6 |
| (1,1,4,4-tetramethyl-tetrahydronaphthalene) | 2-bromophenylboronic acid | IM-YM 16 | 65.7 |
| (1,1,4,4-tetramethyl-tetrahydronaphthalene) | 4-chloro-2-bromophenylboronic acid | IM YM-17 | 60.6 |

2. Synthesis of IM A-1

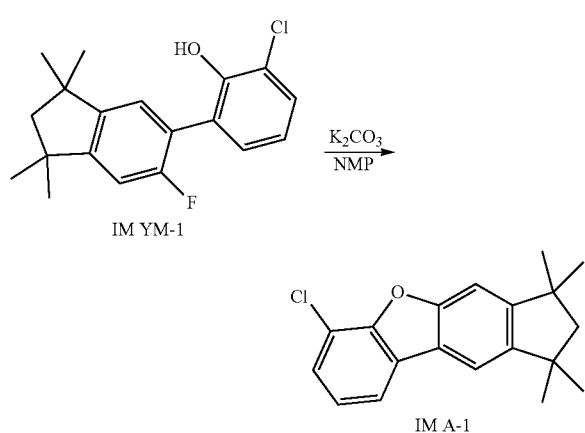

IM YM-1 → IM A-1 (K₂CO₃ / NMP)

In a 250 mL of three-necked flask, IM YM-1 (20 g, 62.7 mmol) was dissolved in 200 mL of N-methyl-2-pyrrolidone, $K_2CO_3$ (17.3 g, 125.4 mmol) was then added, and the mixture was heated to 200° C. and refluxed overnight under a nitrogen atmosphere. After the reaction was completed, the resulting reaction solution was cooled to room temperature, and a solvent was removed by distillation. Then, water was added to the reaction solution, and the mixture was extracted with dichloromethane, drying was performed by using anhydrous magnesium sulfate, and concentration was performed by rotary evaporation. Finally, separation and purification were performed by column chromatography to give IM A-1 (13.5 g, yield: 72.10%).

IM A-y listed in Table 2 was synthesized with reference to the method for IM A-1 except that a raw material 3 was used instead of IM YM-1, where the main raw materials used, IM A-y synthesized and their yields are as shown in Table 2.

TABLE 2
| Raw material 3 | IM A-y | Yield/% |
|---|---|---|
| 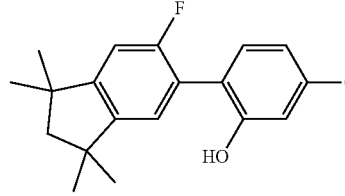<br>IM YM-2 | 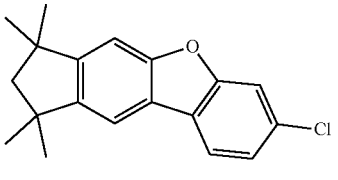 [SMILES: CC1(C)CC(C)(C)c2cc3c(cc21)oc1cc(Cl)ccc13]<br>IM A-2 | 68.2 |
| 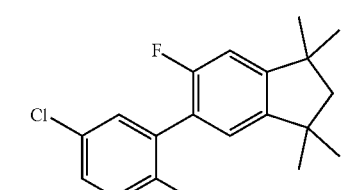<br>IM YM-3 | 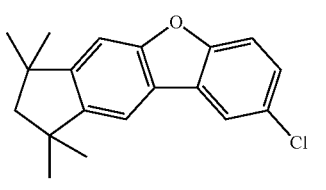 [SMILES: CC1(C)CC(C)(C)c2cc3c(cc21)oc1ccc(Cl)cc13]<br>IM YA-3 | 65.9 |
| 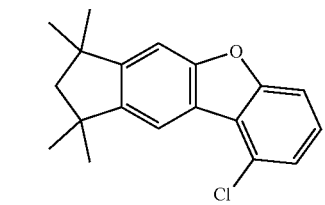 [SMILES: CC1(C)CC(C)(C)c2cc3c(cc21)oc1cccc(Cl)c13]<br>IM YM-4 | 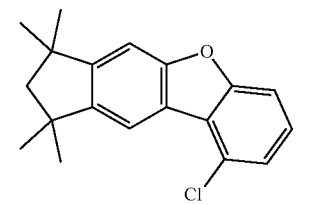 [SMILES: CC1(C)CC(C)(C)c2cc3c(cc21)oc1cccc(Cl)c13]<br>IM YA-4 | 67.6 |
| 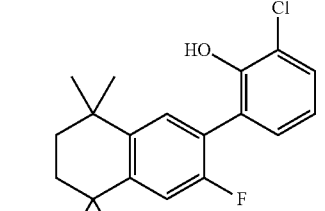<br>IM YM-5 | 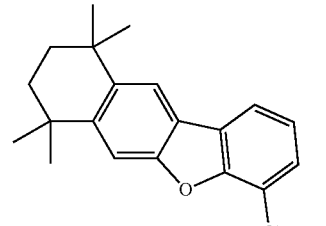<br>IM YA-5 | 67.4 |
| 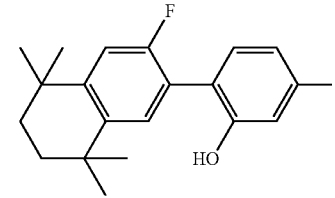<br>IM YM-6 | 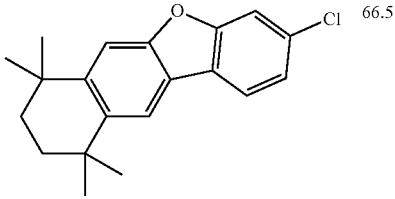<br>IM YA-6 | 66.5 |
| 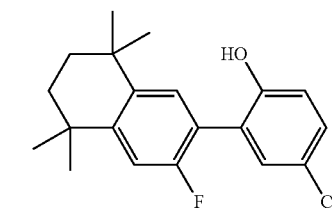<br>IM YM-7 | 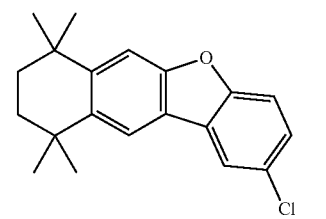 [SMILES: CC1(C)CCC(C)(C)c2cc3c(cc21)oc1ccc(Cl)cc13]<br>IM YA-7 | 65.8 |

TABLE 2-continued

| Raw material 3 | IM A-y | Yield/% |
|---|---|---|
| 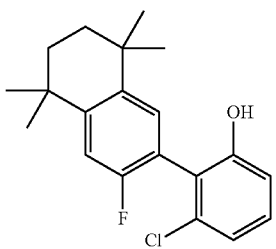 [SMILES: CC1(C)CCC(C)(C)c2cc(-c3c(O)cccc3Cl)c(F)cc21] IM YM-8 | 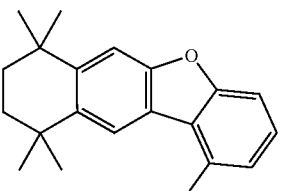 IM YA-8 | 63.6 |

3. Synthesis of IM B-1

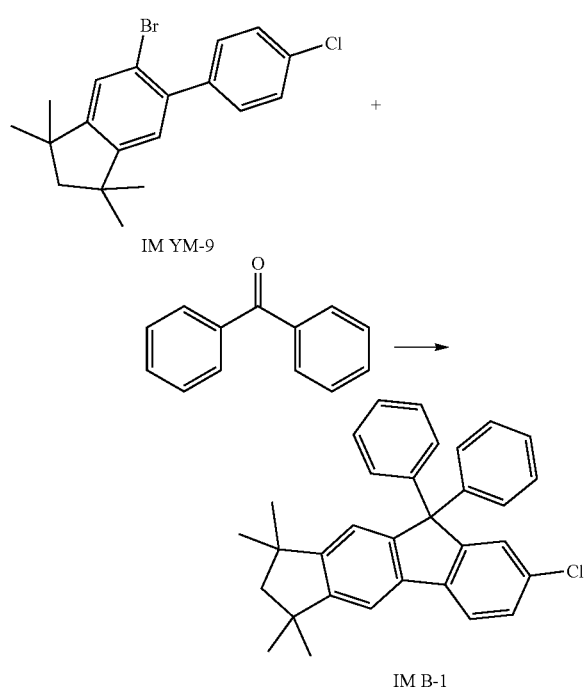

In a three-necked flask, IM YM-9 (20 g, 55 mmol) was dissolved in 50 mL of THF, the resulting solution was cooled to −78° C., then n-BuLi (22 mL, 2.5 M, 55 mmol) was added dropwise, a reaction was carried out for 4 h, benzophenone (10 g, 55 mmol) was added, heat preservation was performed for 30 min, heating was performed to room temperature, a reaction was carried out for 30 min, the reaction was quenched with methanol, and a solvent was removed under reduced pressure. Glacial acetic acid (100 mL) and 25 mL of hydrochloric acid were then added, refluxing was performed for 24 h, cooling was performed to room temperature, the resulting reaction solution was washed with water to be neutral, and a precipitate was filtered, and oven-dried to give IM B-1 (15.4 g, yield: 62.3%).

IM B-z listed in Table 3 was synthesized with reference to the method for IM B-1 except that IM YM-x was used instead of IM YM-9, and a raw material 4 was used instead of benzophenone, where the main raw materials used, IM B-z synthesized, and their yields are as shown in Table 3.

TABLE 3

| IM YM-x | Raw material 4 | IM B-z | Yield/% |
|---|---|---|---|
| 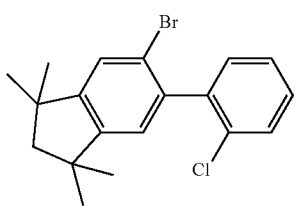 [SMILES: CC1(C)CC(C)(C)c2cc(-c3ccccc3Cl)c(Br)cc21] IM YM-10 | 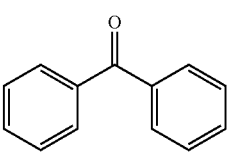 [SMILES: O=C(c1ccccc1)c1ccccc1] | 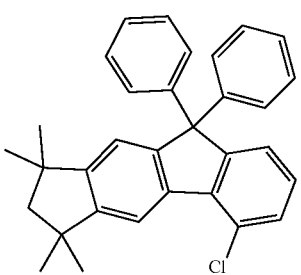 [SMILES: CC1(C)CC(C)(C)c2cc3c(cc21)-c1c(Cl)cccc1C3(c1ccccc1)c1ccccc1] IM B-2 | 59.8 |

TABLE 3-continued
| IM YM-x | Raw material 4 | IM B-z | Yield/% |
|---|---|---|---|
| IM YM-11 | | IM B-3 | 60.4 |
| IM YM-12 | | IM B-4 | 60.7 |
| IM YM-18 | | IM B-6 | 47.3 |
| IM YM-17 | | IM B-5 | 58.1 |
4. Synthesis of IM C-1
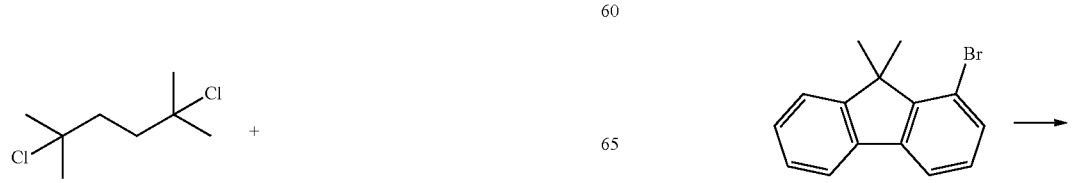

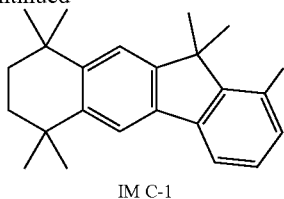

IM C-1

In a 250 mL of three-necked flask, a reactant 2,5-dichloro-2,5-dimethylhexane (10 g, 54.6 mmol) was dissolved in 50 mL of N-dichloroethane (DCE), then the reaction solution was cooled to 0° C., AlCl₃ (7.3 g, 54.6 mmol) was added, a solution of 1-bromo-9,9-dimethyl-9H-fluorene (14.9 g, 54.6 mmol) in DCE (50 mL) was added dropwise under a nitrogen atmosphere, a reaction was carried out for 30 min, the temperature of the reaction solution was raised to 80° C., and a reaction was carried out for 12 h. Then cooling was performed to room temperature, ice (100 g) and HCl (20 mL) were added, and stirring was performed for 20 min. The reaction solution was extracted with dichloromethane for three times, drying was performed by using anhydrous magnesium sulfate, the dried material was allowed to pass through a silica gel column to give a crude product, and finally the crude product was recrystallized by using DCM and MeOH in a ratio of 1:1 (v/v) to give IM C-1 (16.5 g, yield: 78.6%).

IM C-w listed in Table 4 was synthesized with reference to the method for IM C-1 except that a raw material 5 was used instead of 1-bromo-9,9-dimethyl-9H-fluorene, where the main raw materials used, IM C-w synthesized and their yields are as shown in Table 4.

5. Synthesis of IM YD-1

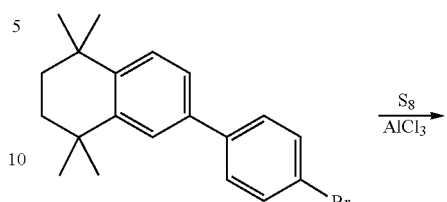

IM YM-15

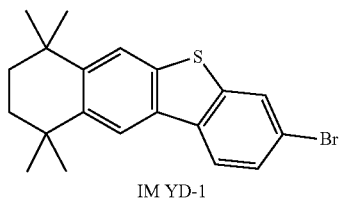

IM YD-1

Under a nitrogen atmosphere, IM YM-15 (15 g, 43.6 mmol) was added to a 10 L of three-necked flask, heating was started to be performed until IM YM-15 was melted, sublimed sulfur (25.8 g, 100.5 mmol) was then added, at this time, the system appeared yellow, heating was continued to be performed to 115-120° C., aluminum trichloride (0.35 g, 2.6 mmol) was then added in batches, where in the process of adding aluminum trichloride, the system gradually turned black, and gave off a large amount of hydrogen sulfide gas, heat preservation was performed for 4 h after the addition of aluminum trichloride was completed, heating was started to be slowly performed to 200-210° C., a reaction was carried

TABLE 4

| Raw material 5 | IM C-w | Yield/% |
|---|---|---|
| ![structure] | ![structure] IM C-2 | 78.2 |
| ![structure] | ![structure] IM C-3 | 75.9 |
| ![structure] | ![structure] IM C-4 | 77.6 | out for 4 h, the reaction solution was poured into a 250 mL of single-necked flask while it was hot, and distilled under reduced pressure, the vacuum degree of an oil pump being about 40 Pa, fractions of 120-130° C. were collected to give 8.2 g of a white crystal, a solid was dissolved in ethanol in a ratio of 1 g:3 mL, crystallization was performed at −20° C., and the above operations were repeated twice to give IM YD-1 (7.9 g, yield: 48.5%).

IM YD-2 listed in Table 5 was synthesized with reference to the method for IM YD-1 except that IM YM-16 was used instead of IM YM-15, where the main raw material used, IM YD-2 synthesized and its yield are shown in Table 5.

TABLE 5

| IM YM-16 | IM YD-2 | Yield/% |
|---|---|---|
| 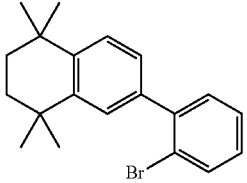 [SMILES: CC1(C)CCC(C)(C)c2cc(-c3ccccc3Br)ccc21]<br>YM-16 | 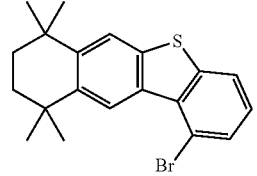 [SMILES: CC1(C)CCC(C)(C)c2cc3c(cc21)sc1cccc(Br)c13]<br>YD-2 | 43.7 |

6. Synthesis of IM F-1

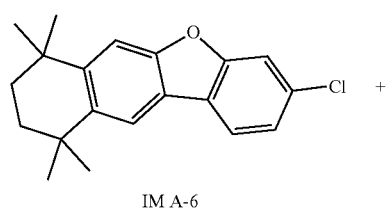

IM A-6

-continued

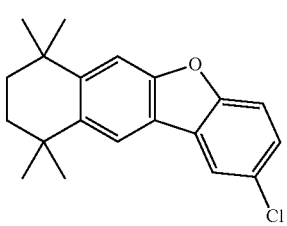 [SMILES: CC1(C)CCC(C)(C)c2cc3c(cc21)oc1ccc(Cl)cc13]

IM F-1

Under a nitrogen atmosphere, IM A-6 (10 g, 31.9 mmol), 4-chlorobenzeneboronic acid (6.0 g, 38.4 mmol), tetrakis(triphenylphosphine)palladium (0.18 g, 0.16 mmol), K$_2$CO$_3$ (11.0 g, 79.8 mmol) and 100 mL of toluene were added to a 250 mL of three-necked flask, and the mixture was heated to 70-80° C., and refluxed overnight. After the reaction was finished, cooling was performed to room temperature, the reaction solution was washed with water for three times, and organic phases were mixed, dried over anhydrous magnesium sulfate, and concentrated under reduced pressure. The obtained solid was recrystallized with ethanol to give IM F-1 (5.3 g, yield: 42.8%).

IM F-x listed in Table 6 was synthesized with reference to the method for IM F-1 except that a raw material 6 was used instead of IM A-6 and a raw material 7 was used instead of 4-chlorobenzeneboronic acid, where the main raw materials used, IM F-x synthesized and their yields are as shown in Table 6.

TABLE 6

| Raw material 6 | Raw material 7 | IM F-x | Yield/% |
|---|---|---|---|
| 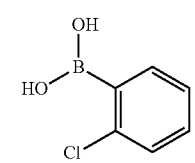<br>IM A-7 | | | 37.1 |
| | | 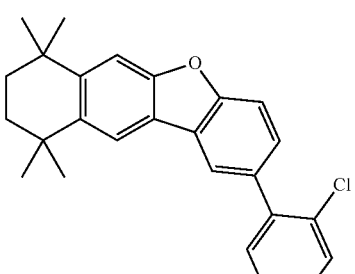<br>IM F-2 | |

TABLE 6-continued

| Raw material 6 | Raw material 7 | IM F-x | Yield/% |
|---|---|---|---|
| IM A-5 | | IM F-4 | 41.8 |
| IM A-6 | | IM F-5 | 39.6 |
| IM A-8 | | IM F-6 | 37.3 |
| | | IM F-13 | 38.7 |

TABLE 6-continued

| Raw material 6 | Raw material 7 | IM F-x | Yield/% |
|---|---|---|---|
| IM A-3 | (2-chloronaphthalen-1-yl)boronic acid | IM F-10 | 38.5 |
| | (5-chloronaphthalen-1-yl)boronic acid | IM F-11 | 39.3 |
| | (5-chloronaphthalen-2-yl)boronic acid | IM F-12 | 40.7 |
| IM C-2 | (6-chloronaphthalen-2-yl)boronic acid | IM F-14 | 40.2 |

TABLE 6-continued

| Raw material 6 | Raw material 7 | IM F-x | Yield/% |
|---|---|---|---|
| 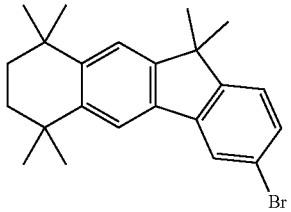<br>IM C-3 | 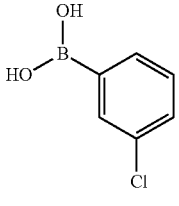 | 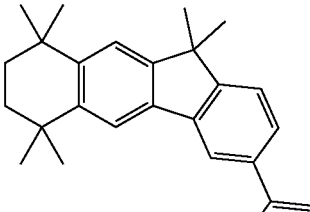<br>IM F-3 | 66.4 |
| 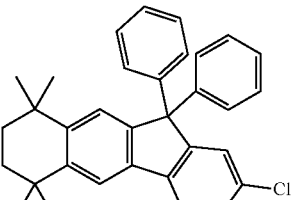<br>IM B-4 | 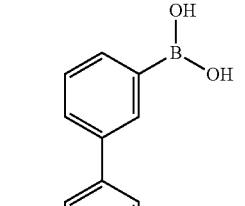 | 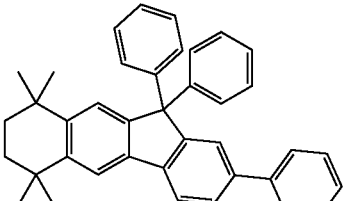<br>IM F-7 | 36.9 |
| 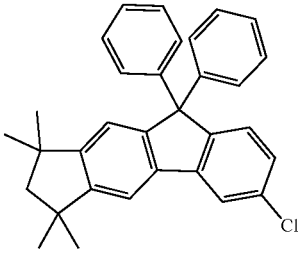<br>IM B-6 | 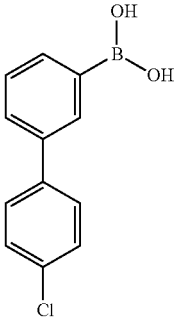 [SMILES: OB(O)c1cccc(-c2ccc(Cl)cc2)c1] | 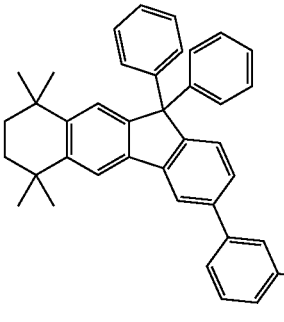<br>IM F-8 | 38.4 |

7. Synthesis of IM D-1

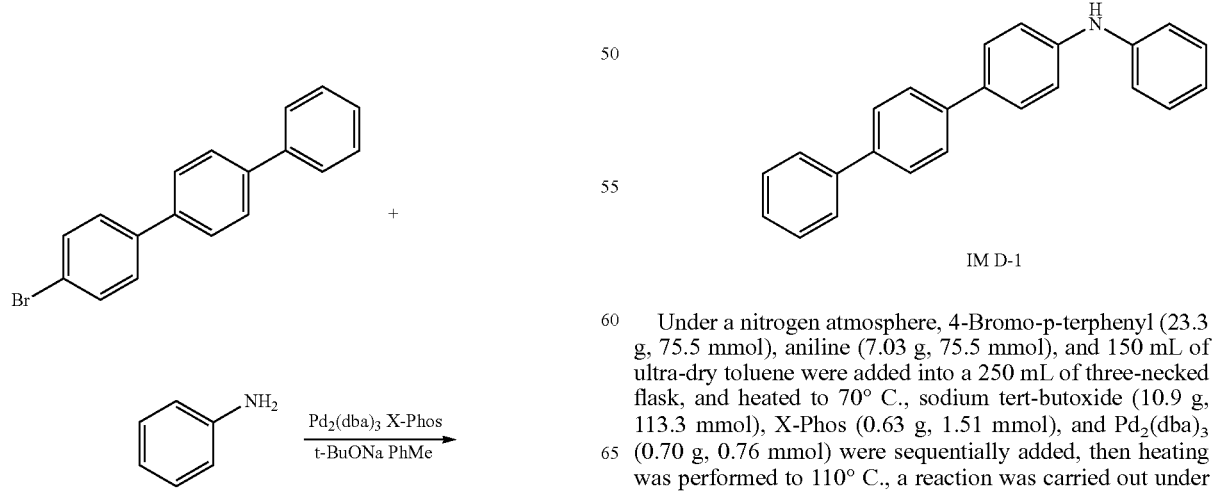

Under a nitrogen atmosphere, 4-Bromo-p-terphenyl (23.3 g, 75.5 mmol), aniline (7.03 g, 75.5 mmol), and 150 mL of ultra-dry toluene were added into a 250 mL of three-necked flask, and heated to 70° C., sodium tert-butoxide (10.9 g, 113.3 mmol), X-Phos (0.63 g, 1.51 mmol), and Pd$_2$(dba)$_3$ (0.70 g, 0.76 mmol) were sequentially added, then heating was performed to 110° C., a reaction was carried out under reflux for 1 h, cooling was performed to room temperature, the reaction solution was washed with water for three times, drying was performed by using anhydrous magnesium sulfate, the dried material was allowed to stand for 30 min, suction filtration was performed, concentration was performed under reduced pressure, and the concentrated material was allowed to pass through a chromatographic column for column chromatography to give IM D-1 (19.5 g, yield: 80.2%).

IM D-x listed in Table 7 was synthesized with reference to the method for IM D-1 except that a raw material 8 was used instead of 4-bromo-p-terphenyl and a raw material 9 was used instead of aniline, where the main raw materials used, IM D-x synthesized and their yields are as shown in Table 7.

TABLE 7

| Raw material 8 | Raw material 9 | IM D-x | Yield/% |
|---|---|---|---|
| 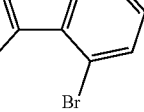 | 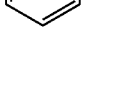 | 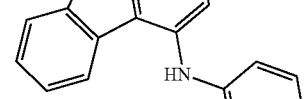<br>IM D-2 | 81.3 |
|  | 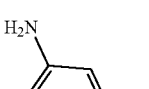 | 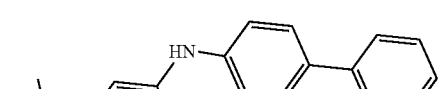<br>IM D-25 | 78.6 |
| |  | 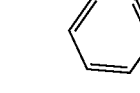<br>IM D-42 | 77.1 |
| |  | <br>IM D-47 | 68.7 |
| | 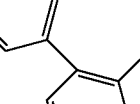 | 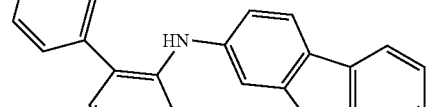<br>IM D-43 | 57.8 |

TABLE 7-continued
| Raw material 8 | Raw material 9 | IM D-x | Yield/% |
|---|---|---|---|
| 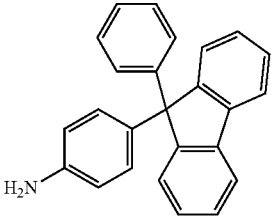 [SMILES: Nc1ccc(C2(c3ccccc3)c3ccccc3-c3ccccc32)cc1] | 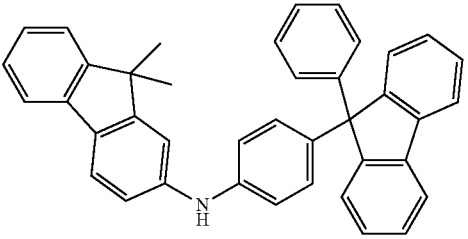 [SMILES: CC1(C)c2ccccc2-c2ccc(Nc3ccc(C4(c5ccccc5)c5ccccc5-c5ccccc54)cc3)cc21] | 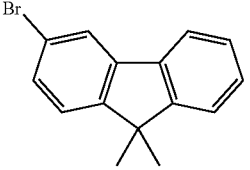 [SMILES: CC1(C)c2ccccc2-c2cc(Br)ccc21] IM D-44 | 58.4 |
| 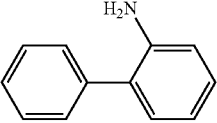 | 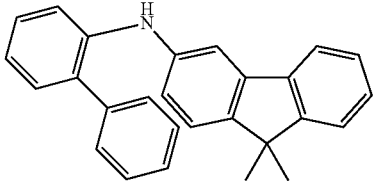 [SMILES: CC1(C)c2ccccc2-c2cc(Nc3ccccc3-c3ccccc3)ccc21] | 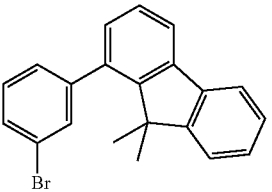 [SMILES: CC1(C)c2ccccc2-c2cccc(-c3cccc(Br)c3)c21] IM D-38 | 72.6 |
| 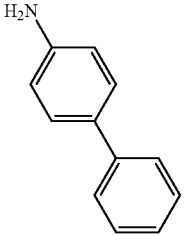 [SMILES: Nc1ccc(-c2ccccc2)cc1] | 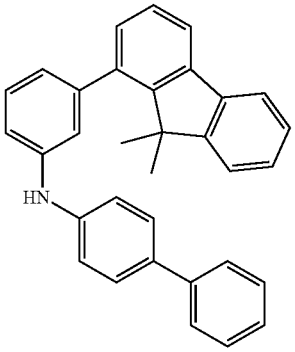 [SMILES: CC1(C)c2ccccc2-c2cccc(-c3cccc(Nc4ccc(-c5ccccc5)cc4)c3)c21] | 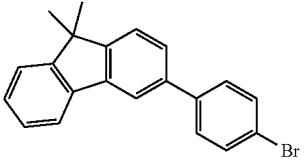 [SMILES: CC1(C)c2ccccc2-c2cc(-c3ccc(Br)cc3)ccc21] IM D-22 | 76.8 |
| 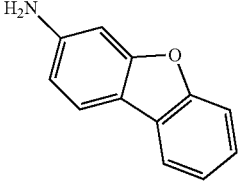 [SMILES: Nc1ccc2c(c1)oc1ccccc12] | 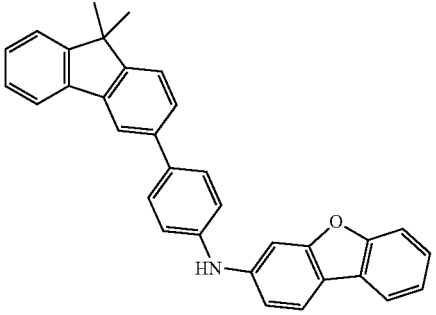 [SMILES: CC1(C)c2ccccc2-c2cc(-c3ccc(Nc4ccc5c(c4)oc4ccccc45)cc3)ccc21] | 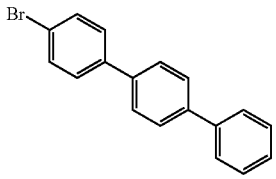 [SMILES: Brc1ccc(-c2ccc(-c3ccccc3)cc2)cc1] IM D-37 | 74.7 |
| 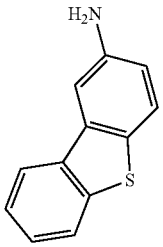 [SMILES: Nc1ccc2sc3ccccc3c2c1] | 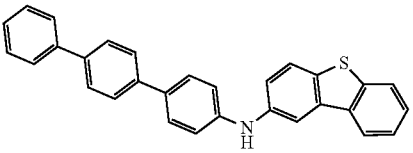 [SMILES: c1ccc(-c2ccc(-c3ccc(Nc4ccc5sc6ccccc6c5c4)cc3)cc2)cc1] |  IM D-3 | 79.6 |

TABLE 7-continued
| Raw material 8 | Raw material 9 | IM D-x | Yield/% |
|---|---|---|---|
| | 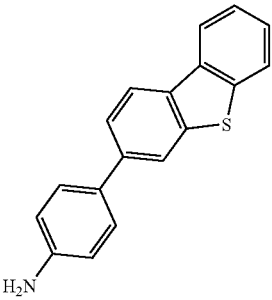 [SMILES: Nc1ccc(-c2ccc3c(c2)sc2ccccc23)cc1] | 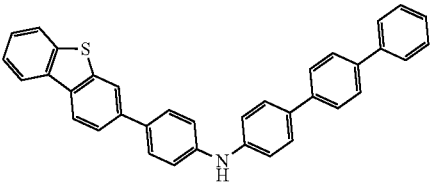 [SMILES: c1ccc(-c2ccc(-c3ccc(Nc4ccc(-c5ccc6c(c5)sc5ccccc56)cc4)cc3)cc2)cc1] IM D-4 | 77.7 |
| | 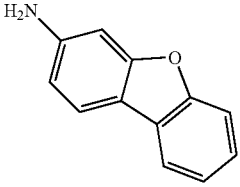 [SMILES: Nc1ccc2c(c1)oc1ccccc12] | 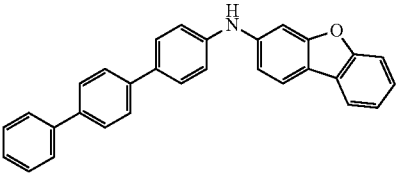 [SMILES: c1ccc(-c2ccc(-c3ccc(Nc4ccc5c(c4)oc4ccccc45)cc3)cc2)cc1] IM D-5 | 79.5 |
| | 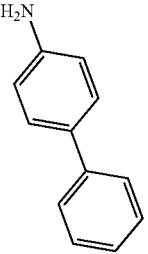 | 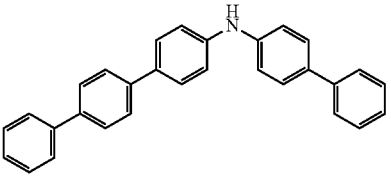 [SMILES: c1ccc(-c2ccc(Nc3ccc(-c4ccc(-c5ccccc5)cc4)cc3)cc2)cc1] IM D-6 | 80.8 |
| 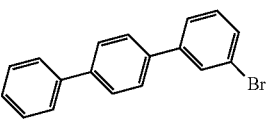 [SMILES: Brc1cccc(-c2ccc(-c3ccccc3)cc2)c1] | 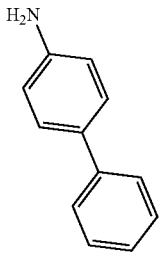 | 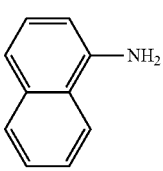 [SMILES: Nc1cccc2ccccc12] IM D-7 | 79.4 |
| | 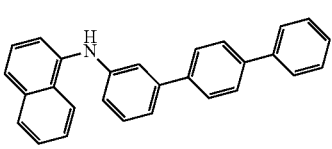 [SMILES: c1ccc(-c2ccc(-c3cccc(Nc4cccc5ccccc45)c3)cc2)cc1] |  IM D-8 | 78.6 |

TABLE 7-continued
| Raw material 8 | Raw material 9 | IM D-x | Yield/% |
|---|---|---|---|
| 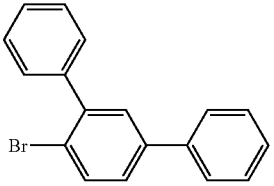 [SMILES: Brc1ccc(-c2ccccc2)cc1-c1ccccc1] | 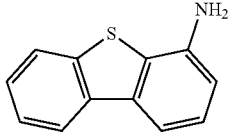 [SMILES: Nc1cccc2c1sc1ccccc12] | 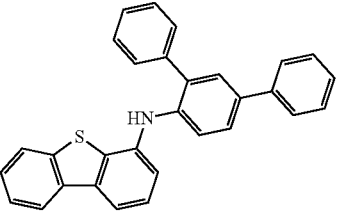 [SMILES: c1ccc(-c2ccc(Nc3cccc4c3sc3ccccc34)c(-c3ccccc3)c2)cc1]<br>IM D-9 | 77.9 |
| | 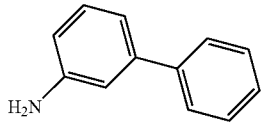 [SMILES: Nc1cccc(-c2ccccc2)c1] | 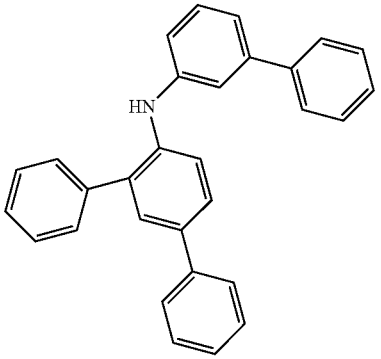 [SMILES: c1ccc(-c2cccc(Nc3ccc(-c4ccccc4)cc3-c3ccccc3)c2)cc1]<br>IM D-45 | 76.7 |
| | 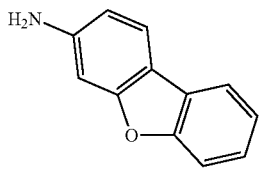 [SMILES: Nc1ccc2c(c1)oc1ccccc12] | 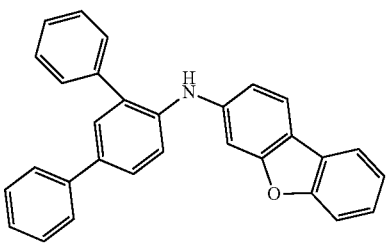 [SMILES: c1ccc(-c2ccc(Nc3ccc4c(c3)oc3ccccc34)c(-c3ccccc3)c2)cc1]<br>IM D-46 | 77.3 |
| 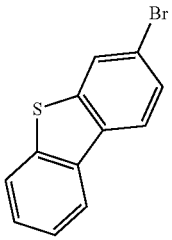 [SMILES: Brc1ccc2c(c1)sc1ccccc12] | 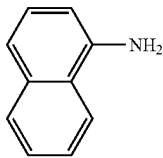 [SMILES: Nc1cccc2ccccc12] | 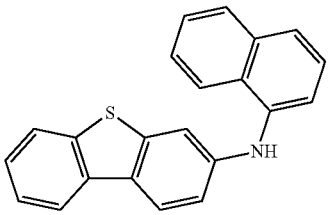 [SMILES: c1ccc2c(Nc3ccc4c(c3)sc3ccccc34)cccc2c1]<br>IM D-13 | 79.7 |
| | 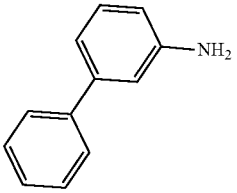 [SMILES: Nc1cccc(-c2ccccc2)c1] | 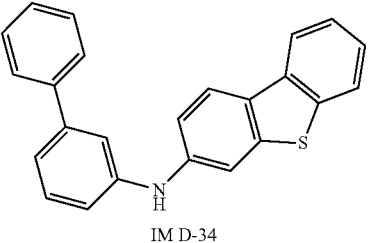 [SMILES: c1ccc(-c2cccc(Nc3ccc4c(c3)sc3ccccc34)c2)cc1]<br>IM D-34 | 76.9 |

TABLE 7-continued
| Raw material 8 | Raw material 9 | IM D-x | Yield/% |
|---|---|---|---|
| | 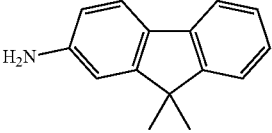 [SMILES: CC1(C)c2ccccc2-c2ccc(N)cc21] | 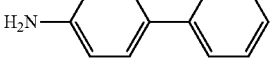<br>IM D-39 | 74.6 |
| 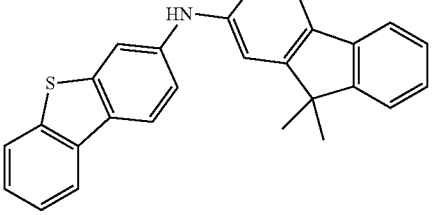 | 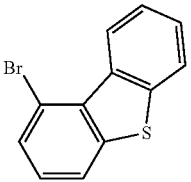 [SMILES: Brc1cccc2sc3ccccc3c12] | 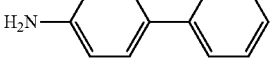<br>IM D-23 | 75.4 |
| 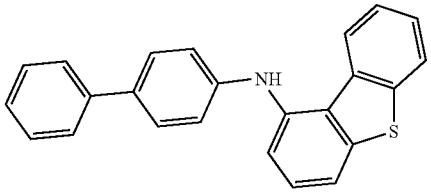 | 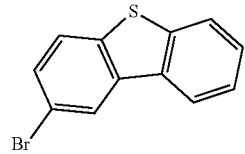 [SMILES: Brc1ccc2sc3ccccc3c2c1] | 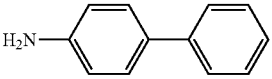<br>IM D-24 | 79.1 |
| | 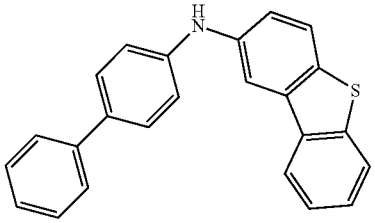 | 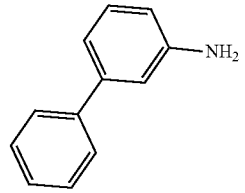 [SMILES: Nc1cccc(-c2ccccc2)c1]<br>IM D-33 | 79.2 |
| 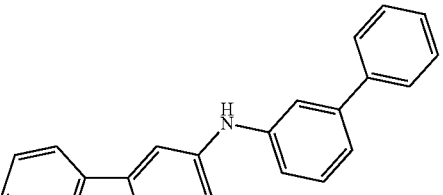 | 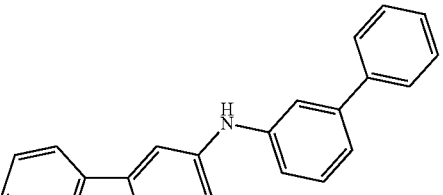 | 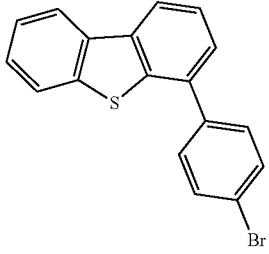 [SMILES: Brc1ccc(-c2cccc3c2sc2ccccc23)cc1]<br>IM D-36 | 75.4 |

TABLE 7-continued
| Raw material 8 | Raw material 9 | IM D-x | Yield/% |
|---|---|---|---|
|  |  | <br>IM D-55 | 67.9 |
|  |  | <br>IM D-14 | 80.5 |
|  |  | 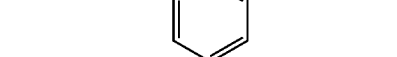<br>IM D-49 | 79.6 |
| |  | 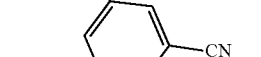<br>IM D-17<br>IM D-17 | 81.8 |

TABLE 7-continued
| Raw material 8 | Raw material 9 | IM D-x | Yield/% |
|---|---|---|---|
| | 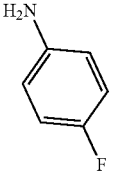 | 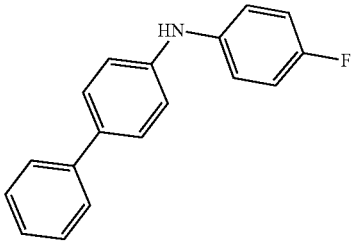 IM D-50 | 80.9 |
| | 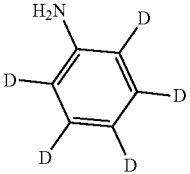 | 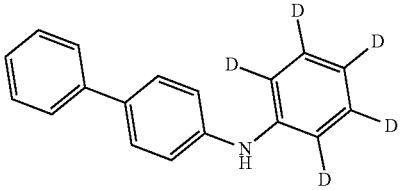 [SMILES: [2H]c1c([2H])c([2H])c(Nc2ccc(-c3ccccc3)cc2)c([2H])c1[2H]] IM D-53 | 70.8 |
| 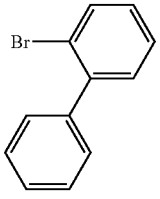 [SMILES: Brc1ccccc1-c1ccccc1] | 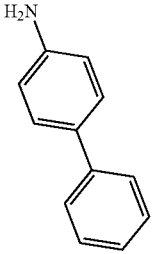 [SMILES: Nc1ccc(-c2ccccc2)cc1] | 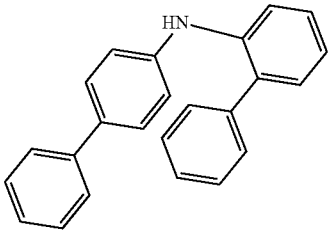 [SMILES: c1ccc(-c2ccc(Nc3ccccc3-c3ccccc3)cc2)cc1] IM D-21 | 78.3 |
| 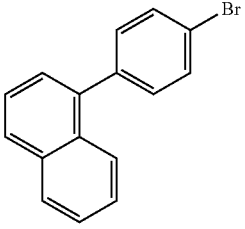 [SMILES: Brc1ccc(-c2cccc3ccccc23)cc1] | | 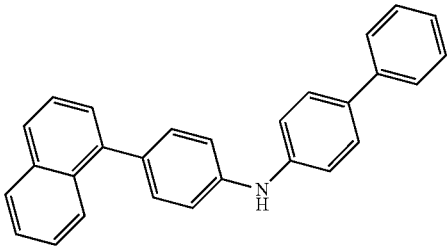 [SMILES: c1ccc(-c2ccc(Nc3ccc(-c4cccc5ccccc45)cc3)cc2)cc1] IM D-16 | 78.7 |
| 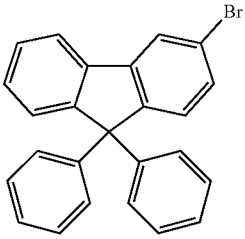 [SMILES: Brc1ccc2c(c1)-c1ccccc1C2(c1ccccc1)c1ccccc1] | | 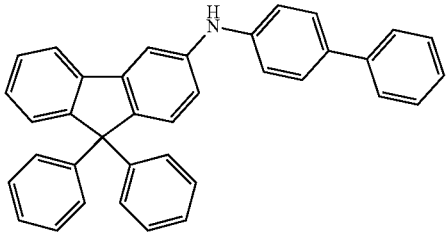 [SMILES: c1ccc(-c2ccc(Nc3ccc4c(c3)-c3ccccc3C4(c3ccccc3)c3ccccc3)cc2)cc1] IM D-15 | 73.5 |

TABLE 7-continued
| Raw material 8 | Raw material 9 | IM D-x | Yield/% |
|---|---|---|---|
| 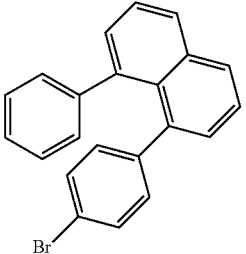 [SMILES: Brc1ccc(-c2cccc3cccc(-c4ccccc4)c23)cc1] | | 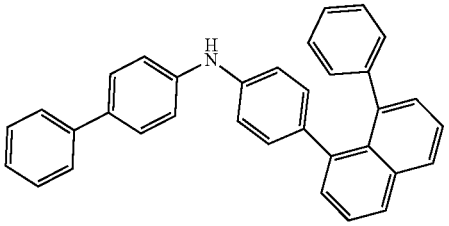 [SMILES: c1ccc(-c2ccc(Nc3ccc(-c4cccc5cccc(-c6ccccc6)c45)cc3)cc2)cc1]<br>IM D-51 | 78.2 |
| 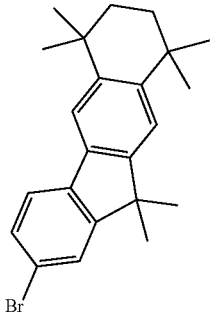 [SMILES: CC1(C)CCC(C)(C)c2cc3c(cc21)-c1ccc(Br)cc1C3(C)C] | | 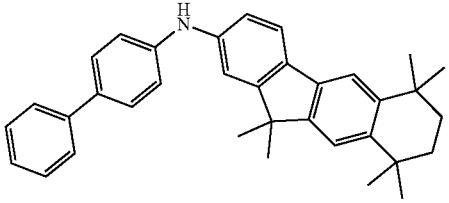 [SMILES: CC1(C)CCC(C)(C)c2cc3c(cc21)-c1ccc(Nc2ccc(-c4ccccc4)cc2)cc1C3(C)C]<br>IM D-52 | 76.9 |
| 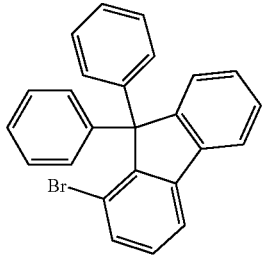 [SMILES: Brc1cccc2c1C(c1ccccc1)(c1ccccc1)c1ccccc1-2] | | 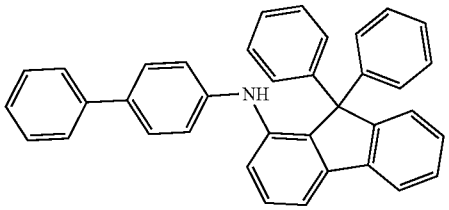 [SMILES: c1ccc(-c2ccc(Nc3cccc4c3C(c3ccccc3)(c3ccccc3)c3ccccc3-4)cc2)cc1]<br>IM D-18 | 73.7 |
| 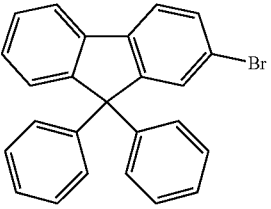 [SMILES: Brc1ccc2c(c1)C(c1ccccc1)(c1ccccc1)c1ccccc1-2] | | 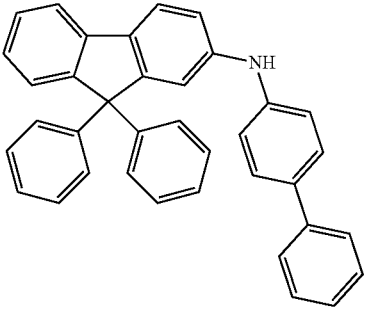 [SMILES: c1ccc(-c2ccc(Nc3ccc4c(c3)C(c3ccccc3)(c3ccccc3)c3ccccc3-4)cc2)cc1]<br>IM D-19 | 72.6 |

TABLE 7-continued

| Raw material 8 | Raw material 9 | IM D-x | Yield/% |
|---|---|---|---|
| (structure) | (structure) | IM D-32 | 72.4 |
| (structure) | (structure) | IM D-20 | 74.1 |
| (structure) | (structure) | IM D-26 | 74.5 |
| (structure) | (structure) | IM D-40 | 71.5 |
| (structure) | | IM D-41 | 72.7 |

TABLE 7-continued

| Raw material 8 | Raw material 9 | IM D-x | Yield/% |
|---|---|---|---|
| (2-bromotriphenylene) | (dibenzothiophen-2-amine) | IM D-27 | 75.2 |
| (2-bromodibenzofuran) | (9,9-dimethyl-9H-fluoren-2-amine) | IM D-28 | 73.9 |
| | (9,9-dimethyl-9H-fluoren-1-amine) | IM D-29 | 72.7 |
| | (dibenzothiophen-3-amine) | IM D-30 | 73.4 |
| | (2-aminobiphenyl) | IM D-31 | 75.6 |

TABLE 7-continued
| Raw material 8 | Raw material 9 | IM D-x | Yield/% |
|---|---|---|---|
| | 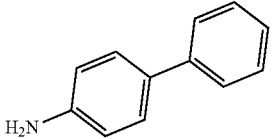 [SMILES: Nc1ccc(-c2ccccc2)cc1] | 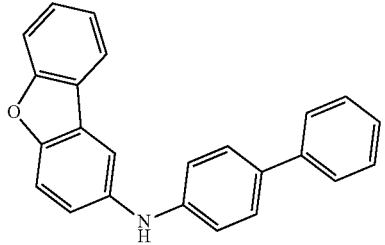 [SMILES: c1ccc(-c2ccc(Nc3ccc4oc5ccccc5c4c3)cc2)cc1]<br>IM D-47 | 75.4 |
| 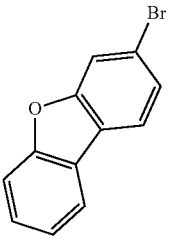 [SMILES: Brc1ccc2c(c1)oc1ccccc12] | 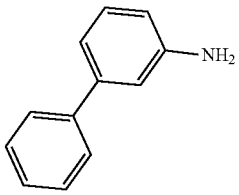 [SMILES: Nc1cccc(-c2ccccc2)c1] | 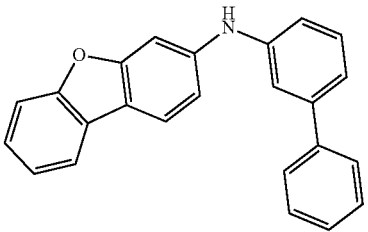<br>IM D-35 | 77.4 |
| 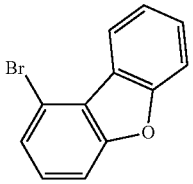 [SMILES: Brc1cccc2oc3ccccc3c12] | 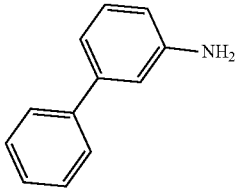 [SMILES: Nc1cccc(-c2ccccc2)c1] | 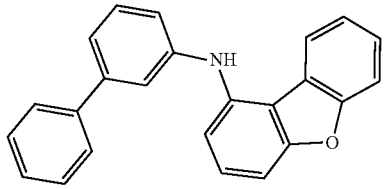<br>IM D-10 | 76.5 |
| | 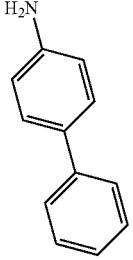 [SMILES: Nc1ccc(-c2ccccc2)cc1] | 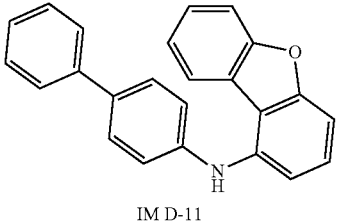<br>IM D-11 | 75.2 |
| 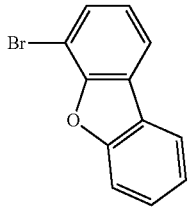 [SMILES: Brc1cccc2c1oc1ccccc12] | 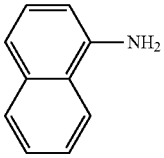 [SMILES: Nc1cccc2ccccc12] | 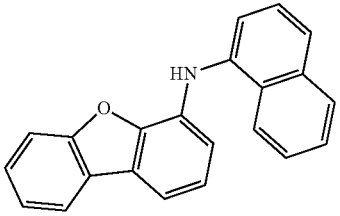<br>IM D-12 | 76.4 |

TABLE 7-continued

| Raw material 8 | Raw material 9 | IM D-x | Yield/% |
|---|---|---|---|
| 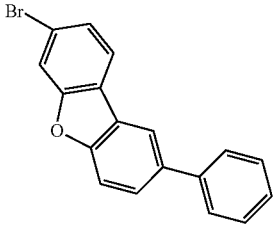 [SMILES: Brc1ccc2c(c1)oc1ccc(-c3ccccc3)cc12] | | 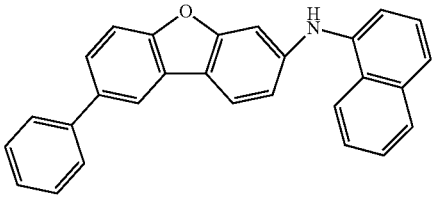 [SMILES: c1ccc(-c2ccc3oc4cc(Nc5cccc6ccccc56)ccc4c3c2)cc1] IM D-54 | 67.8 |

8. Synthesis of Compound 4

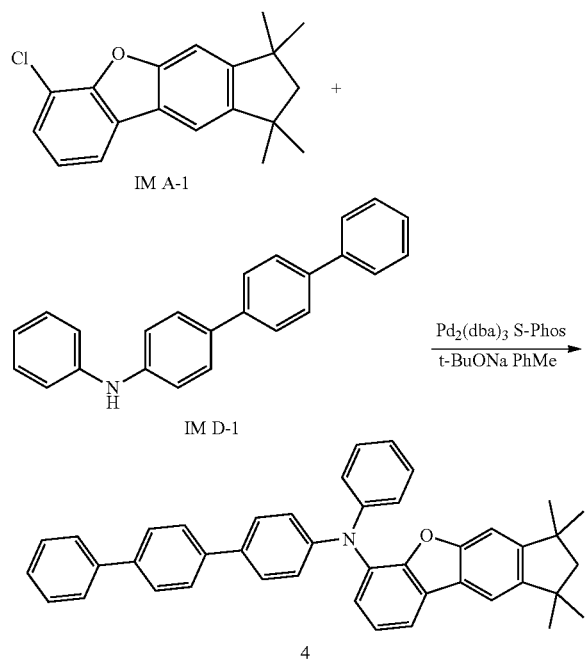

Under a nitrogen atmosphere, IM A-1 (5 g, 16.7 mmol), IM D-1 (5.4 g, 16.7 mmol), and 50 mL of toluene were added to a 100 mL of three-necked flask, the mixture was heated to 70° C., sodium tert-butoxide (2.4 g, 25.05 mmol), S-Phos (0.14 g, 0.33 mmol), and $Pd_2(dba)_3$ (0.16 g, 0.17 mmol) were sequentially added, then heating was performed to 110° C., a reaction was carried out under reflux for 2 h, cooling was performed to room temperature, the reaction solution was washed with water for three times, drying was performed by using anhydrous magnesium sulfate, the dried material was allowed to stand for 30 min, suction filtration was performed, concentration was performed under reduced pressure, the concentrated material was allowed to pass through a chromatographic column for column chromatography, and finally recrystallization was performed by using n-heptane to give a compound 4 (5.5 g, yield: 56.2%); mass spectrum (m/z)=584.29 $[M+H]^+$.

Compounds X listed in Table 8 were synthesized with reference to the method for the compound 4 except that a raw material 10 was used instead of IM A-1 and a raw material 11 was used instead of IM D-1, where the main raw materials used, compounds X synthesized and their yields and mass spectra are as shown in Table 8.

TABLE 8

| Raw material 10 | Raw material 11 | Compound X | Yield/% | Mass spectrum (m/z) [M + H]+ |
|---|---|---|---|---|
| IM A-1 | IMD-12 | 5 | 51.3 | 572.25 |
| | IMD-49 | 373 | 67.7 | 533.25 |

TABLE 8-continued
| Raw material 10 | Raw material 11 | Compound X | Yield/% | Mass spectrum (m/z)/ [M + H]+ |
|---|---|---|---|---|
| | 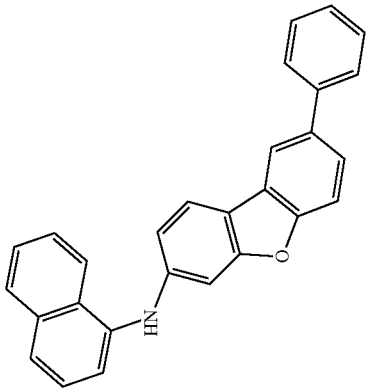 IMD-54 | 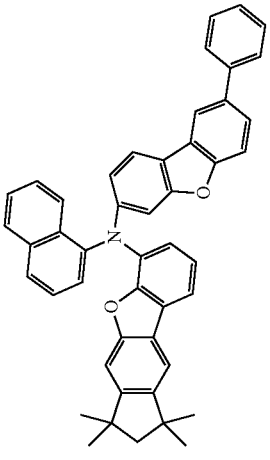 399 | 58.4 | 648.28 |
| 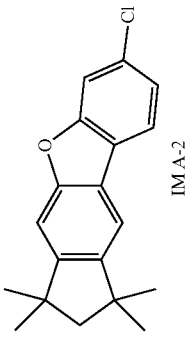 IMA-2 | 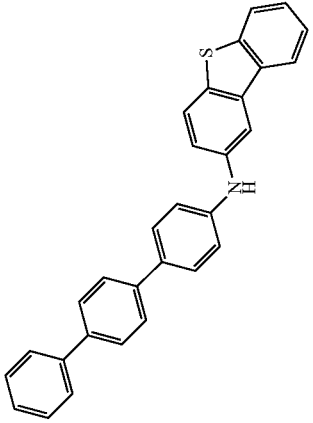 IMD-3 | 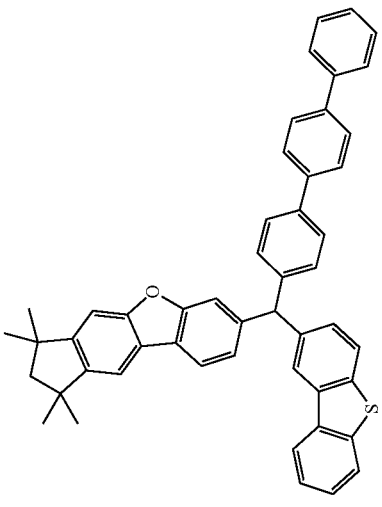 6 | 53.6 | 690.28 |

TABLE 8-continued

| Raw material 10 | Raw material 11 | Compound X | Yield/% | Mass spectrum (m/z)/ [M + H]+ |
|---|---|---|---|---|
| IMA-3 | Raw material 11 structure | Compound 13 | 53.8 | 660.32 |
| IMD-7 | IMD-15 | Compound 7 | 52.9 | 748.35 |

TABLE 8-continued
| Raw material 10 | Raw material 11 | Compound X | Yield/% | Mass spectrum (m/z)/ [M + H]+ |
|---|---|---|---|---|
| | 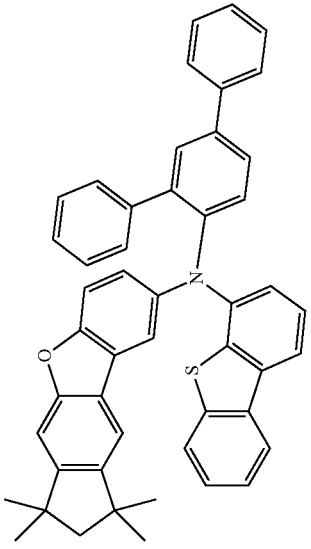 IMD-9 | 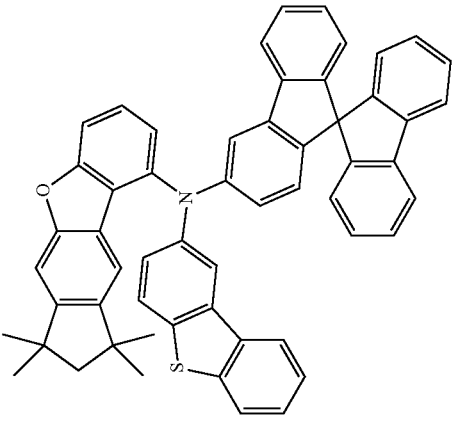 12 | 53.4 | 690.28 |
| 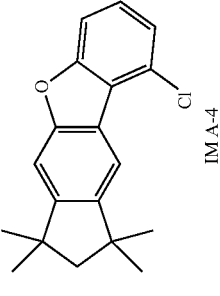 IMA-4 | 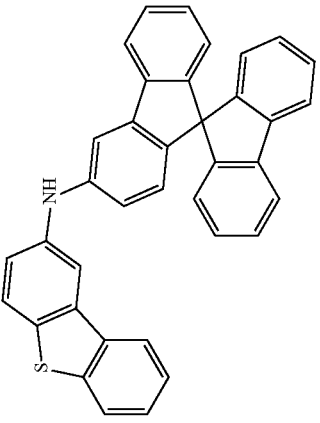 IMD-26 | 8 | 56.1 | 776.29 |

TABLE 8-continued

| Raw material 10 | Raw material 11 | Compound X | Yield/% | Mass spectrum (m/z)/ [M + H]+ |
|---|---|---|---|---|
| | IMD-10 | 16 | 52.9 | 598.27 |
| IMB-1 | IMD-16 | 49 | 54.1 | 784.39 |

TABLE 8-continued
| Raw material 10 | Raw material 11 | Compound X | Yield/% | Mass spectrum (m/z)/ [M + H]+ |
|---|---|---|---|---|
| 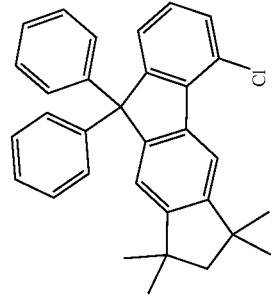 IM B-2 | 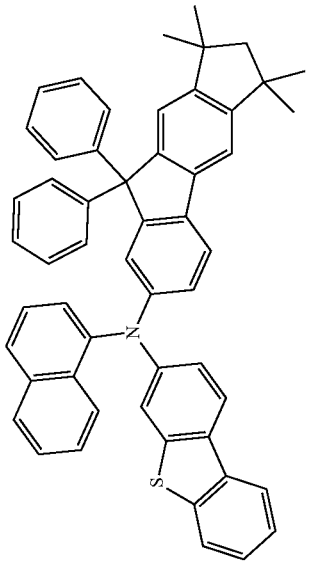 IM D-13 | 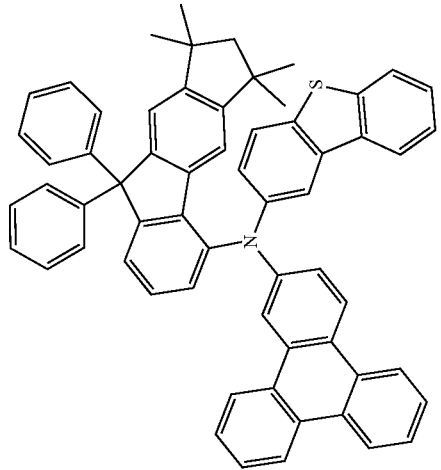 56 | 53.8 | 738.31 |
| | 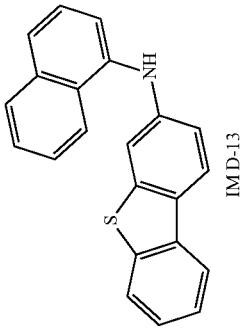 IM D-27 | 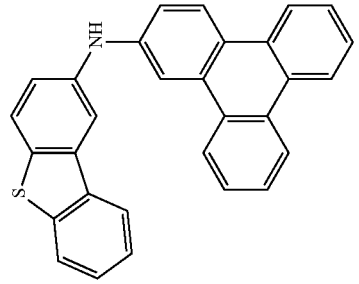 60 | 52.5 | 838.34 |

TABLE 8-continued
| Raw material 10 | Raw material 11 | Compound X | Yield/ % | Mass spectrum (m/z)/ [M + H]+ |
|---|---|---|---|---|
| 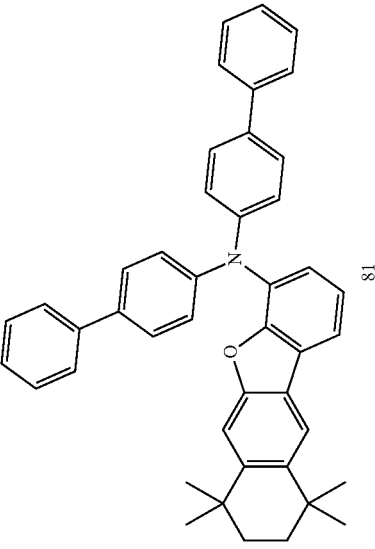 IMD-28 | 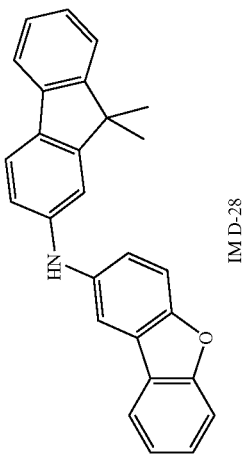 62 | 54.2 | 788.38 |
| 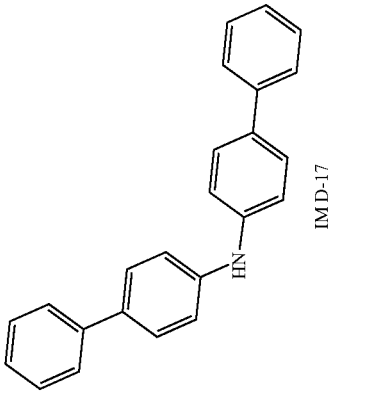 IMA-5 | 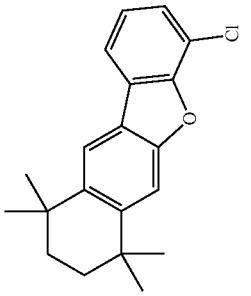 IMD-17 | 81 | 56.3 | 598.30 |

TABLE 8-continued

| Raw material 10 | Raw material 11 | Compound X | Yield/% | Mass spectrum (m/z) [M + H]+ |
|---|---|---|---|---|
| IM A-7 | IM D-18 | 86 | 49.8 | 762.37 |
| IM A-8 | IM D-19 | 96 | 51.6 | 762.37 |

TABLE 8-continued

| Raw material 10 | Raw material 11 | Compound X | Yield/% | Mass spectrum (m/z)/ [M + H]+ |
|---|---|---|---|---|
| IMC-1 | IMD-36 | 114 | 53.4 | 704.33 |
| IMC-2 | IMD-4 | 117 | 55.2 | 806.37 |

TABLE 8-continued
| Raw material 10 | Raw material 11 | Compound X | Yield/% | Mass spectrum (m/z)/ [M + H]+ |
|---|---|---|---|---|
| 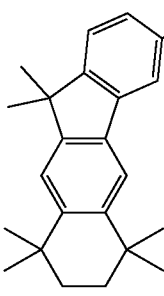 IMC-3 | 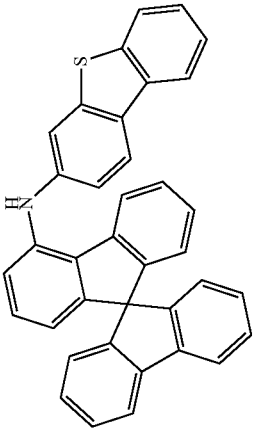 IMD-40 | 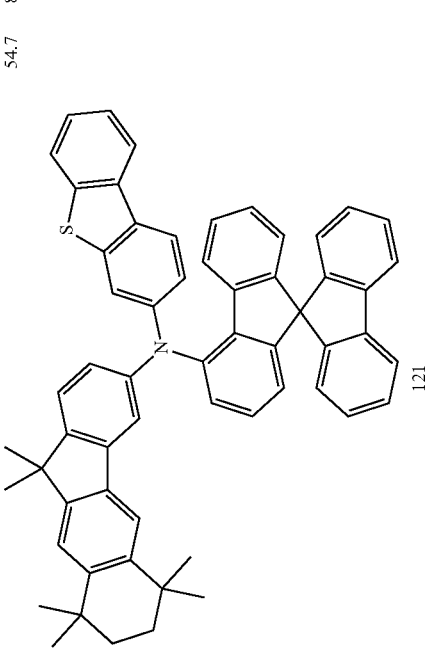 121 | 54.7 | 816.36 |
| 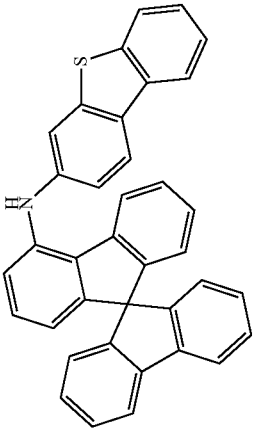 IMC-4 | 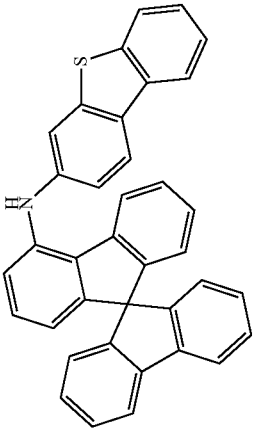 IMD-20 | 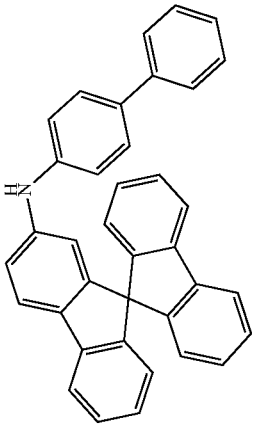 125 | 53.9 | 786.40 |

TABLE 8-continued

| Raw material 10 | Raw material 11 | Compound X | Yield/% | Mass spectrum (m/z) [M + H]+ |
|---|---|---|---|---|
| IMB-4 | IMD-29 | 126 | 54.8 | 678.37 |
| IMB-4 | IMD-17 | 130 | 49.7 | 748.39 |

TABLE 8-continued
| Raw material 10 | Raw material 11 | Compound X | Yield/% | Mass spectrum (m/z)/ [M + H]+ |
|---|---|---|---|---|
| 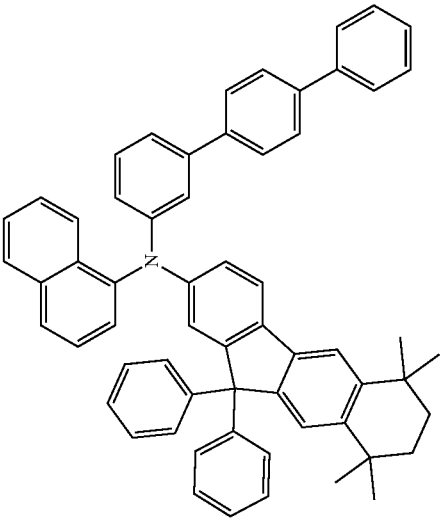 IMB-3 | 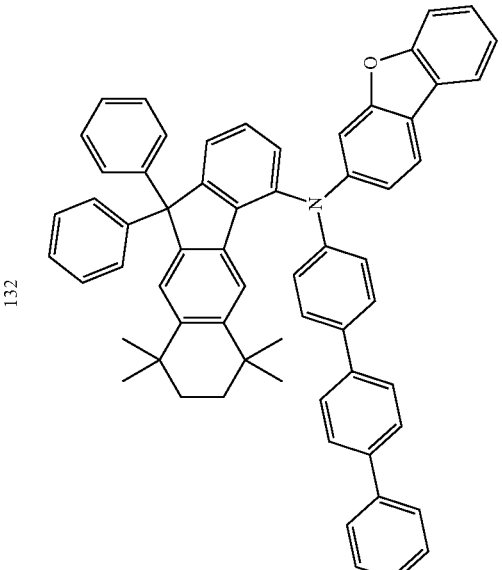 IMD-8 | 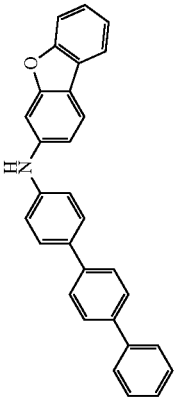 132 | 48.8 | 798.40 |
| 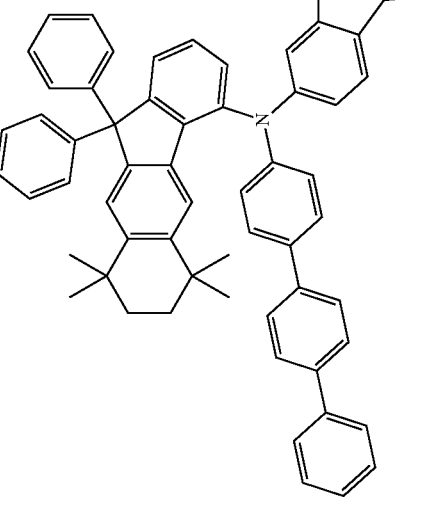 IMB-3 | 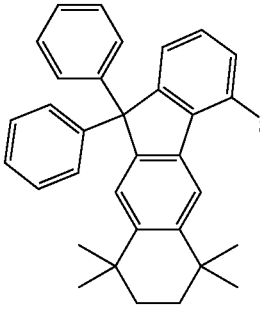 IMD-5 | 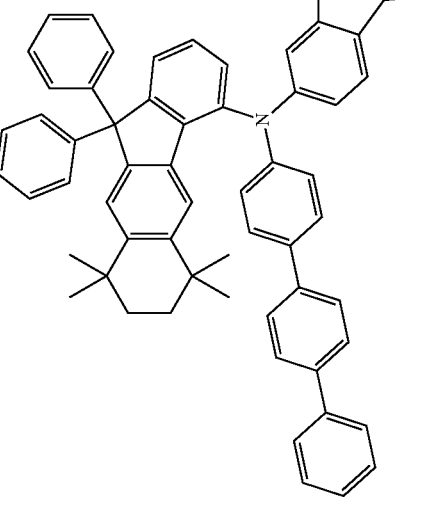 135 | 53.3 | 838.40 |

TABLE 8-continued
| Raw material 10 | Raw material 11 | Compound X | Yield/% | Mass spectrum (m/z) [M + H]+ |
|---|---|---|---|---|
| 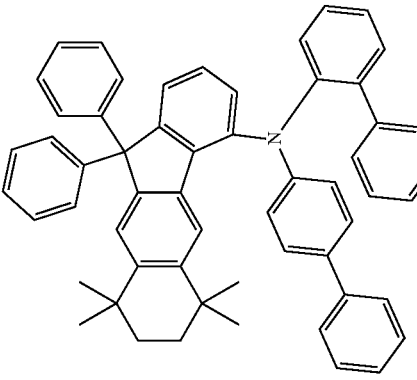 IMD-21 | 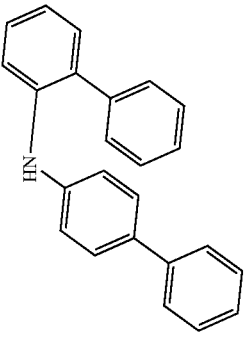 | 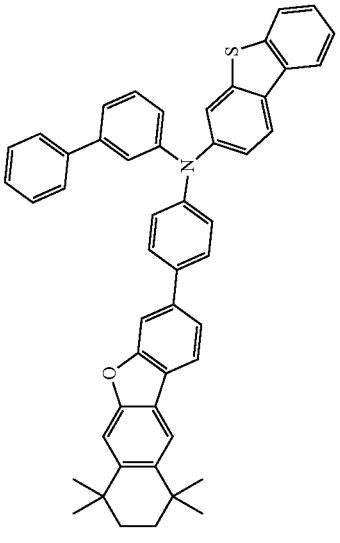 134 | 52.8 | 748.39 |
| 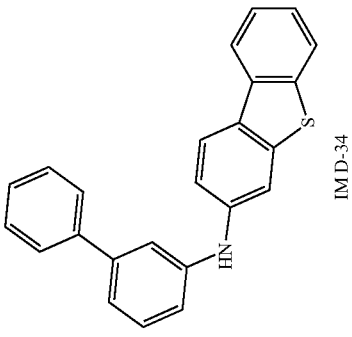 IMF-1 | 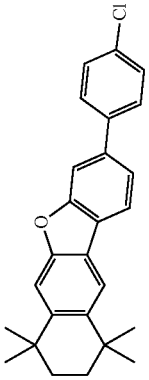 IMD-34 | 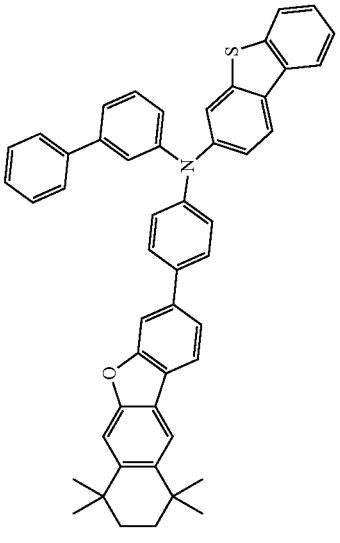 156 | 53.4 | 704.29 |

TABLE 8-continued
| Raw material 10 | Raw material 11 | Compound X | Yield/% | Mass spectrum (m/z)/ [M + H]+ |
|---|---|---|---|---|
| 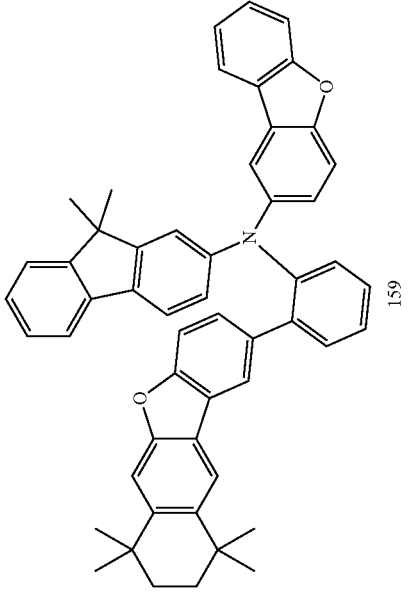 IM F-2 | 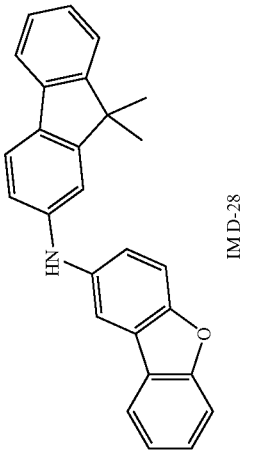 IM D-28 | 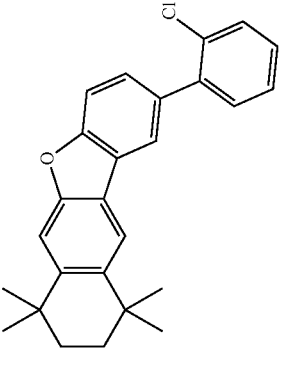 159 | 54.8 | 728.35 |
| | 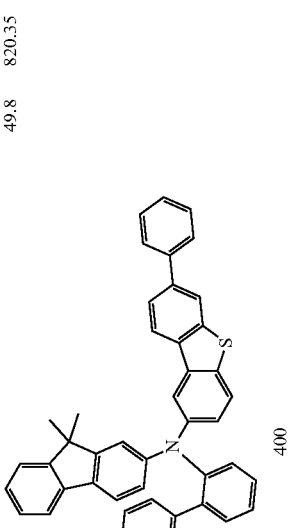 IM D-55 | 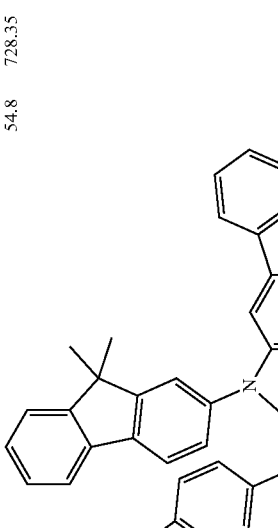 400 | 49.8 | 820.35 |

TABLE 8-continued
| Raw material 10 | Raw material 11 | Compound X | Yield/% | Mass spectrum (m/z)/ [M + H]+ |
|---|---|---|---|---|
| 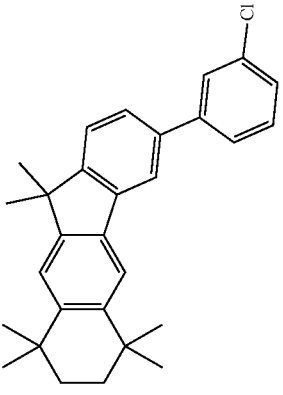 IM F-3 | 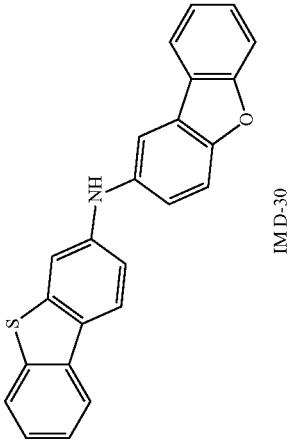 IM D-30 | 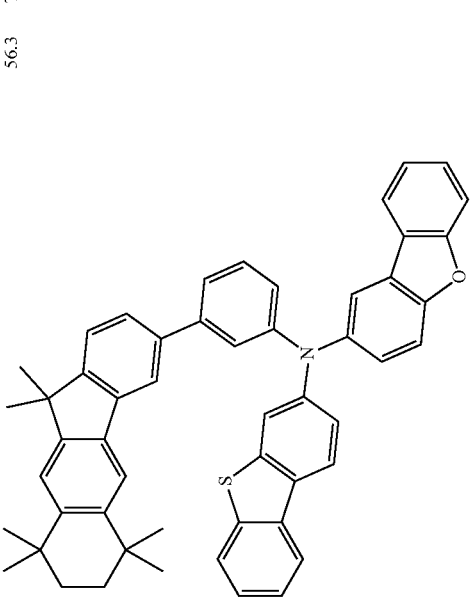 184 | 56.3 | 744.32 |
| 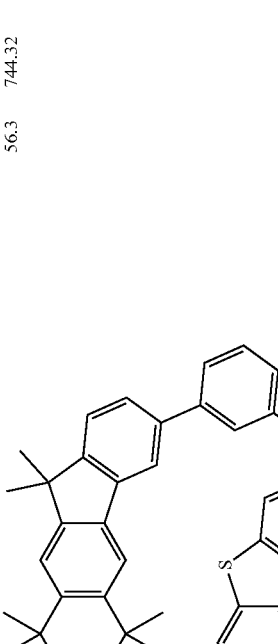 IM F-5 | 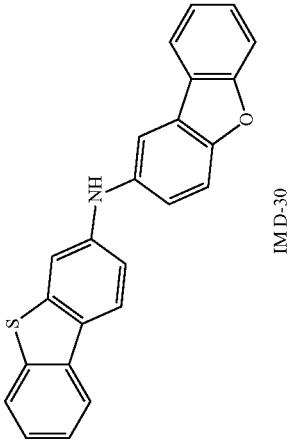 IM D-31 | 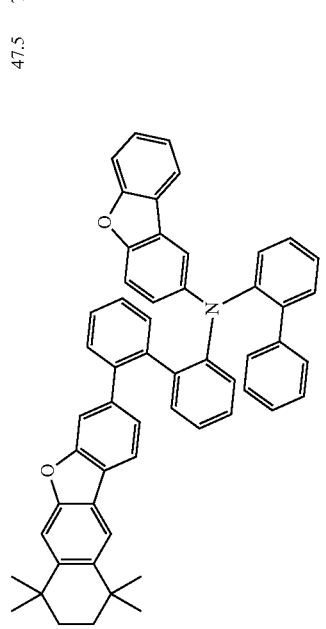 215 | 47.5 | 764.35 |

TABLE 8-continued
| Raw material 10 | Raw material 11 | Compound X | Yield/% | Mass spectrum (m/z)/ [M + H]+ |
|---|---|---|---|---|
| 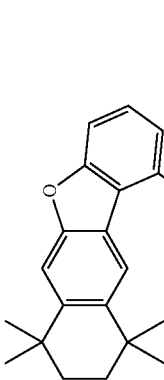 IMF-6 | 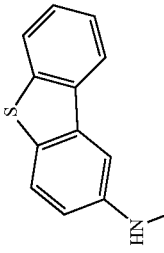 IMD-24 | 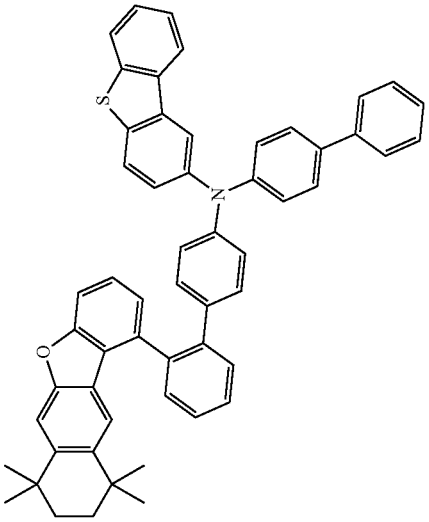 223 | 50.5 | 780.32 |
| 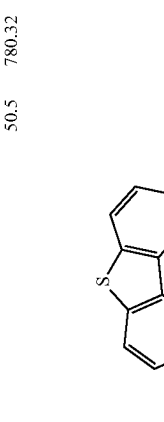 IMF-7 | 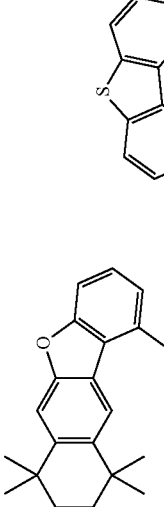 IMD-2 | 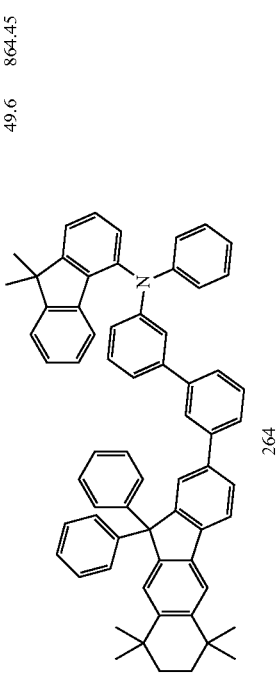 264 | 49.6 | 864.45 |

TABLE 8-continued

| Raw material 10 | Raw material 11 | Compound X | Yield/% | Mass spectrum (m/z) [M + H]+ |
|---|---|---|---|---|
| IM F-8 | IM D-35 | 266 | 53.2 | 900.41 |
| IM F-10 | IM D-11 | 293 | 50.7 | 724.31 |

TABLE 8-continued
| Raw material 10 | Raw material 11 | Compound X | Yield/ % | Mass spectrum (m/z)/ [M + H]+ |
|---|---|---|---|---|
| IM F-11 | IM D-39 | 294 | 52.5 | 780.32 |
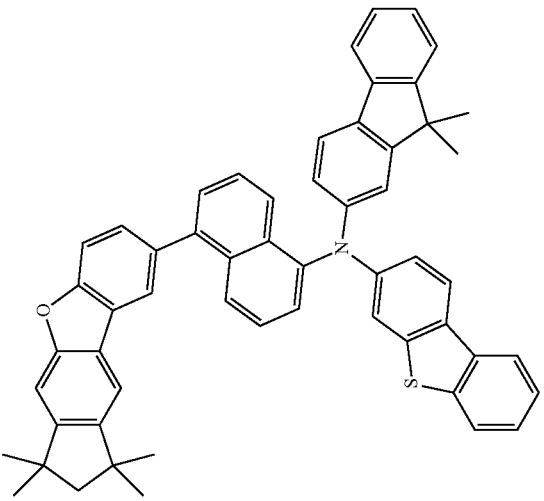

TABLE 8-continued

| Raw material 10 | Raw material 11 | Compound X | Yield/ % | Mass spectrum (m/z)/ [M + H]+ |
|---|---|---|---|---|
| IMF-12 | IMD-6 | 295 | 54.4 | 800.38 |

TABLE 8-continued

| Raw material 10 | Raw material 11 | Compound X | Yield/% | Mass spectrum (m/z)/ [M + H]+ |
|---|---|---|---|---|
| IM F-13 | IM D-14 | 300 | 56.7 | 698.33 |
| IM F-14 | IM D-41 | 318 | 46.8 | 942.41 |

TABLE 8-continued
| Raw material 10 | Raw material 11 | Compound X | Yield/% | Mass spectrum (m/z)/ [M + H]+ |
|---|---|---|---|---|
| 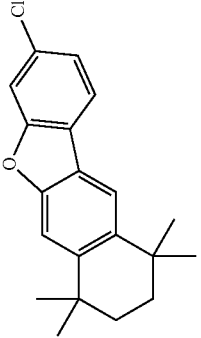<br>IM A-6 | 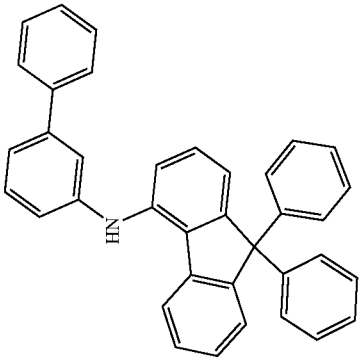<br>IM D-32 | 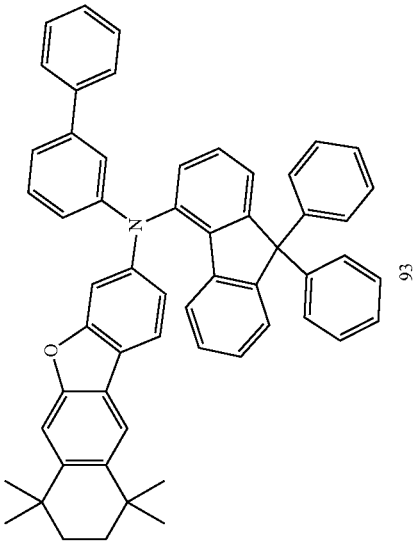<br>93 | 50.3 | 762.37 |
| | 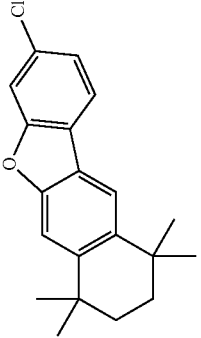<br>IM D-47 | 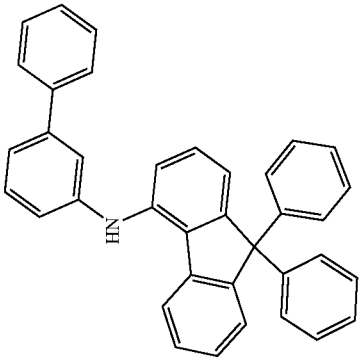<br>364 | 50.7 | 612.28 |

TABLE 8-continued
| Raw material 10 | Raw material 11 | Compound X | Yield/% | Mass spectrum (m/z) [M + H]+ |
|---|---|---|---|---|
| 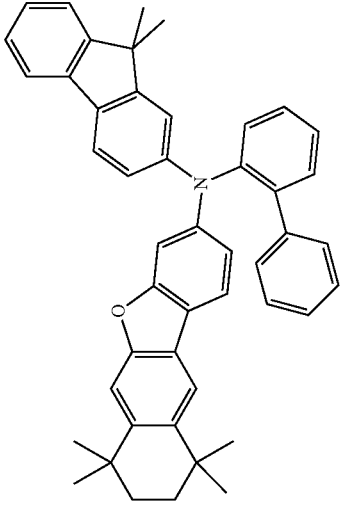 IM D-42 | | 365 | 61.2 | 638.33 |
| 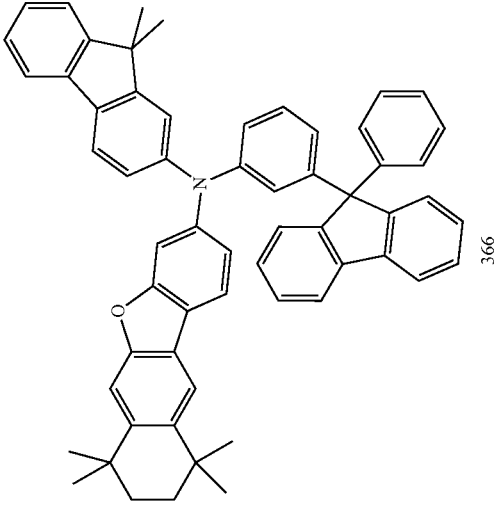 IM D-43 | | 366 | 54.9 | 802.40 |

TABLE 8-continued
| Raw material 10 | Raw material 11 | Compound X | Yield/% | Mass spectrum (m/z) [M + H]+ |
|---|---|---|---|---|
| 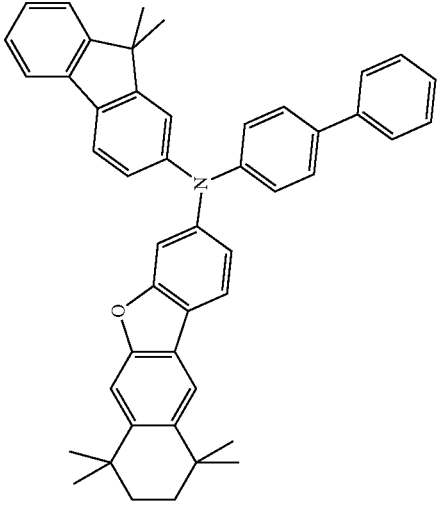 IMD-25 | 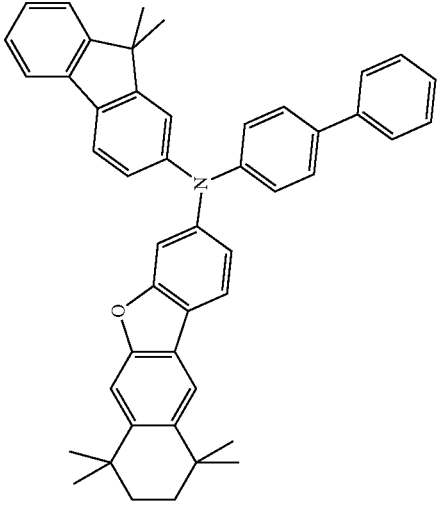 | 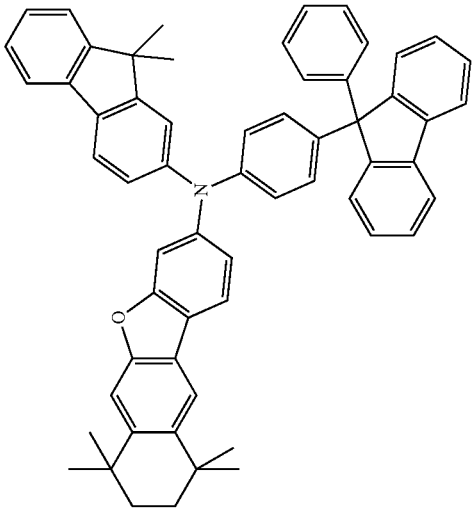 367 | 58.1 | 638.33 |
| 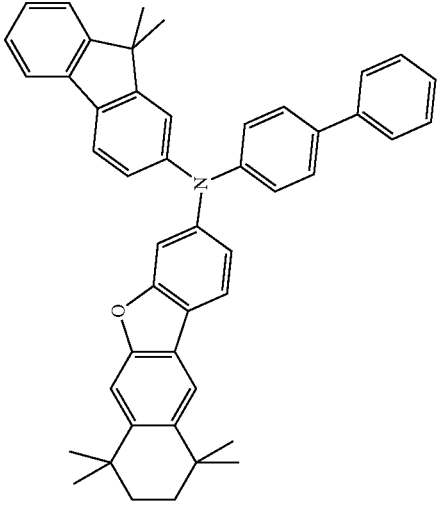 IMD-44 | 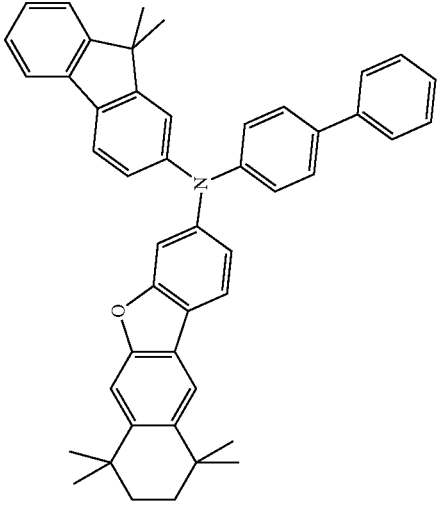 | 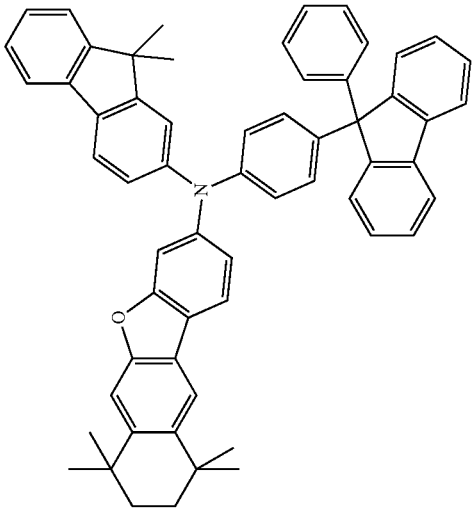 368 | 64.2 | 802.40 |

TABLE 8-continued

| Raw material 10 | Raw material 11 | Compound X | Yield/% | Mass spectrum (m/z)/ [M + H]+ |
|---|---|---|---|---|
| | IMD-45 | 369 | 55.7 | 674.33 |
| | IMD-46 | 372 | 61.2 | 688.31 |

TABLE 8-continued

| Raw material 10 | Raw material 11 | Compound X | Yield/% | Mass spectrum (m/z)/ [M + H]+ |
|---|---|---|---|---|
| | IMD-51 | 379 | 52.4 | 724.35 |

TABLE 8-continued

| Raw material 10 | Raw material 11 | Compound X | Yield/% | Mass spectrum (m/z) [M + H]+ |
|---|---|---|---|---|
| | IMD-52 | 389 | 51.9 | 748.44 |
| | IMD-53 | 389 | 50.7 | 527.30 |

TABLE 8-continued
| Raw material 10 | Raw material 11 | Compound X | Yield/% | Mass spectrum (m/z)/ [M + H]+ |
|---|---|---|---|---|
| 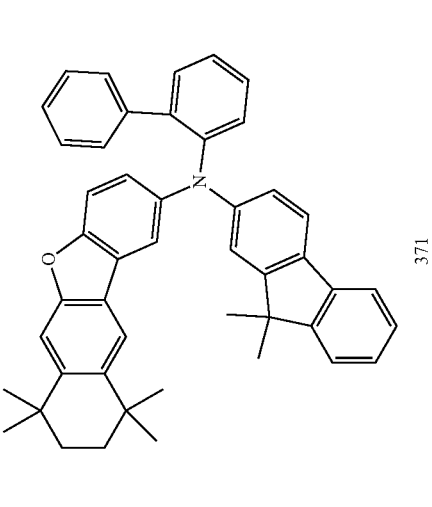 IM A-7 | 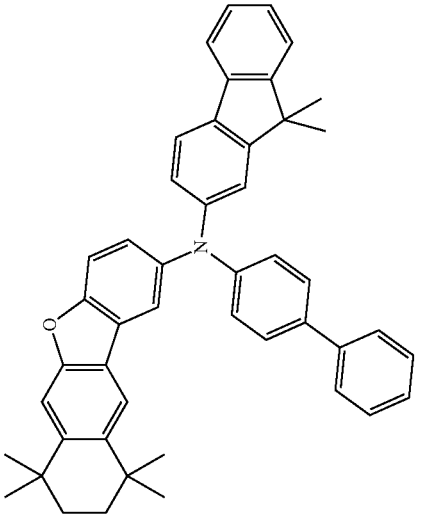 IM D-25 | 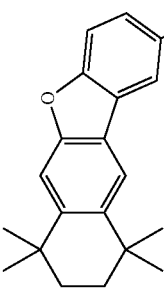 370 | 58.9 | 638.33 |
| | 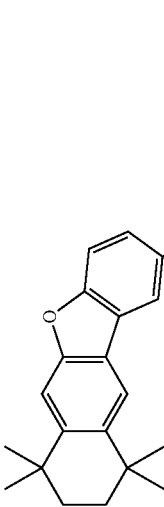 IM D-42 | 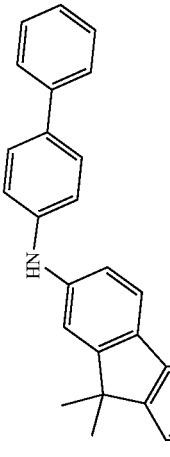 371 | 59.3 | 638.33 |

TABLE 8-continued

| Raw material 10 | Raw material 11 | Compound X | Yield/% | Mass spectrum (m/z) [M + H]+ |
|---|---|---|---|---|
| IMD-50 | | 374 | 46.8 | 540.36 |
| IMYD-1 | | 101 | 47.4 | 654.31 |

TABLE 8-continued
| Raw material 10 | Raw material 11 | Compound X | Yield/% | Mass spectrum (m/z)/[M + H]+ |
|---|---|---|---|---|
| 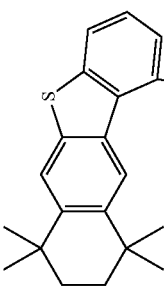 IMYD-2 | 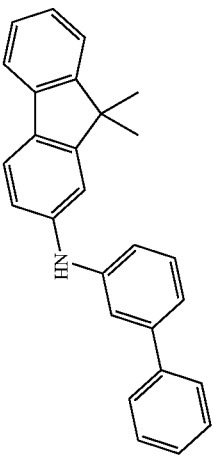 | 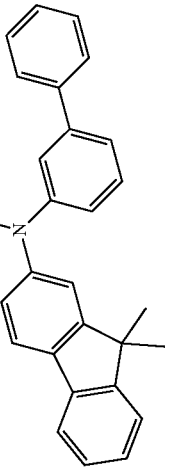 112 | 46.9 | 654.31 |
| 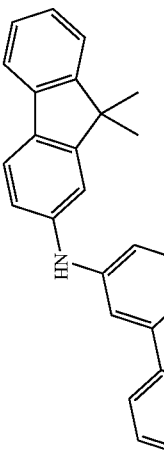 IMB-5 | 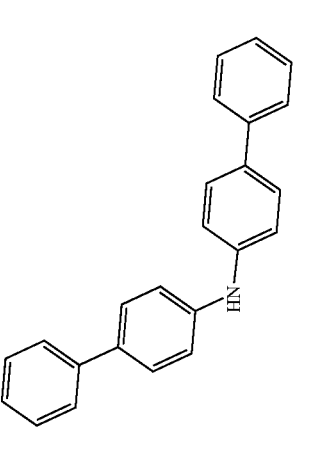 | 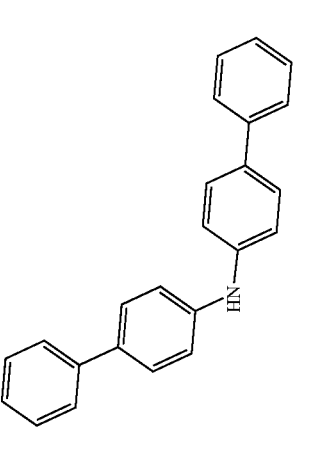 363 | 47.1 | 746.37 |

NMR data or the compound 4:

$^1$H-NMR (CDCl$_3$, 400 MHz): 7.66-7.51 (m, 13H), 7.43-7.21 (m, 4H), 6.65-6.47 (m, 6H), 2.04 (s, 2H), 1.43-1.40 (d, 12H).

NMR data for a compound 81:

$^1$H-NMR (CDCl$_3$, 400 MHz): 7.63-7.38 (m, 16H), 7.25-7.21 (m, 1H), 7.15 (s, 1H), 6.71-6.69 (d, 1H), 6.50-6.48 (d, 4H), 1.94-1.86 (m, 2H), 1.75-1.66 (m, 2H), 1.47-1.44 (d, 12H).

Example 1: Red Organic Electroluminescent Device

A 1500 Å ITO substrate (manufactured by Corning) was cut into a size of 40 mm (length)×40 mm (width)×0.7 mm (height) to be prepared into an experimental substrate with an anode and an insulating layer pattern by adopting a photoetching process, and surface treatment was performed by utilizing ultraviolet ozone and O$_2$:N$_2$ plasma to increase the work function of the anode, and the surface of the ITO substrate was cleaned with an organic solvent to remove impurities and oil on the surface of the ITO substrate.

First, F4-TCNQ was evaporated on the anode of the experimental substrate by a vacuum evaporation method to form a hole injection layer having a thickness of 100 Å, and NPB was evaporated on the hole injection layer to form a hole transporting layer having a thickness of 1150 Å.

The compound 4 of the present application was vacuum evaporated on the hole transporting layer to form a hole adjusting layer having a thickness of 750 Å.

CBP and Ir(piq)$_2$(acac) were evaporated on the hole adjusting layer at a weight ratio of 98%:2% to form an organic luminescence layer having a thickness of 400 Å.

ET-01 and LiQ were evaporated on the organic luminescence layer at a weight ratio of 1:1 to form an electron transporting layer having a thickness of 300 Å, Yb was evaporated on the electron transporting layer to form an electron injection layer having a thickness of 15 Å, and then magnesium (Mg) and silver (Ag) were vacuum evaporated on the electron injection layer at an evaporation rate of 1:9 to form a cathode having a thickness of 125 Å.

Finally, CP-1 was evaporated on the cathode to form an organic capping layer having a thickness of 600 Å, thereby completing the manufacture of an organic luminescence device.

Examples 2 to 56

An organic electroluminescent device was manufactured by the same method as that in Example 1 except that compounds shown in Table 10 below were used instead of the compound 4 when forming the hole adjusting layer.

Comparative Examples 1 to 4

An organic electroluminescent device was manufactured by the same method as that in Example 1 except that the compound 4 was replaced by Compound A, Compound B, Compound C, and Compound D, respectively when forming the hole adjusting layer.

The structures of main materials used in the examples and the comparative examples are shown in Table 9 below.

TABLE 9

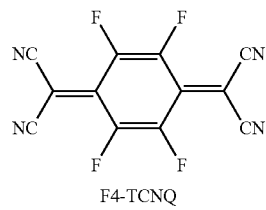 [SMILES: N#CC(C#N)=c1c(F)c(F)c(=C(C#N)C#N)c(F)c1F]

F4-TCNQ

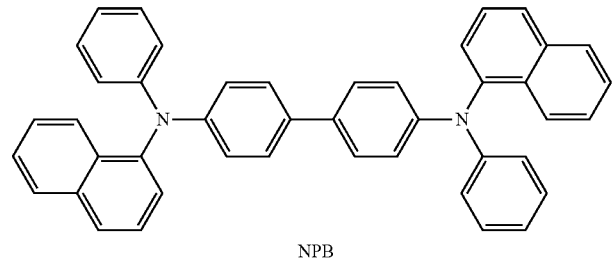 [SMILES: c1ccc(N(c2ccc(-c3ccc(N(c4ccccc4)c4cccc5ccccc45)cc3)cc2)c2cccc3ccccc23)cc1 ; "NPB"]

NPB

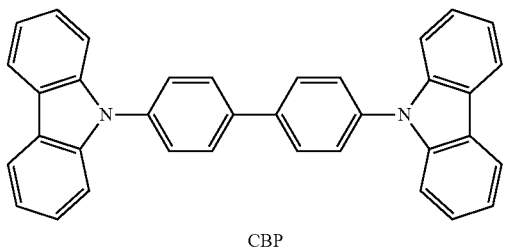 [SMILES: c1ccc2c(c1)c1ccccc1n2-c1ccc(-c2ccc(-n3c4ccccc4c4ccccc43)cc2)cc1 ; "CBP"]

CBP

TABLE 9-continued
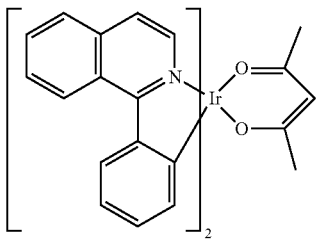
Ir(piq)₂(acac)
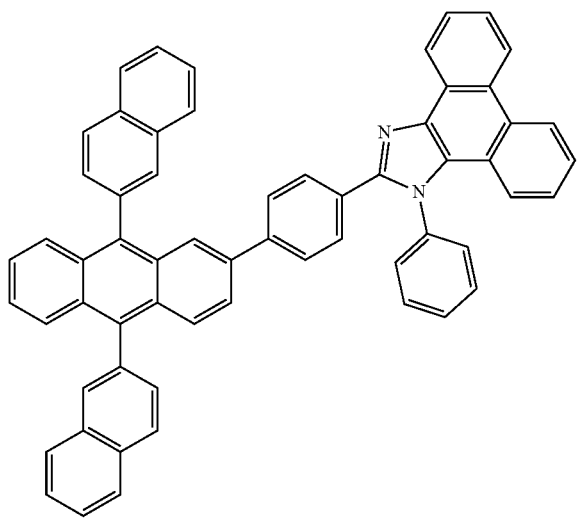
ET-01
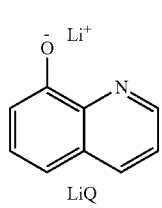
LiQ
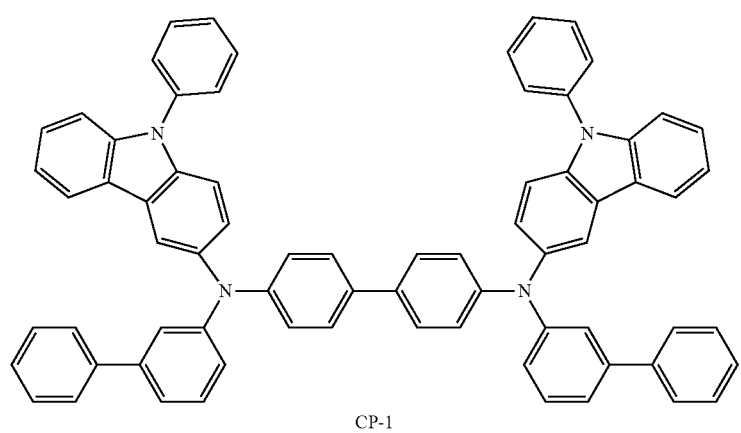 [SMILES: c1ccc(-c2cccc(N(c3ccc(-c4ccc(N(c5cccc(-c6ccccc6)c5)c5ccc6c(c5)c5ccccc5n6-c5ccccc5)cc4)cc3)c3ccc4c(c3)c3ccccc3n4-c3ccccc3)c2)cc1 ; "CP-1"]
CP-1

TABLE 9-continued
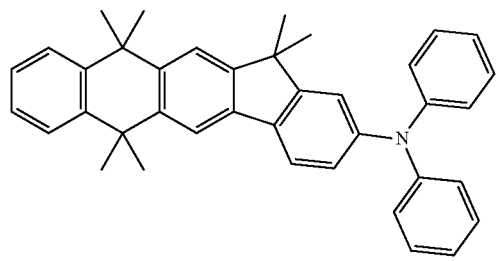
Compound A
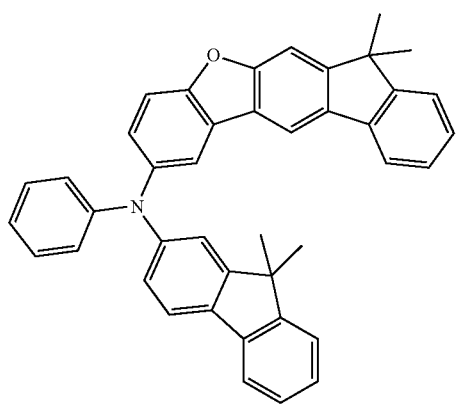
Compound B
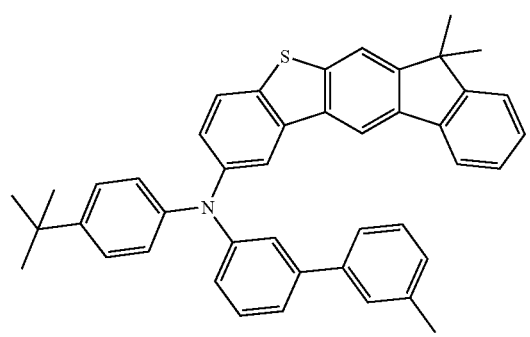
Compound C TABLE 9-continued

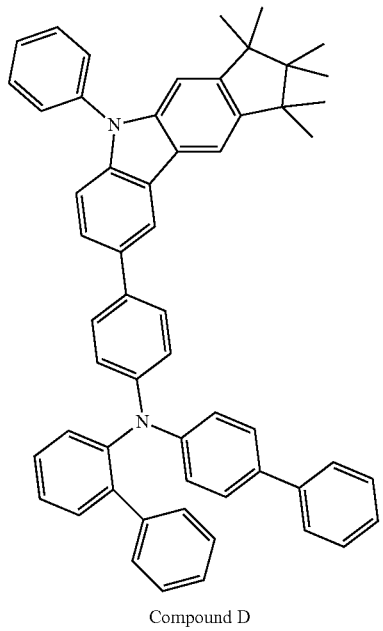 [SMILES: CC1(C)c2cc3c4cc(-c5ccc(N(c6ccc(-c7ccccc7)cc6)c6ccccc6-c6ccccc6)cc5)ccc4n(-c4ccccc4)c3cc2C(C)(C)C1(C)C]

Compound D

The performance of the organic electroluminescent devices manufactured above was analyzed under the condition of 20 mA/cm², and the results are shown in Table 10 below.

TABLE 10

| Example No. | Hole adjusting layer | Driving voltage (V) | Luminescence efficiency (Cd/A) | Power efficiency (lm/W) | Chromaticity coordinate CIE-x, CIE-y | External quantum efficiency (EQE %) | T95 (h) |
|---|---|---|---|---|---|---|---|
| Example 1 | Compound 4 | 3.89 | 38.16 | 28.83 | 0.680, 0.320 | 24.39 | 458 |
| Example 2 | Compound 5 | 3.97 | 37.58 | 29.74 | 0.680, 0.320 | 25.55 | 459 |
| Example 3 | Compound 6 | 3.95 | 37.54 | 29.87 | 0.680, 0.320 | 25.53 | 482 |
| Example 4 | Compound 13 | 3.99 | 37.14 | 29.24 | 0.680, 0.320 | 25.26 | 481 |
| Example 5 | Compound 7 | 3.98 | 37.81 | 28.05 | 0.680, 0.320 | 24.17 | 476 |
| Example 6 | Compound 12 | 3.82 | 37.18 | 29.04 | 0.680, 0.320 | 24.45 | 480 |
| Example 7 | Compound 8 | 3.99 | 37.33 | 29.39 | 0.680, 0.320 | 25.38 | 482 |
| Example 8 | Compound 16 | 3.92 | 36.95 | 28.74 | 0.680, 0.320 | 24.35 | 477 |
| Example 9 | Compound 49 | 3.82 | 35.81 | 30.36 | 0.680, 0.320 | 25.11 | 473 |
| Example 10 | Compound 56 | 3.82 | 35.18 | 28.93 | 0.680, 0.320 | 23.92 | 463 |
| Example 11 | Compound 60 | 3.93 | 35.89 | 28.69 | 0.680, 0.320 | 24.41 | 474 |
| Example 12 | Compound 62 | 3.99 | 35.39 | 29.27 | 0.680, 0.320 | 25.29 | 473 |
| Example 13 | Compound 81 | 3.83 | 37.89 | 29.59 | 0.680, 0.320 | 24.53 | 470 |
| Example 14 | Compound 86 | 3.89 | 36.78 | 29.42 | 0.680, 0.320 | 24.76 | 479 |
| Example 15 | Compound 93 | 3.90 | 37.16 | 29.93 | 0.680, 0.320 | 25.27 | 460 |
| Example 16 | Compound 96 | 3.86 | 36.96 | 29.48 | 0.680, 0.320 | 24.63 | 469 |
| Example 17 | Compound 114 | 3.92 | 36.22 | 29.62 | 0.680, 0.320 | 25.13 | 440 |
| Example 18 | Compound 117 | 3.85 | 35.35 | 28.84 | 0.680, 0.320 | 24.04 | 475 |
| Example 19 | Compound 121 | 3.84 | 36.63 | 29.97 | 0.680, 0.320 | 24.91 | 449 |
| Example 20 | Compound 125 | 3.82 | 36.52 | 30.49 | 0.680, 0.320 | 25.21 | 462 |
| Example 21 | Compound 126 | 3.94 | 35.87 | 29.63 | 0.680, 0.320 | 25.37 | 451 |
| Example 22 | Compound 130 | 3.97 | 35.58 | 29.13 | 0.680, 0.320 | 25.03 | 476 |
| Example 23 | Compound 132 | 3.91 | 36.76 | 29.53 | 0.680, 0.320 | 25.41 | 477 |
| Example 24 | Compound 135 | 3.83 | 36.57 | 30.10 | 0.680, 0.320 | 24.87 | 467 |
| Example 25 | Compound 134 | 3.82 | 35.54 | 30.27 | 0.680, 0.320 | 25.33 | 471 |
| Example 26 | Compound 156 | 3.95 | 36.82 | 29.28 | 0.680, 0.320 | 25.04 | 485 |
| Example 27 | Compound 159 | 3.96 | 36.59 | 29.03 | 0.680, 0.320 | 24.88 | 469 |
| Example 28 | Compound 184 | 3.93 | 36.07 | 29.47 | 0.680, 0.320 | 25.02 | 478 |
| Example 29 | Compound 215 | 3.85 | 37.51 | 28.85 | 0.680, 0.320 | 24.02 | 468 |
| Example 30 | Compound 223 | 3.92 | 37.08 | 29.02 | 0.680, 0.320 | 24.62 | 468 |
| Example 31 | Compound 264 | 3.95 | 35.33 | 29.83 | 0.680, 0.320 | 25.51 | 466 |
| Example 32 | Compound 266 | 3.91 | 36.21 | 29.34 | 0.680, 0.320 | 24.83 | 457 |
| Example 33 | Compound 293 | 3.98 | 36.84 | 29.08 | 0.680, 0.320 | 25.05 | 470 |
| Example 34 | Compound 294 | 3.98 | 36.93 | 28.63 | 0.680, 0.320 | 24.64 | 479 |

TABLE 10-continued

| Example No. | Hole adjusting layer | Driving voltage (V) | Luminescence efficiency (Cd/A) | Power efficiency (lm/W) | Chromaticity coordinate CIE-x, CIE-y | External quantum efficiency (EQE %) | T95 (h) |
|---|---|---|---|---|---|---|---|
| Example 35 | Compound 295 | 3.89 | 37.17 | 30.02 | 0.680, 0.320 | 25.28 | 484 |
| Example 36 | Compound 300 | 3.94 | 37.85 | 28.27 | 0.680, 0.320 | 24.11 | 465 |
| Example 37 | Compound 318 | 3.88 | 35.45 | 28.81 | 0.680, 0.320 | 24.19 | 472 |
| Example 38 | Compound 364 | 3.86 | 39.15 | 30.37 | 0.680, 0.320 | 25.17 | 483 |
| Example 39 | Compound 365 | 3.93 | 37.98 | 28.73 | 0.680, 0.320 | 24.39 | 487 |
| Example 40 | Compound 366 | 3.90 | 38.81 | 29.67 | 0.680, 0.320 | 24.87 | 475 |
| Example 41 | Compound 367 | 3.87 | 39.21 | 29.86 | 0.680, 0.320 | 24.91 | 486 |
| Example 42 | Compound 368 | 3.92 | 39.34 | 30.14 | 0.680, 0.320 | 25.37 | 479 |
| Example 43 | Compound 369 | 3.88 | 37.95 | 29.77 | 0.680, 0.320 | 24.98 | 478 |
| Example 44 | Compound 370 | 3.85 | 38.91 | 28.97 | 0.680, 0.320 | 25.16 | 483 |
| Example 45 | Compound 371 | 3.92 | 37.83 | 28.88 | 0.680, 0.320 | 25.32 | 480 |
| Example 46 | Compound 372 | 3.91 | 38.56 | 29.31 | 0.680, 0.320 | 25.29 | 481 |
| Example 47 | Compound 363 | 3.86 | 36.78 | 28.79 | 0.680, 0.320 | 24.86 | 476 |
| Example 48 | Compound 101 | 3.91 | 34.89 | 29.88 | 0.680, 0.320 | 25.01 | 427 |
| Example 49 | Compound 112 | 3.94 | 34.96 | 29.36 | 0.680, 0.320 | 25.45 | 431 |
| Example 50 | Compound 373 | 3.87 | 38.34 | 28.79 | 0.680, 0.320 | 24.41 | 456 |
| Example 51 | Compound 399 | 3.90 | 37.47 | 29.84 | 0.680, 0.320 | 25.75 | 466 |
| Example 52 | Compound 400 | 3.89 | 37.59 | 29.03 | 0.680, 0.320 | 24.78 | 471 |
| Example 53 | Compound 379 | 3.90 | 37.45 | 28.94 | 0.680, 0.320 | 25.89 | 460 |
| Example 54 | Compound 389 | 3.86 | 36.89 | 27.99 | 0.680, 0.320 | 26.87 | 473 |
| Example 55 | Compound 398 | 3.92 | 37.67 | 27.86 | 0.680, 0.320 | 25.78 | 453 |
| Example 56 | Compound 374 | 3.88 | 38.91 | 28.34 | 0.680, 0.320 | 26.57 | 456 |
| Comparative example 1 | Compound A | 4.23 | 28.61 | 21.31 | 0.680, 0.320 | 19.55 | 342 |
| Comparative example 2 | Compound B | 4.22 | 29.62 | 22.07 | 0.680, 0.320 | 20.11 | 351 |
| Comparative example 3 | Compound C | 4.20 | 29.03 | 21.76 | 0.680, 0.320 | 19.73 | 371 |
| Comparative example 4 | Compound D | 4.18 | 29.12 | 21.81 | 0.680, 0.320 | 19.81 | 360 |

As can be seen from the results in Table 10, compared with Comparative examples 1 to 4 of devices corresponding to well-known compounds, Examples 1 to 56 in which the organic compound of the present application was used have the advantages that for the above organic electroluminescent devices manufactured with the organic compound of the present application as a hole adjusting layer, the luminescence efficiency (Cd/A) was improved by at least 17.8%, the external quantum efficiency was improved by at least 18.9%, and the service life was improved by at least 15.1%; and in addition, the devices manufactured in Examples 1-56 also had lower driving voltages.

The preferred embodiments of the present application are described in detail above in combination with the drawings, however, the present application is not limited to the specific details in the above embodiments, in the technical concept range of the present application, the technical solution of the present application can be subjected to various simple variations, and these simple variations all belong to the protection range of the present application. In addition, it should be noted that the specific technical features described in the above specific embodiments can be combined in any appropriate mode without contradiction, and in order to avoid unnecessary repetition, various possible combinations are not described any more in the present application. In addition, various different embodiments of the present application can also be combined at will, and as long as they do not violate the idea of the present application, they also should be regarded as the contents disclosed by the present application.

What is claimed is:

1. An organic compound having a structure as shown in Formula I:

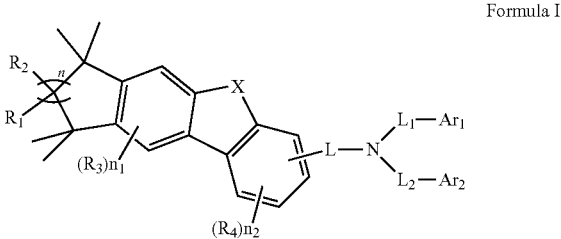

Formula I wherein $R_1$ and $R_2$ are the same or different, and are each independently selected from hydrogen, deuterium, a methyl or a phenyl;

n is selected from 1 or 2;

X is selected from $C(R_5R_6)$, O or S;

$R_5$ and $R_6$ are the same or different, and are each independently selected from a methyl, an ethyl, an isopropyl, a tert-butyl, a phenyl, a naphthyl, or a biphenyl; and optionally, $R_5$ and $R_6$ are connected to each other to form a cyclopentane, a cyclohexane, a norbornane or a fluorene ring;

L is selected from a single bond, a substituted or unsubstituted phenylene, a substituted or unsubstituted biphenylene, or a substituted or unsubstituted naphthylene;

$L_1$ and $L_2$ are the same or different, and are each independently selected from a single bond, a substituted or unsubstituted phenylene, a substituted or unsubstituted biphenylene, a substituted or unsubstituted naphthylene, a substituted or unsubstituted dibenzofurylene, or a substituted or unsubstituted dibenzothienylene;

substituents of L, L₁ and L₂ are the same or different, and are each independently selected from deuterium, a fluorine, a cyano, an alkyl with 1 to 5 carbon atoms, a trimethylsilyl, or a phenyl;

Ar₁ and Ar₂ are the same or different, and are each independently selected from a substituted or unsubstituted group V, or a substituted or unsubstituted group W;

wherein the unsubstituted group V is selected from the group consisting of the following groups:

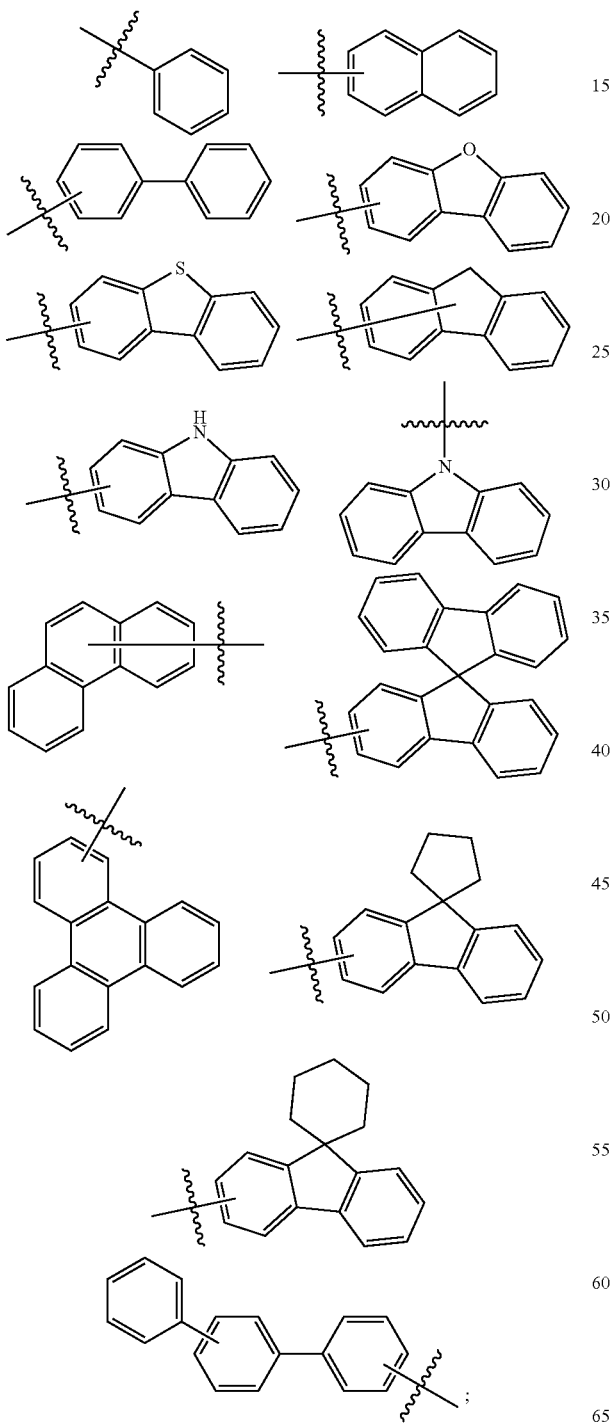

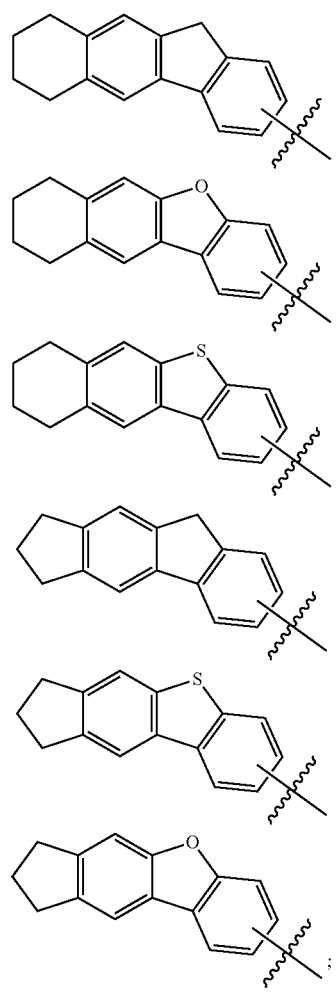

wherein ⁑ represents a chemical bond; the substituted group V has one or two or more substituents, the substituents are each independently selected from deuterium, a fluorine, a cyano, a methyl, an ethyl, an isopropyl, a tert-butyl, a trifluoromethyl, a trimethylsilyl, a phenyl, a naphthyl, a cyclopentyl, a cyclohexyl, or an adamantyl; and when the number of the substituents is greater than 1, the substituents are the same or different;

the unsubstituted group W is selected from the group consisting of the following groups:

wherein ⁑ represents a chemical bond: the substituted group W has one or two or more substituents, the substituents are independently selected from deuterium, a fluorine, a cyano, a methyl, an ethyl, an isopropyl, or a tert-butyl; and when the number of the substituents is greater than 1, the substituents are the same or different;

R₃ and R₄ are the same or different, and are each independently selected from deuterium, a cyano, a fluorine, a methyl, an ethyl, an isopropyl, a tert-butyl, a phenyl, a trimethylsilyl, or a trifluoromethyl;

n₁ represents the number of R₃, and is selected from 0, 1 or 2, and when n₁ is 2, each R₃ is the same or different; and n₂ represents the number of R₄, and is selected from 0, 1, 2 or 3, and when $n_2$ is greater than 1, each $R_4$ is the same or different.
2. The organic compound of claim 1, wherein $Ar_1$ and $Ar_2$ are each independently selected from the group consisting of the following groups:
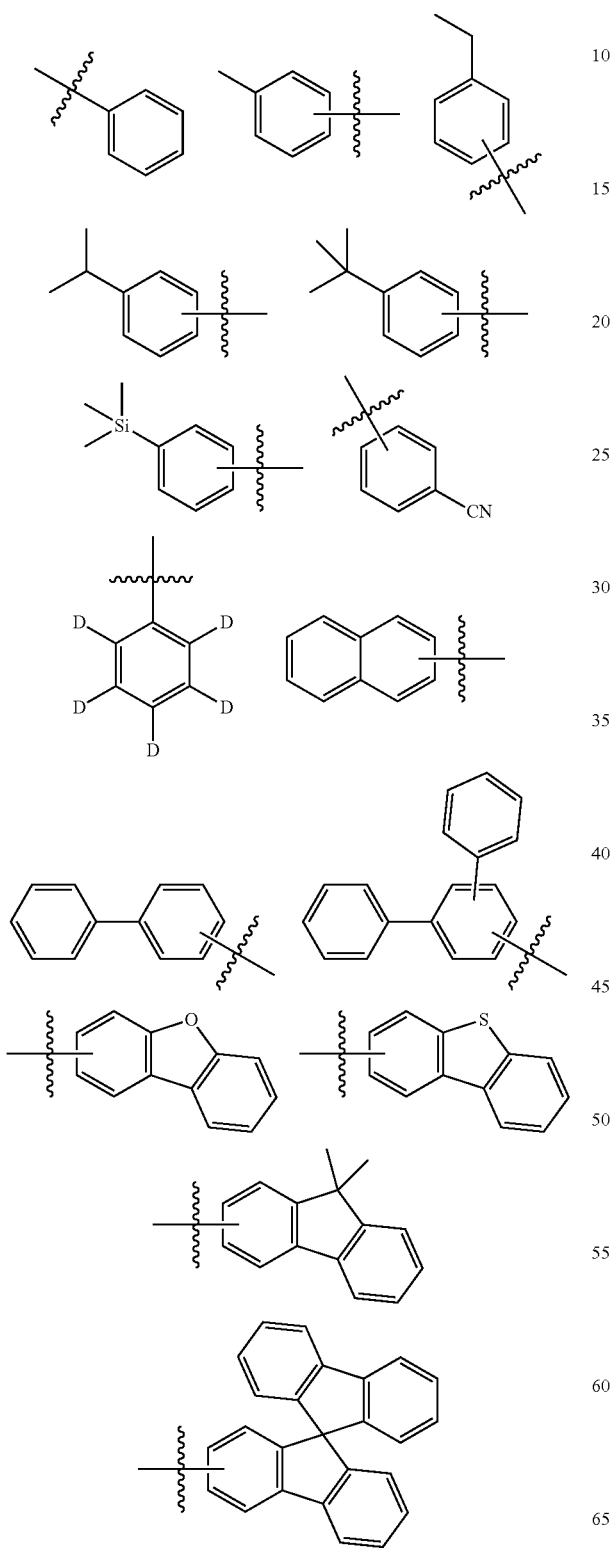
-continued
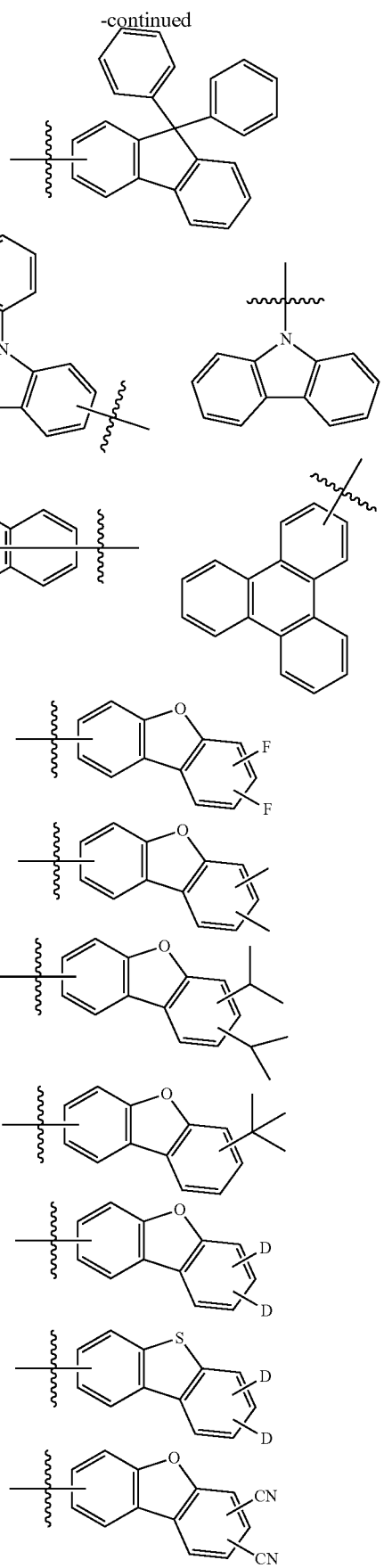

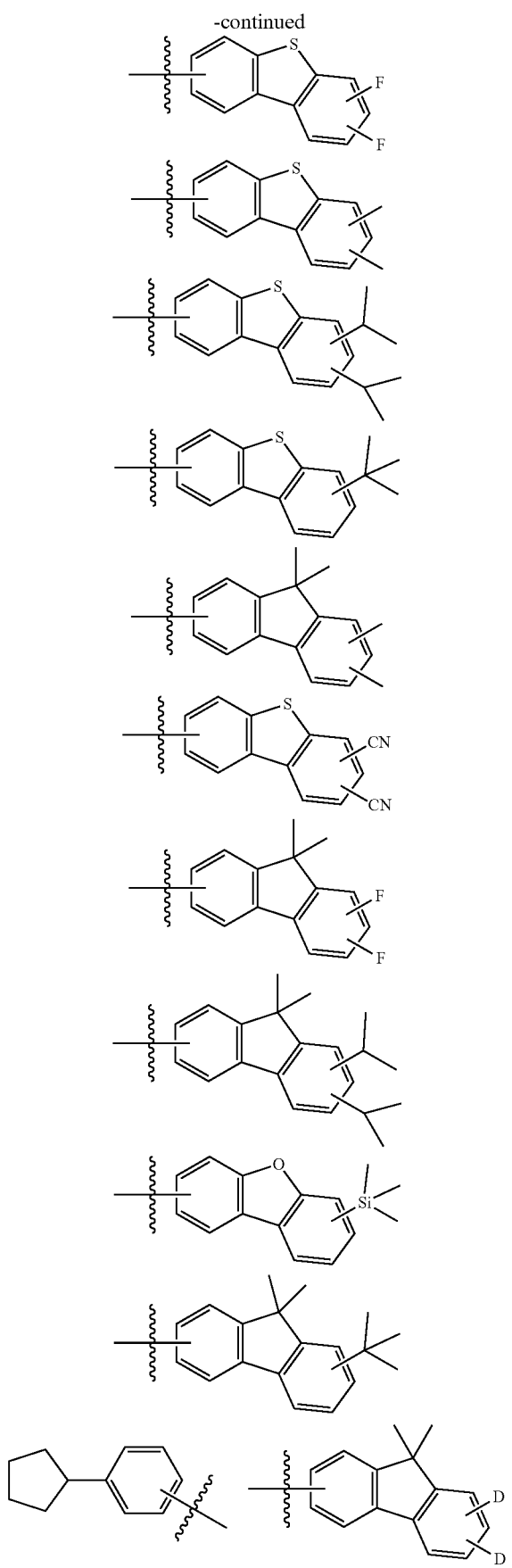
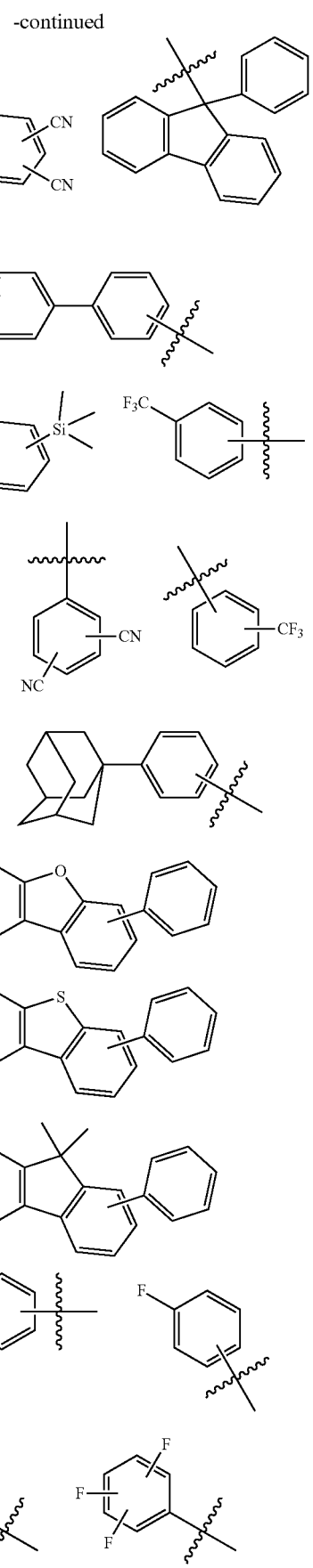

-continued
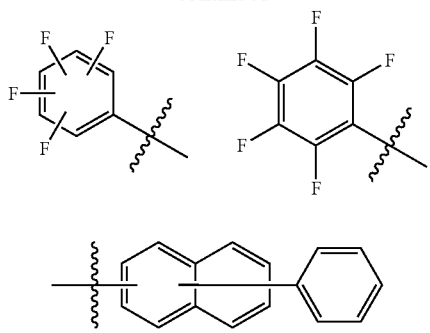
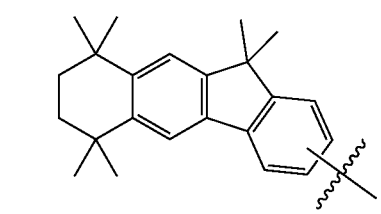
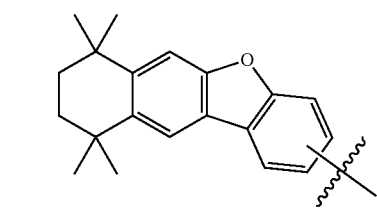
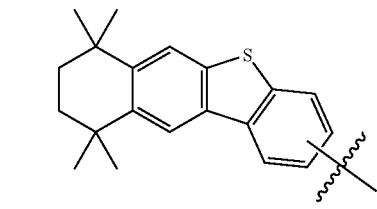
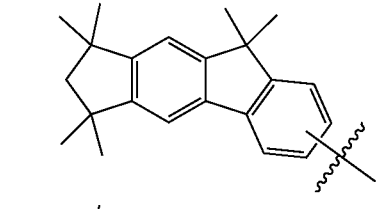
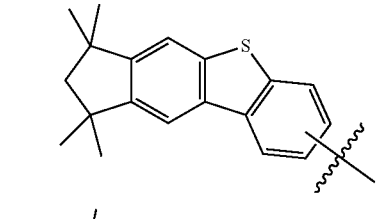
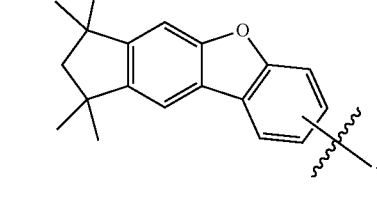
Formula I-1-A
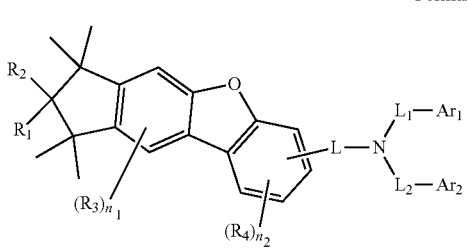
Formula I-2-A
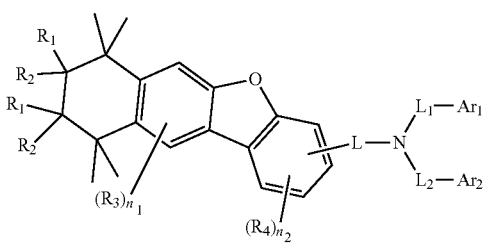
Formula I-1-B
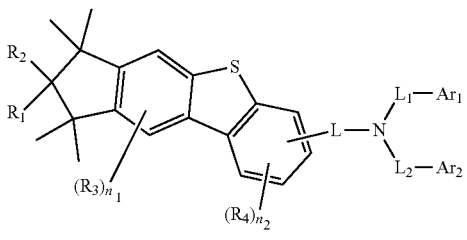
Formula I-2-B
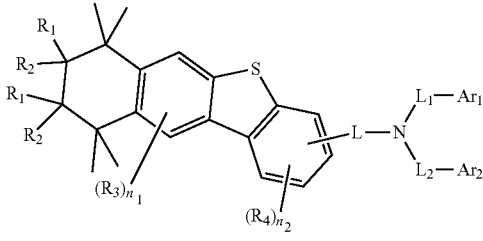
Formula I-1-C
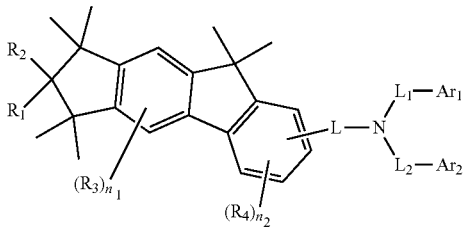
Formula I-2-C
3. The organic compound of claim 1, wherein the structure of the organic compound is selected from the group consisting of the following structural formulas:

Formula I-1-D
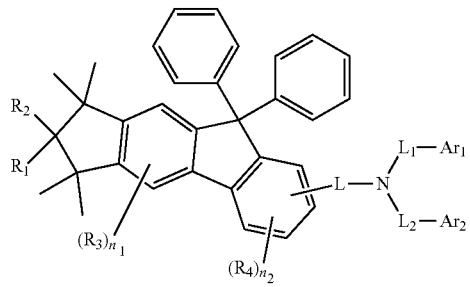
Formula I-2-D
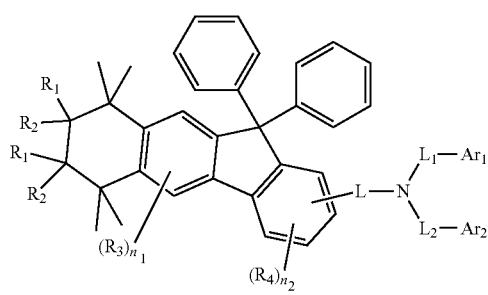
Formula I-1-E
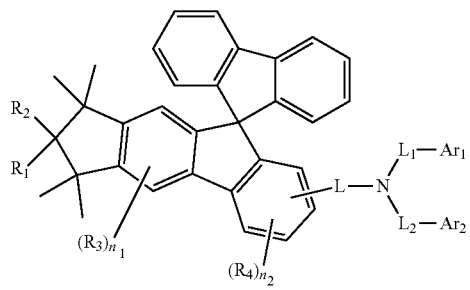
Formula I-2-E
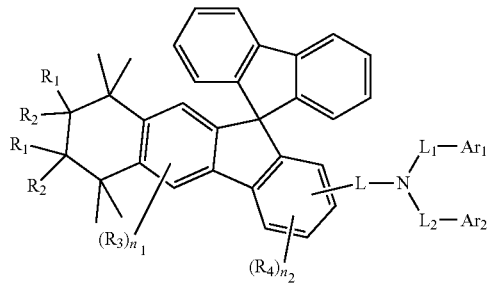
Formula I-1-F
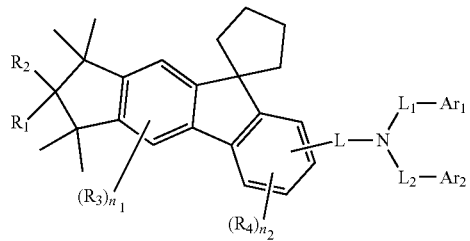
Formula I-2-F
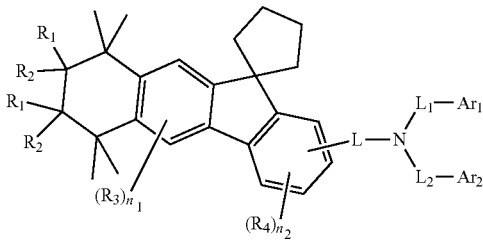
Formula I-1-G
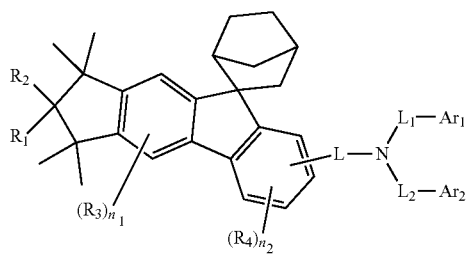
Formula I-2-G
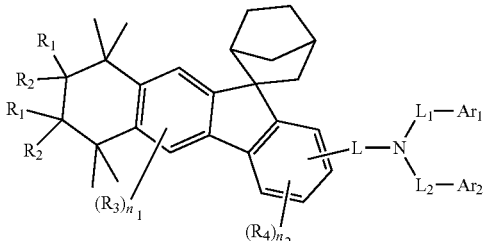
Formula I-1-H
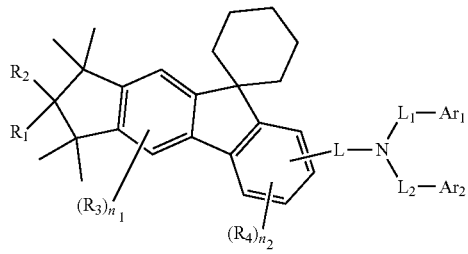
Formula I-2-H
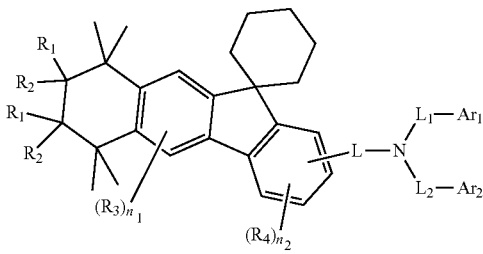
4. The organic compound of claim 1, wherein the organic compound is selected from the group consisting of the following compounds:

317 318
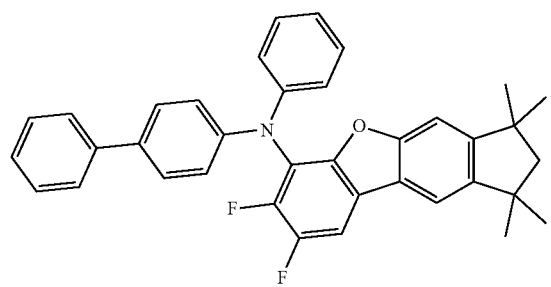
1
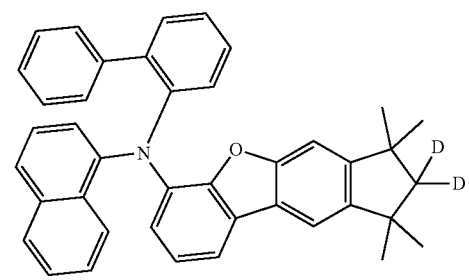
2
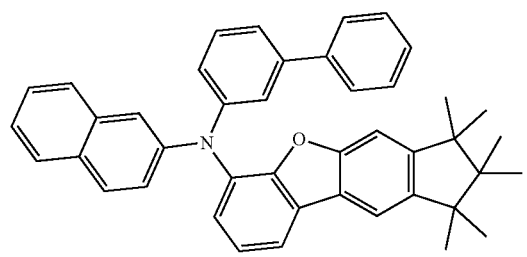
3
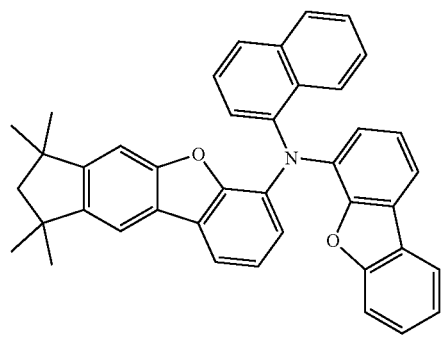
4
5
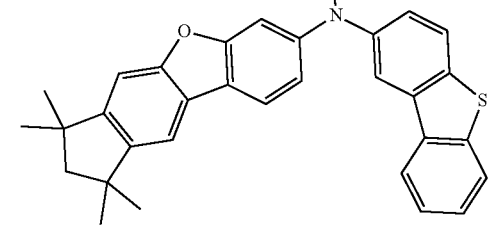
6
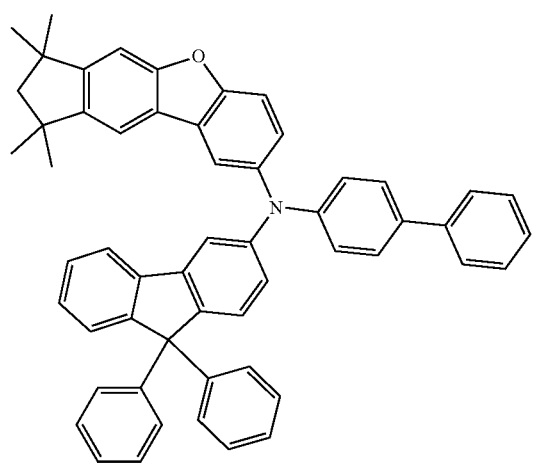
7
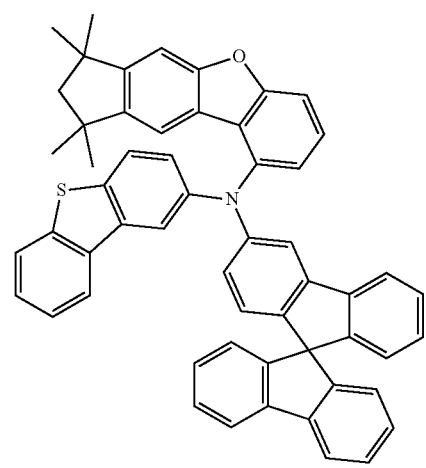
8

9
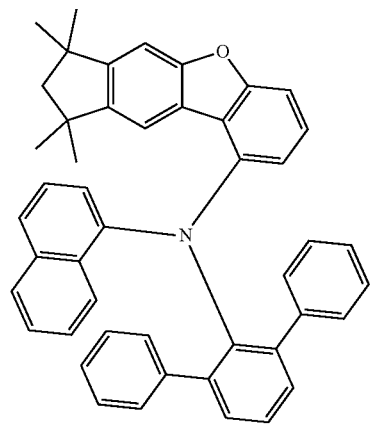
10
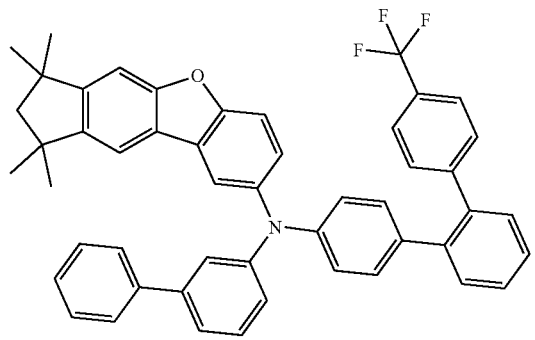
11
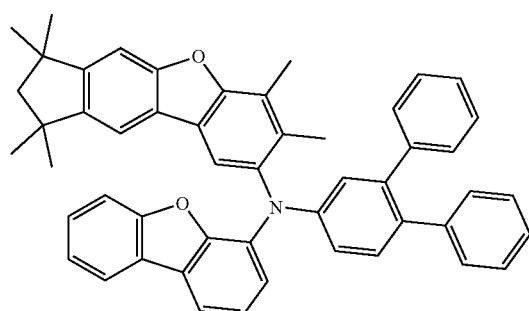
12
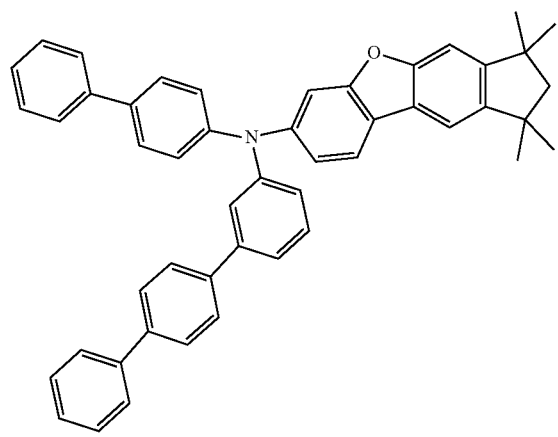
13
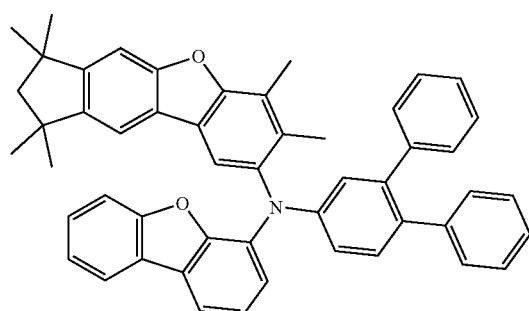
14
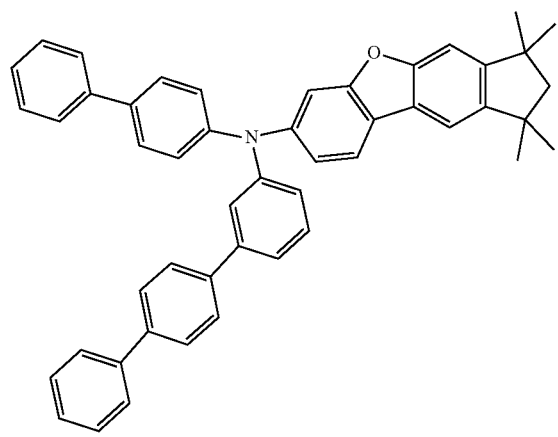
15
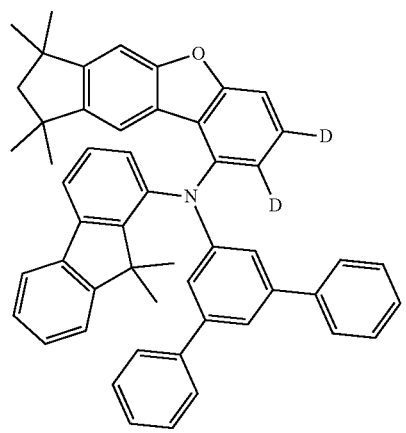
16
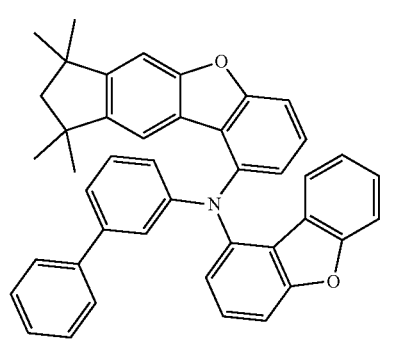

-continued
17
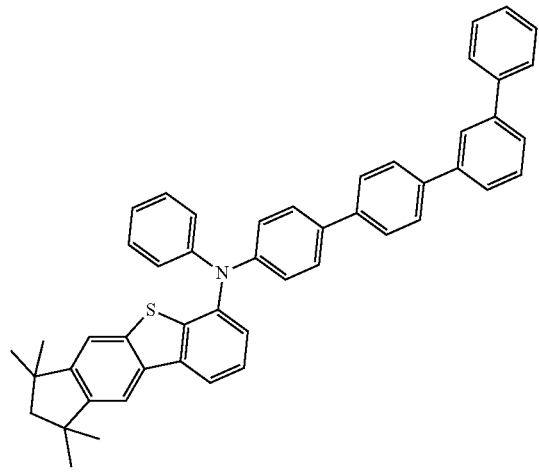
18
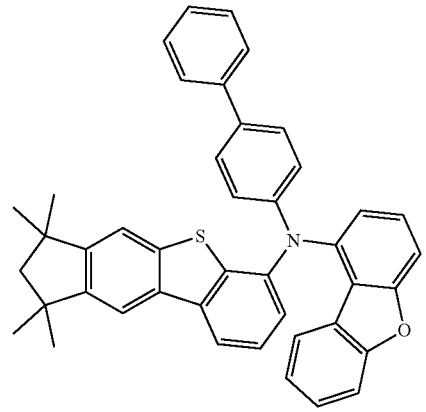
19
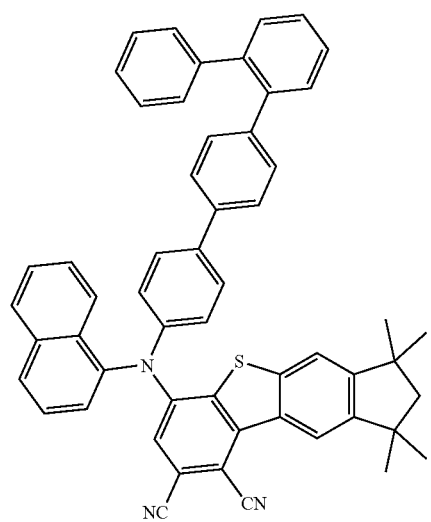
20
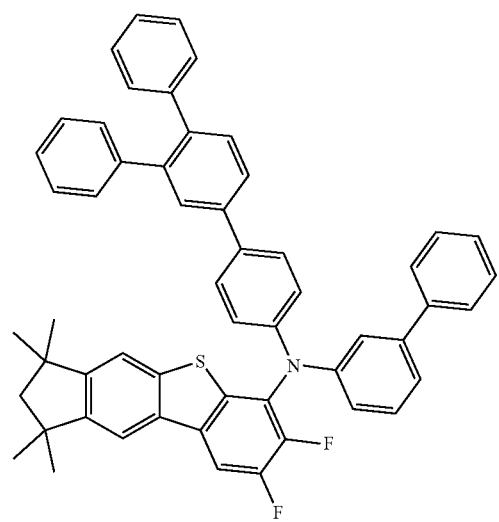
21
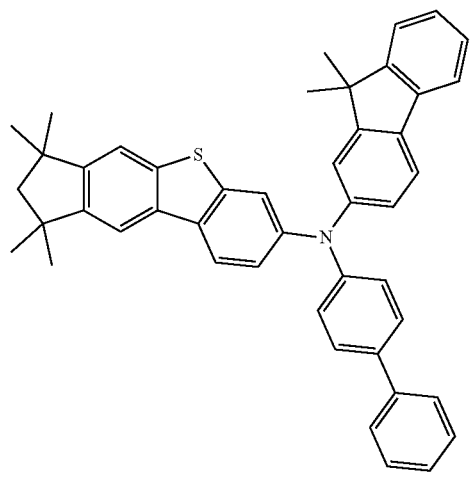
22
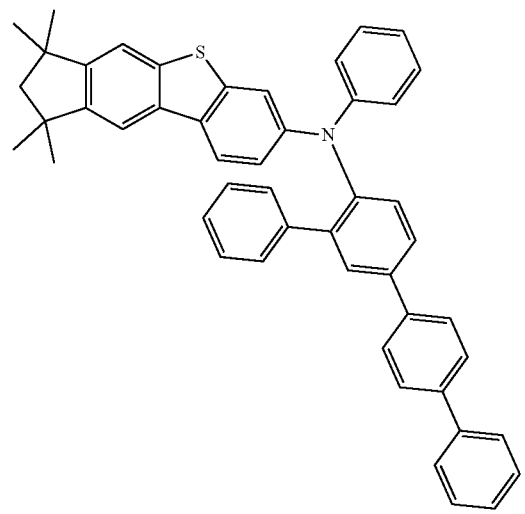

-continued
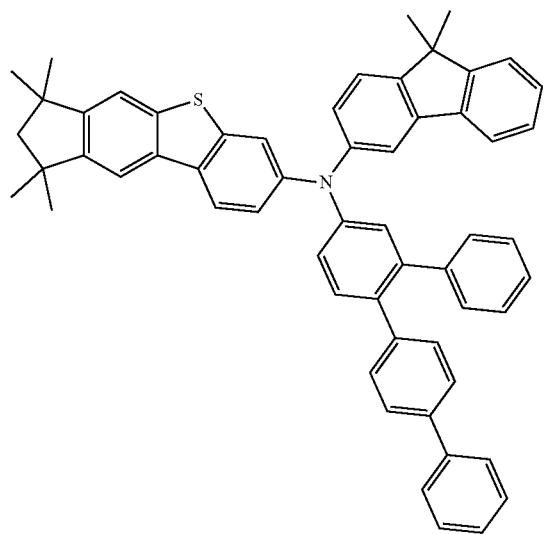
23
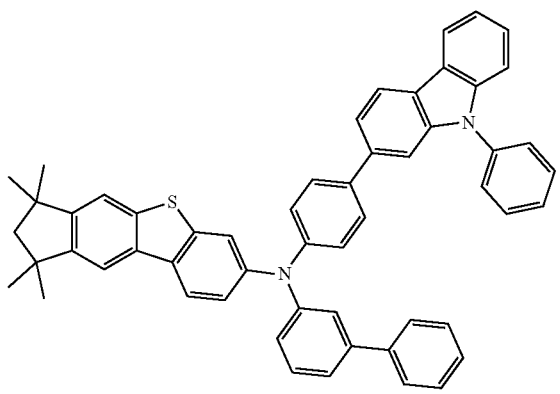
24
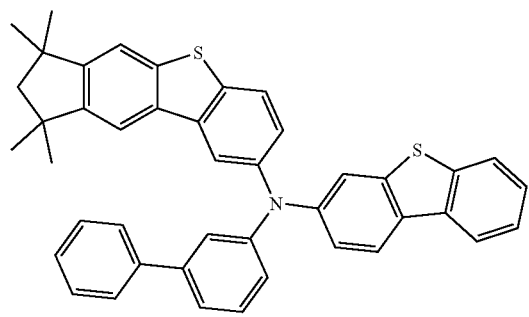
25
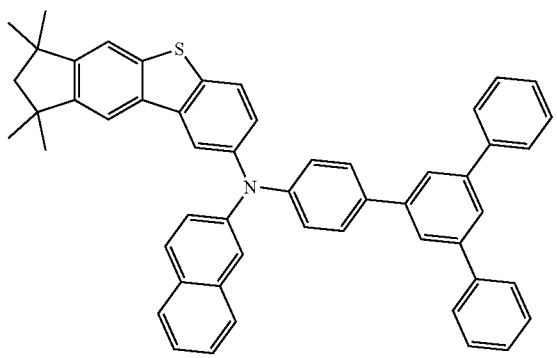
26
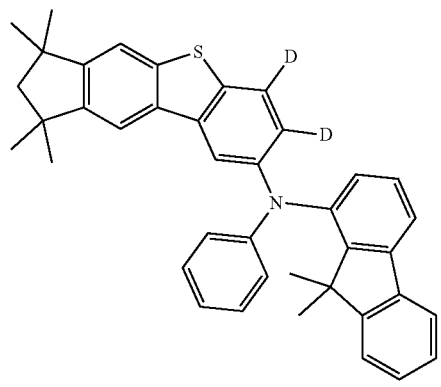
27
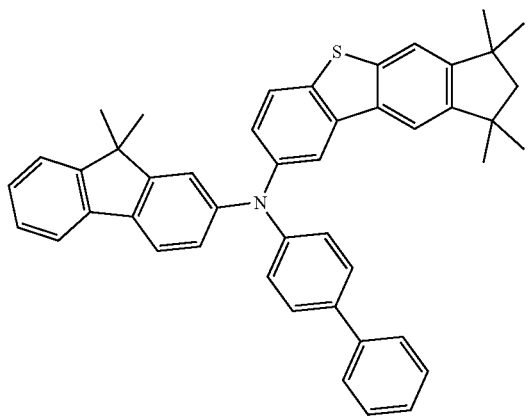
28

-continued
29
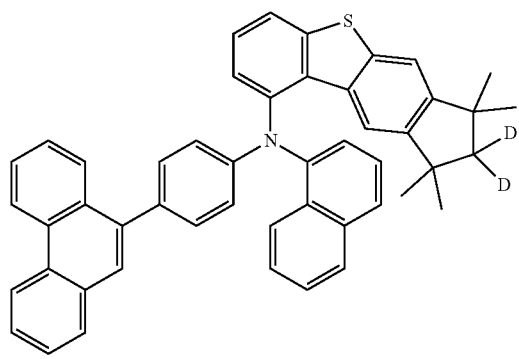
30
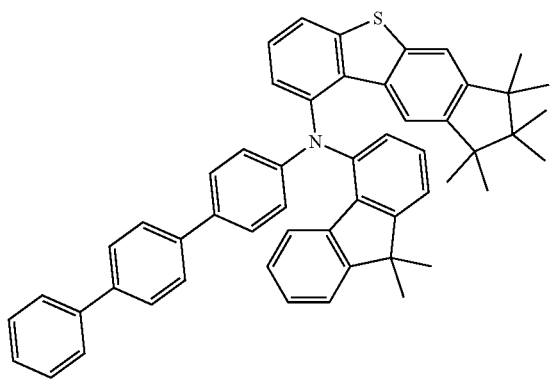
31
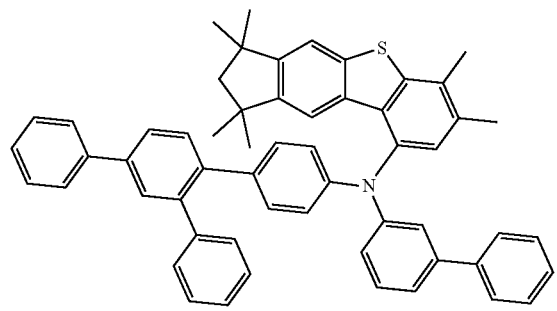
32
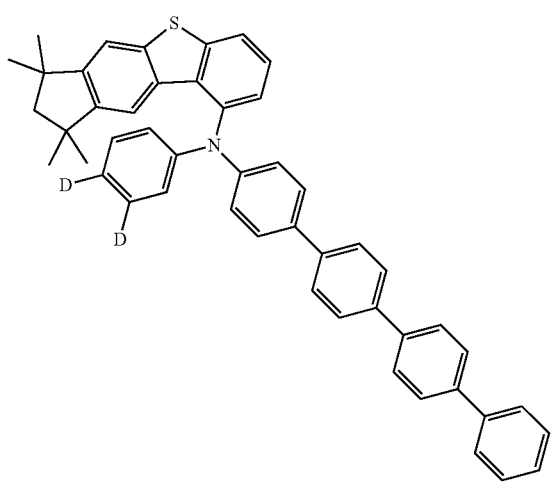
33
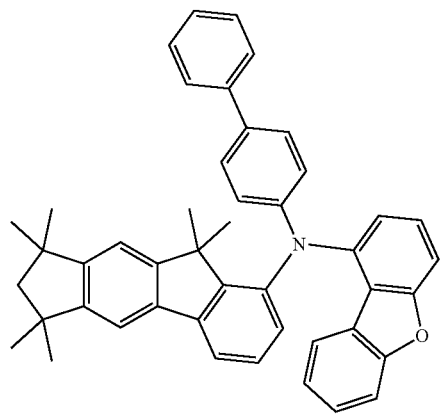
34
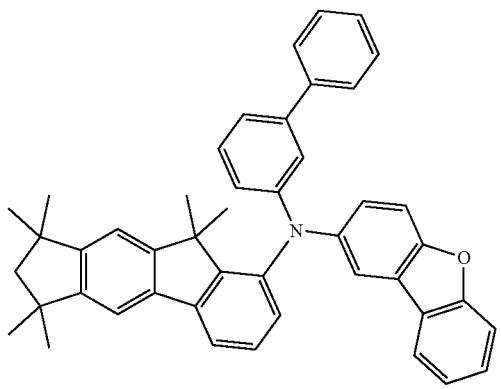

327 328
35 36
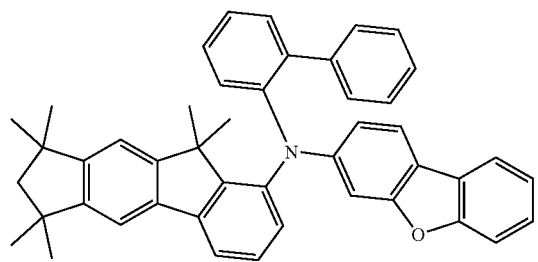 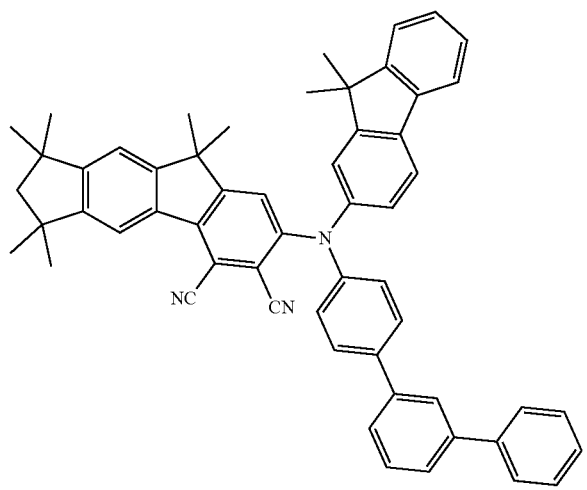
37 38
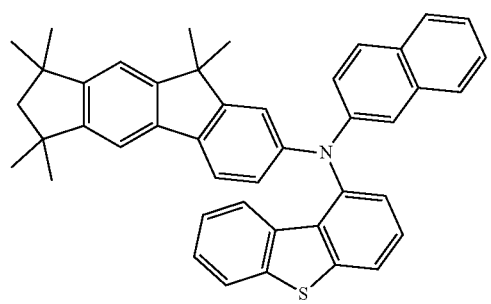 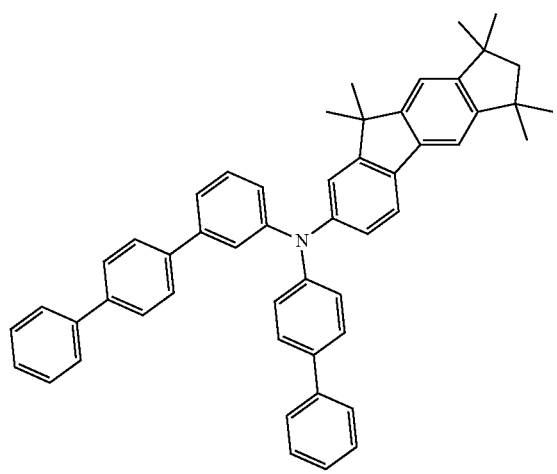
39 40
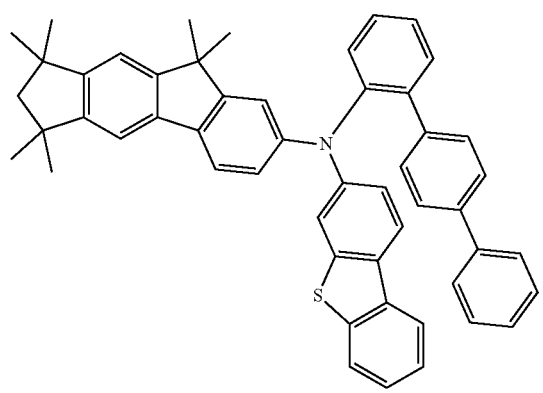 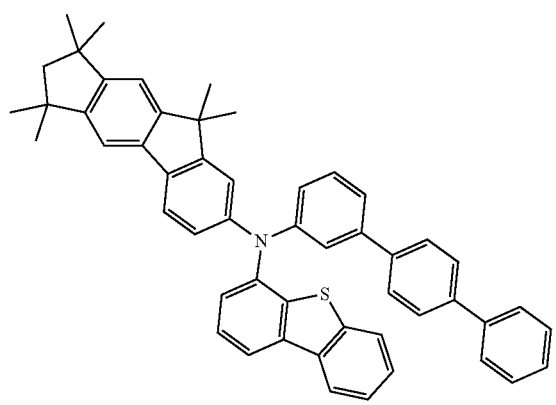

-continued
41
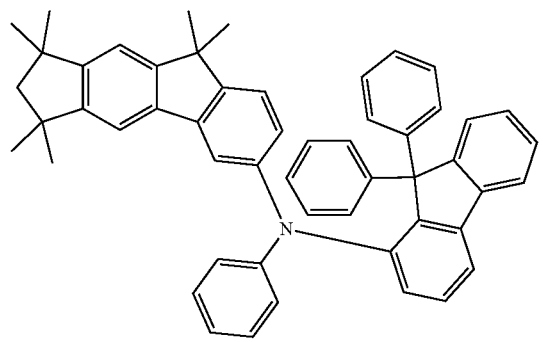
42
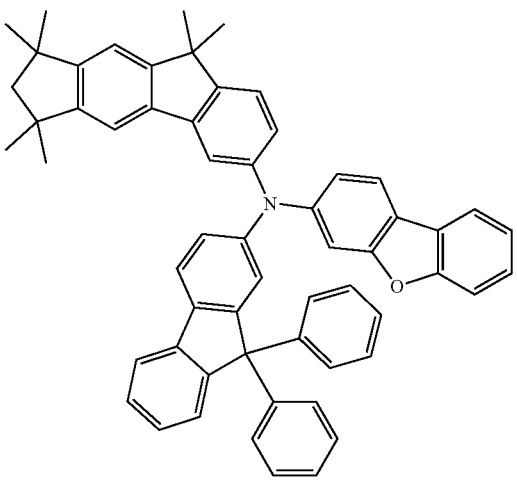
43
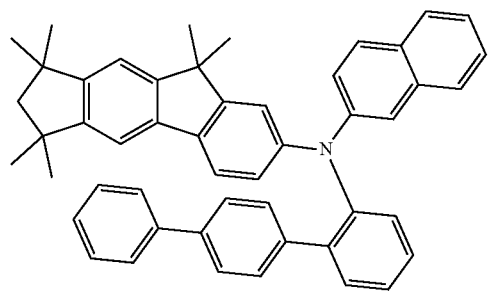
44
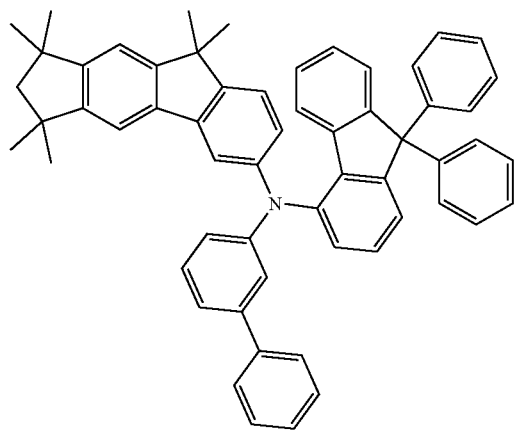
45
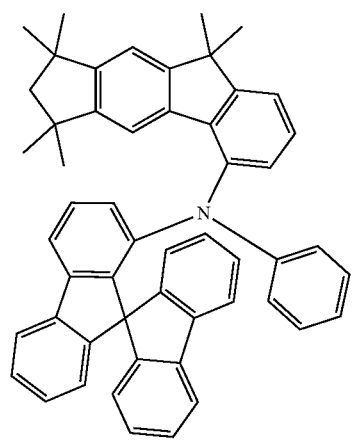
46
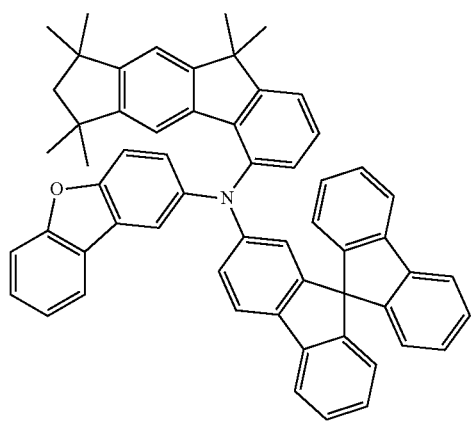

-continued
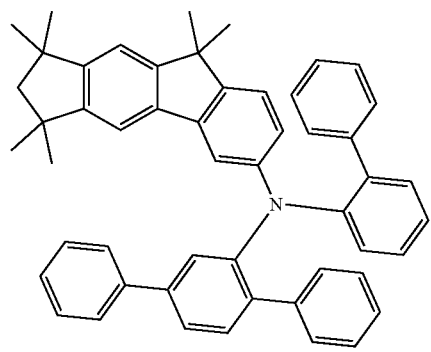
47
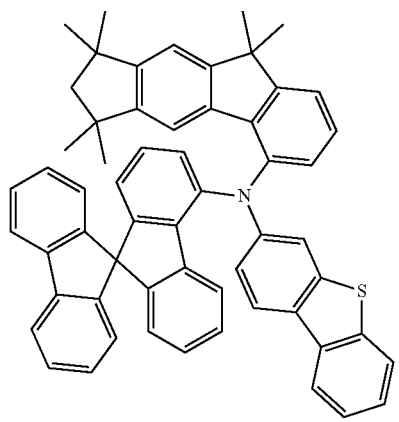
48
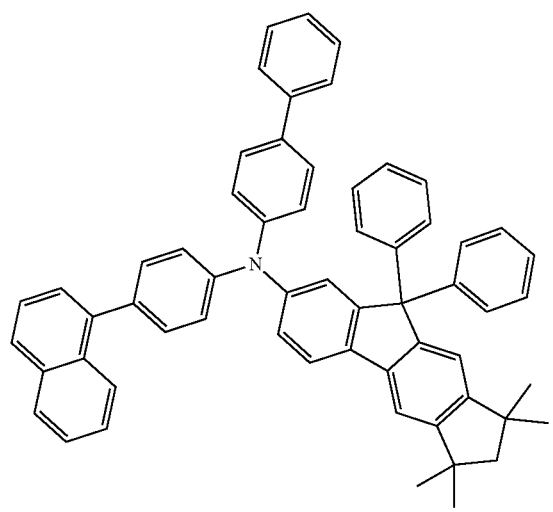
49
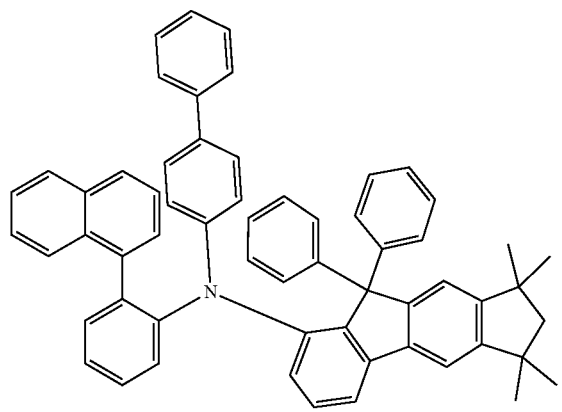
51
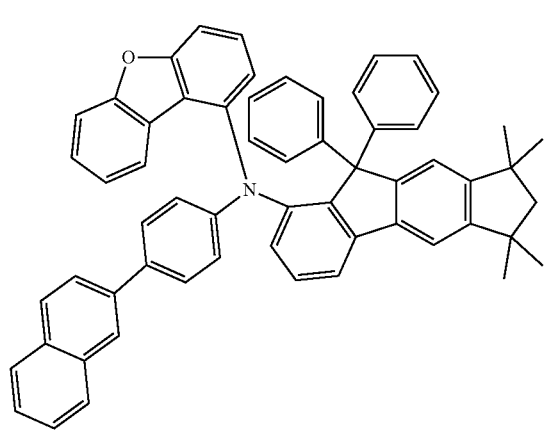
52

333    334
-continued
53
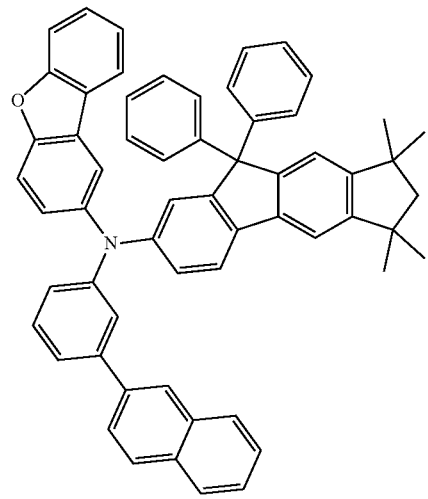
54
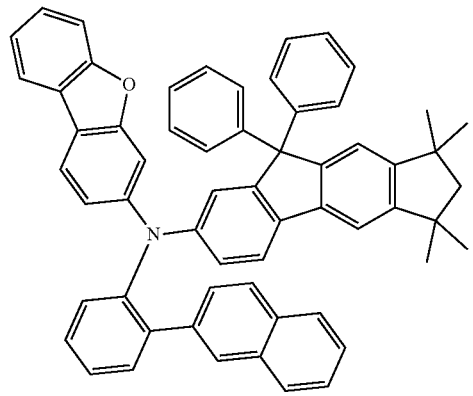
55
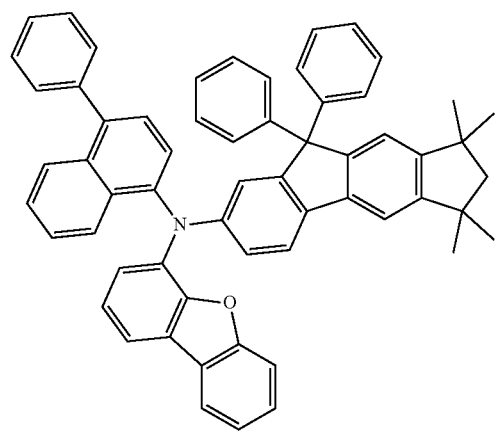
56
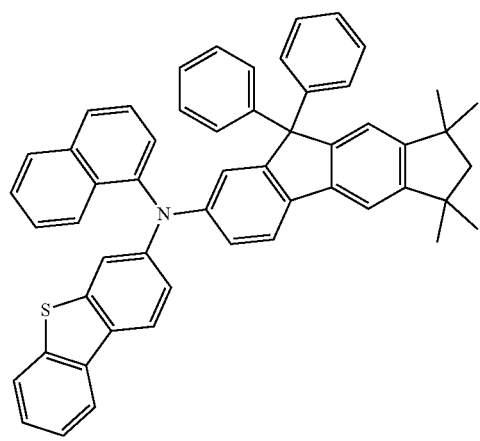
57
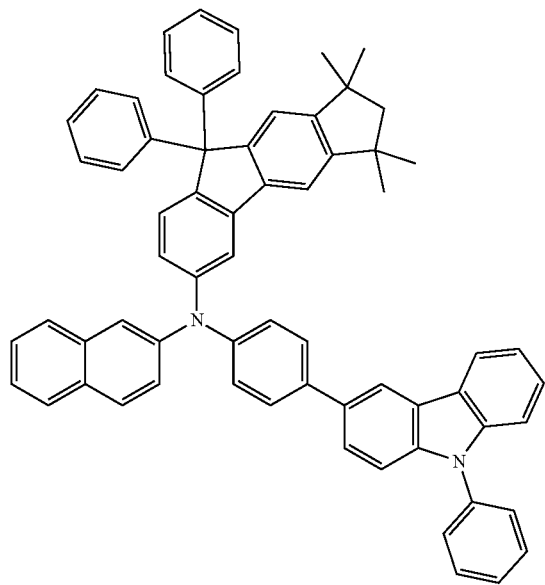
58
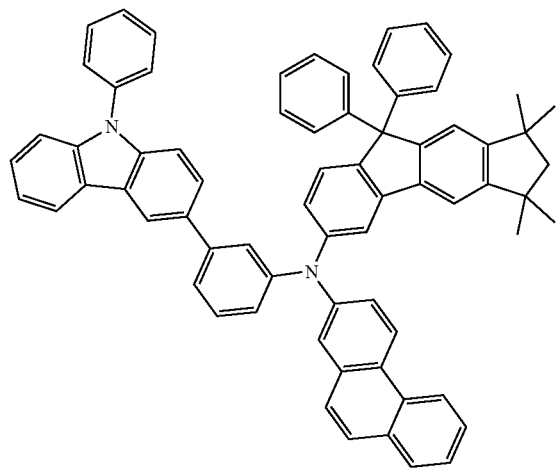

-continued
59
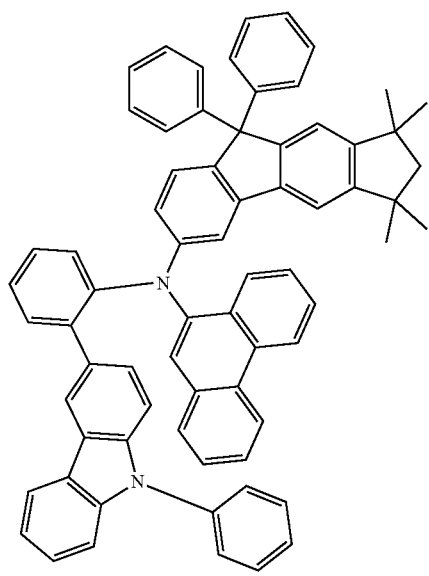
60
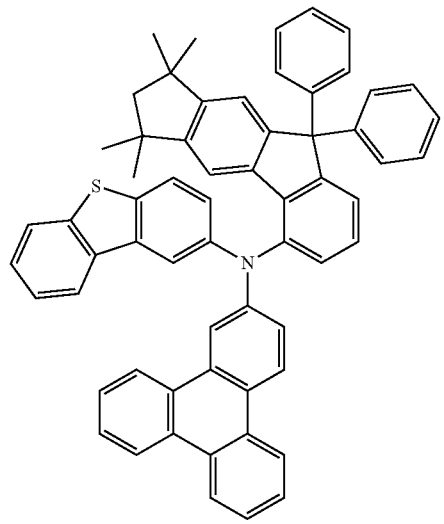
61
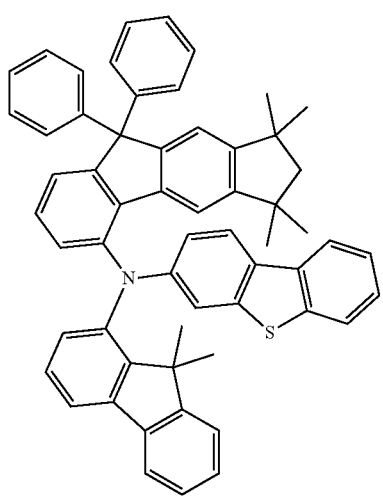
62
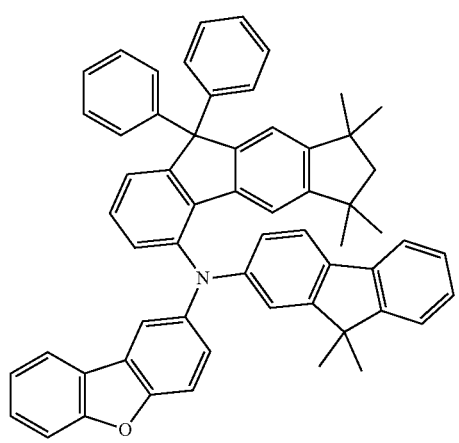
63
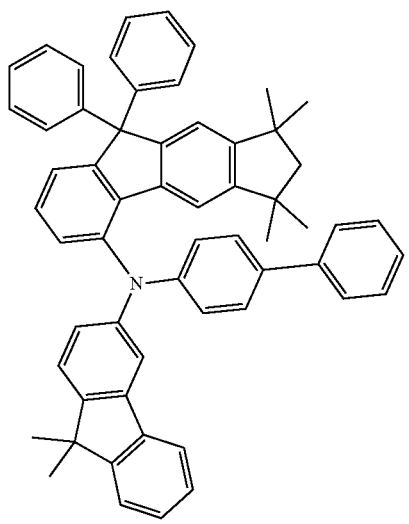
64
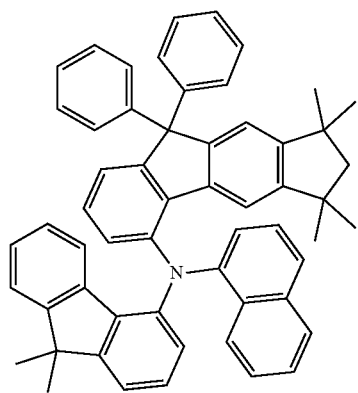

-continued
65
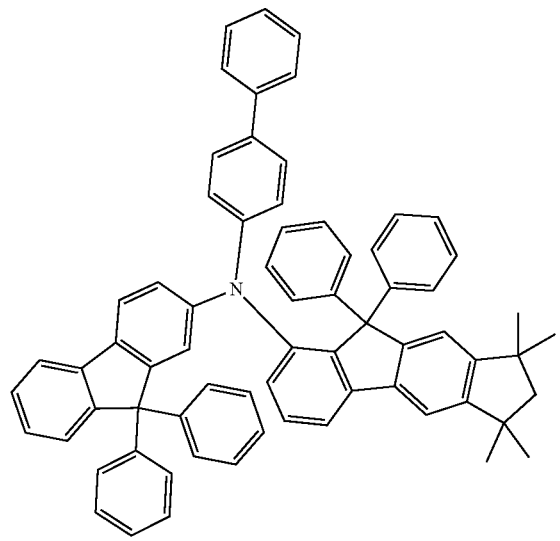
66
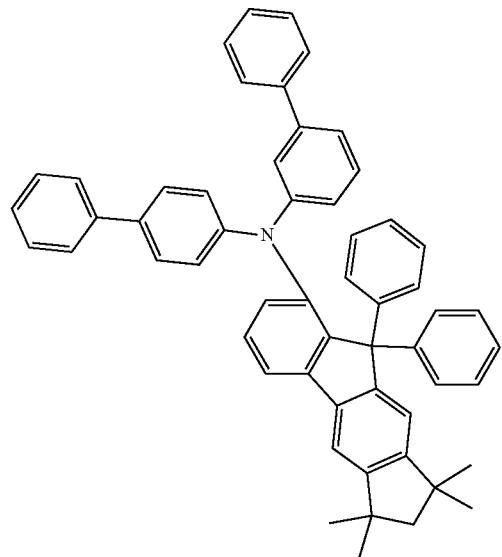
67
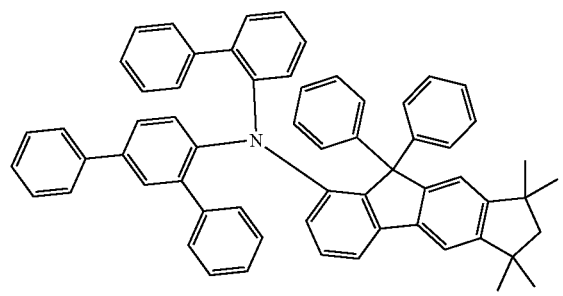
68
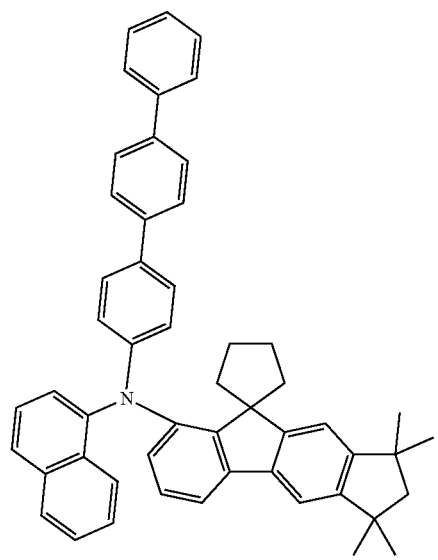
69
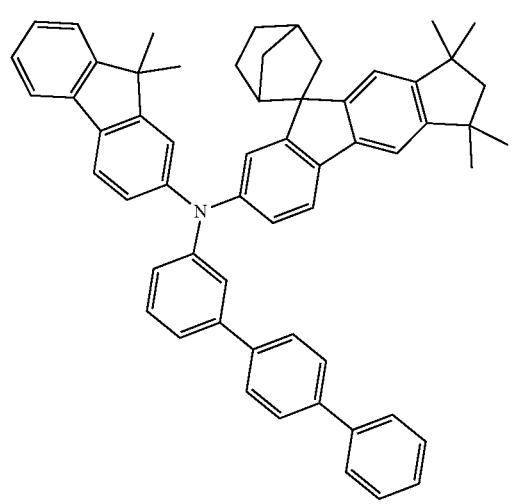
70
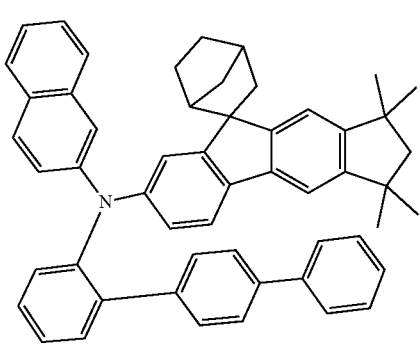

-continued
71
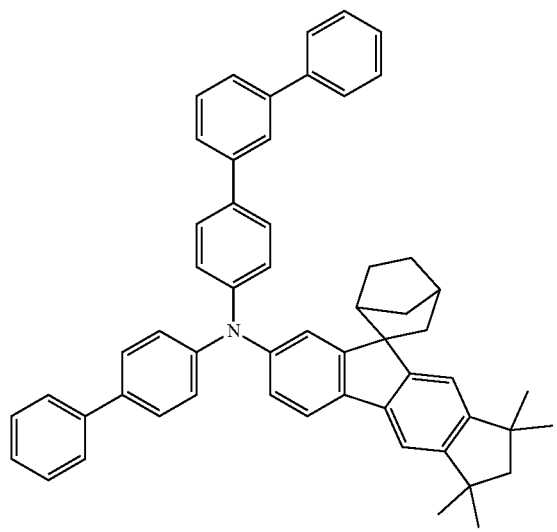
72
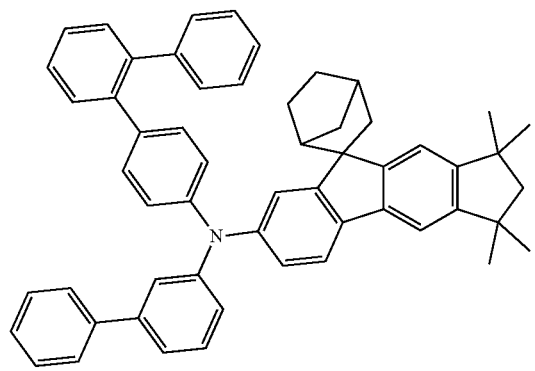
73
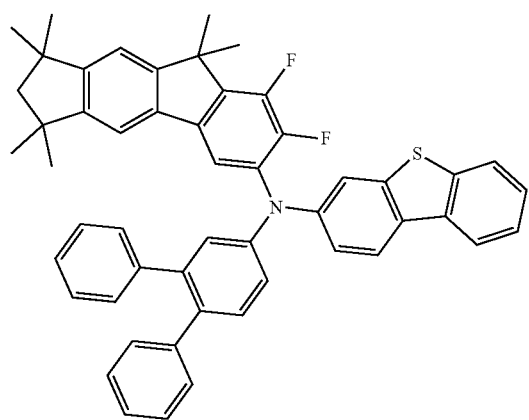
74
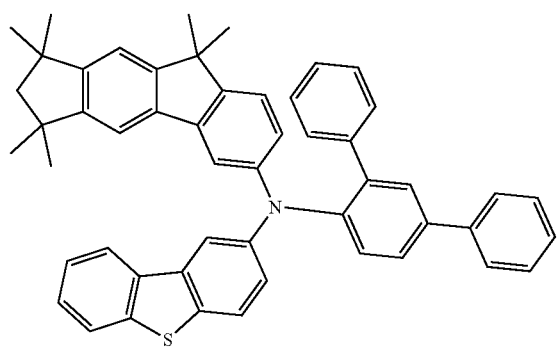
75
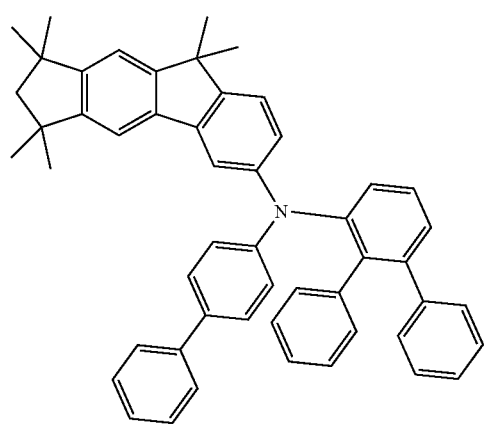
76
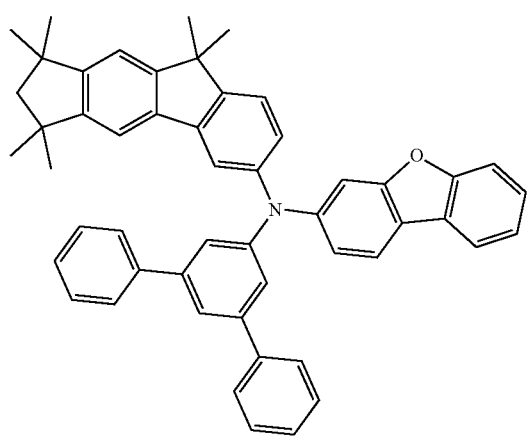

-continued
77
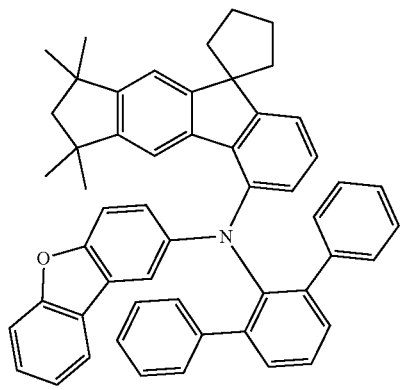
78
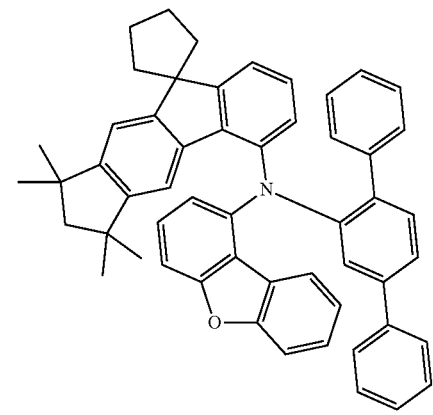
79
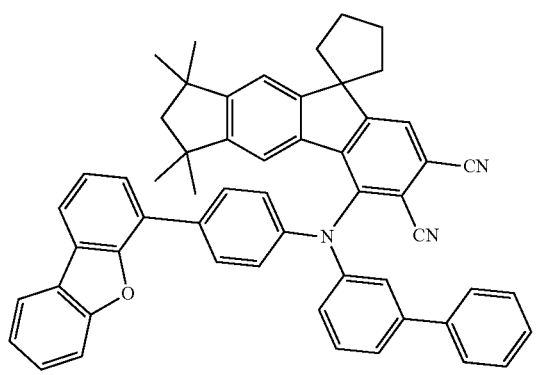
80
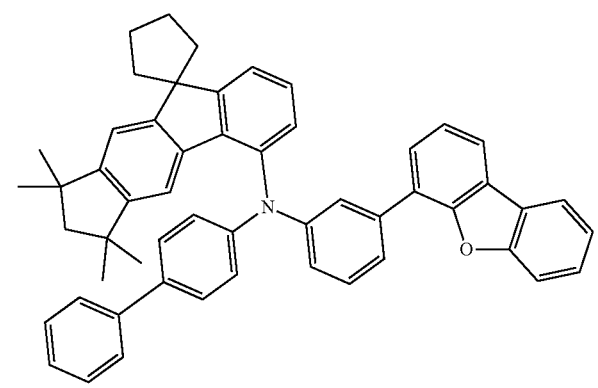
81
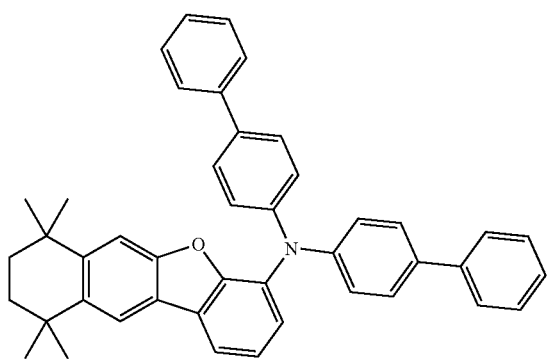
82
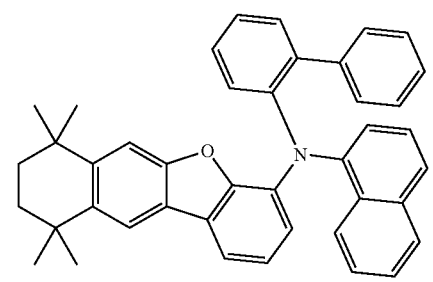
83
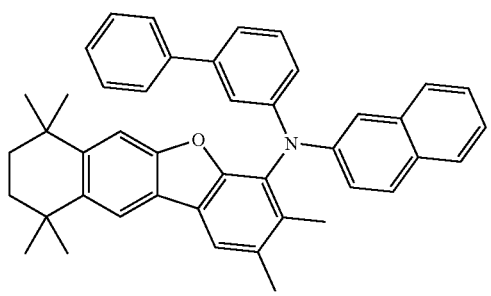
84
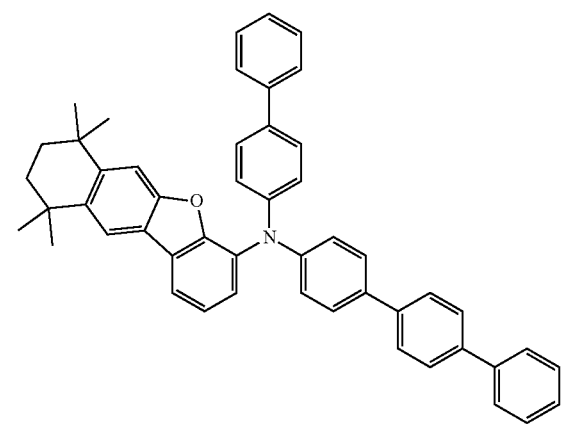

-continued
85
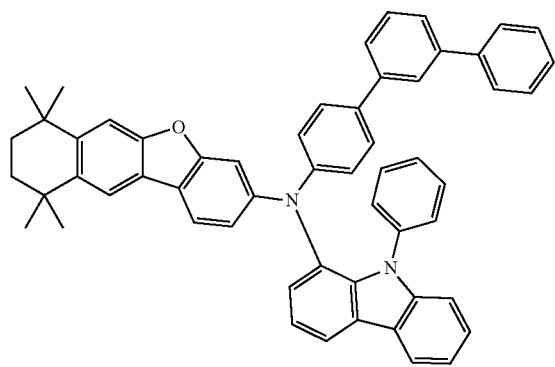
86
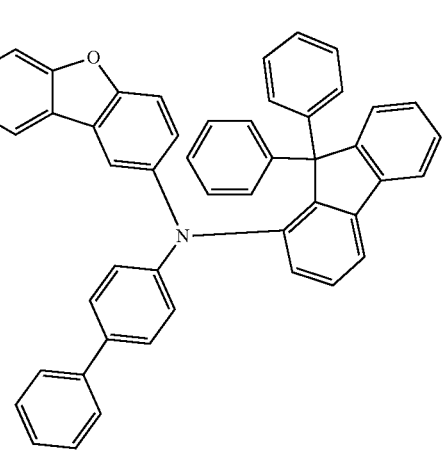
87
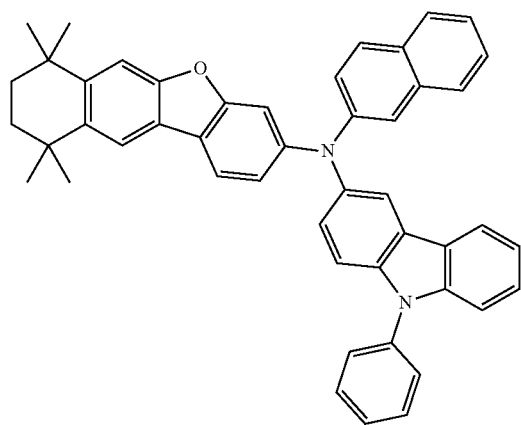
88
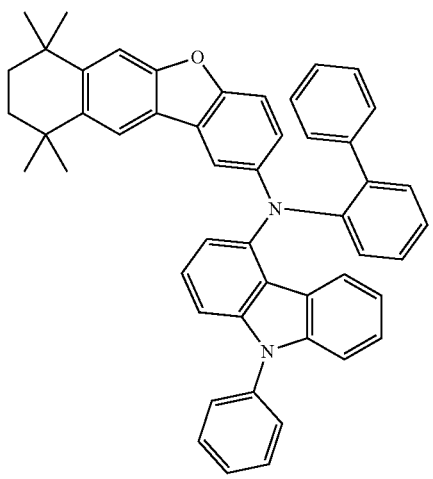
89
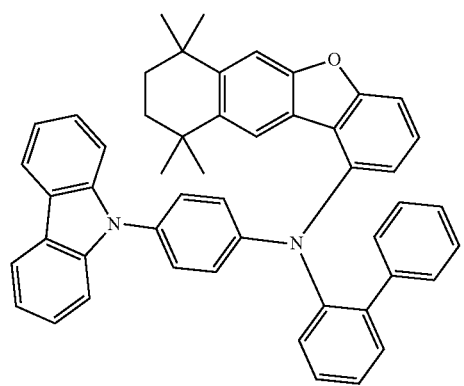
90
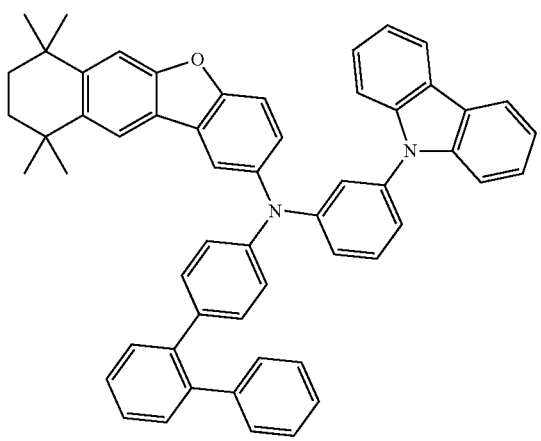

91
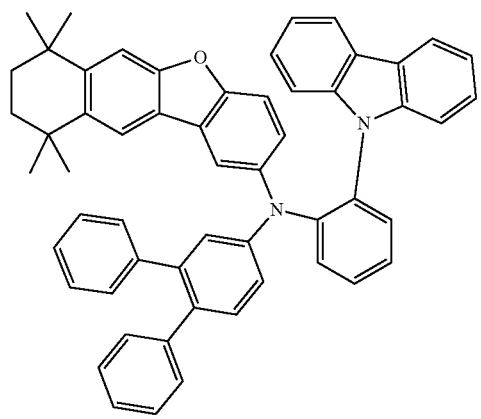
92
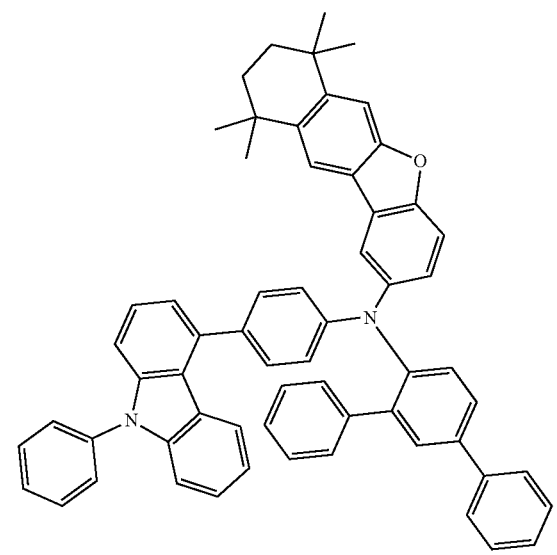
93
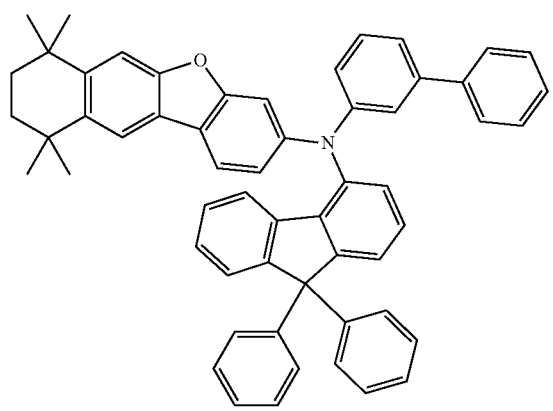
94
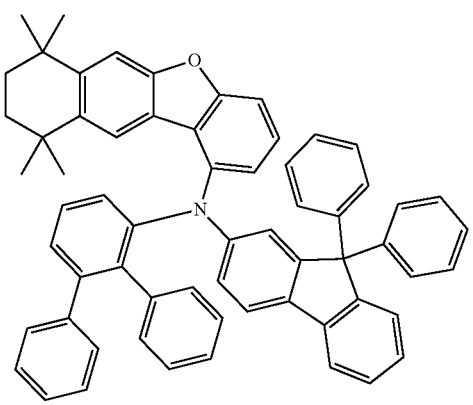
95
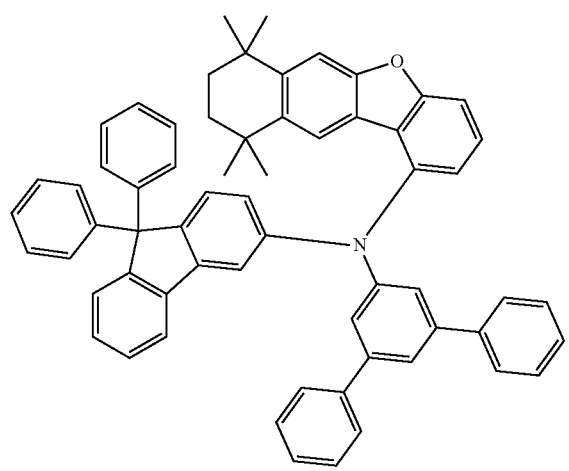
96
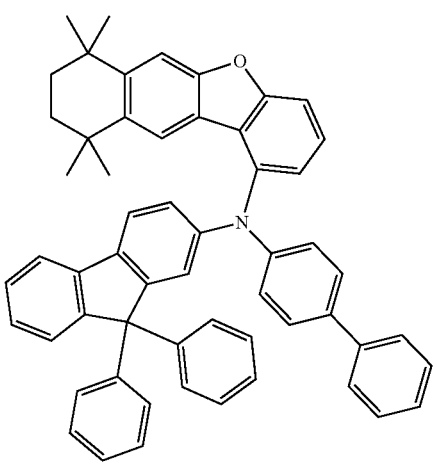

-continued
97
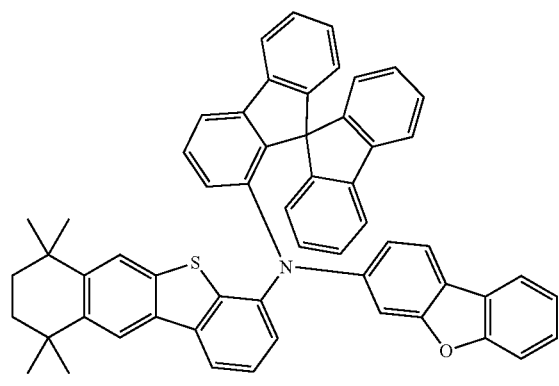
98
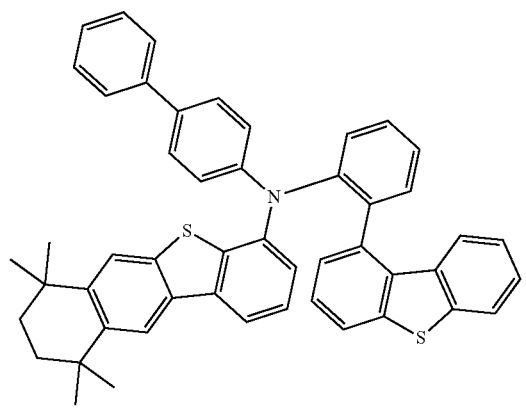
99
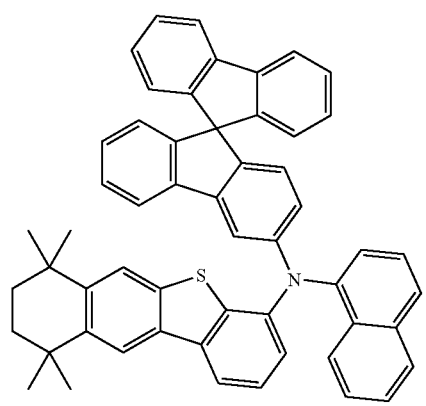
100
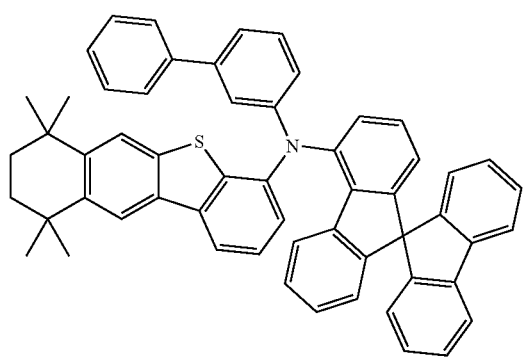
101
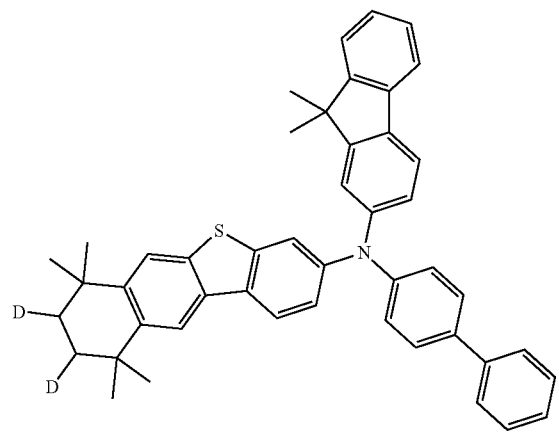
102
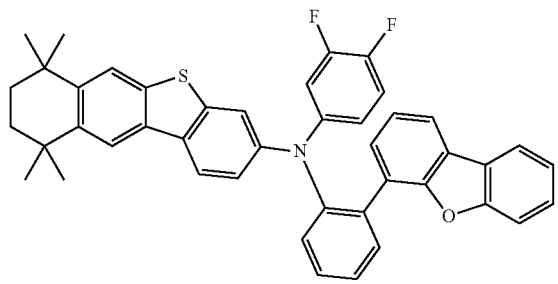

-continued
103
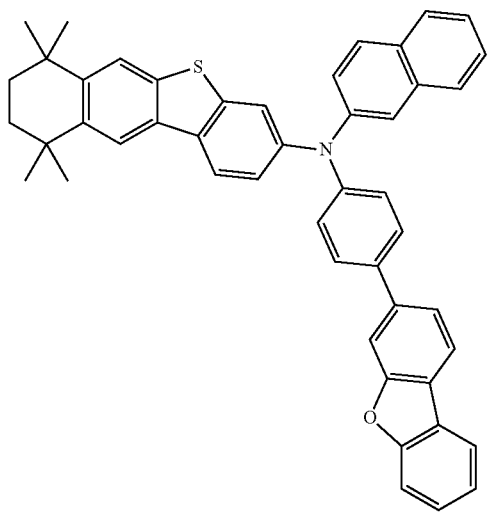
104
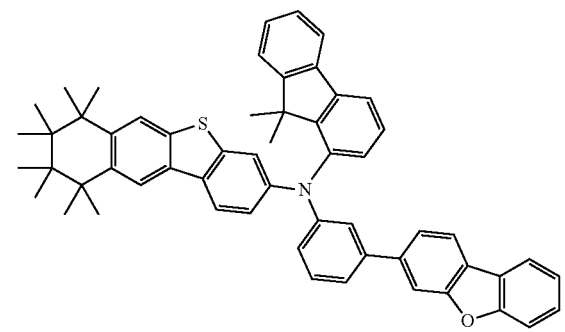
105
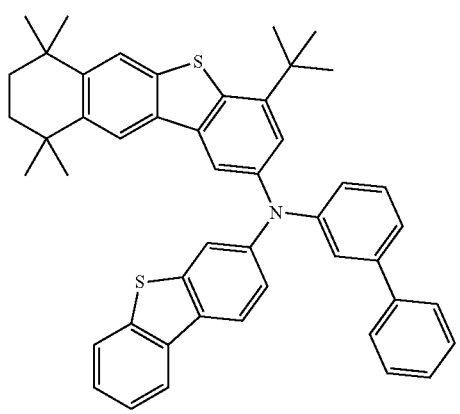
106
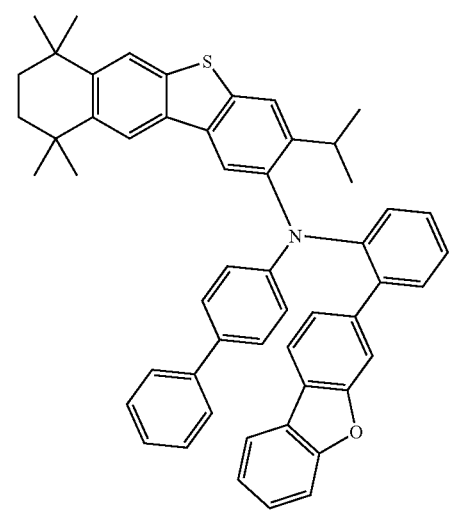
107
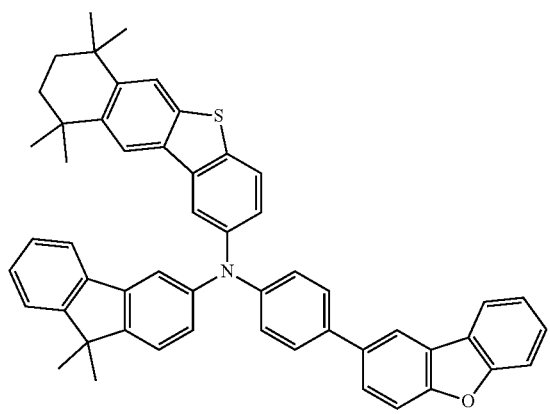
108
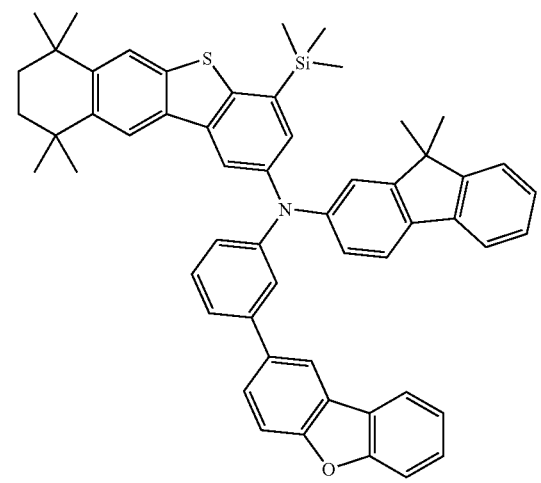

-continued
109
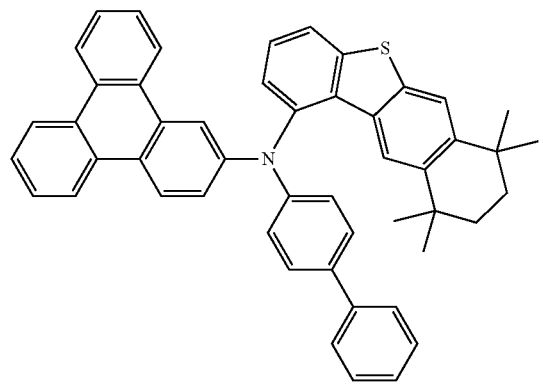
110
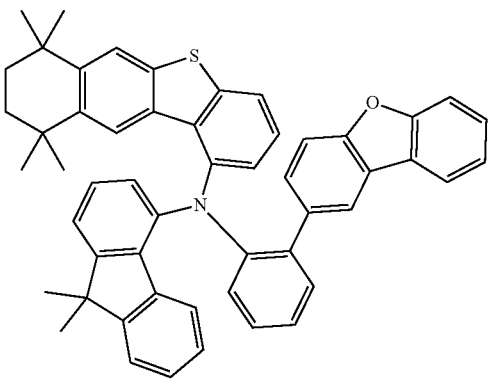
111
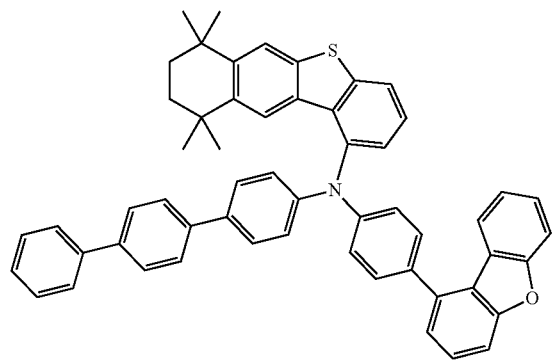
112
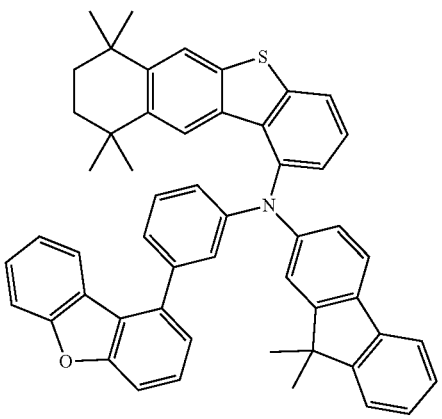
113
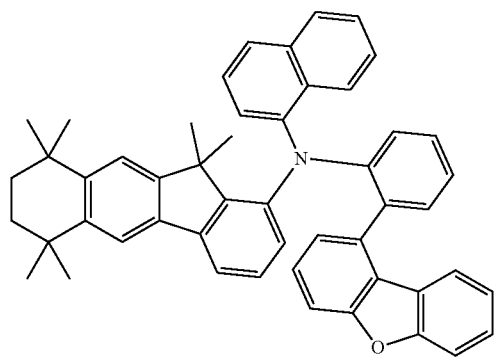
114
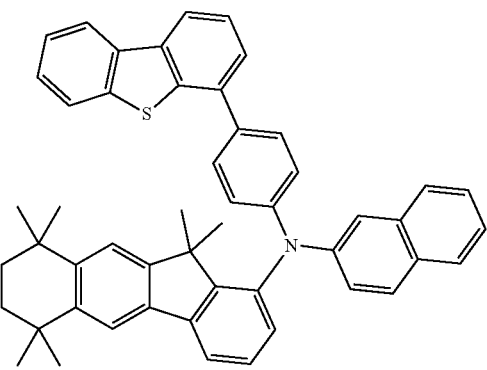
115
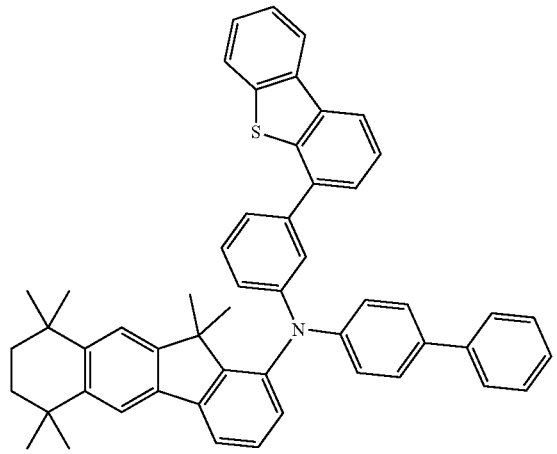
116
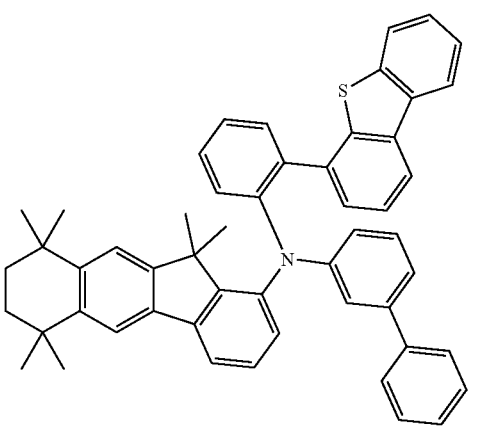

-continued
117
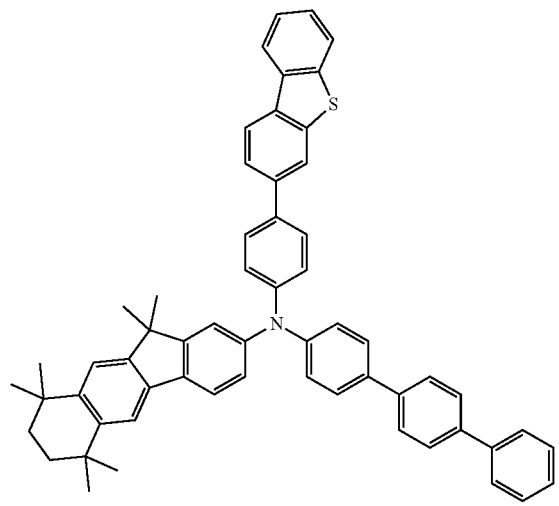
118
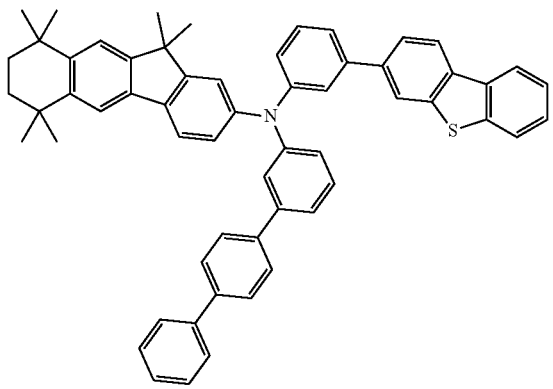
119
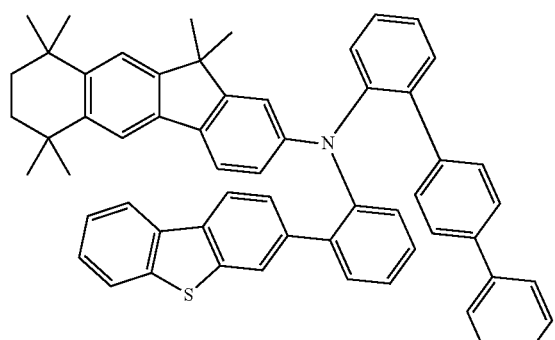
120
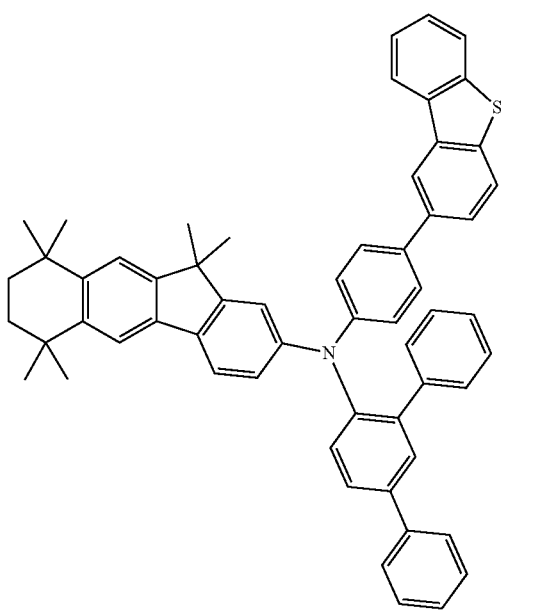
121
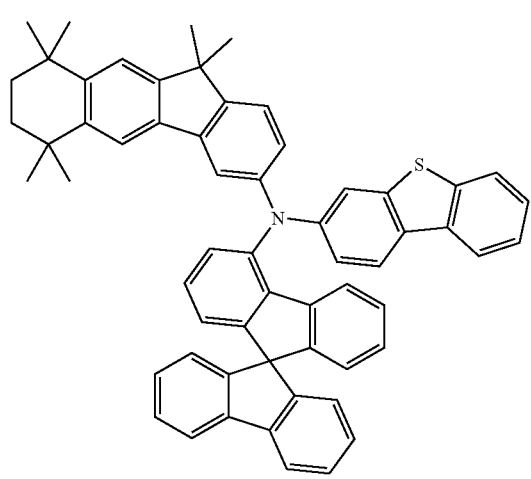
122
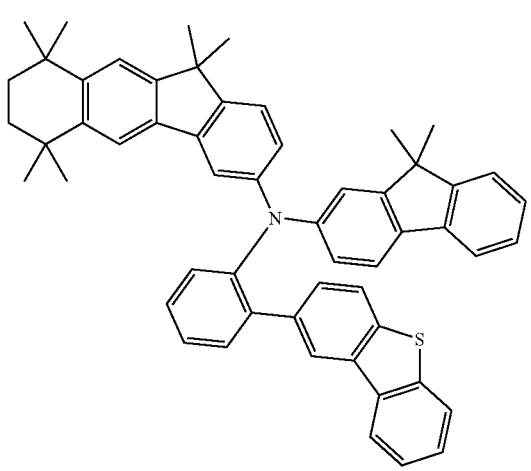

-continued
123
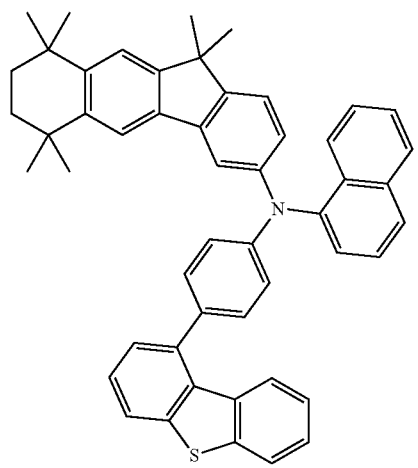
124
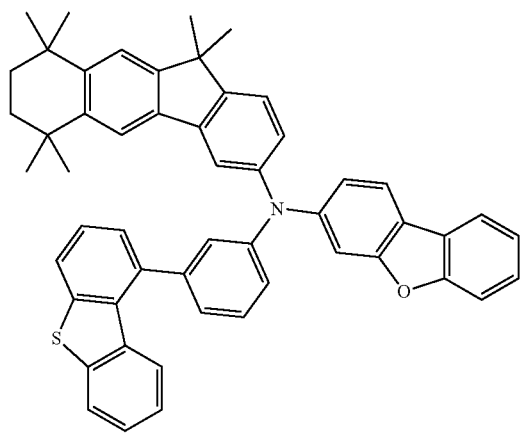
125
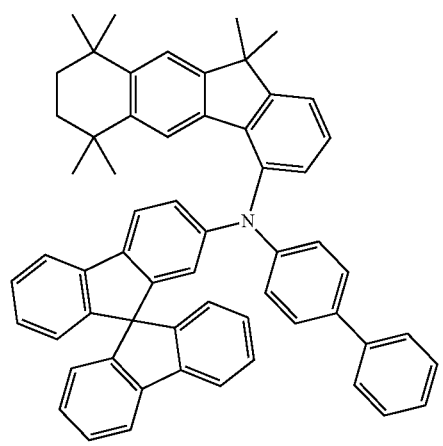
126
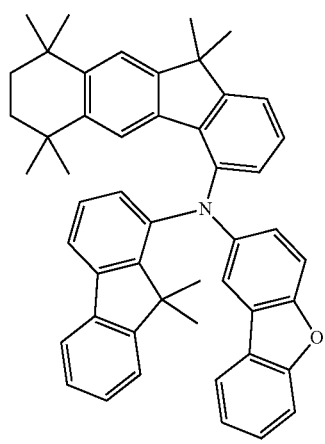
127
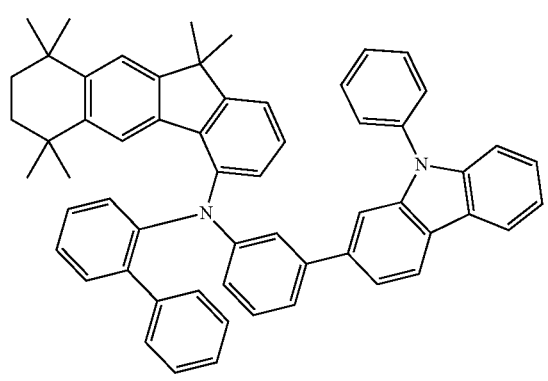
128
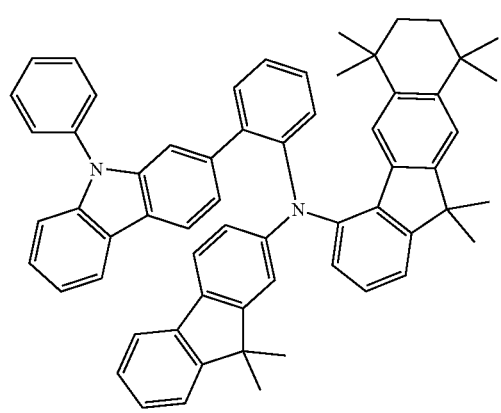

-continued
129
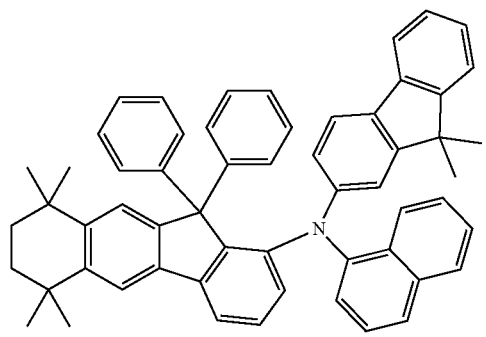
130
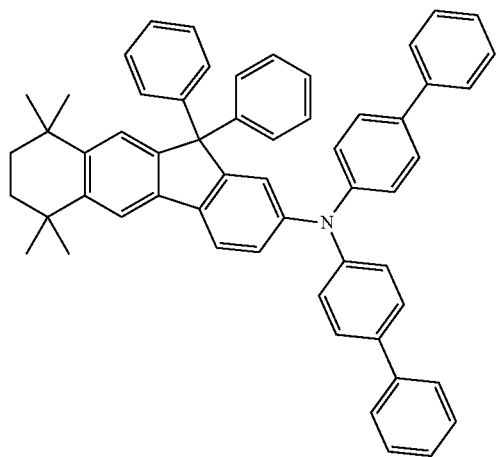
131
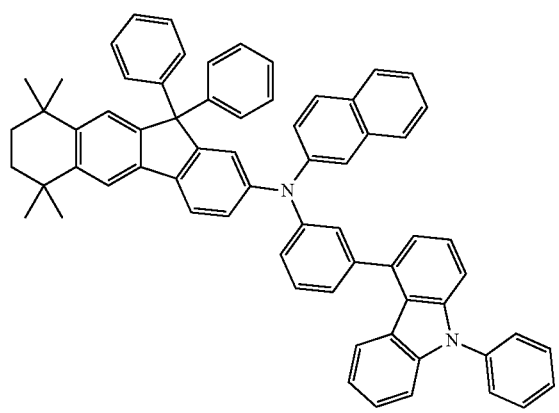
132
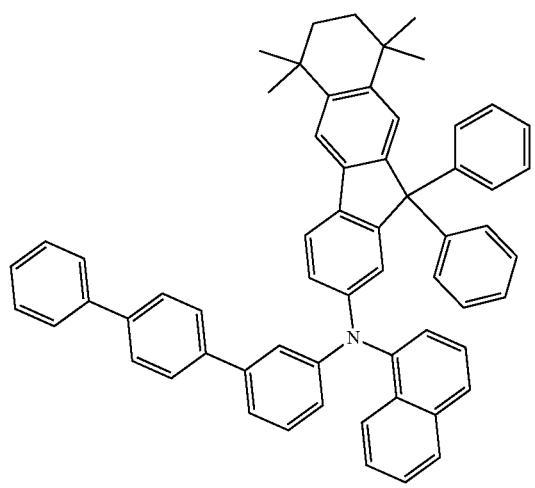
133
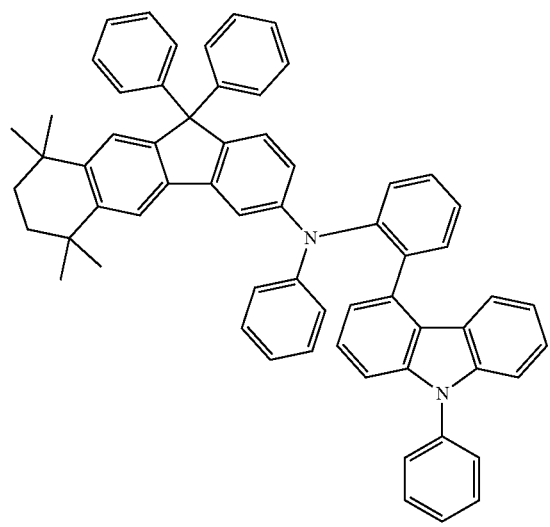
134
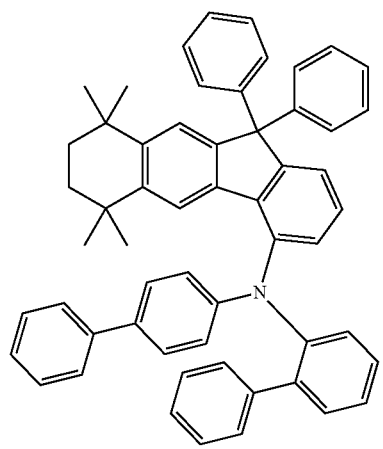

135
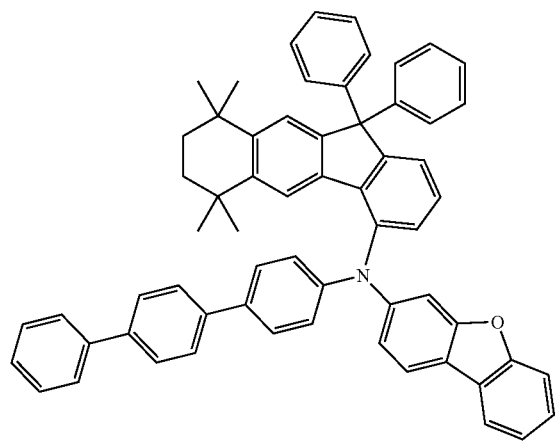
136
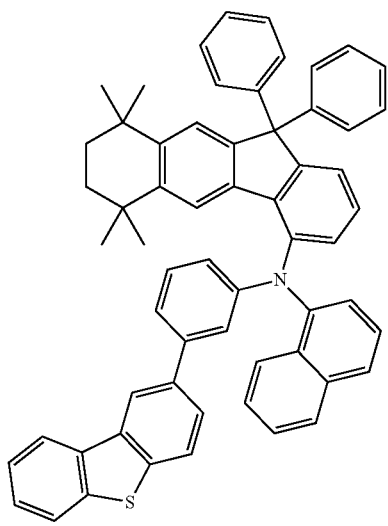
137
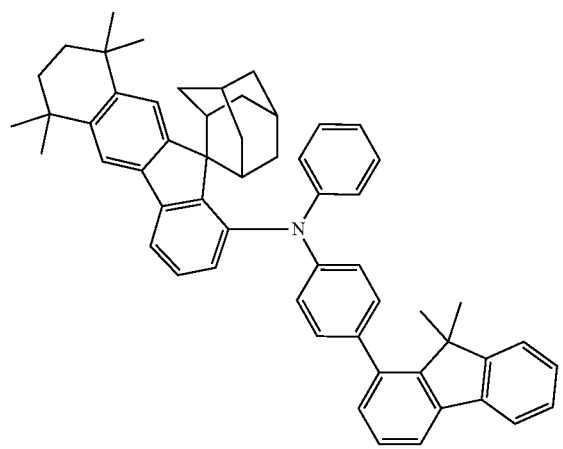
138
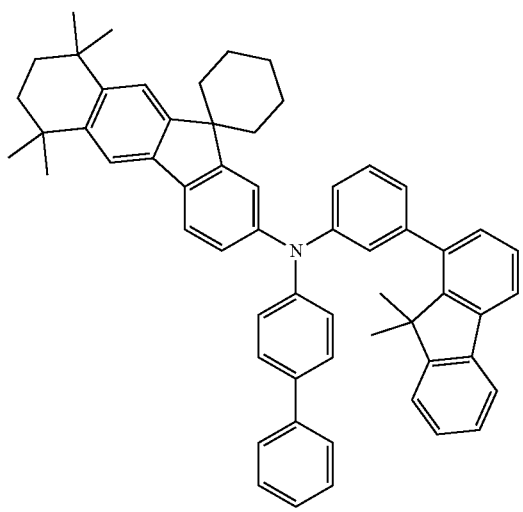
139
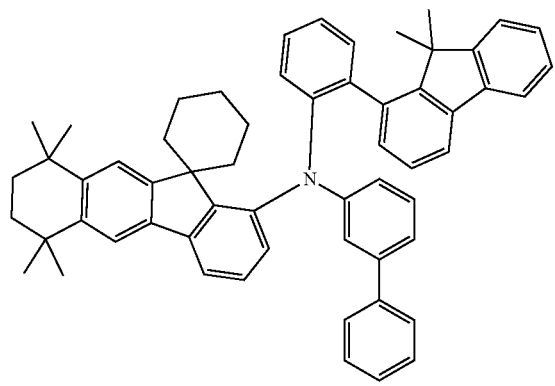
140
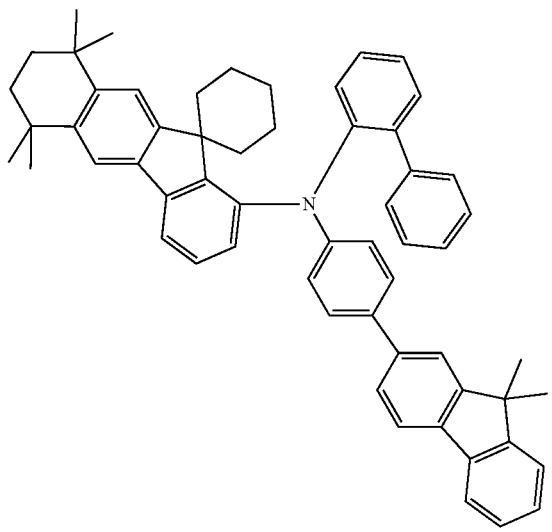

-continued
141
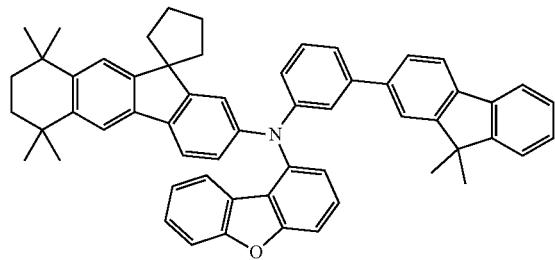
142
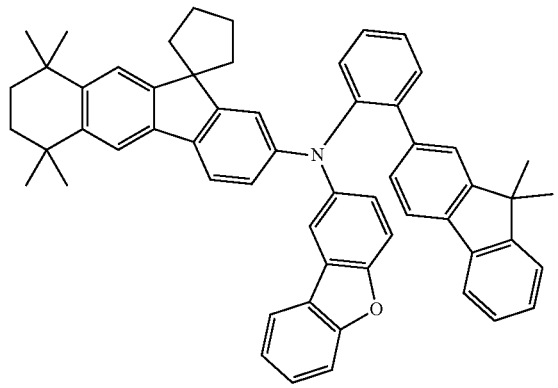
143
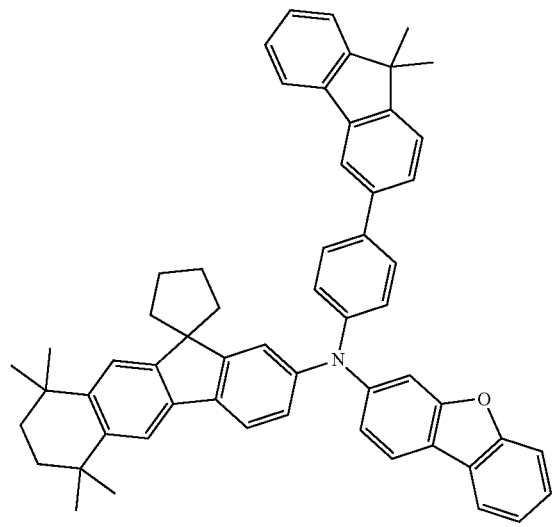
144
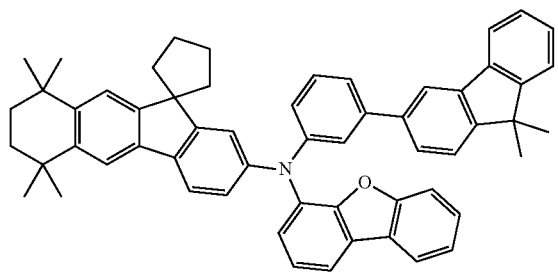
145
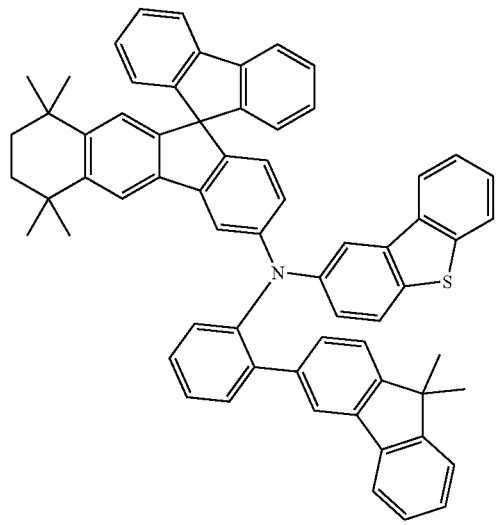
146
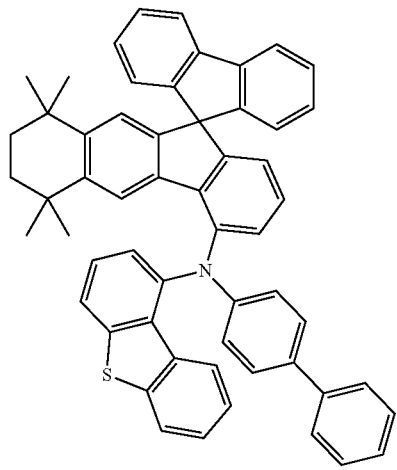

-continued
147
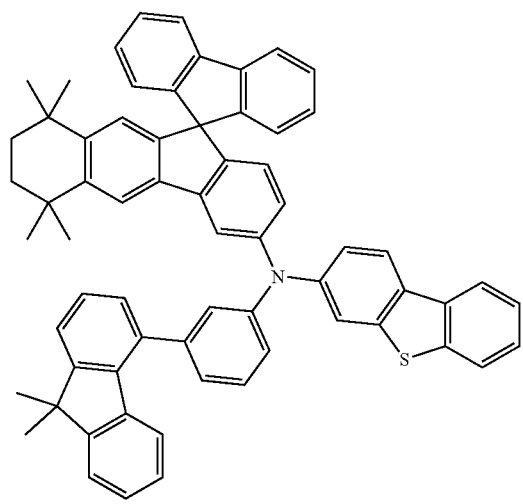
148
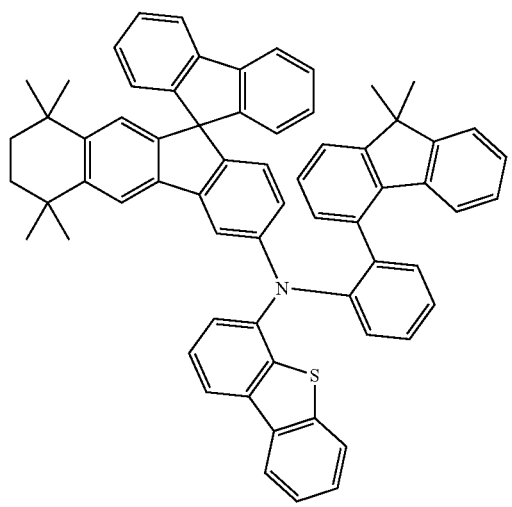
149
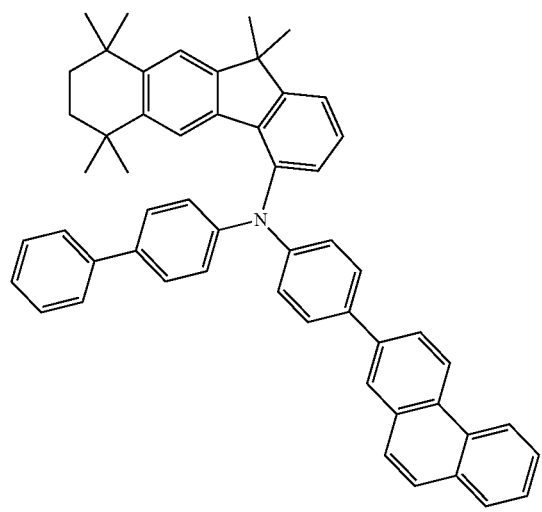
150
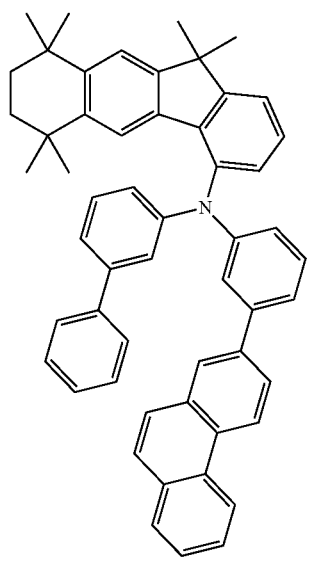
151
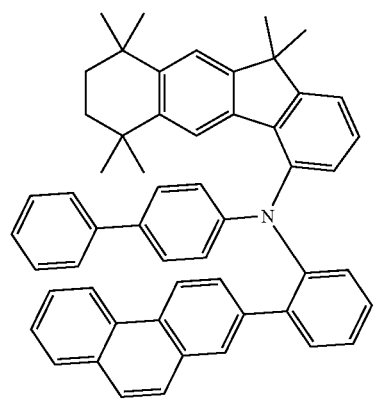
152
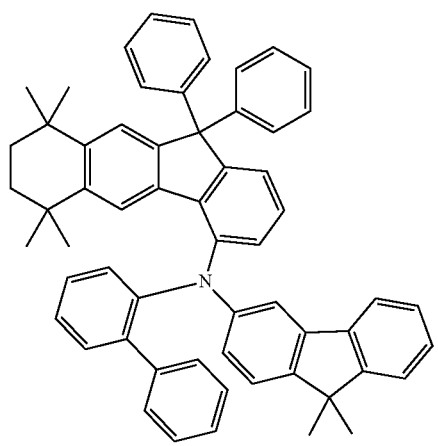

-continued
153
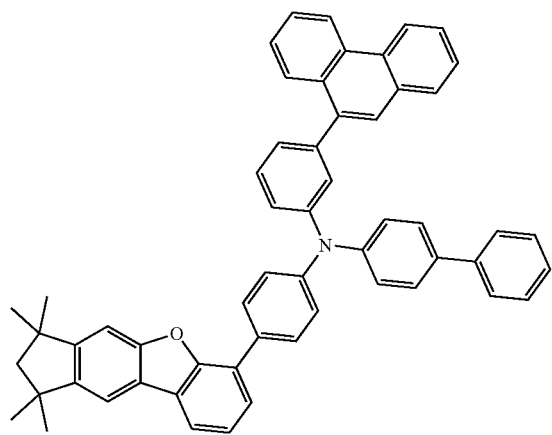
154
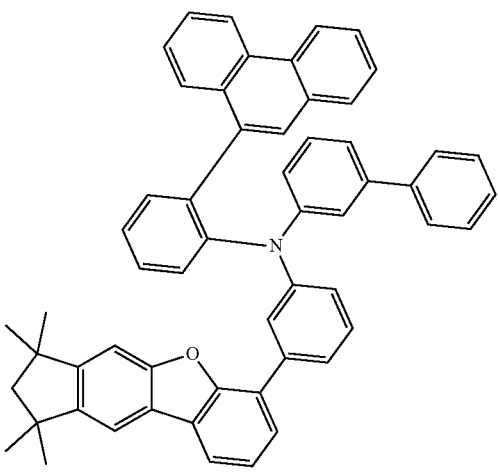
155
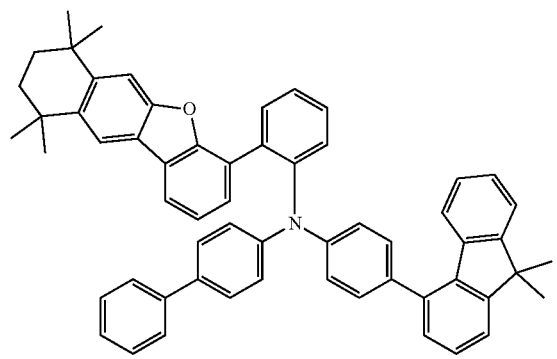
156
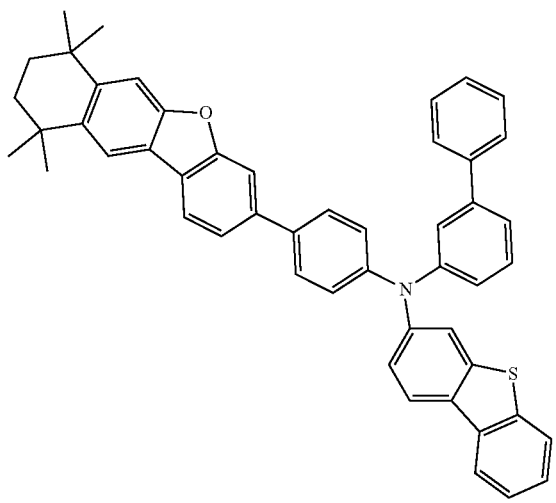
157
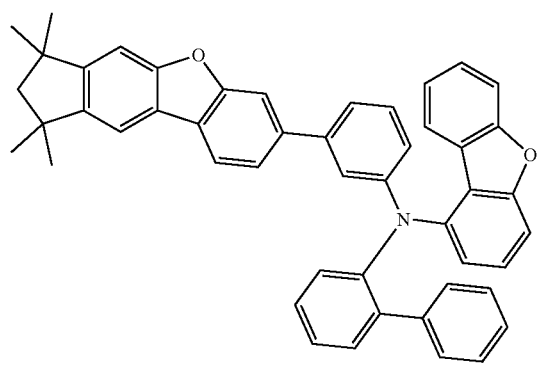
158
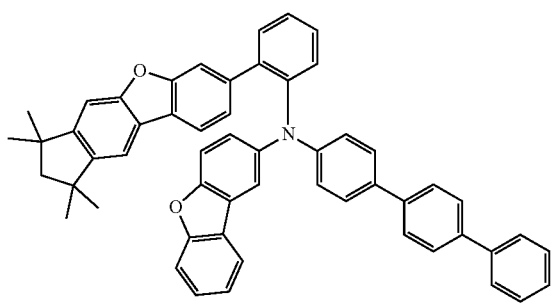

-continued
159
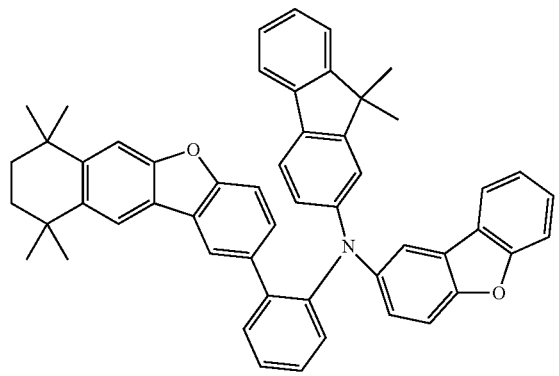
160
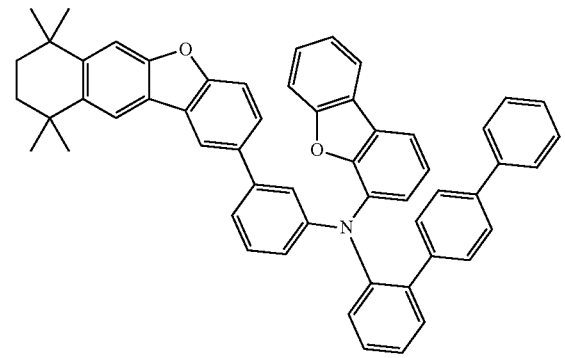
161
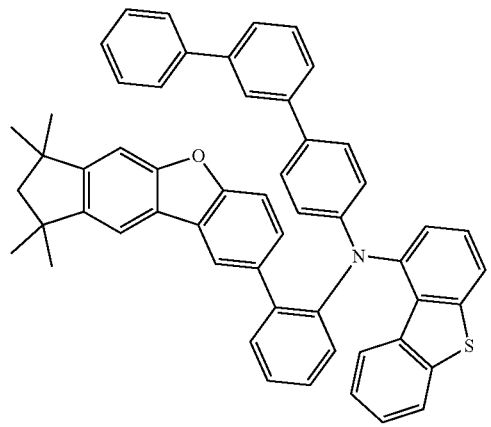
162
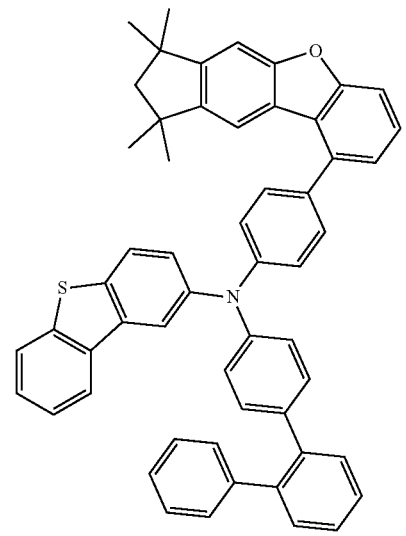
163
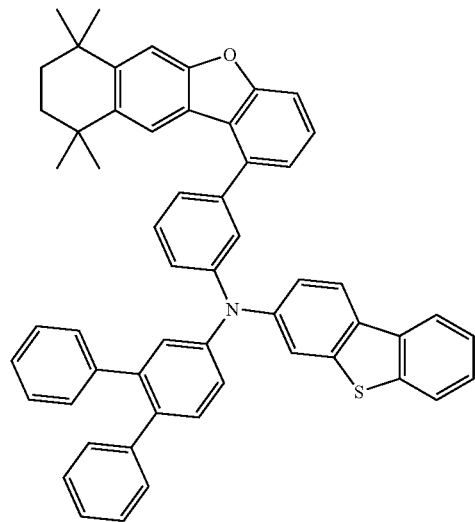
164
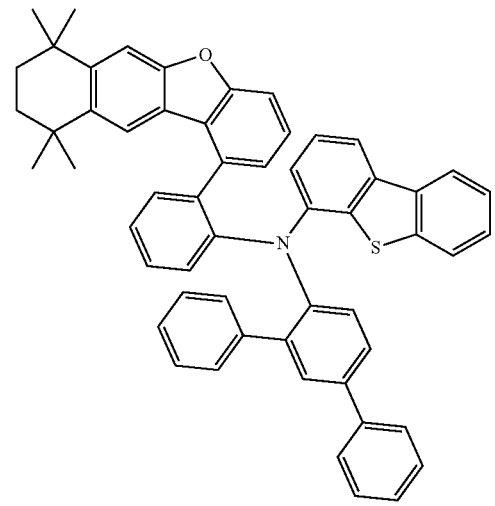

-continued
165
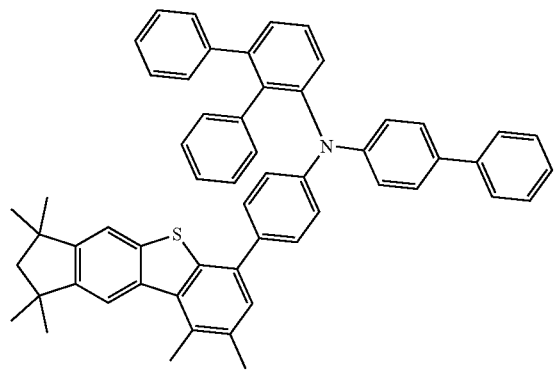
166
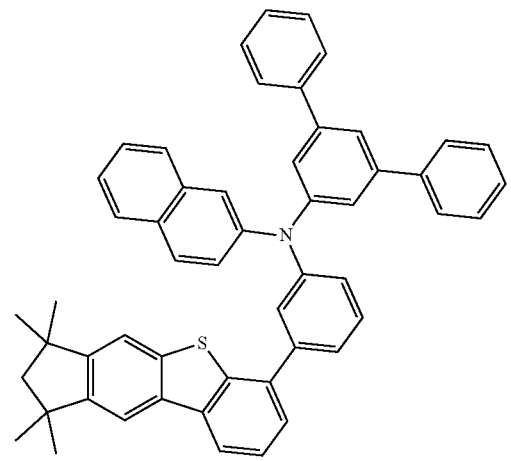
167
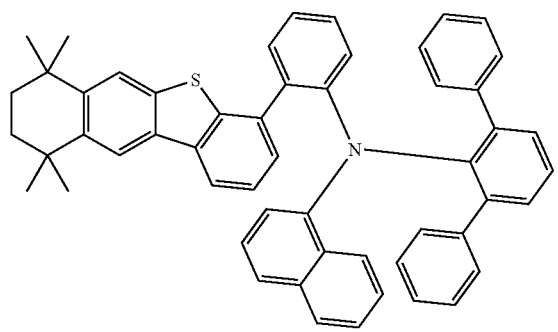
168
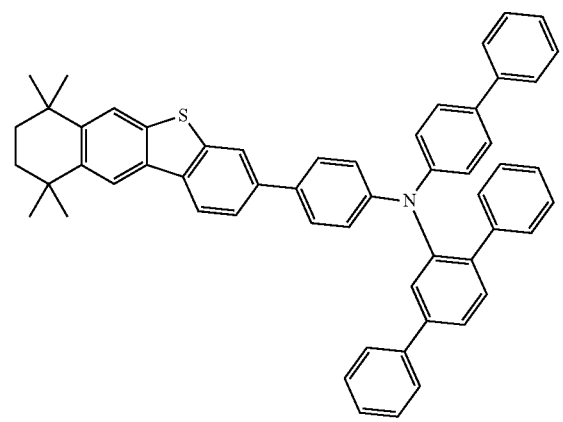
169
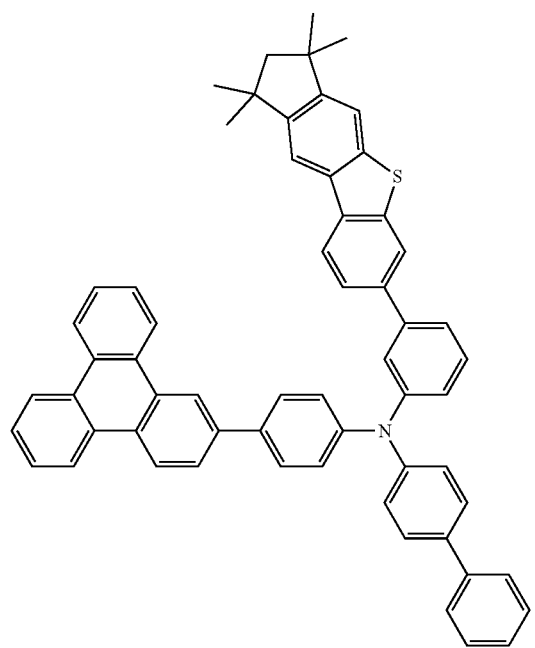
170
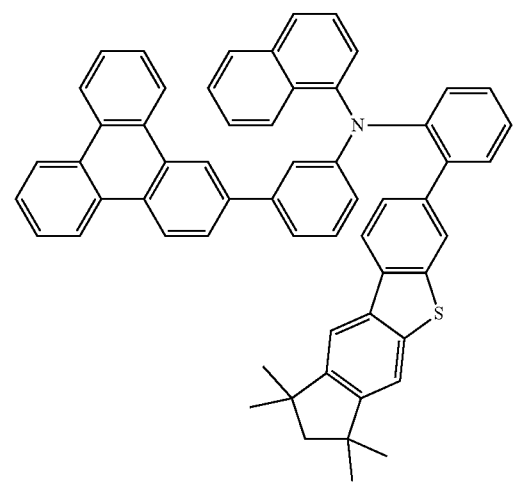

-continued
171
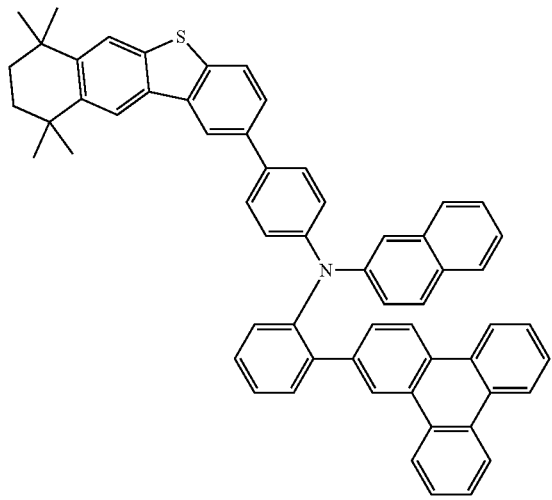
172
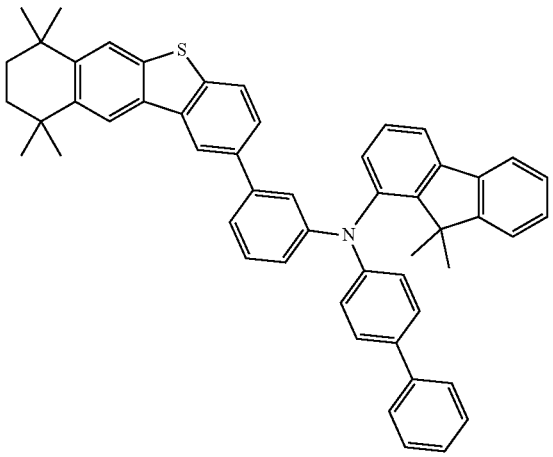
173
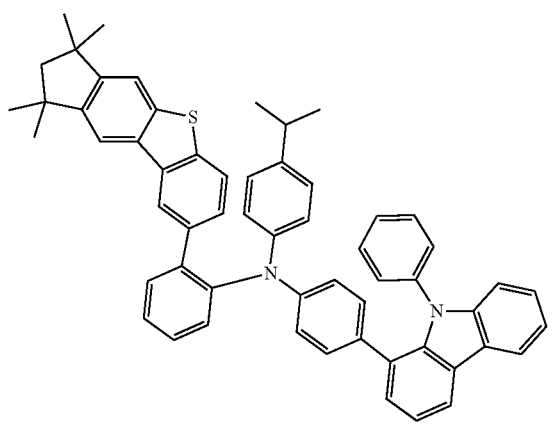
174
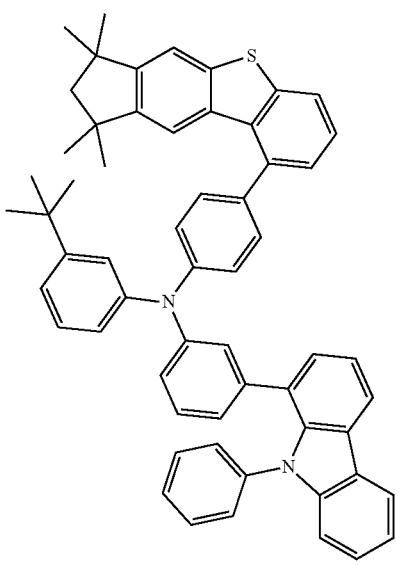
175
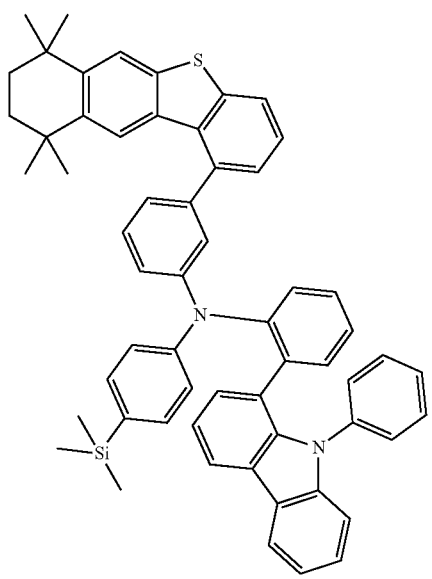
176
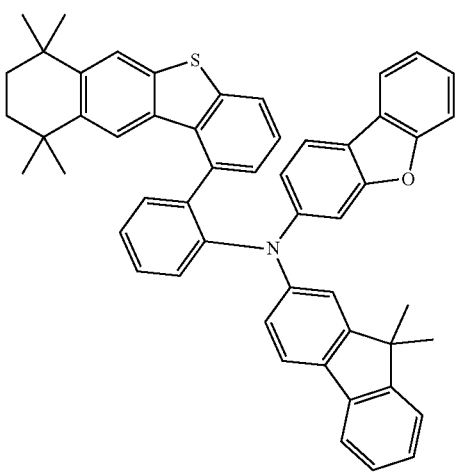

373 374
-continued
177
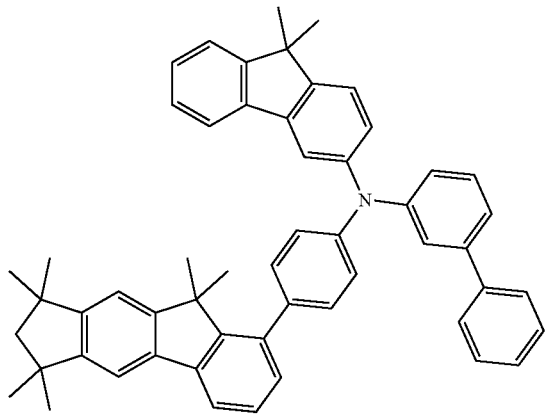
178
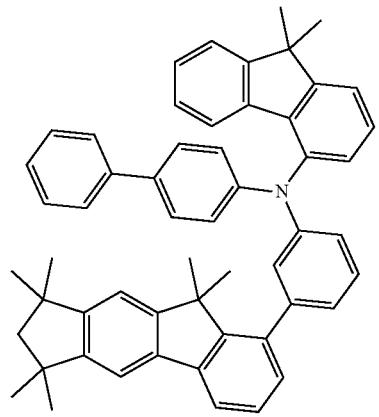
179
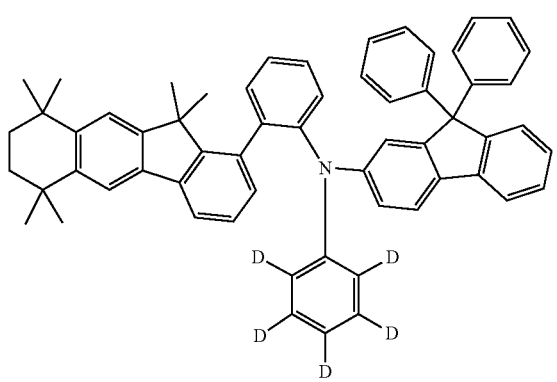
180
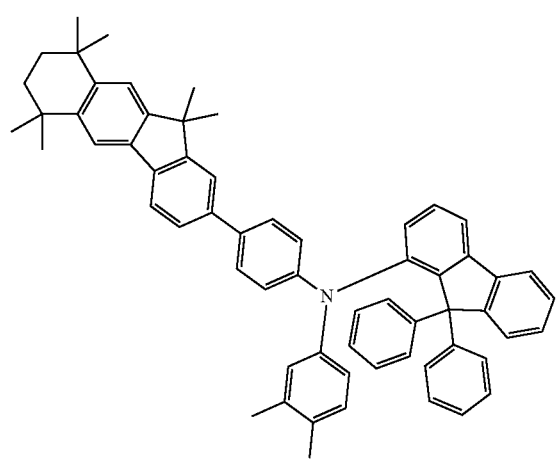
181
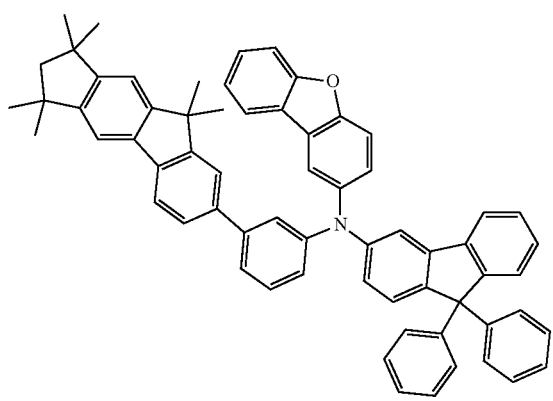
182
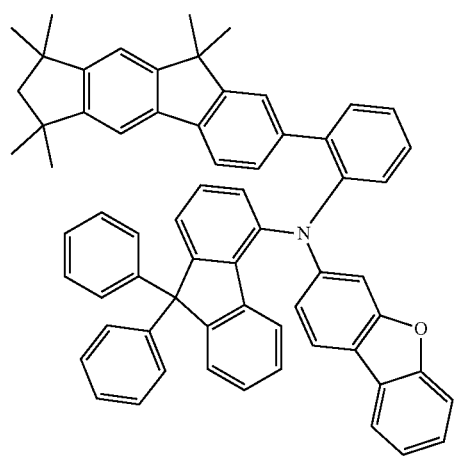

-continued
183
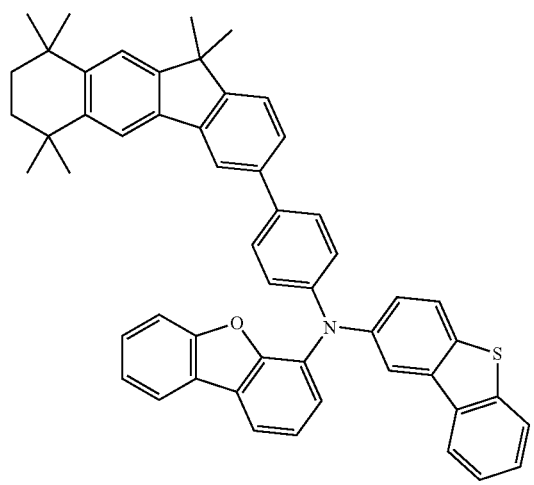
184
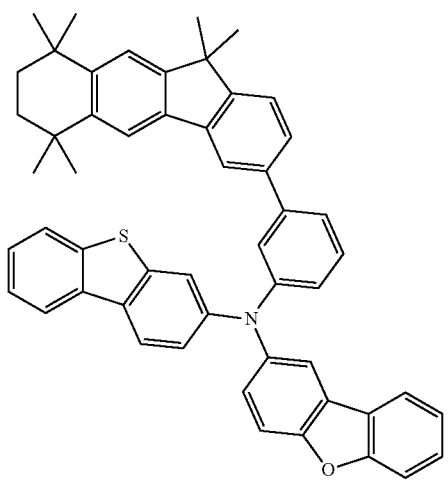
185
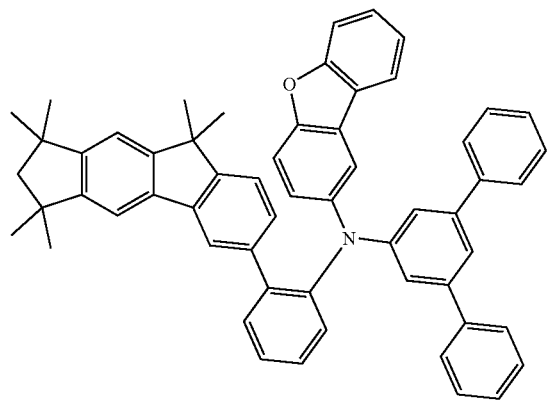
186
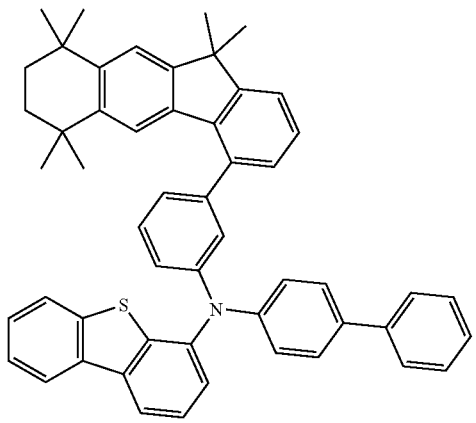
187
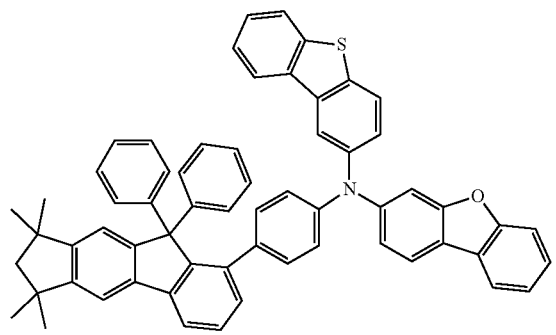
188
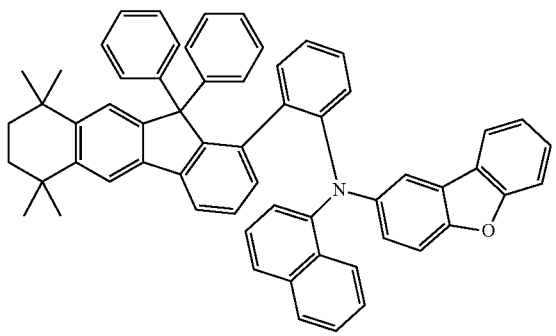

-continued
189
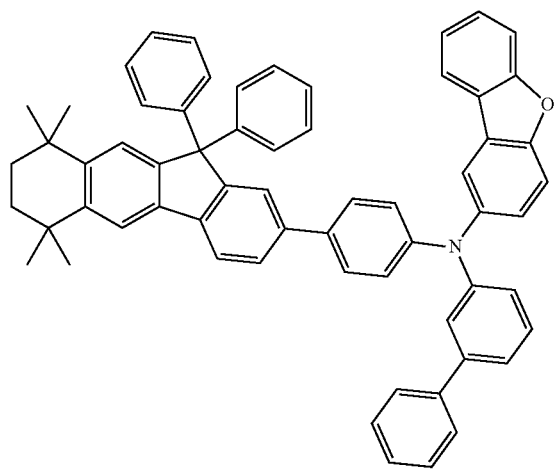
190
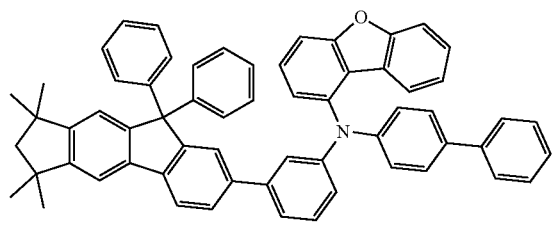
191
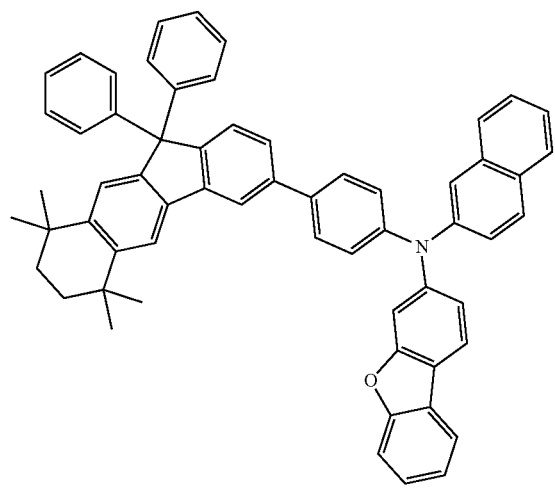
192
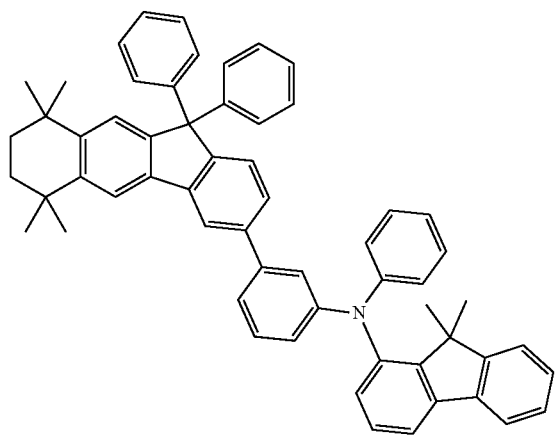
193
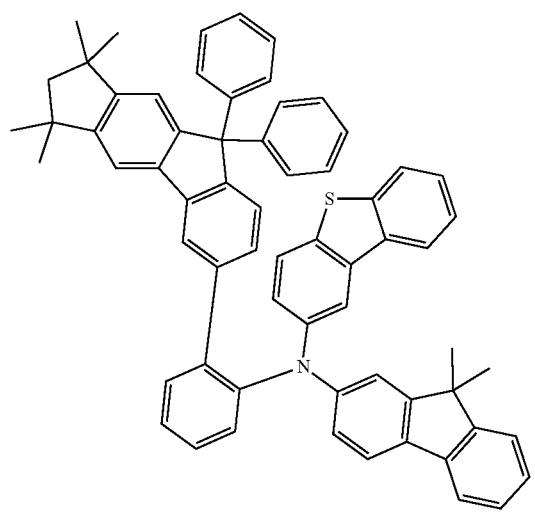
194
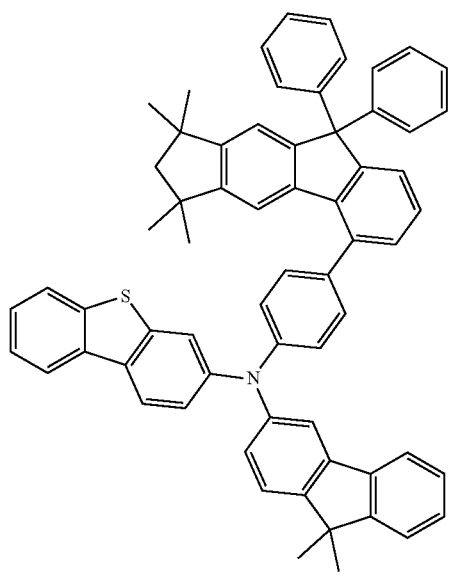

-continued
195
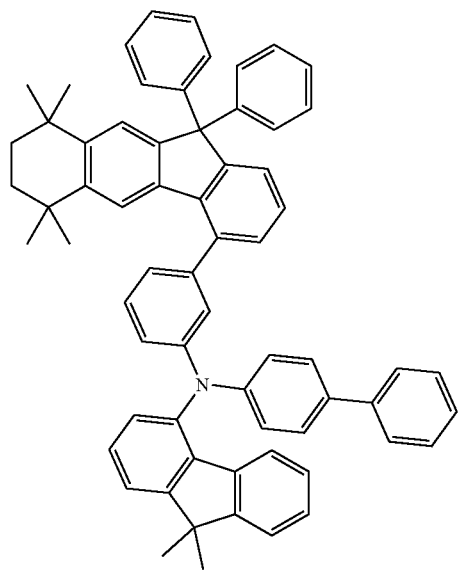
196
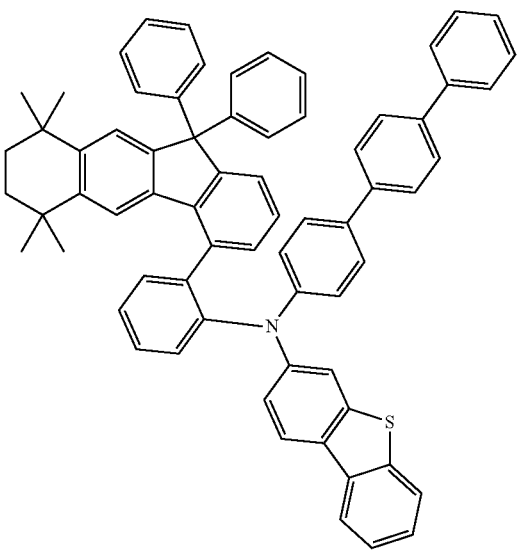
197
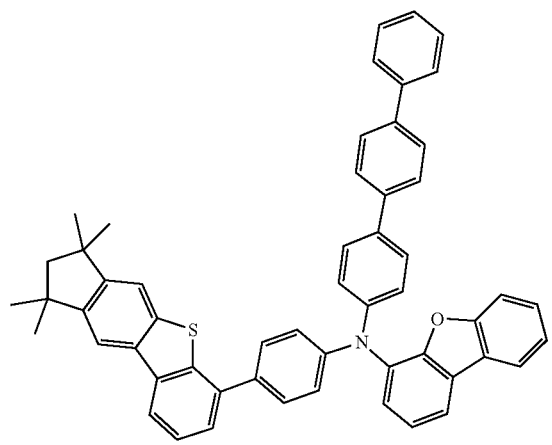
198
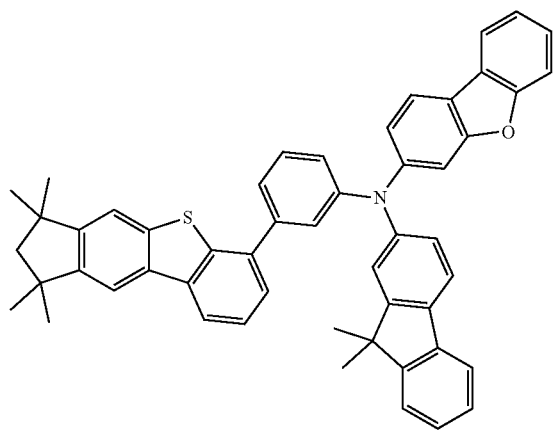
199
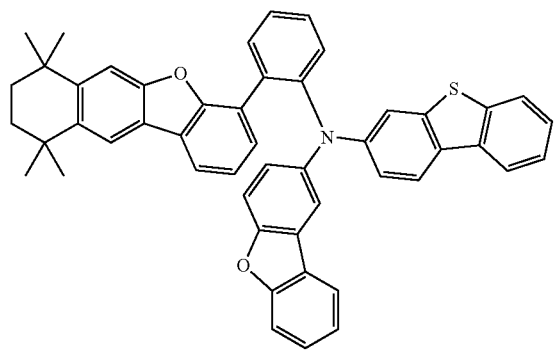
200
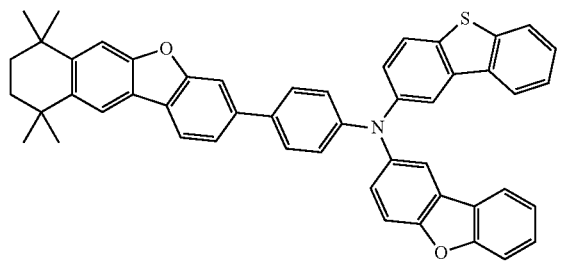

-continued
201
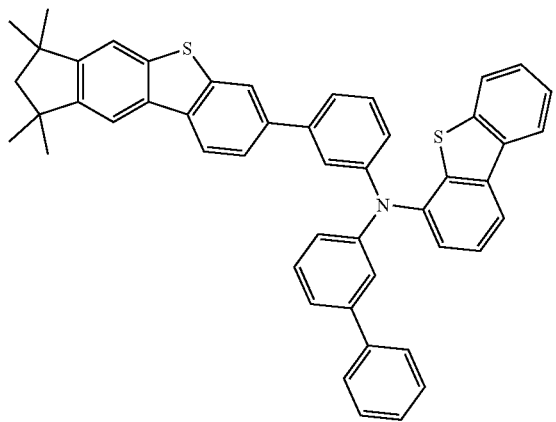
202
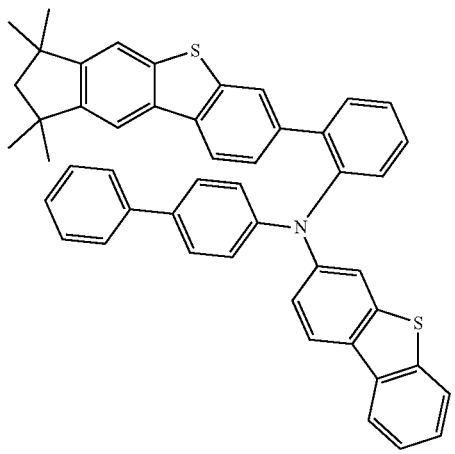
203
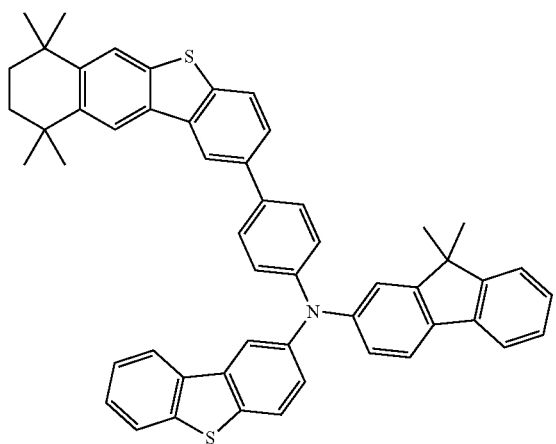
204
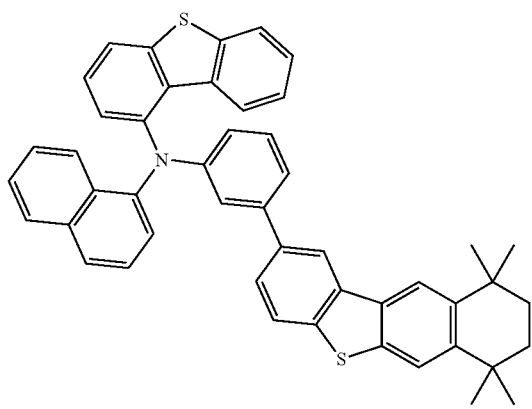
205
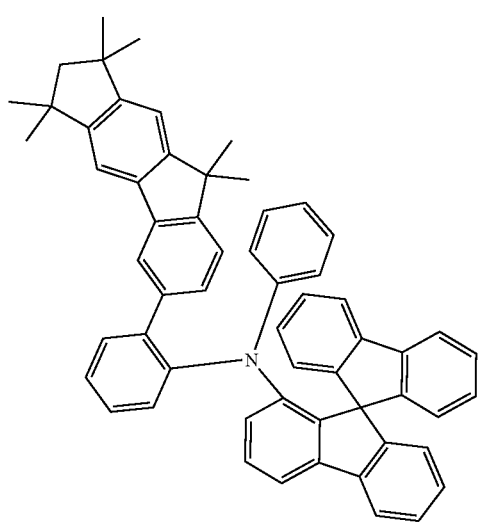
206
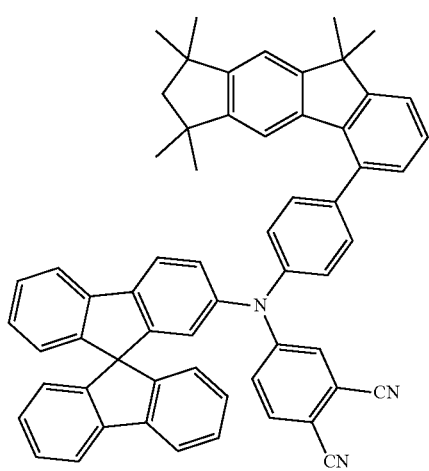

-continued
207
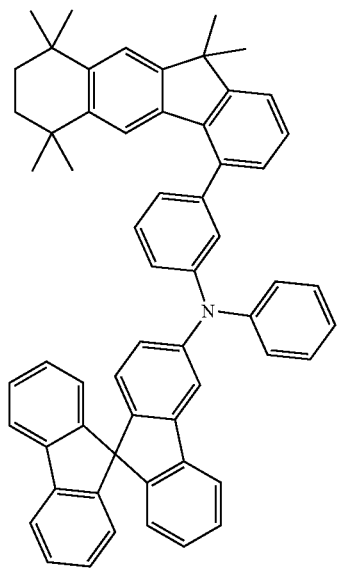
208
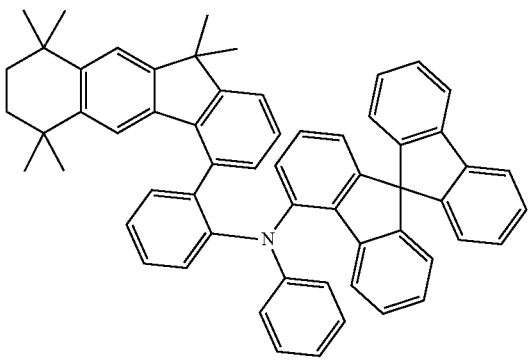
209
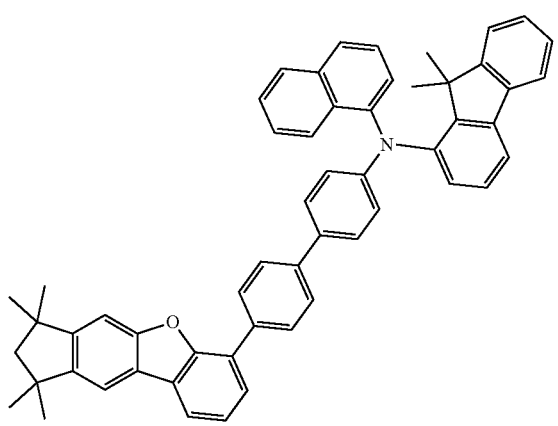
210
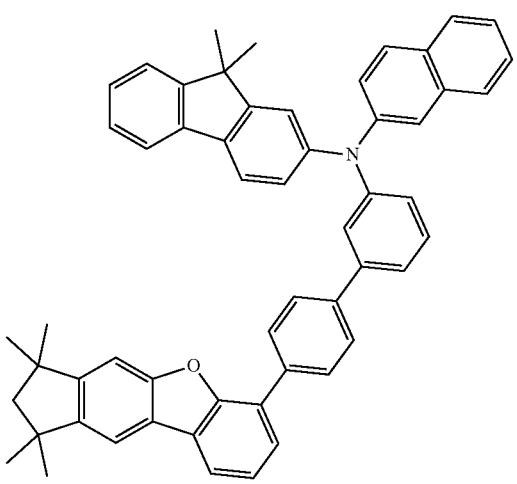
211
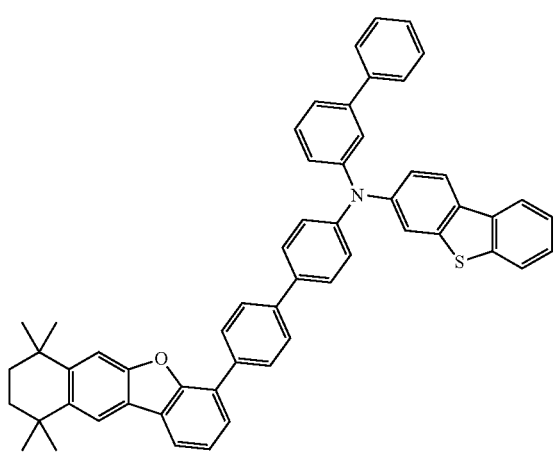
212
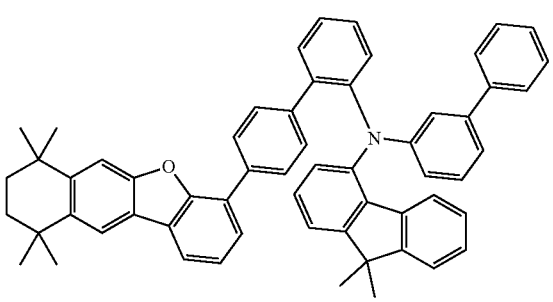

-continued
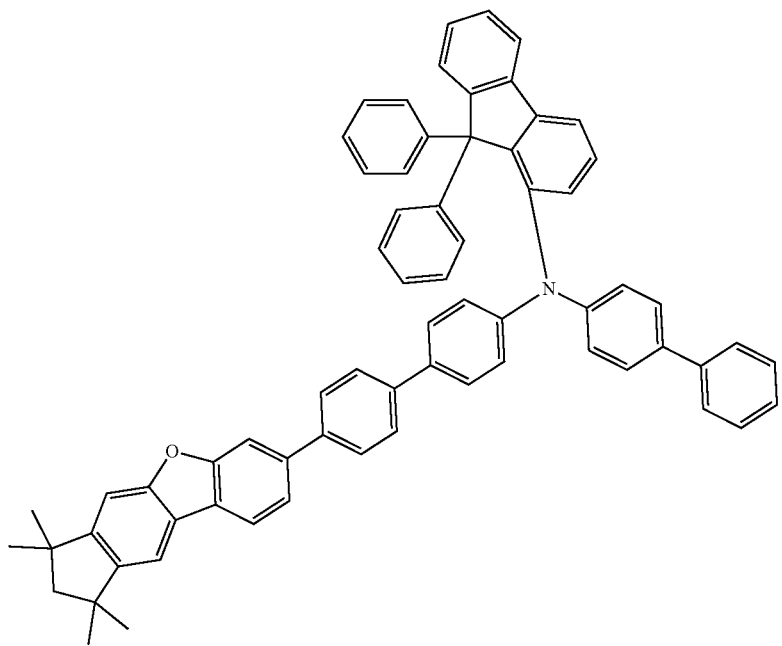
213
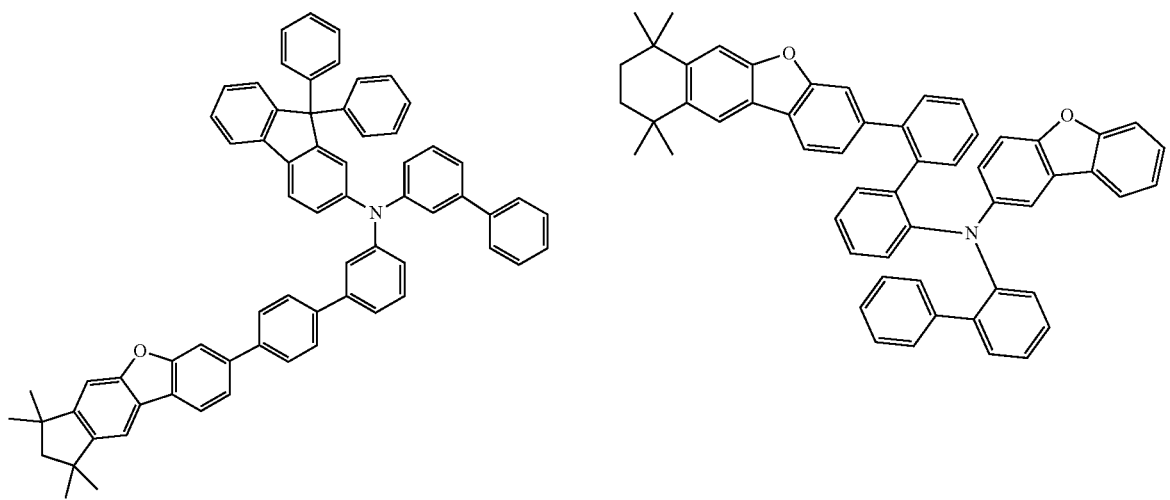
214 215

-continued
387 216 388 217
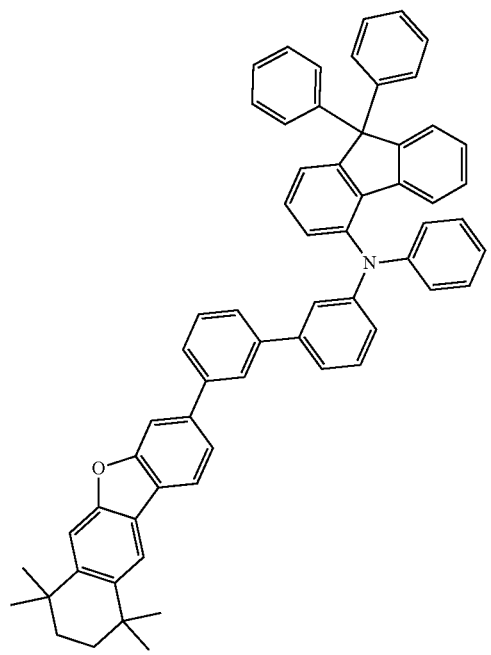 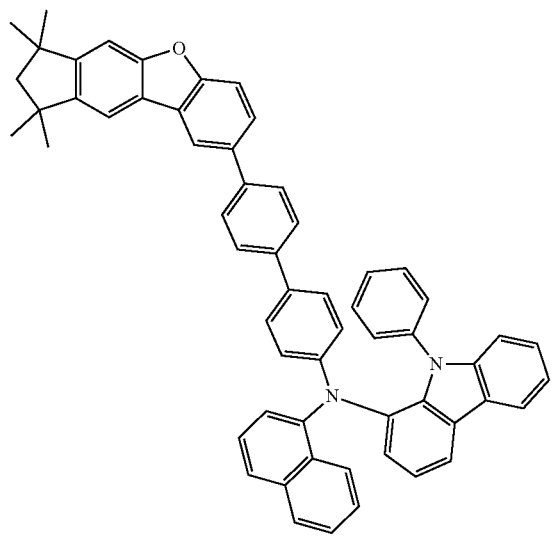
218 219
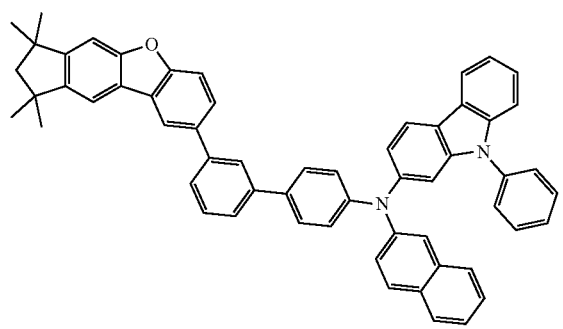 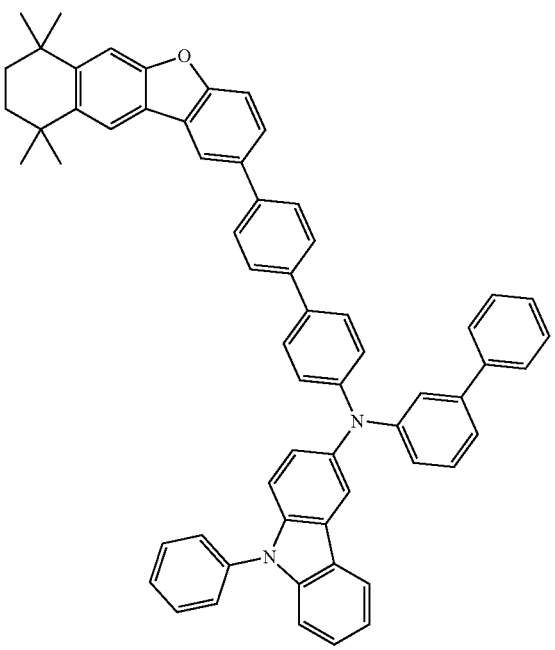

220
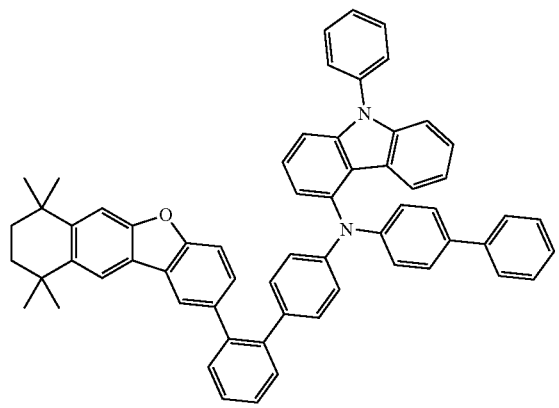
221
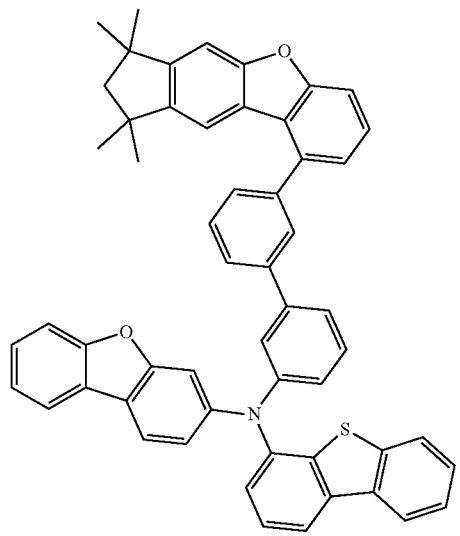
222
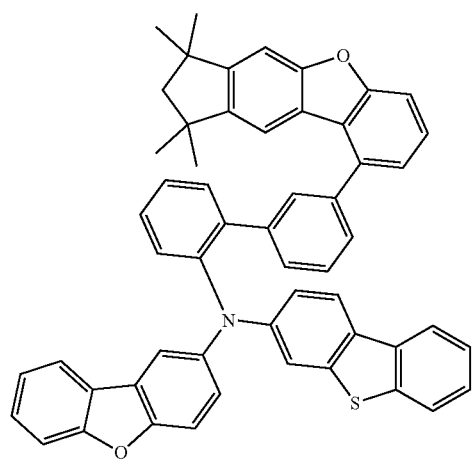
223
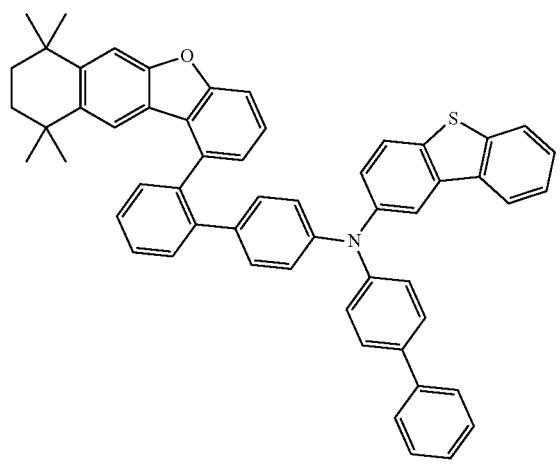
224
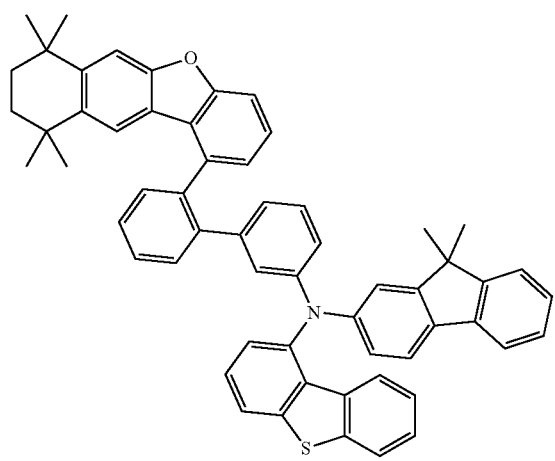
225
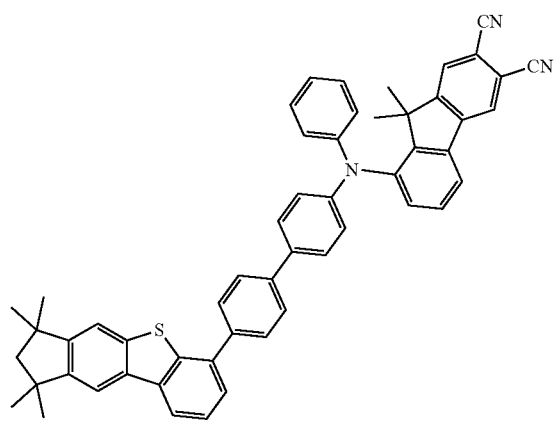

-continued
226
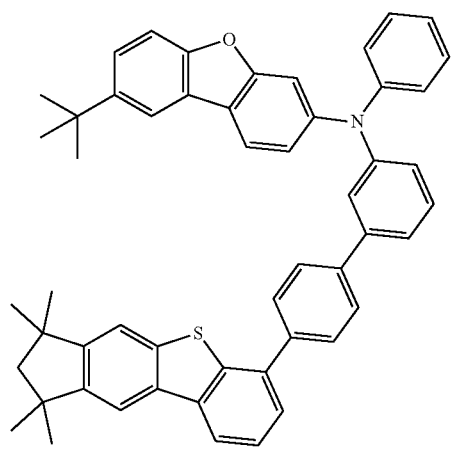
227
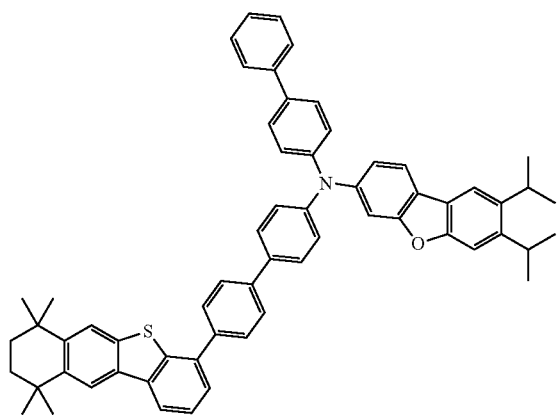
228
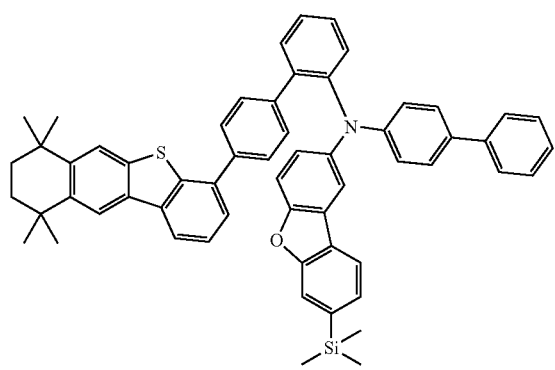
229
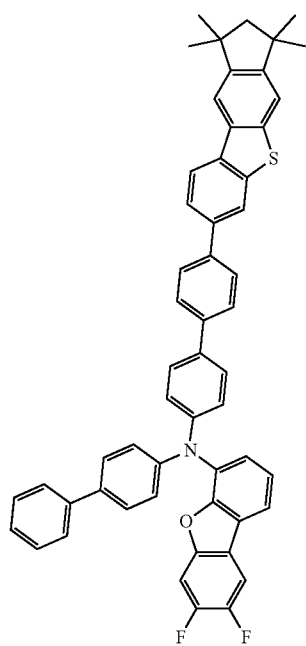

393
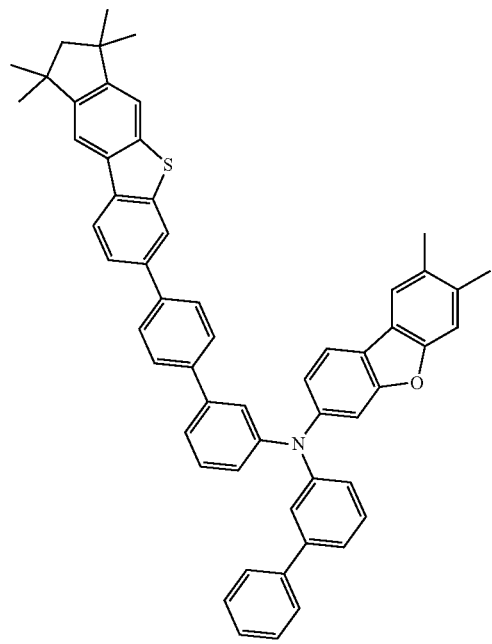
230
394
-continued
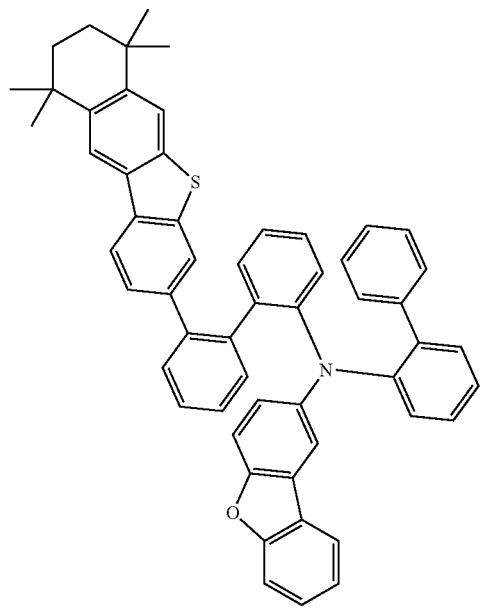
231
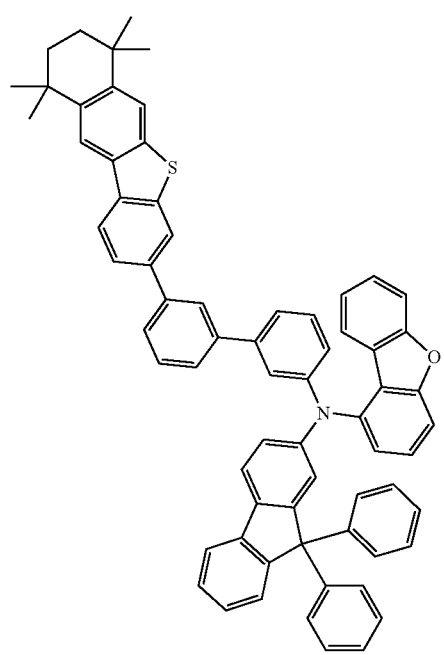
232
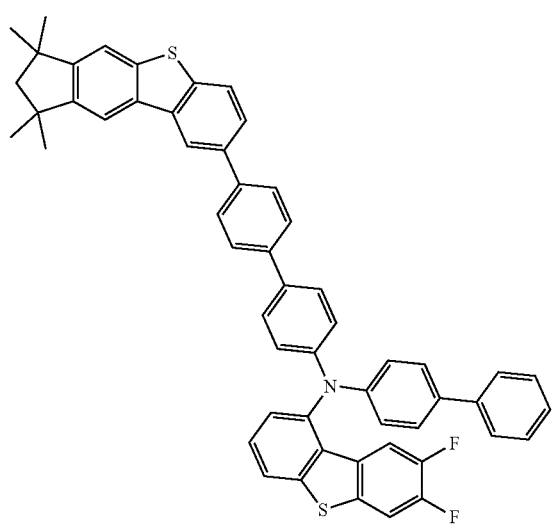
233

-continued
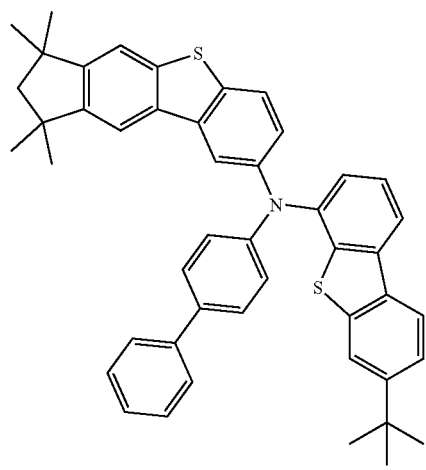
234
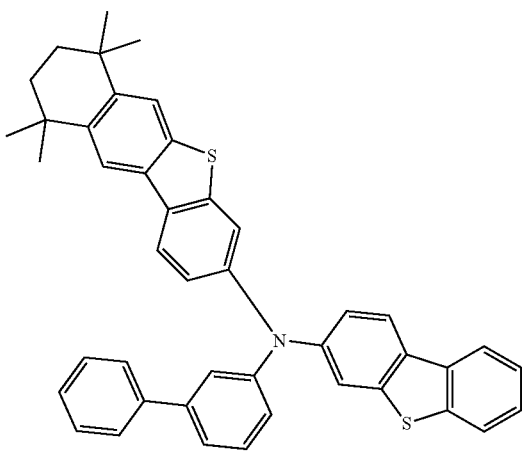
235
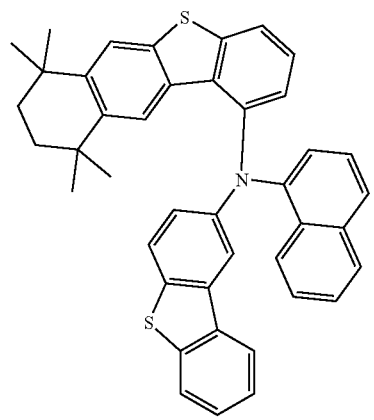
236
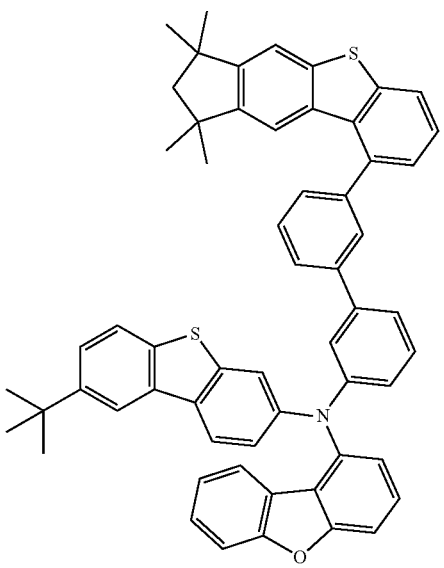
237
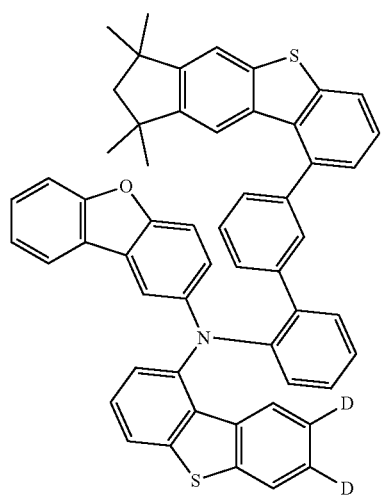
238
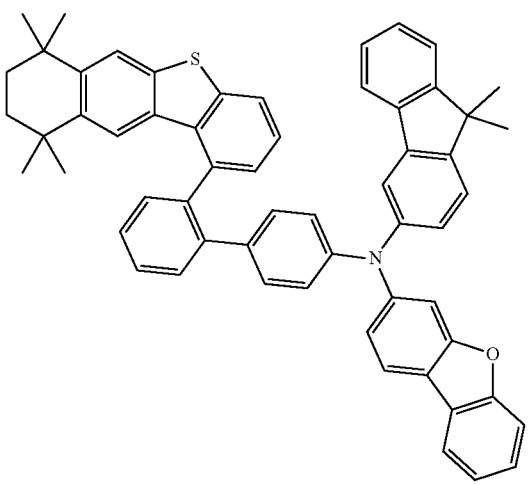
239

397
398
240
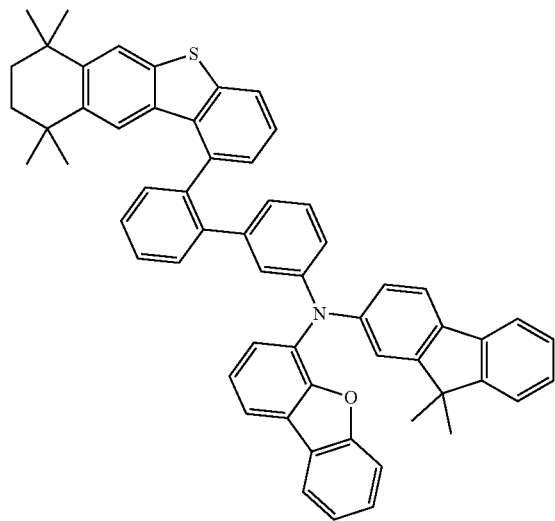
241
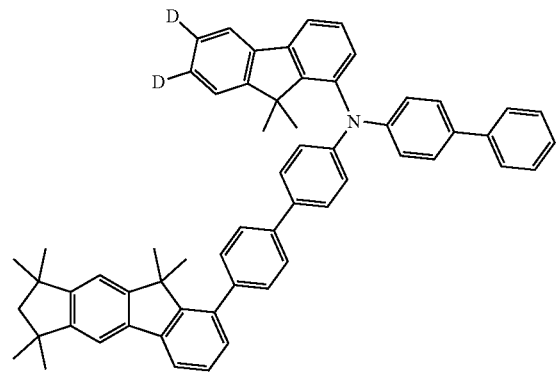
242
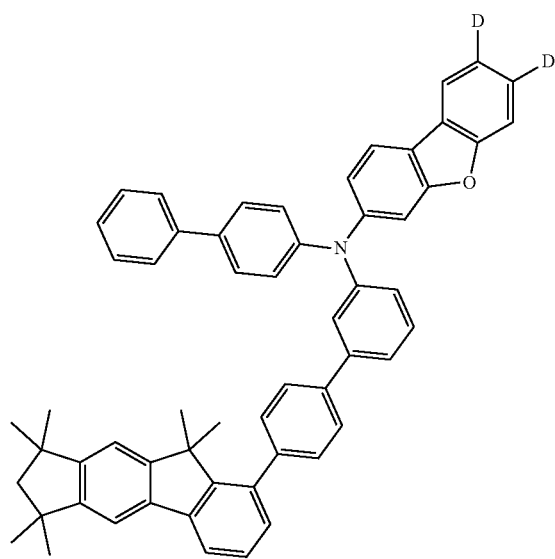
243
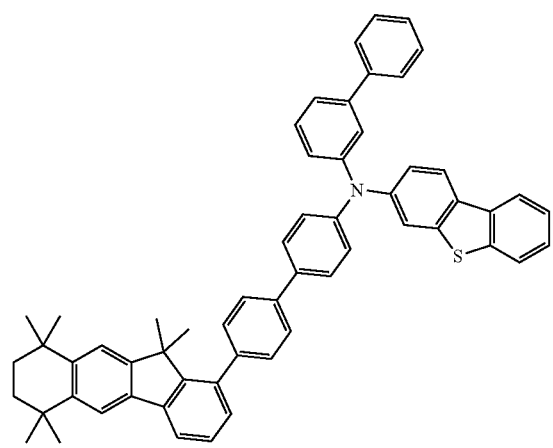

244
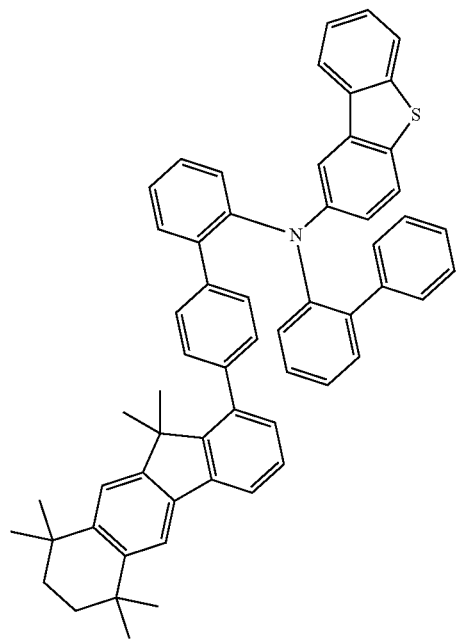
245
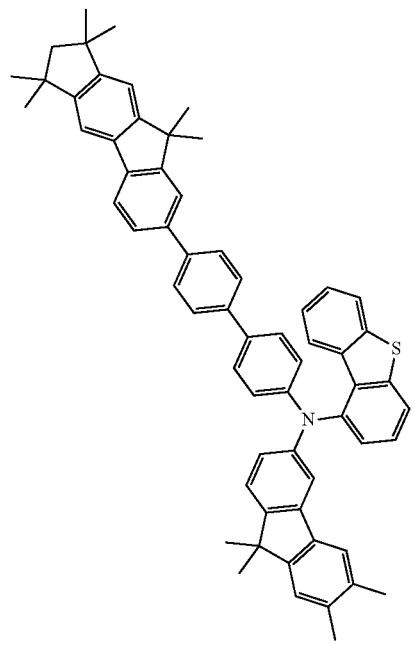
246
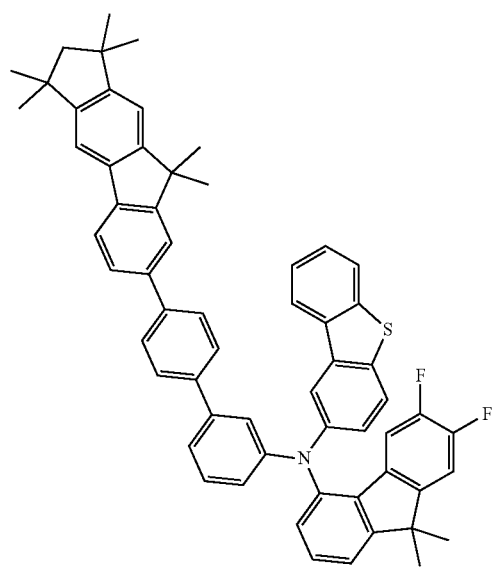
247
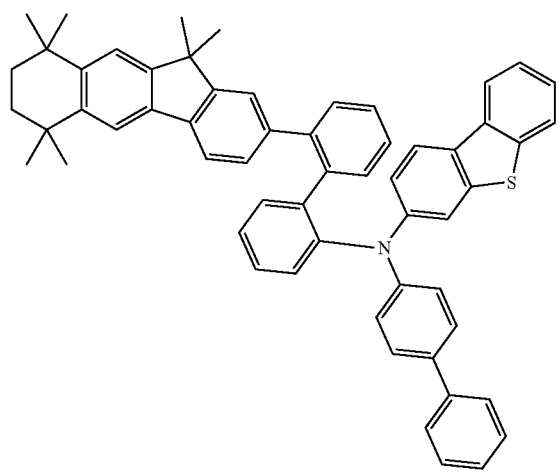

401
248
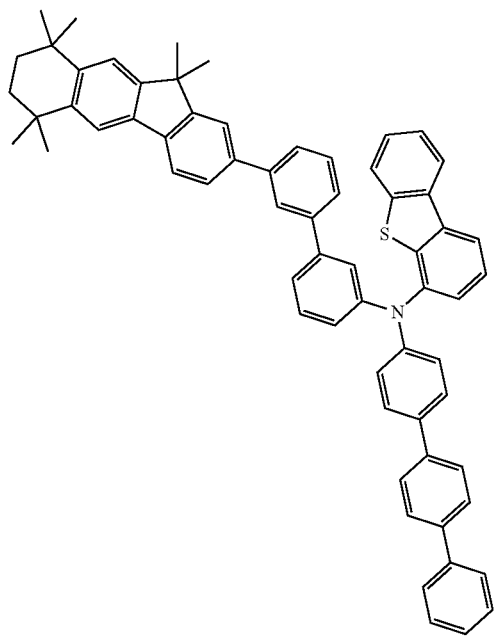
402
249
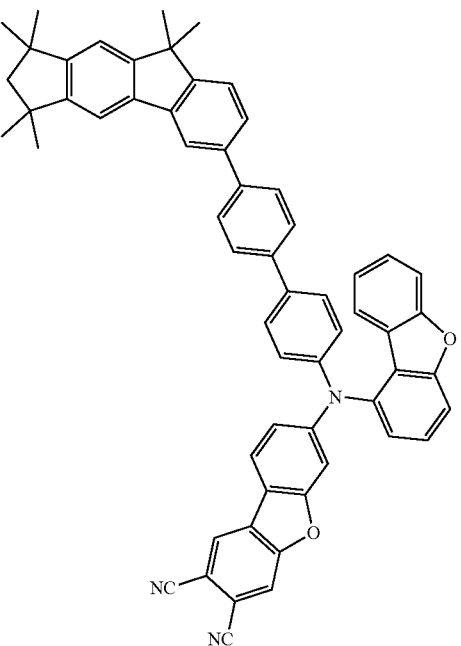
250
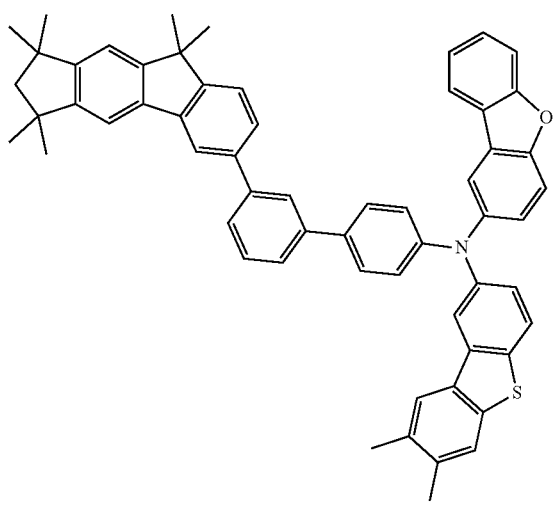
251
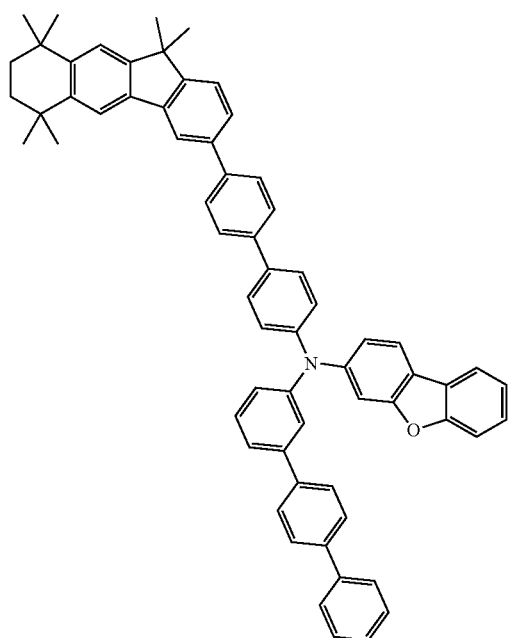

-continued
252
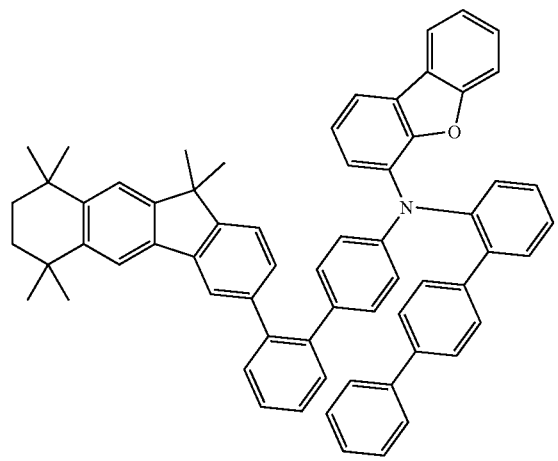
253
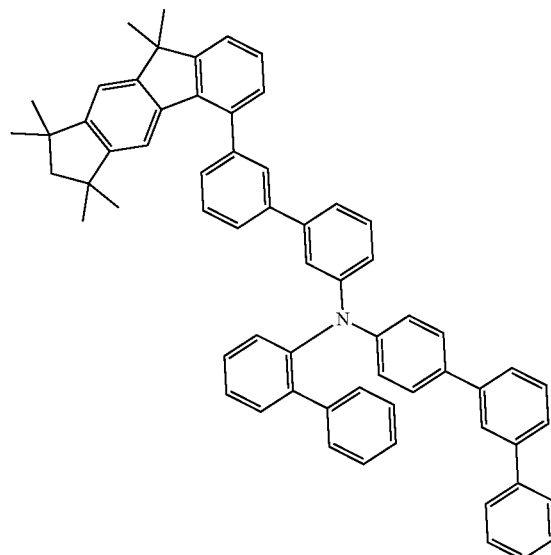
254
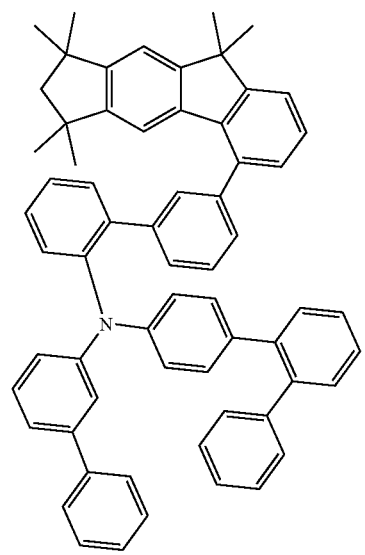
255
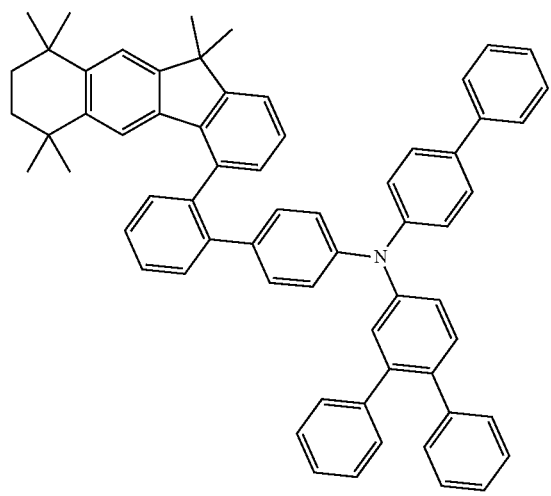

256
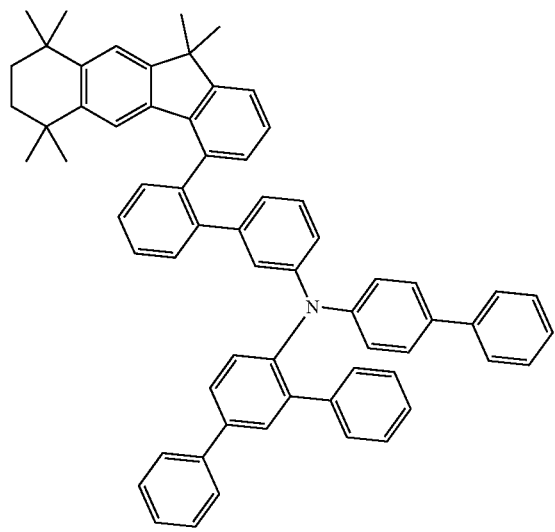
257
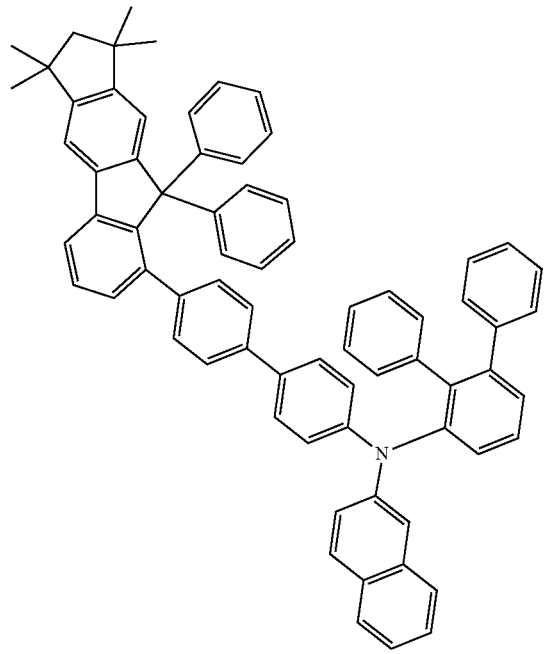
258
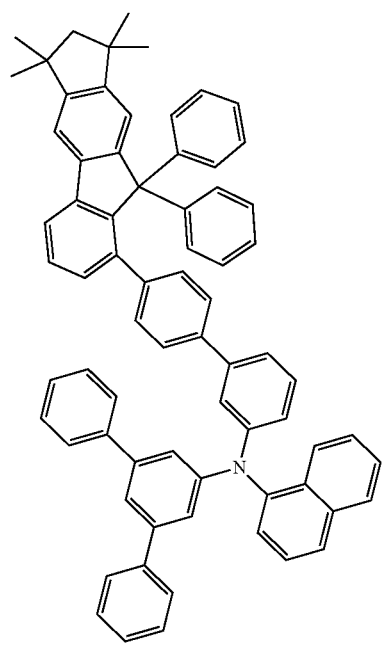
259
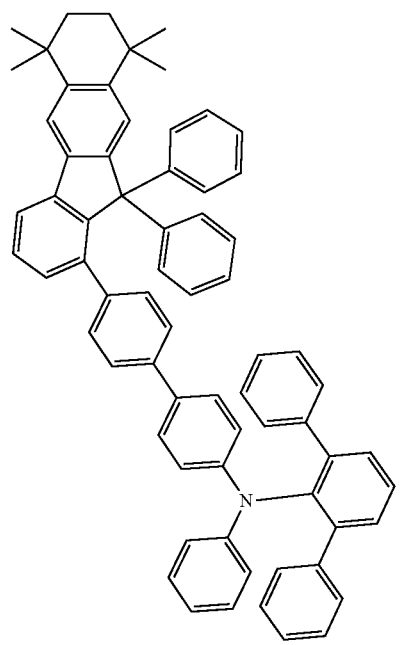

-continued
260
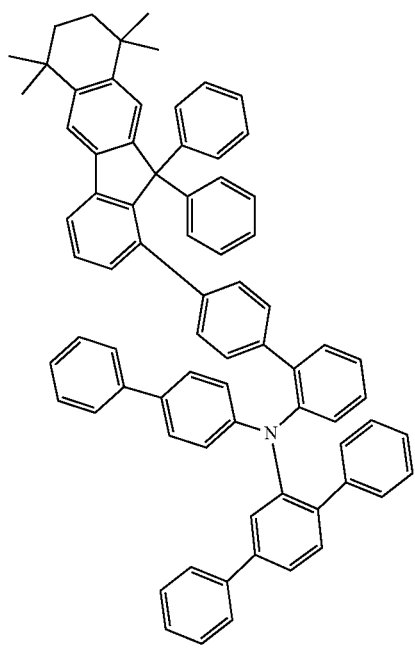
261
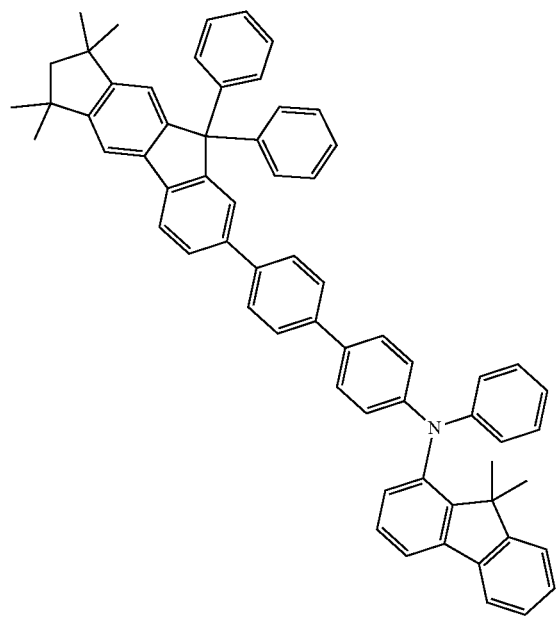
262
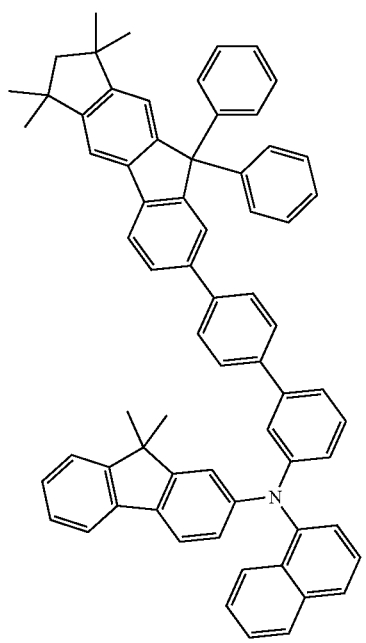
263
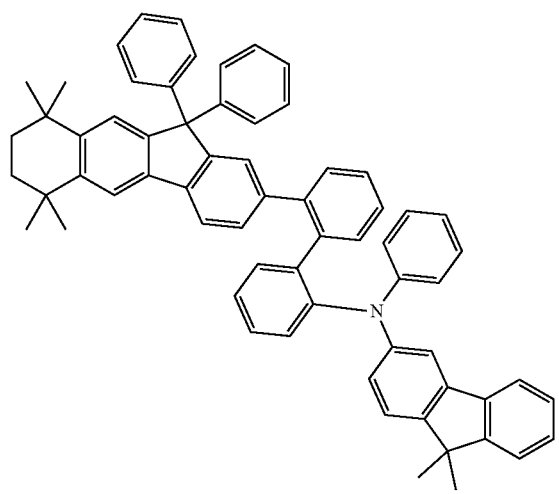

264
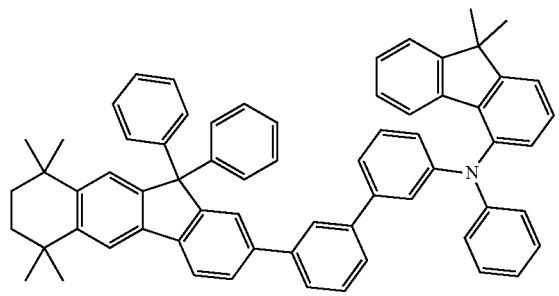
265
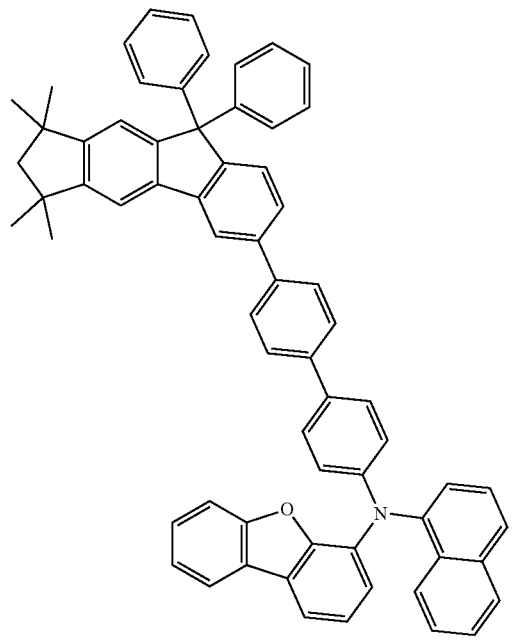
266
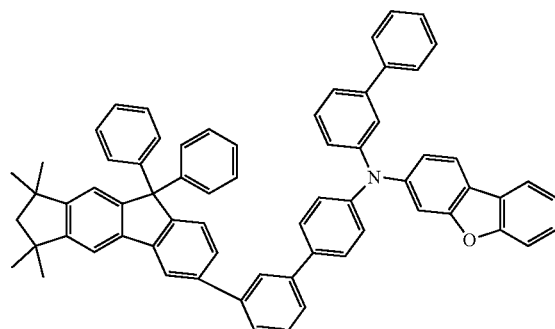
267
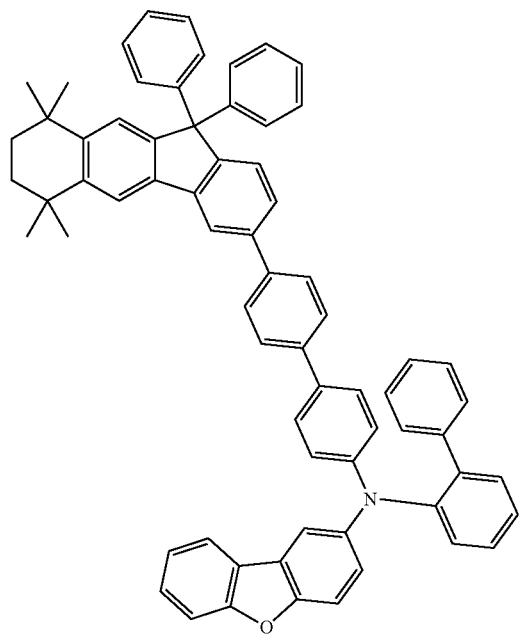

-continued
268
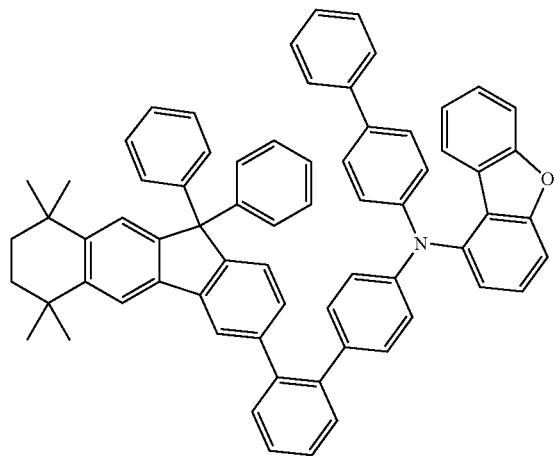
269
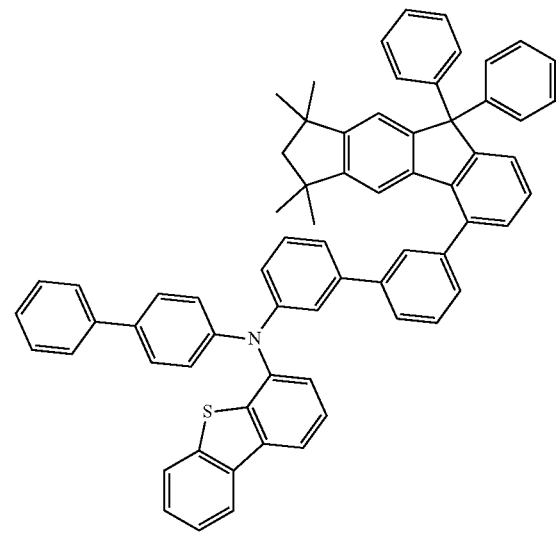
270
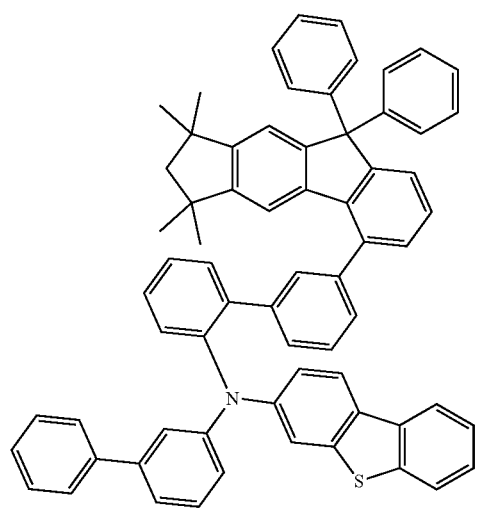
271
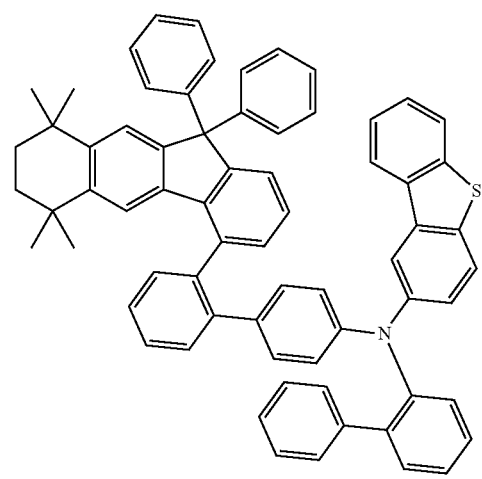
272
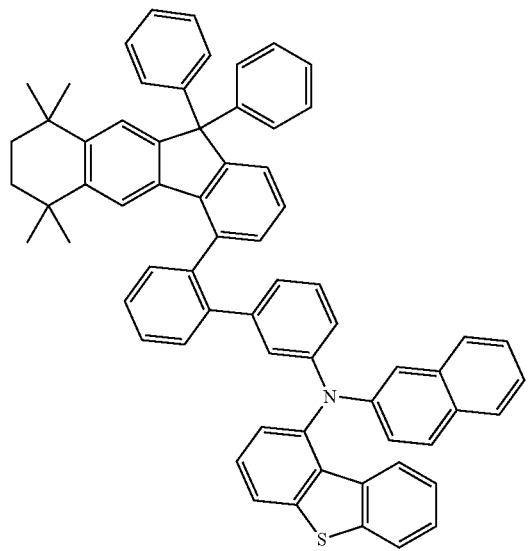
273
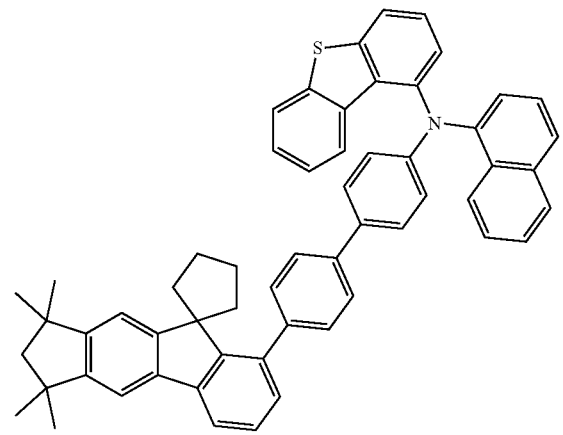

-continued
274
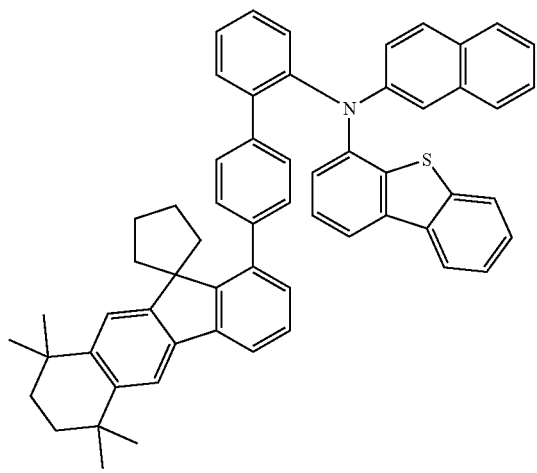
275
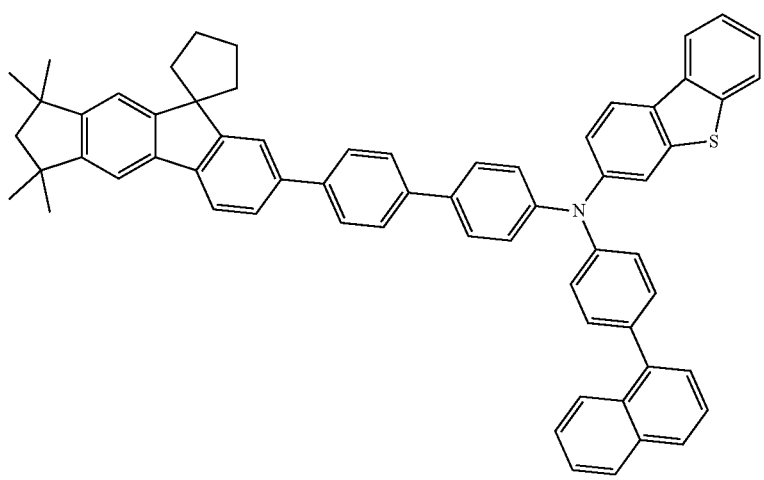
276
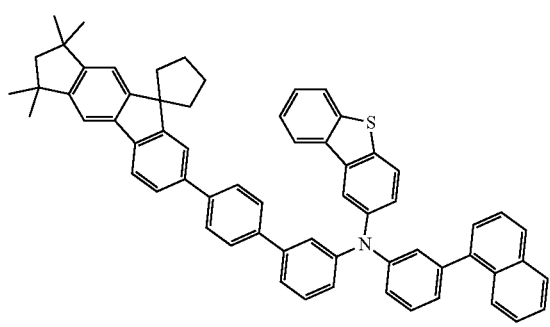
277
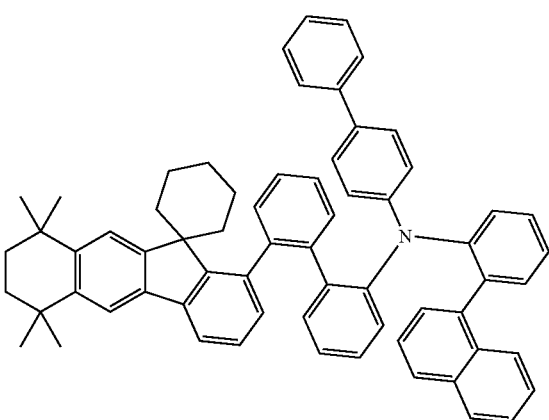

278
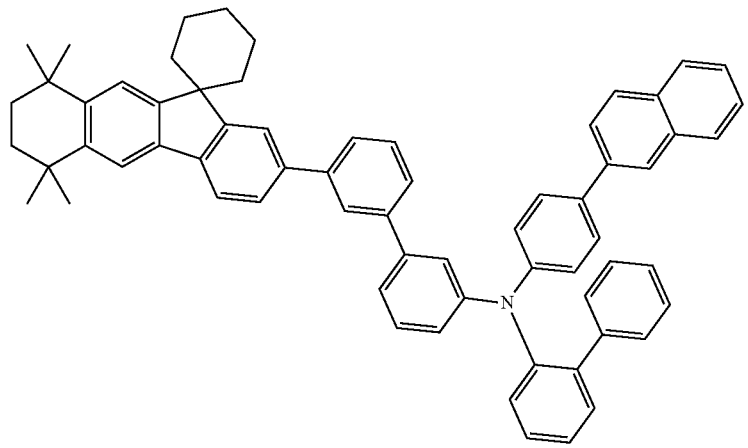
279
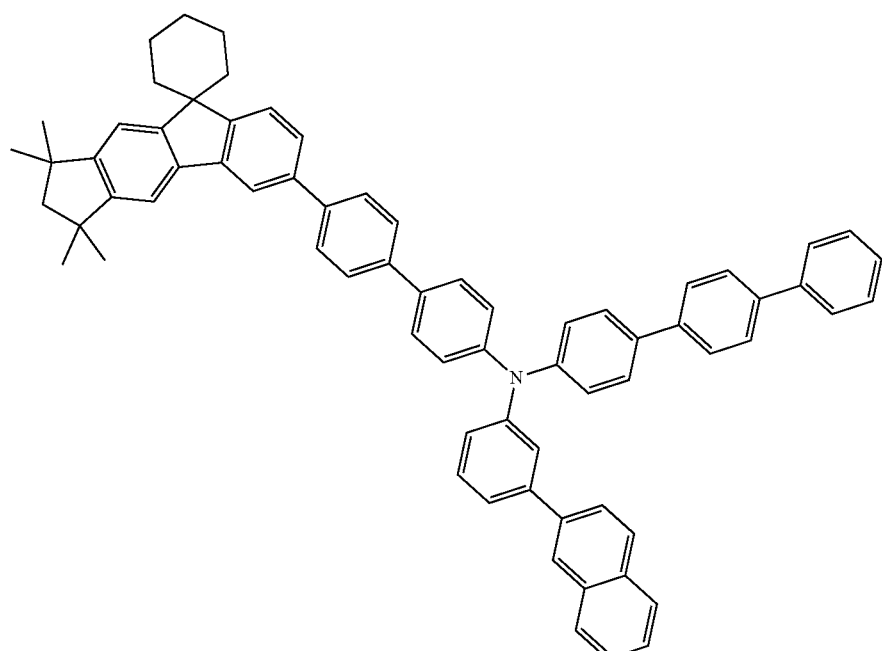
280
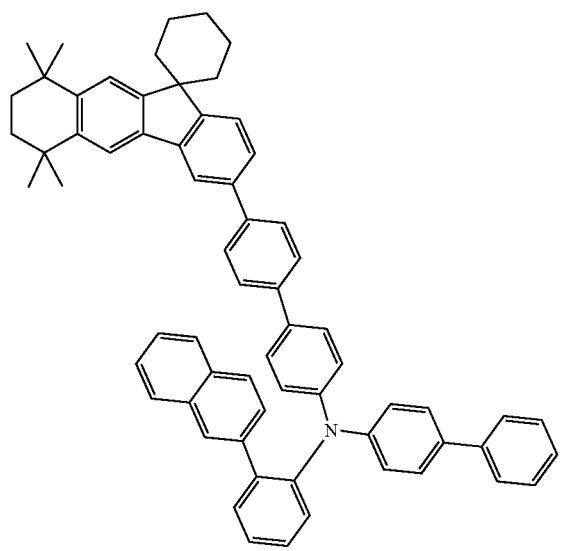
281
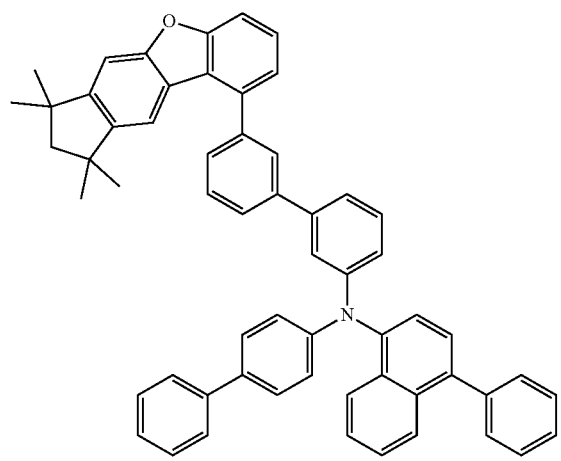

-continued
282
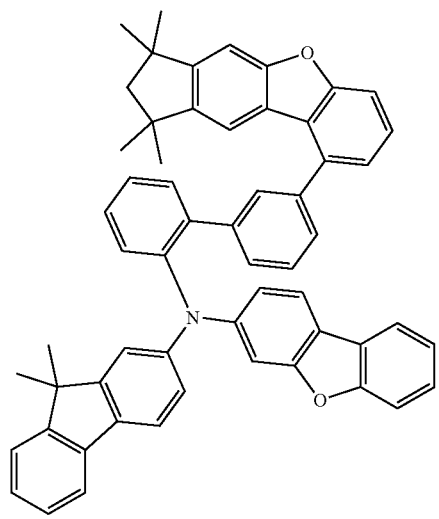
283
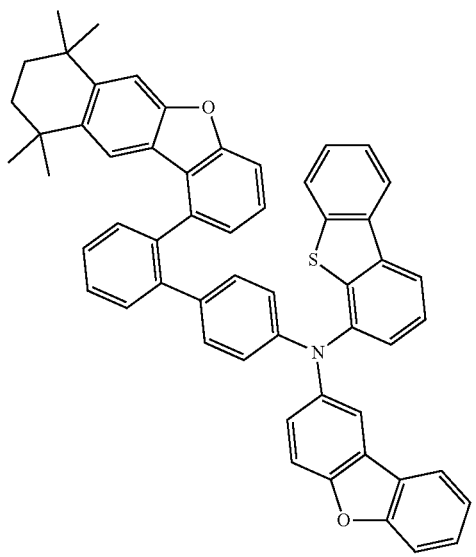
284
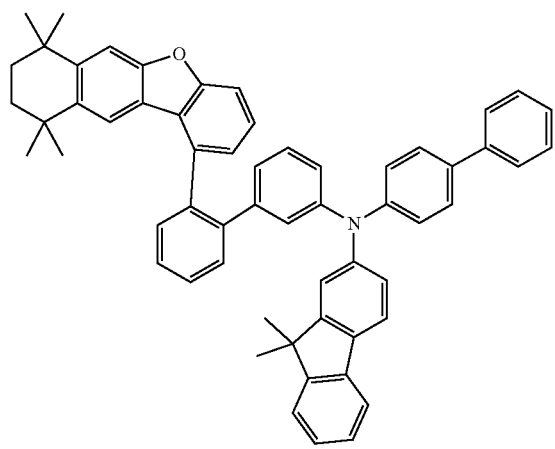
285
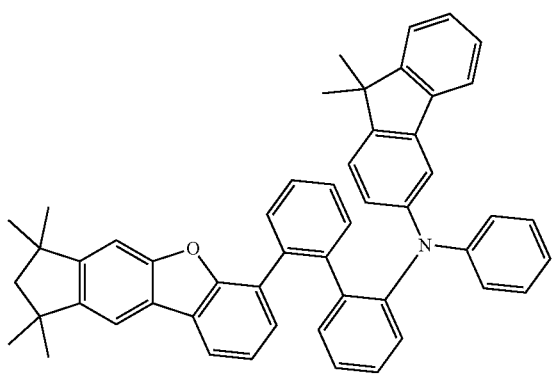
286
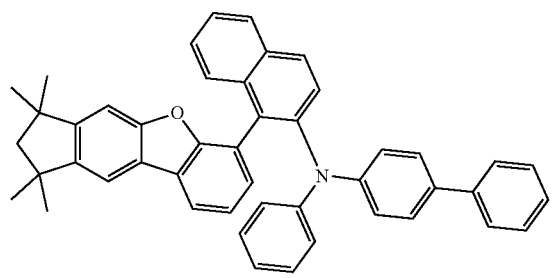
287
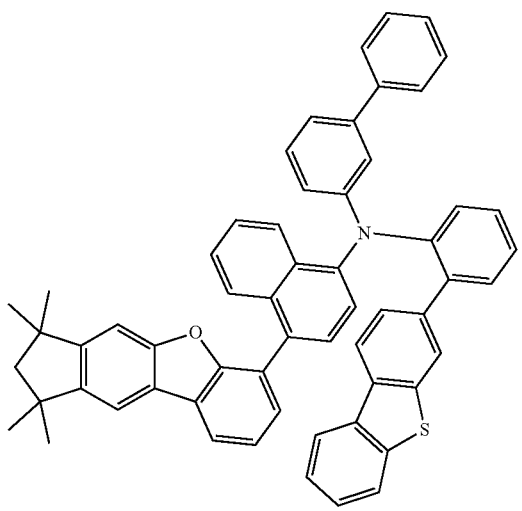

-continued
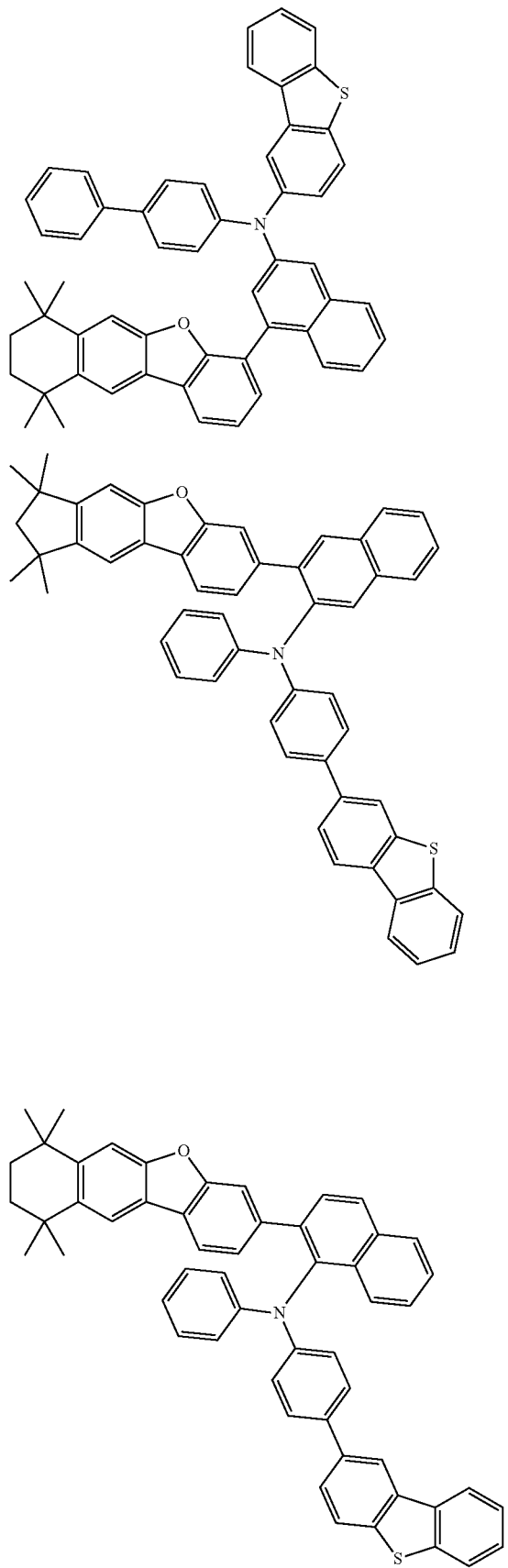
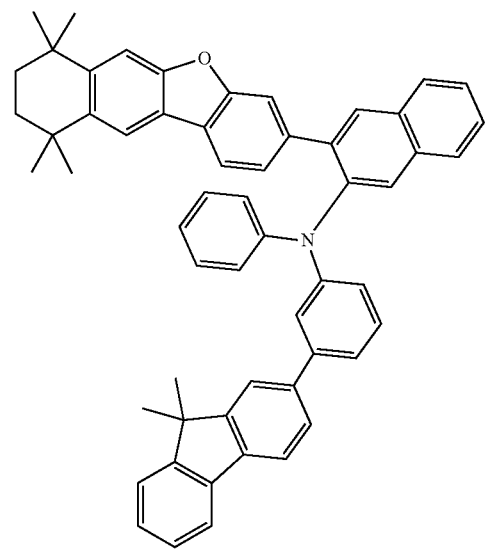
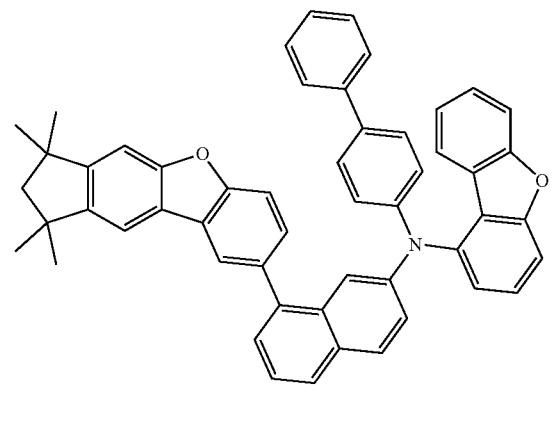

421
294
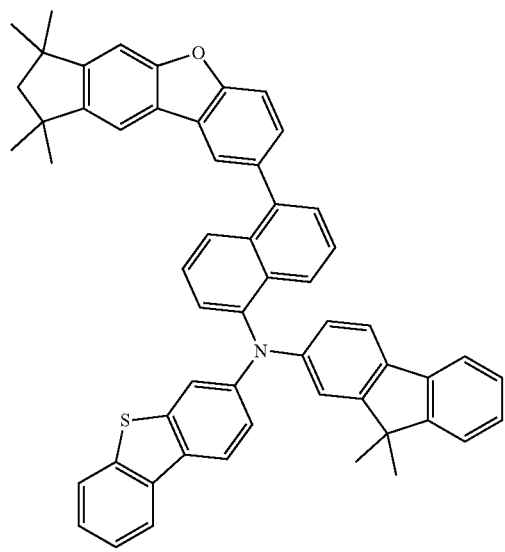
422
295
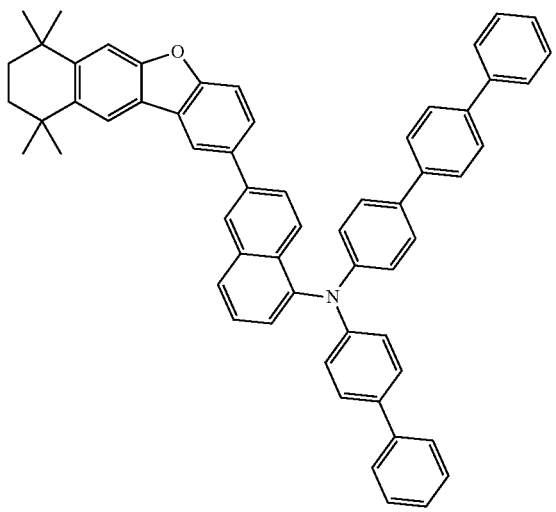
296
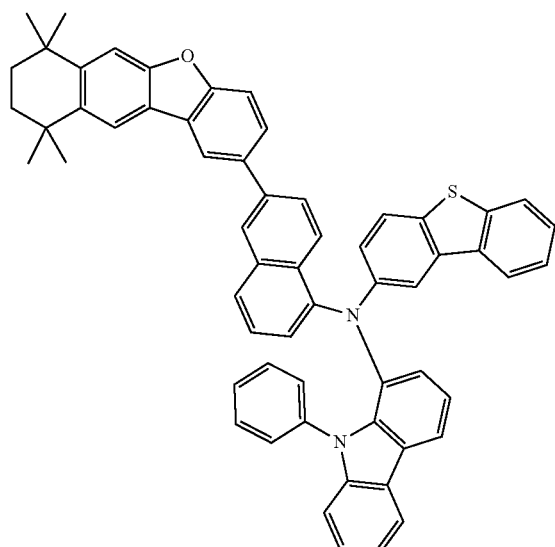
297
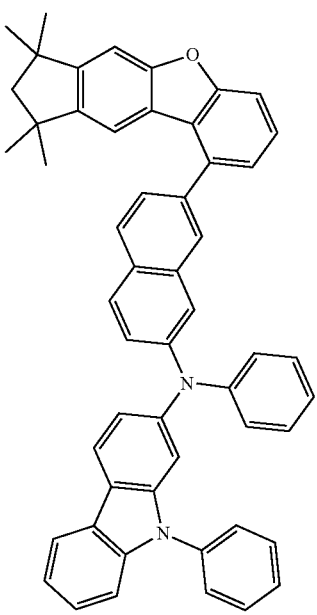

-continued
298
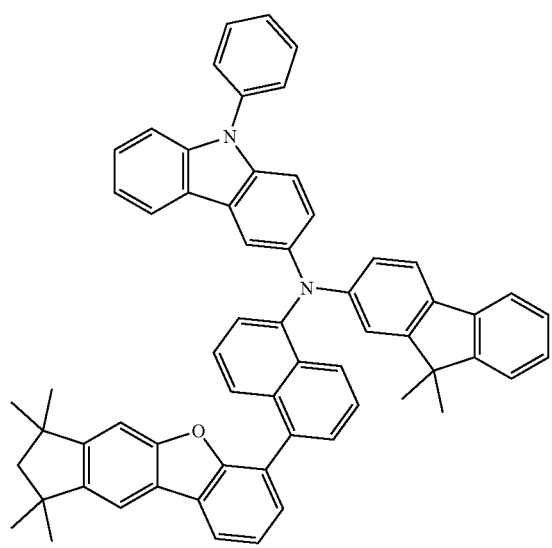
299
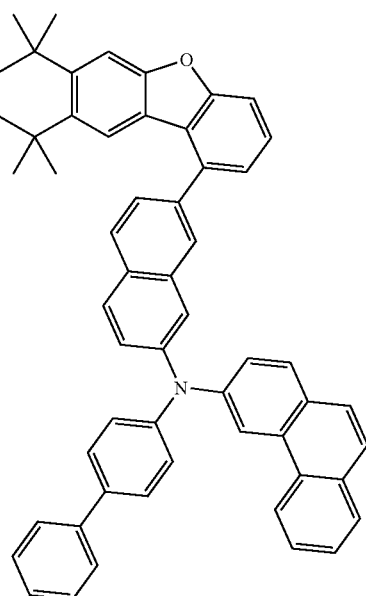
300
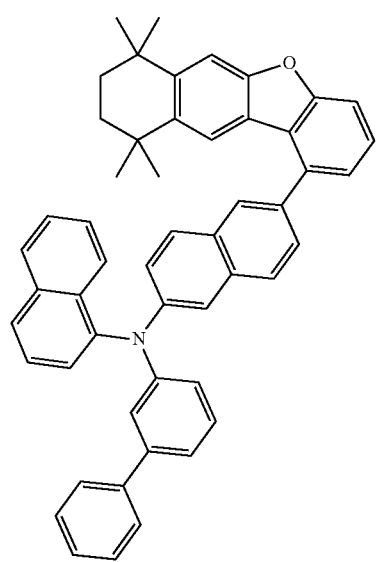
301
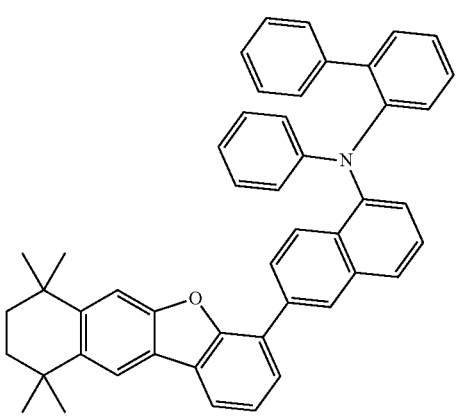

-continued
302
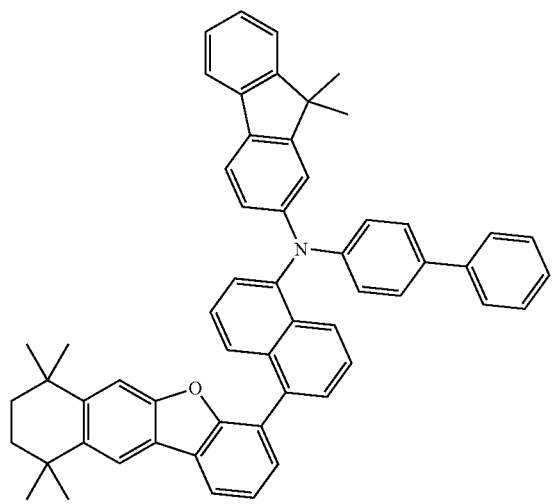
303
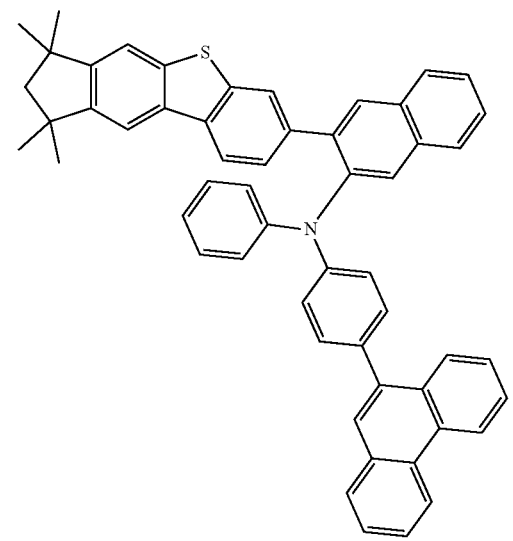
304
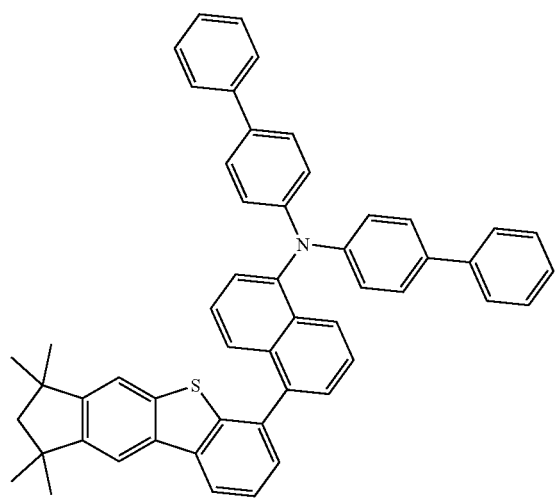
305
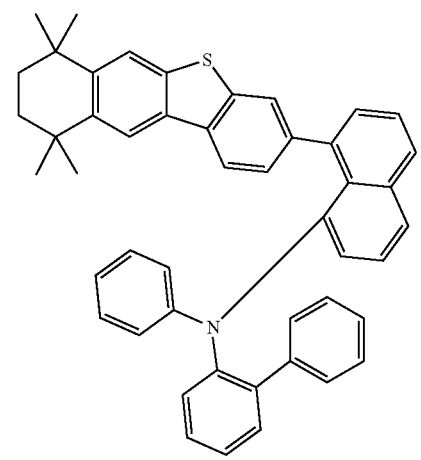
306
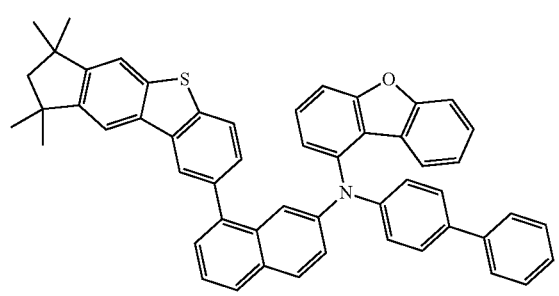
307
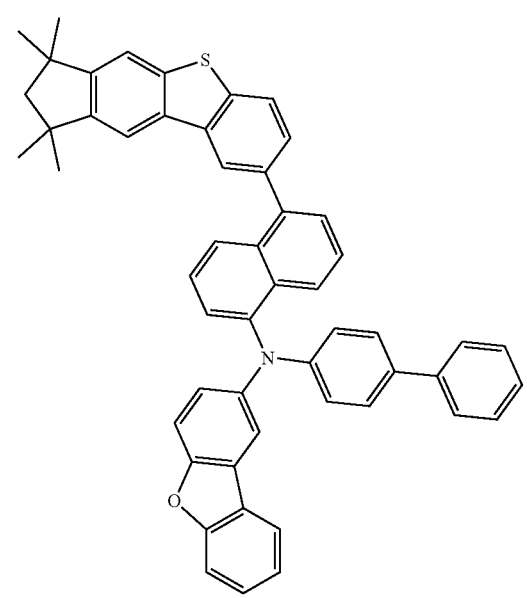

-continued
308
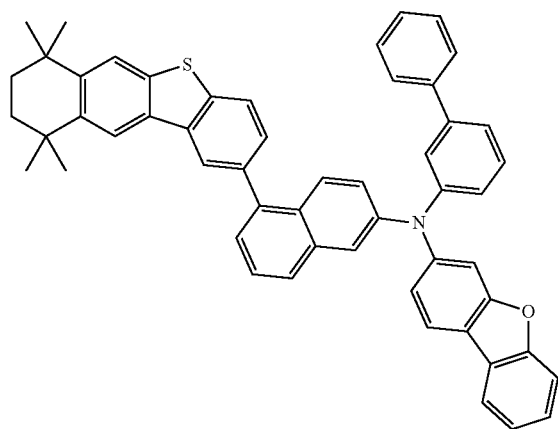
309
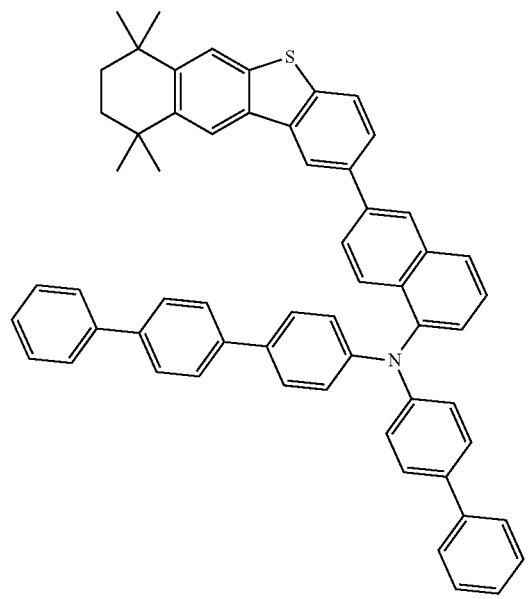
310
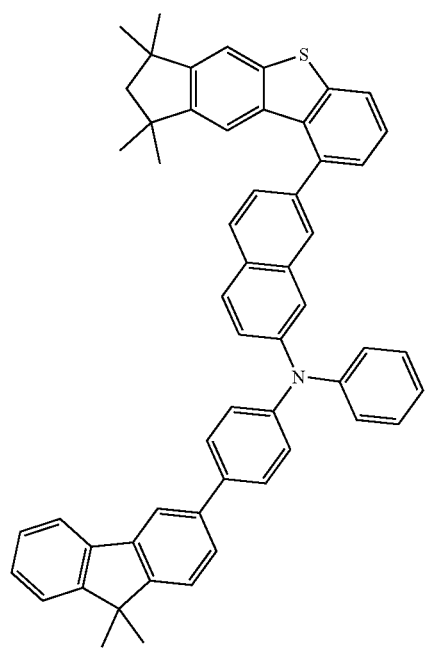
311
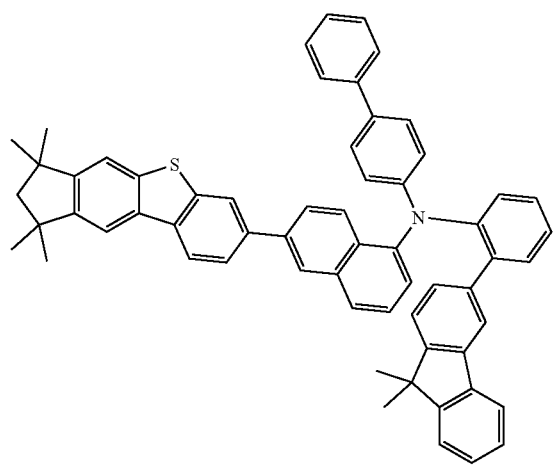

-continued
3312
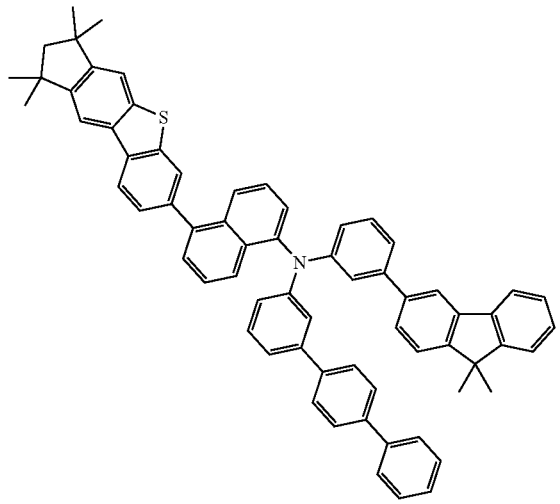
313
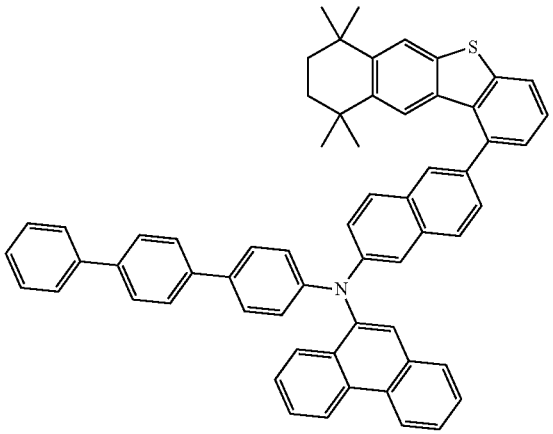
314
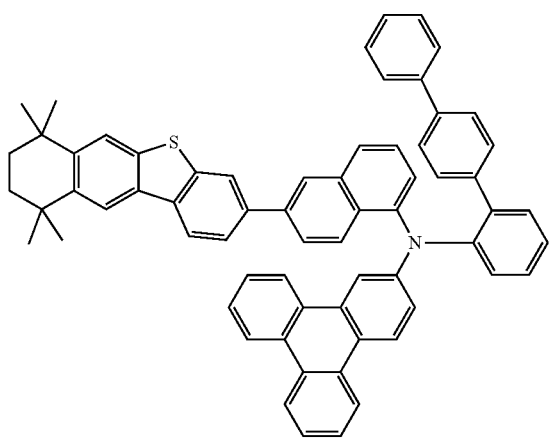
315
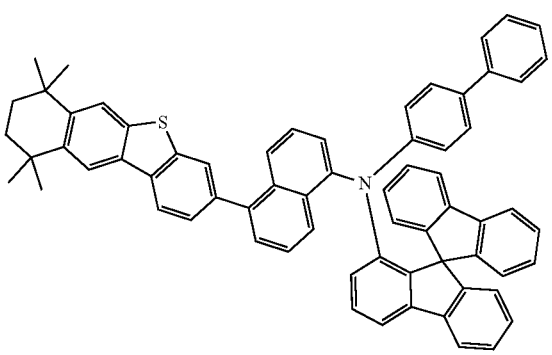
316
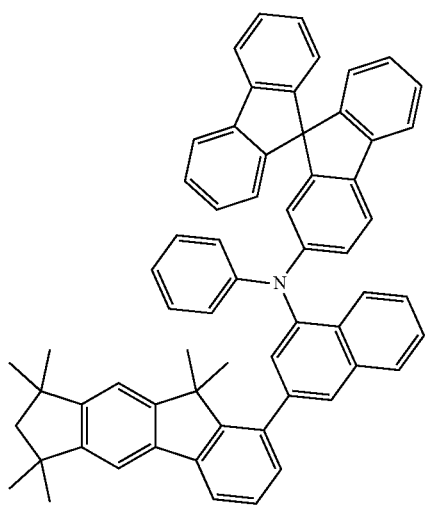
317
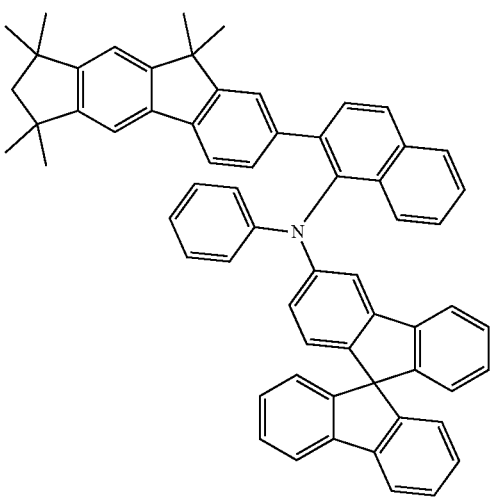

-continued
318
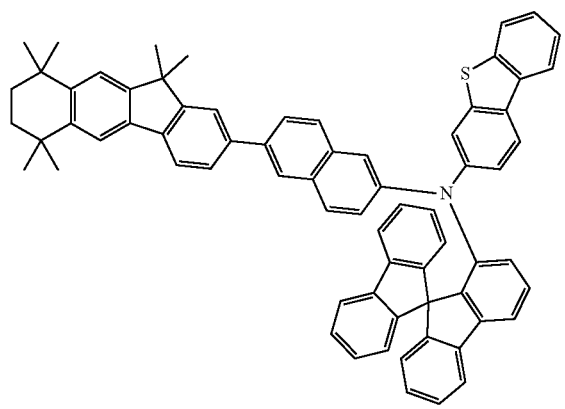
319
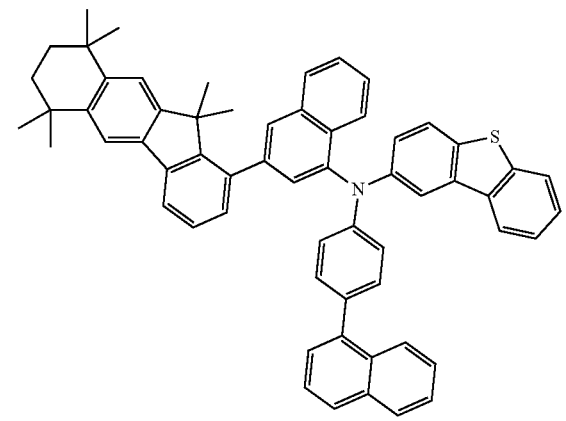
320
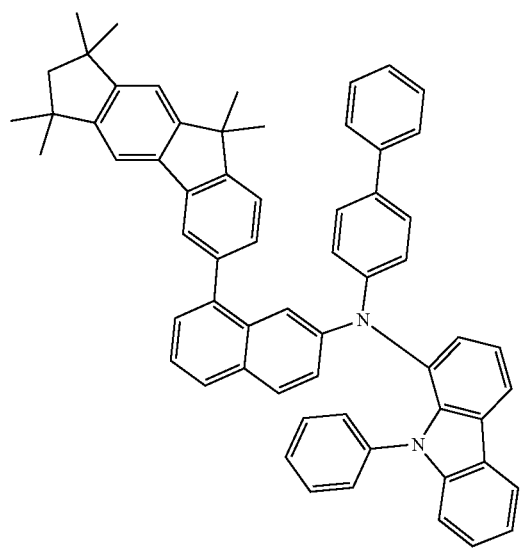
321
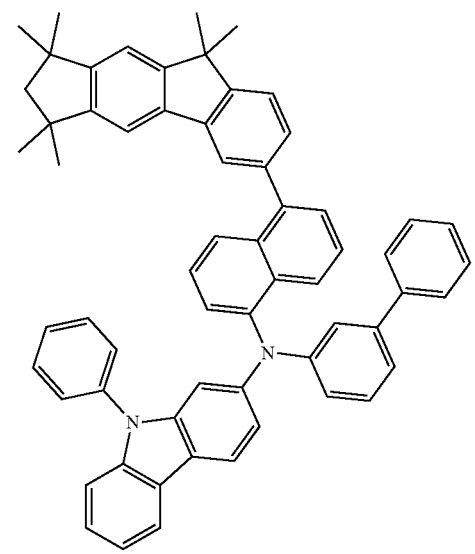
322
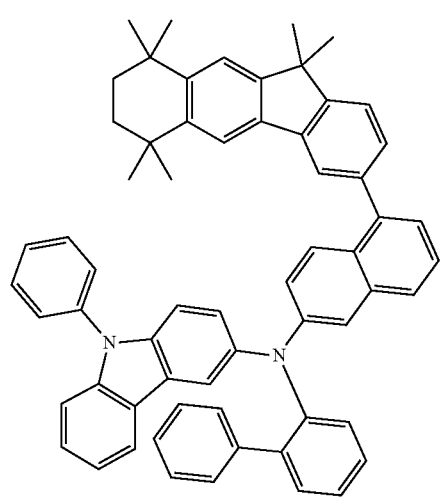
323
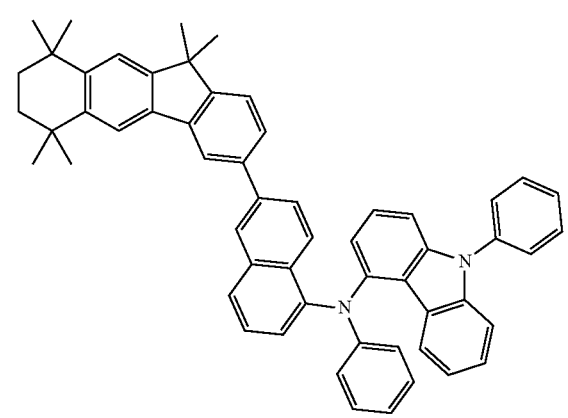

-continued
324
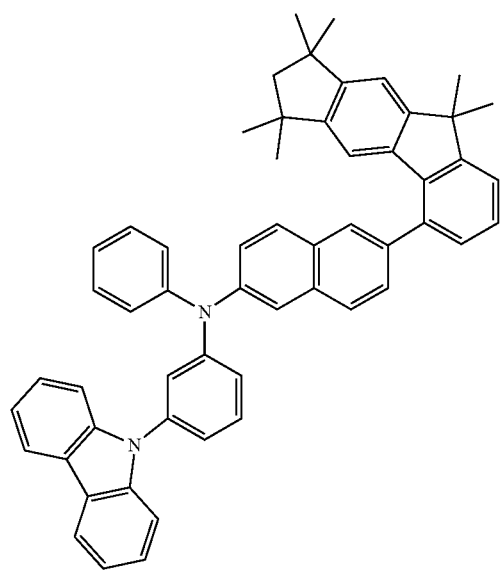
325
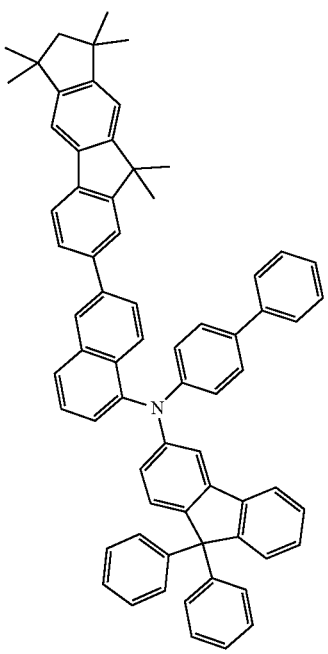
326
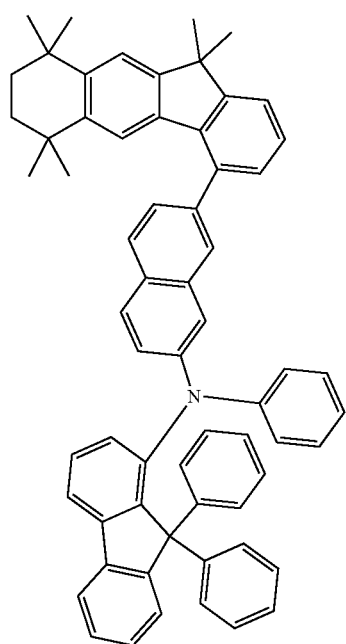
327
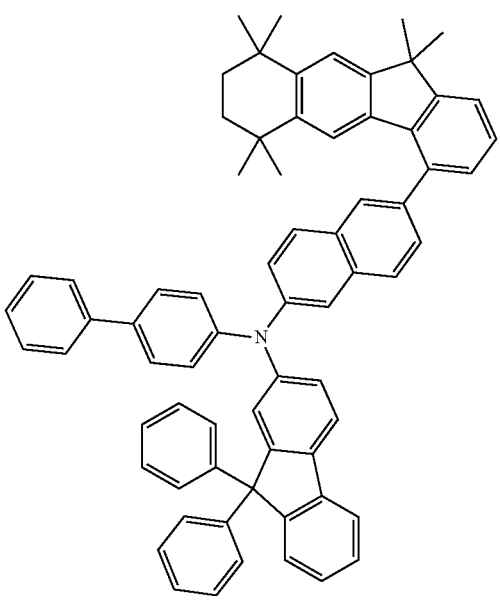

-continued
328
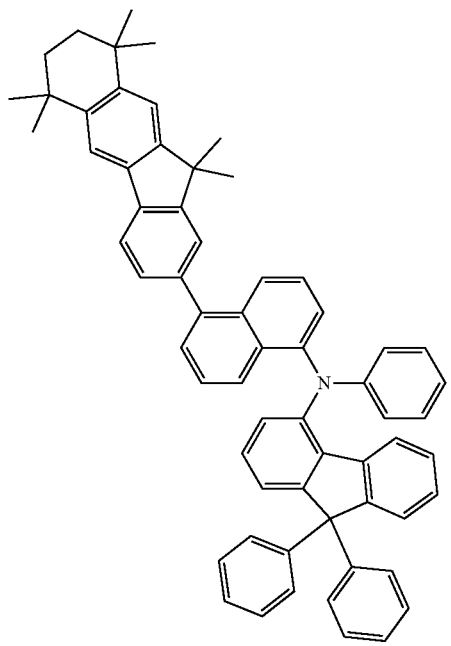
329
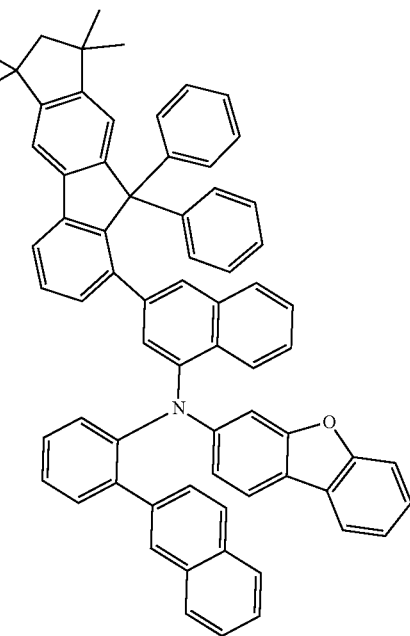
330
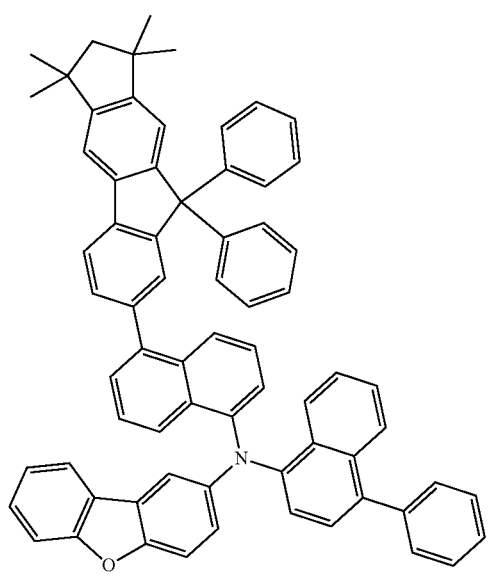
331
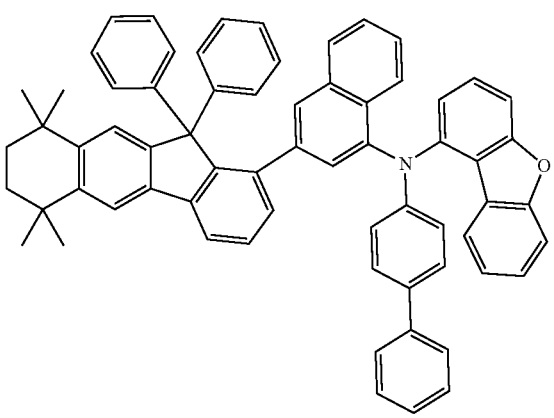

437 438
-continued
332 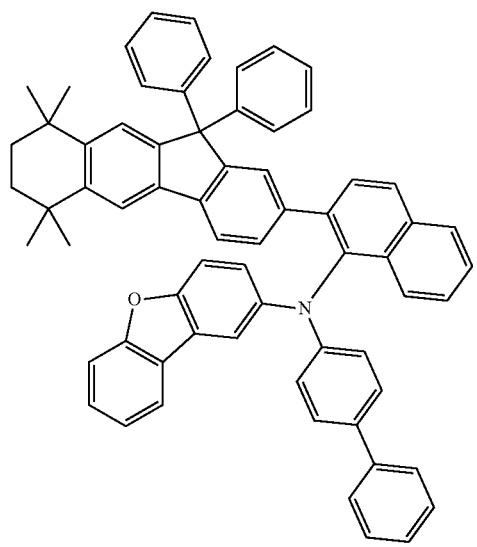 333 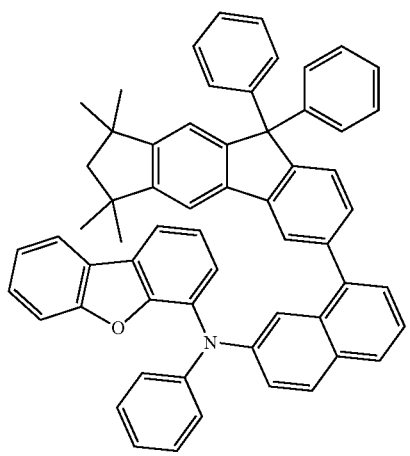
334 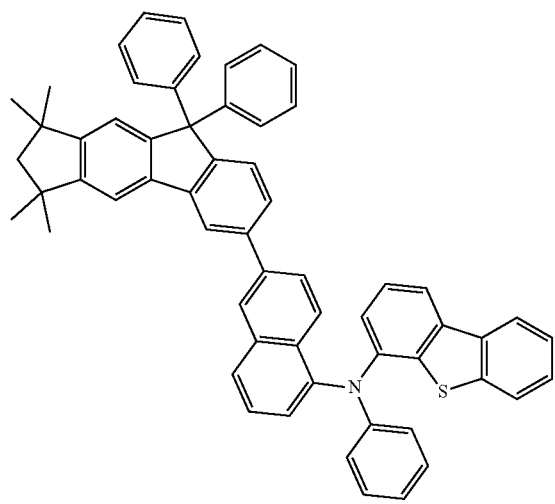 335 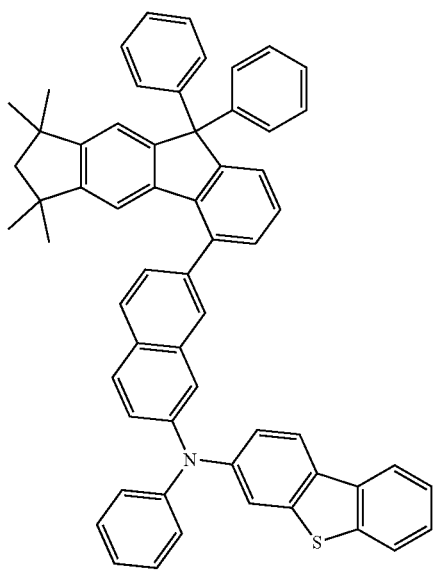

-continued
336
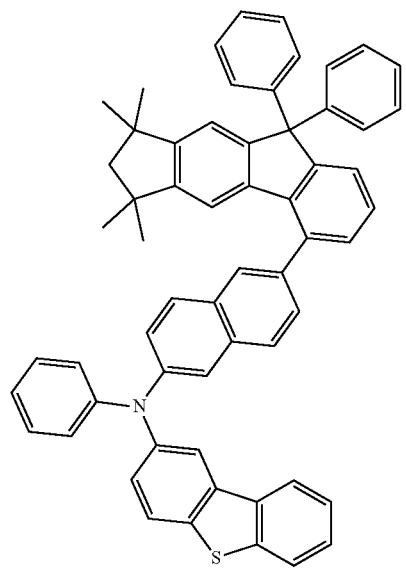
337
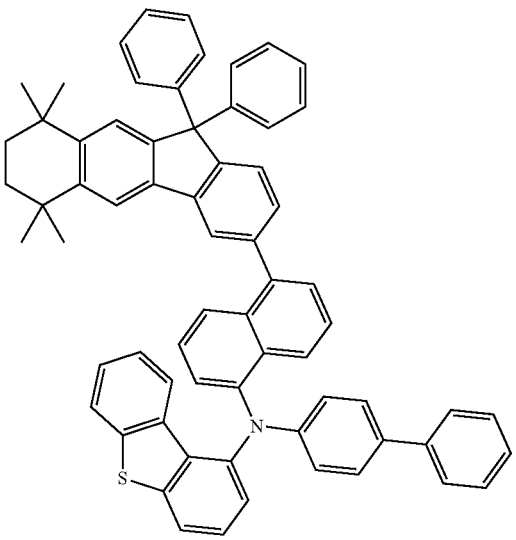
338
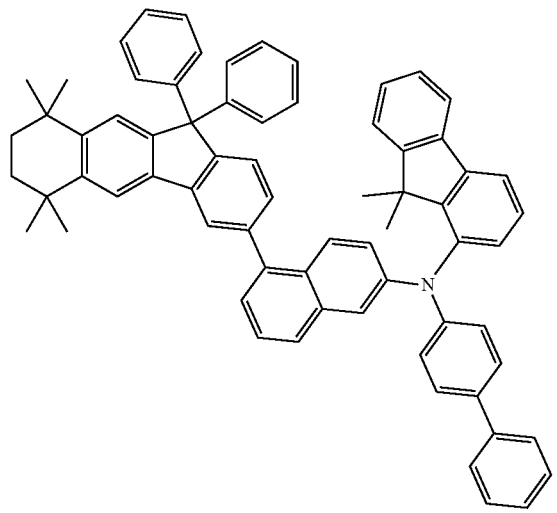
339
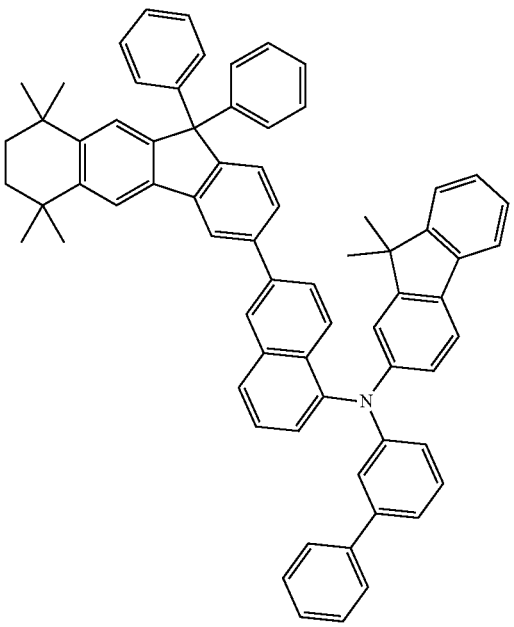

340
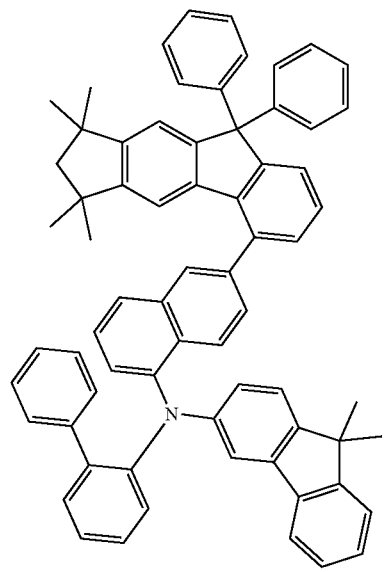
341
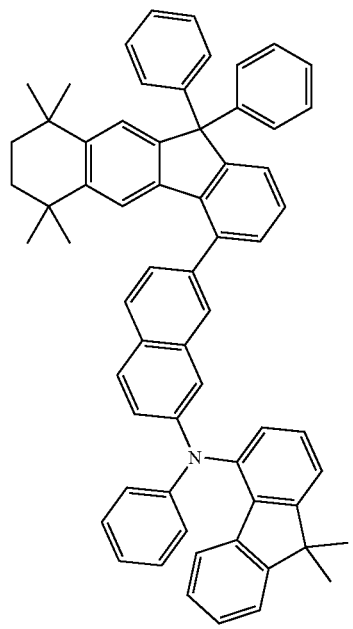
342
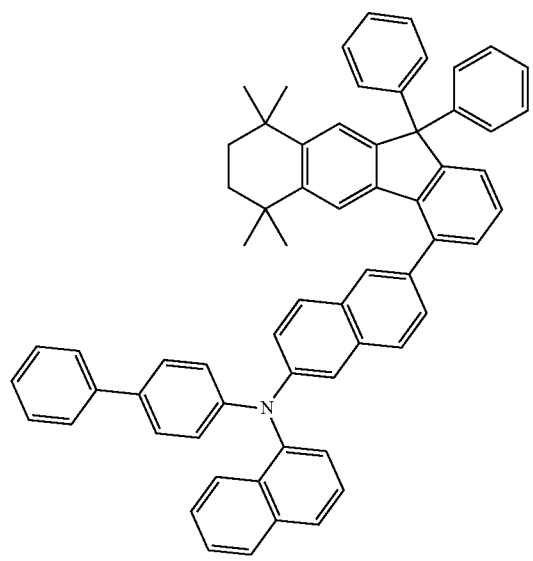
343
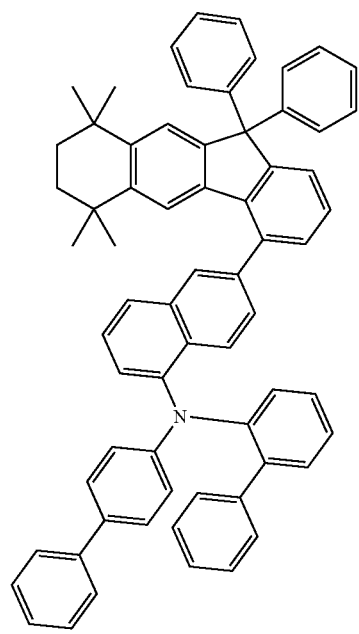

344
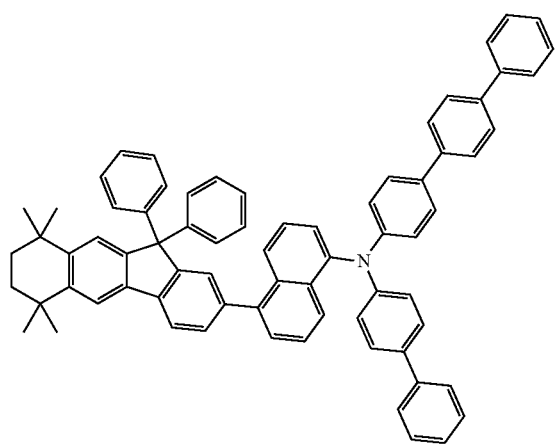
345
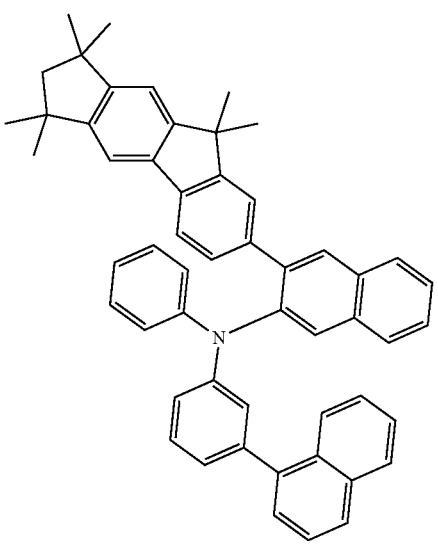
346
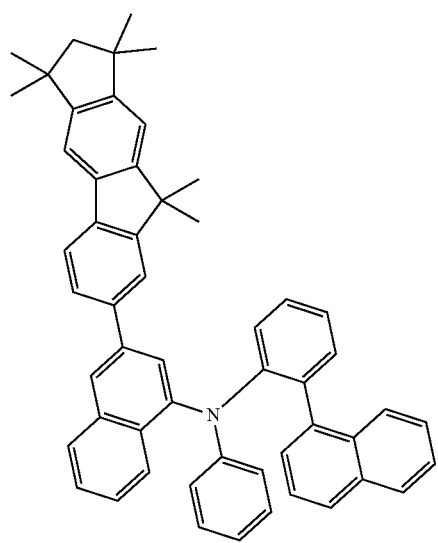
347
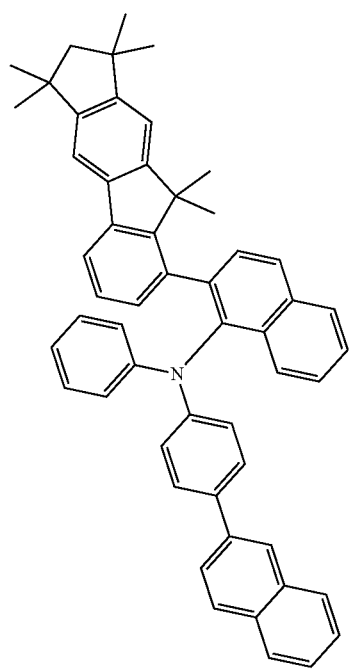

445 446
-continued
348 349
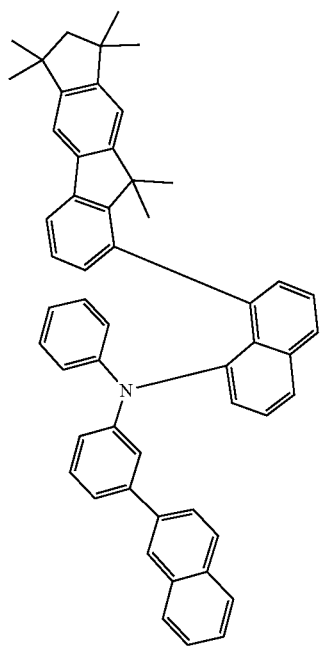
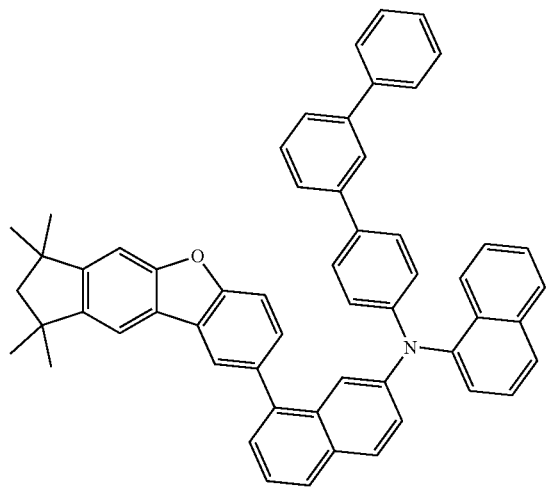
350 351
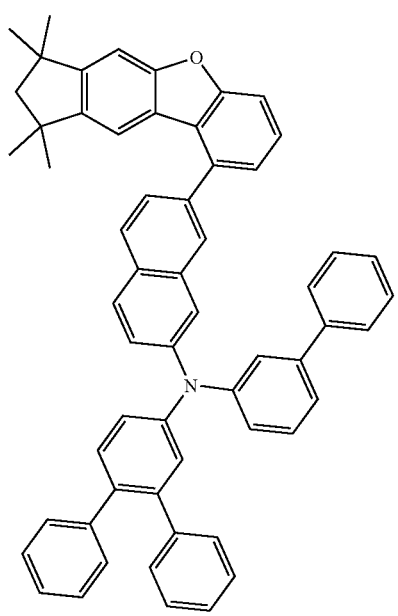
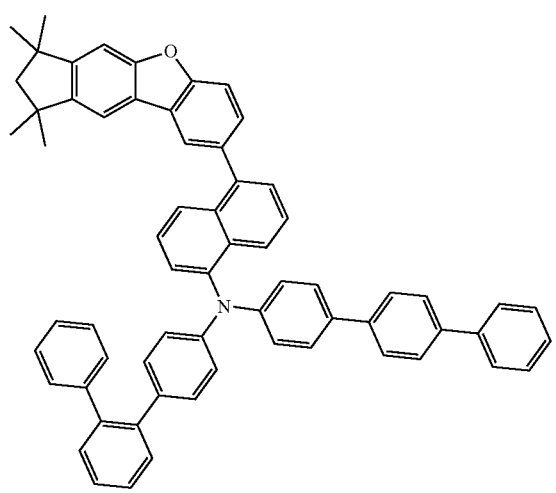

352
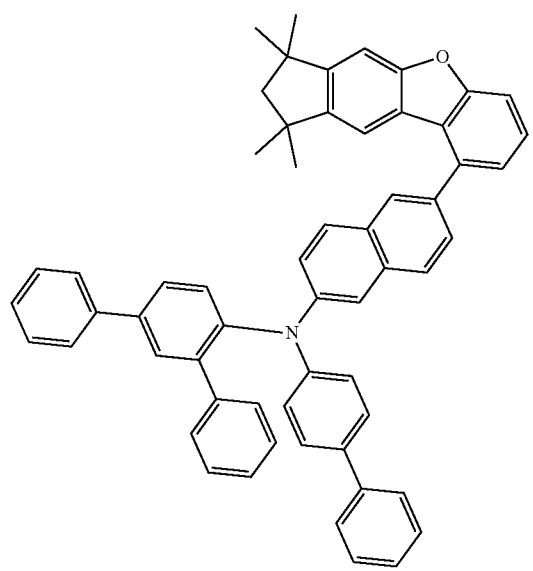
353
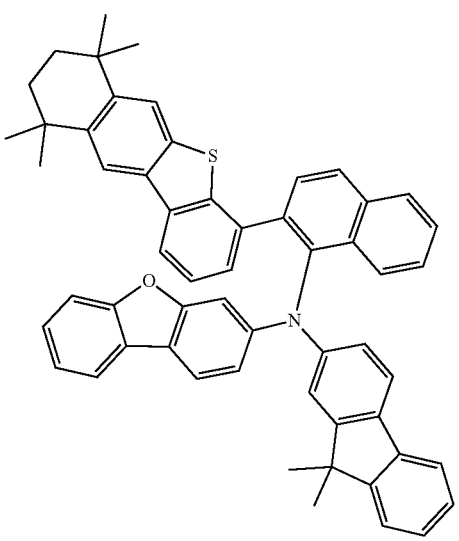
354
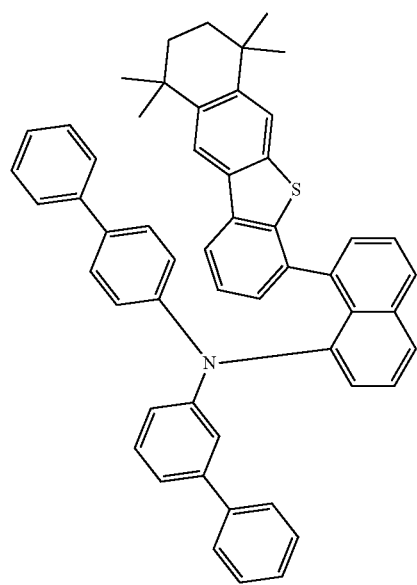
355
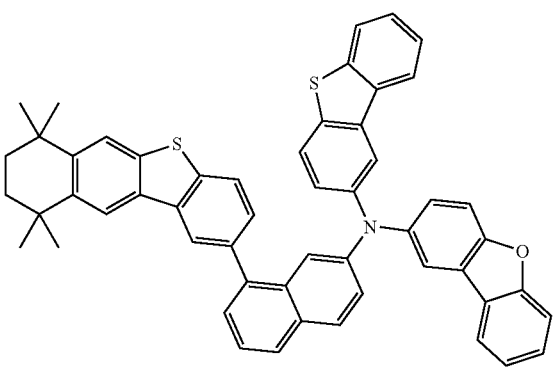

-continued
356
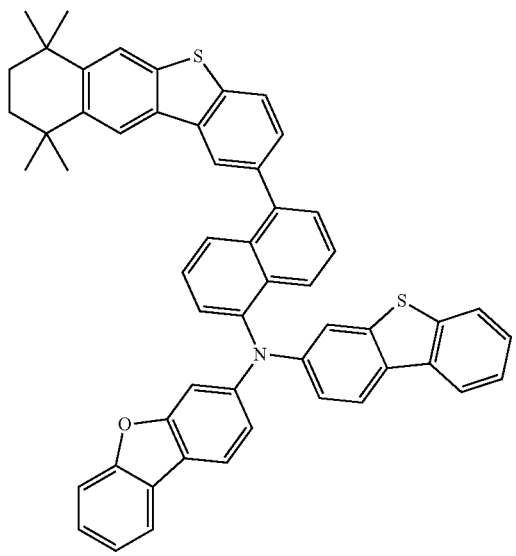
357
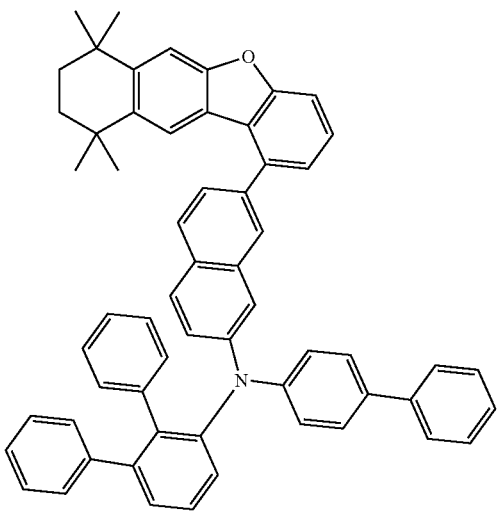
358
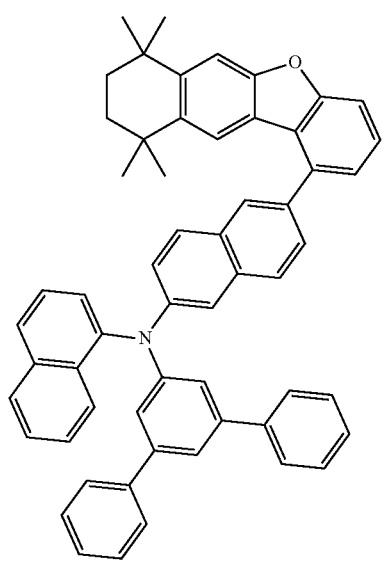
359
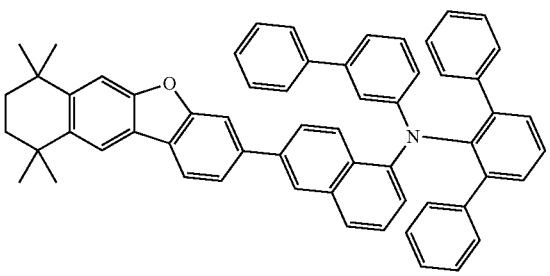
360
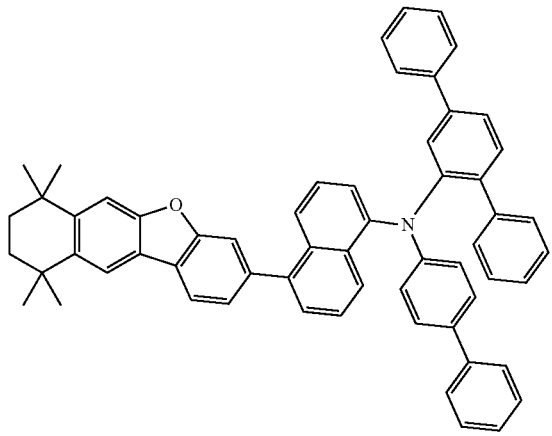
361
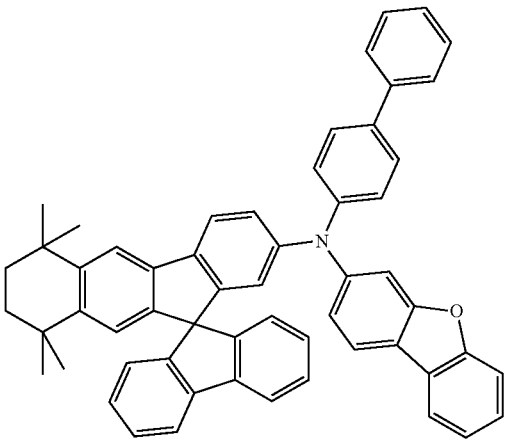

-continued
362
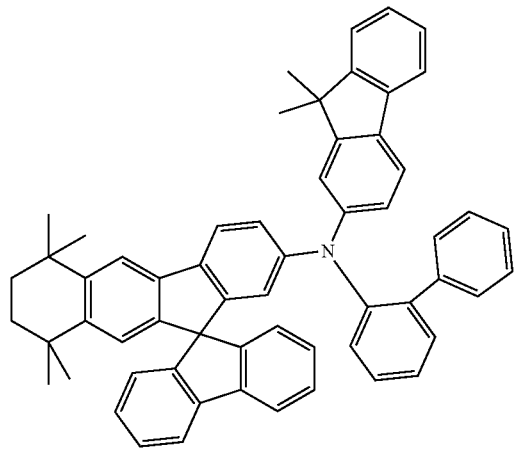
363
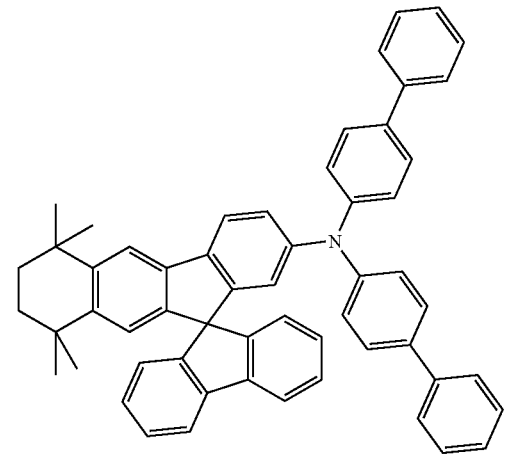
364
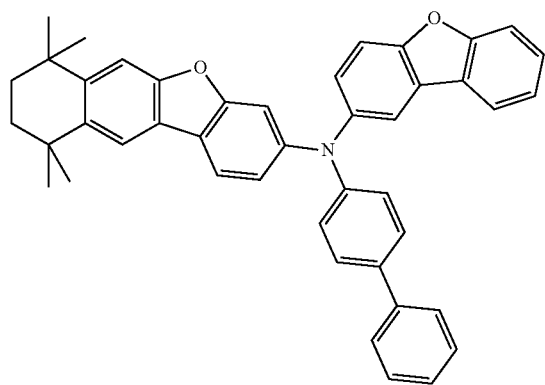
365
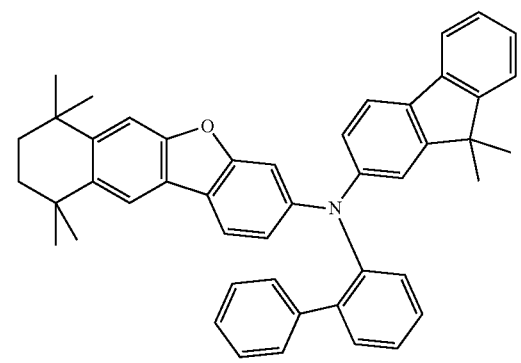
366
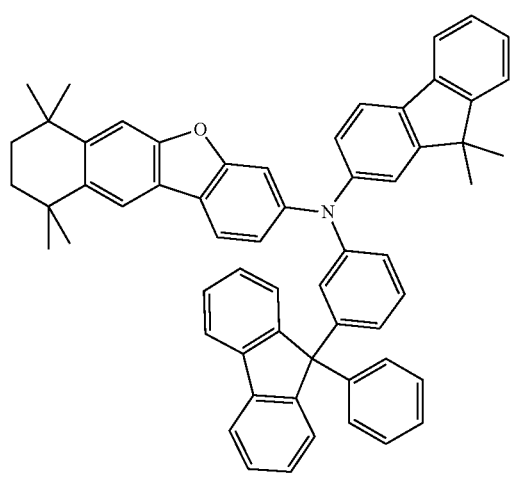
367
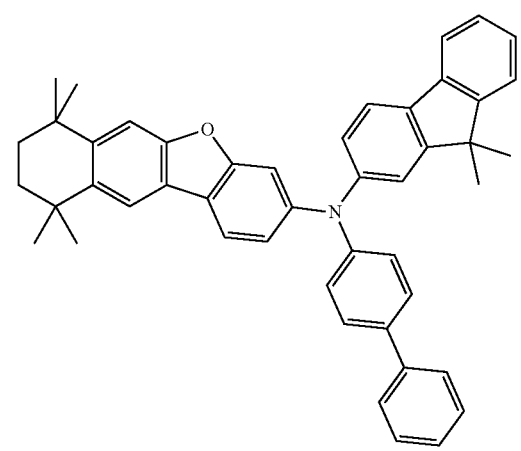

-continued
368
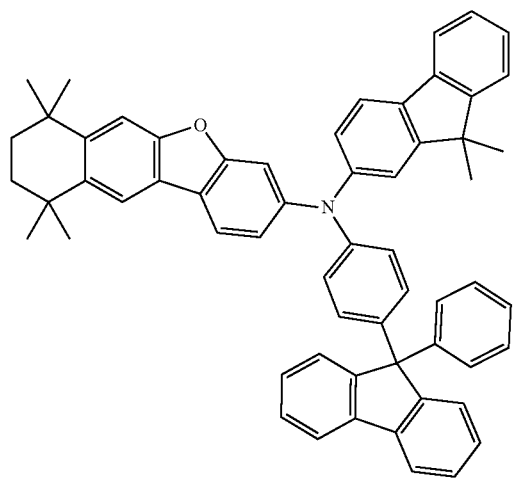
369
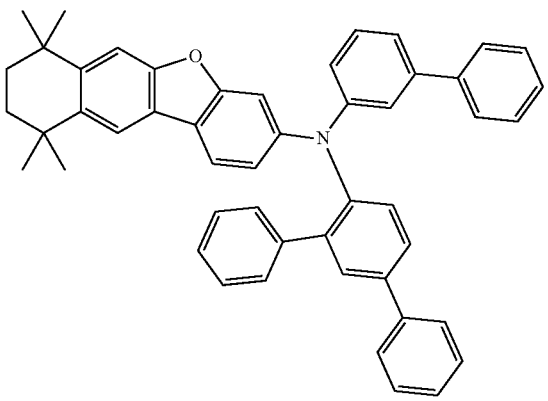
370
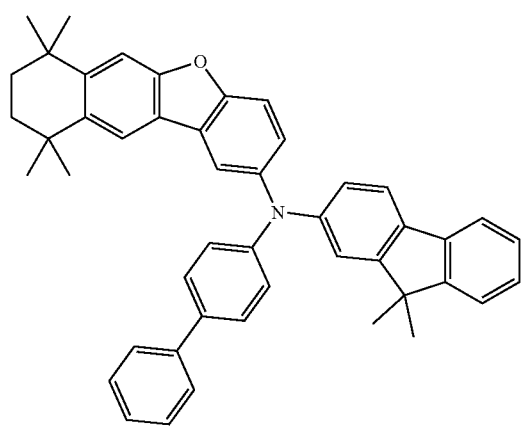
371
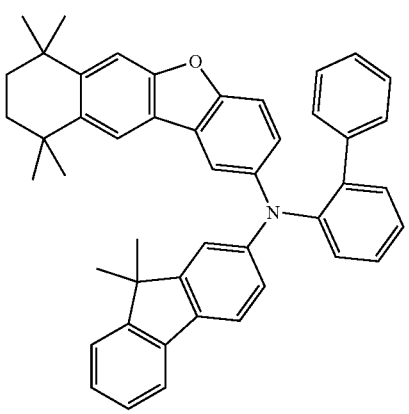
372
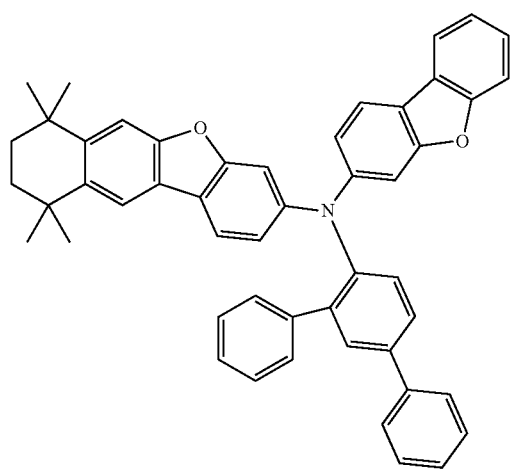
373
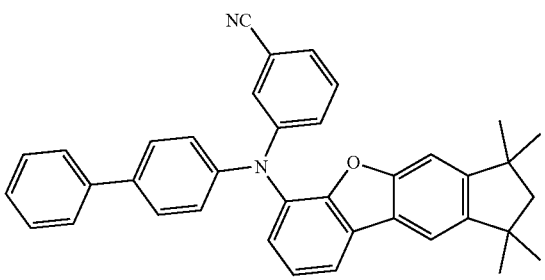

-continued
455
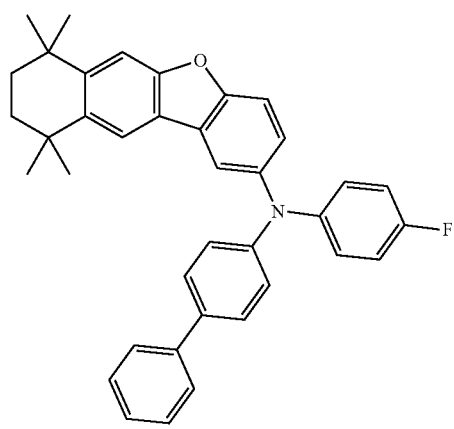
374
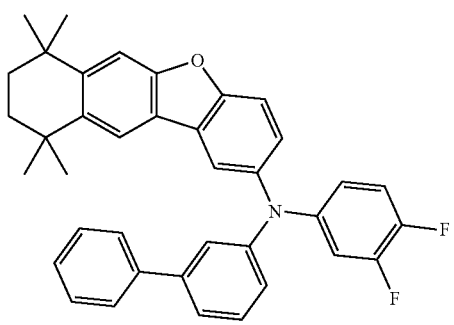
375
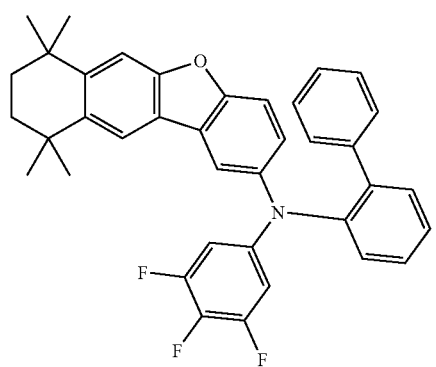
376
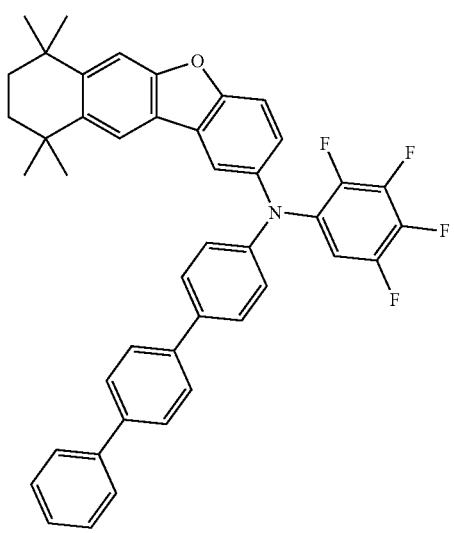
377
456
378
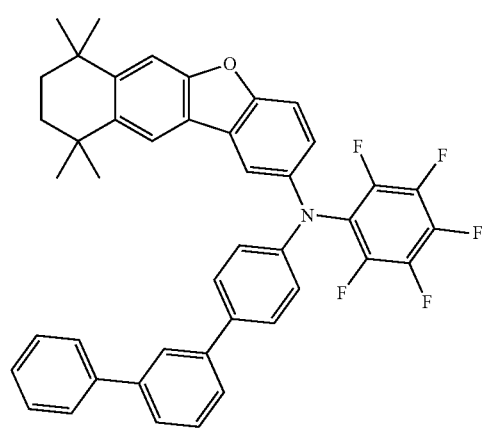
379
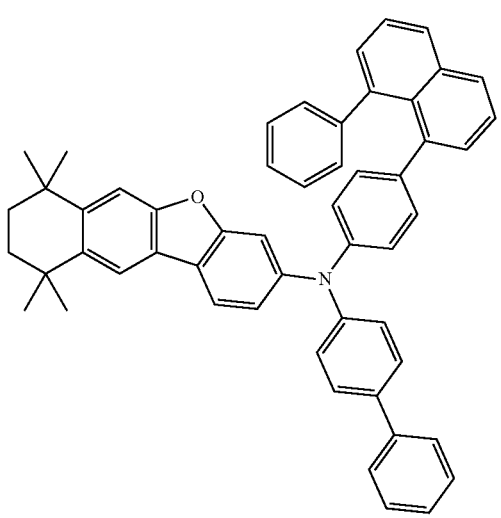

-continued
380
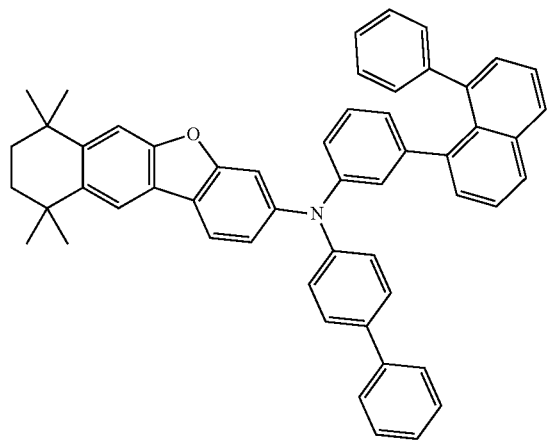
381
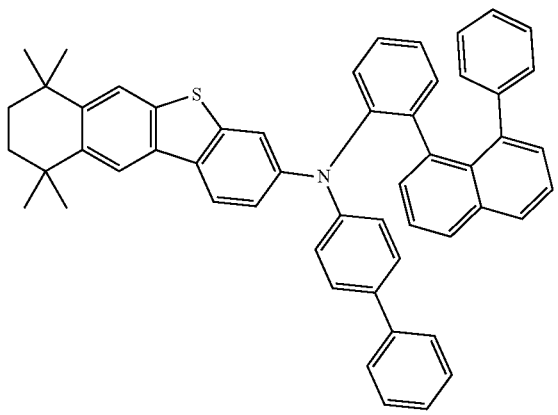
382
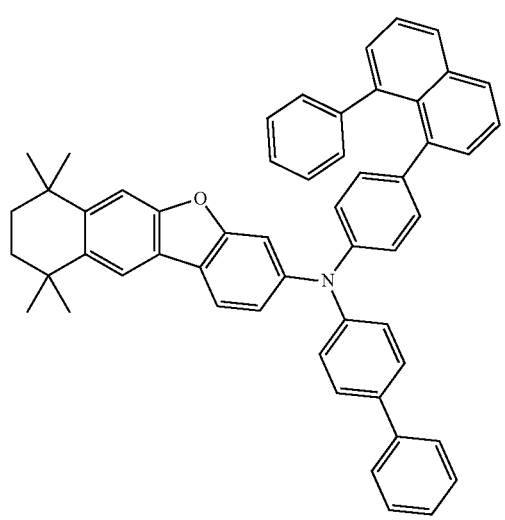
383
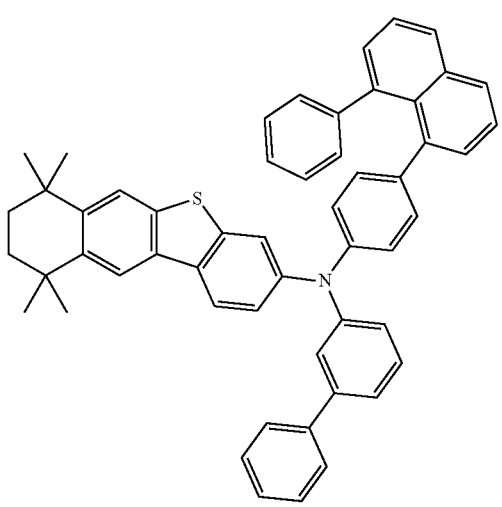
384
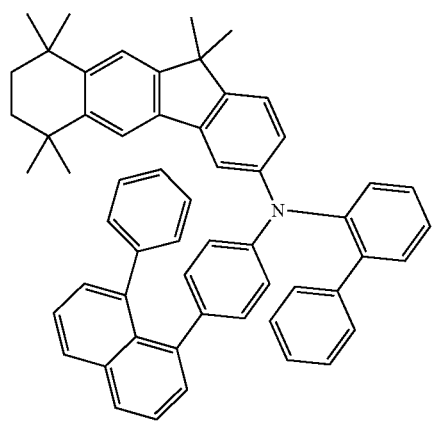
385
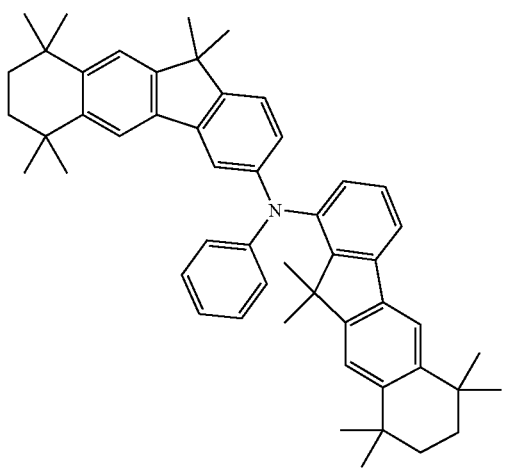

-continued
386
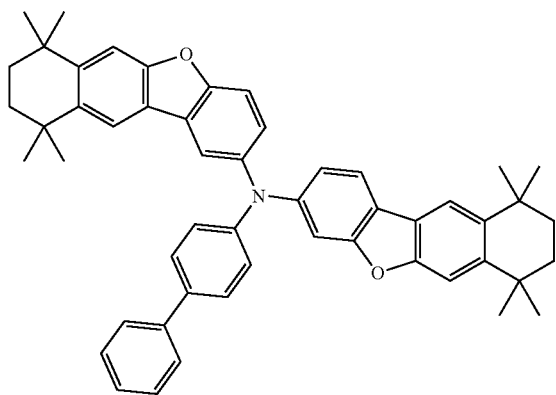
387
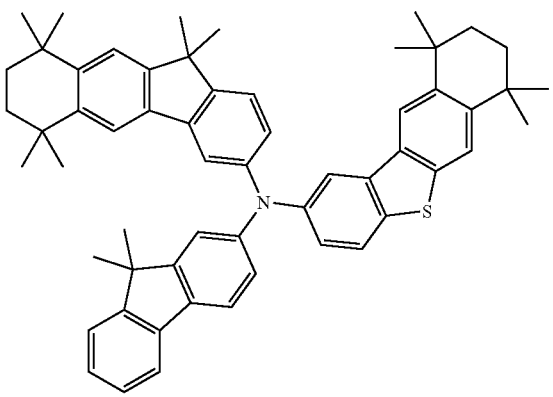
388
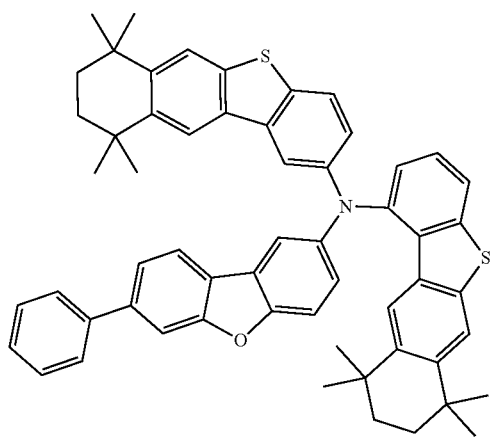
389
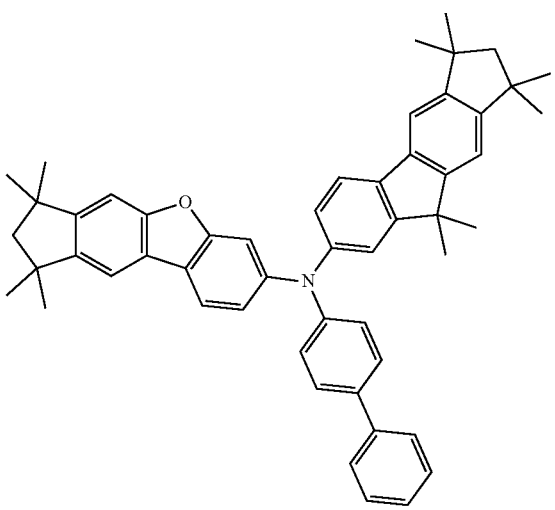
390
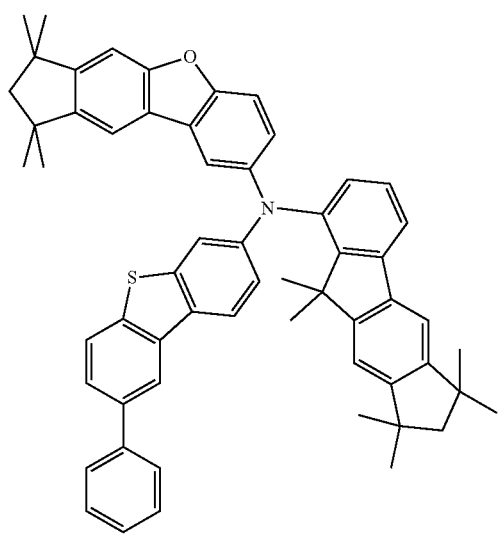
391
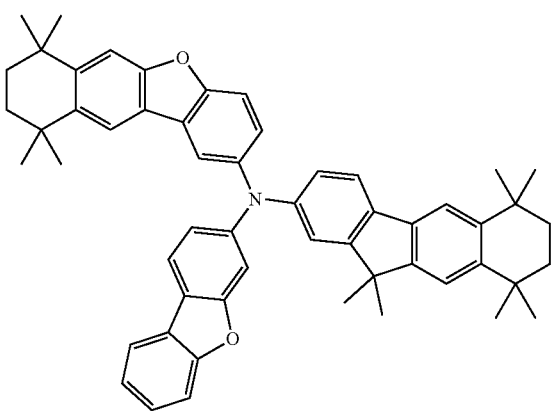

-continued
392
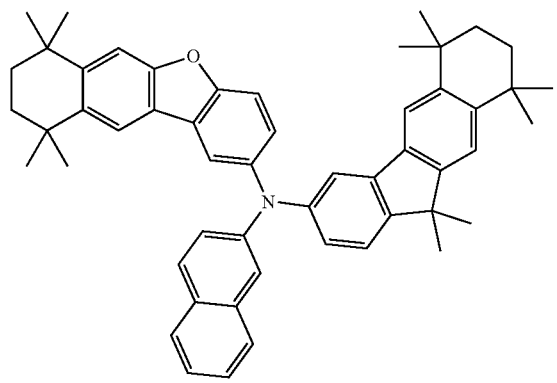
393
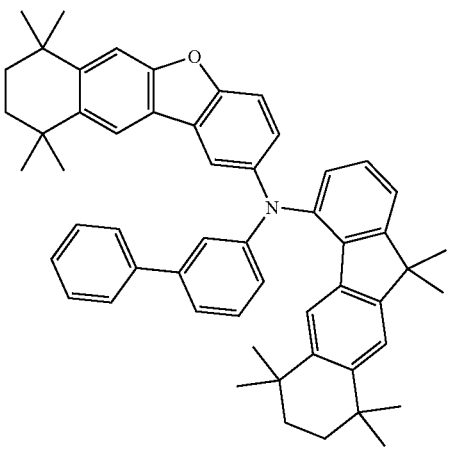
394
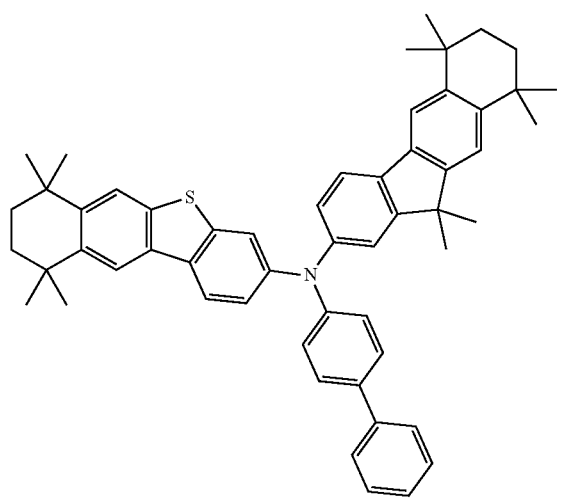
395
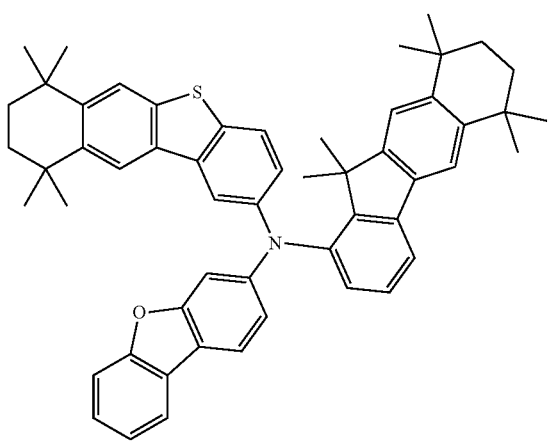
396
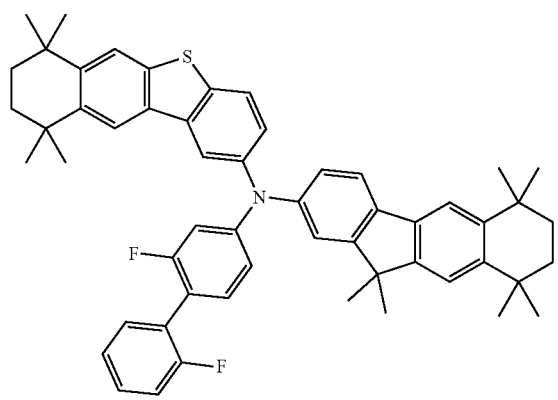
397
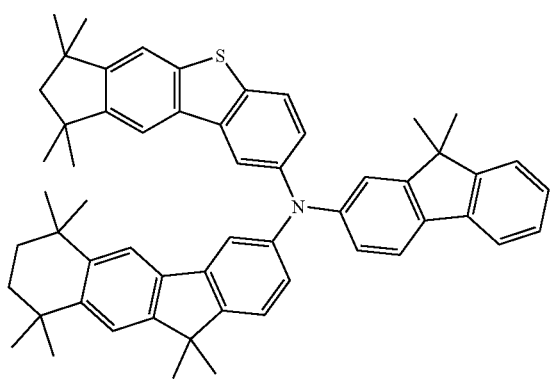

-continued

398
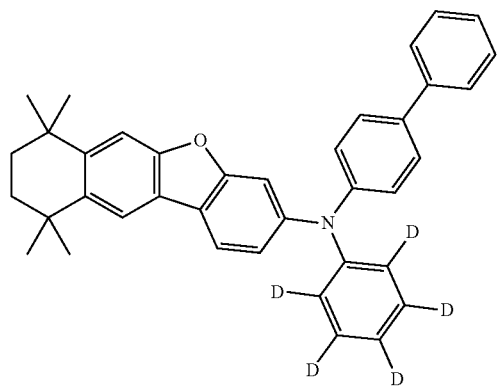

399
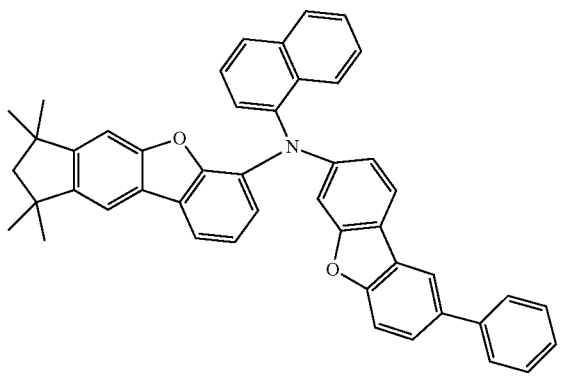

400
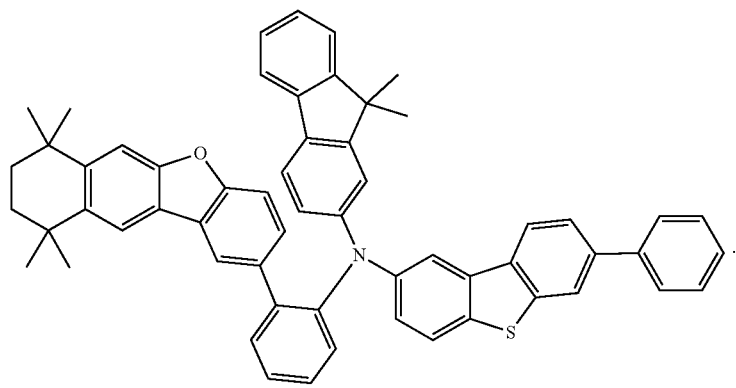

5. An electronic element, comprising an anode and a cathode which are oppositely disposed, and a functional layer disposed between the anode and the cathode; wherein the functional layer comprises the organic compound of claim 1.

6. The electronic element of claim 5, wherein the electronic element is an organic electroluminescent device or a photoelectric conversion device.

7. The electronic element of claim 5, wherein the electronic element is an organic electroluminescent device, and the functional layer comprises a hole adjusting layer comprising the organic compound.

8. An electronic device, comprising the electronic element of claim 5.

9. The organic compound of claim 3, wherein $R_1$ and $R_2$ are the same or different, and are each independently selected from hydrogen or a methyl.

10. The organic compound of claim 3, wherein $n_1+n_2=0$, 1 or 2.

* * * * *